US010184884B2

(12) United States Patent
Anderson et al.

(10) Patent No.: US 10,184,884 B2
(45) Date of Patent: Jan. 22, 2019

(54) ASSAY CARTRIDGES AND METHOD OF USING THE SAME

(75) Inventors: Nicholas Anderson, Ijamsville, MD (US); Jeffery Debad, Ijamsville, MD (US); Eli N. Glezar, Chevy Chase, MD (US); Sudeep Kumar, Gaithersburg, MD (US); Noel Lawrence, Gaithersburg, MD (US); Kenneth Page, Germantown, MD (US); George Sigal, Rockville, MD (US); Sharon West, Rockville, MD (US)

(73) Assignee: Meso Scale Technologies, LLC, Gaithersburg, MD (US)

( * ) Notice: Subject to any disclaimer, the term of this patent is extended or adjusted under 35 U.S.C. 154(b) by 0 days.

(21) Appl. No.: 12/959,952

(22) Filed: Dec. 3, 2010

(65) Prior Publication Data

US 2011/0201099 A1    Aug. 18, 2011

Related U.S. Application Data

(60) Provisional application No. 61/283,677, filed on Dec. 7, 2009, provisional application No. 61/283,927, filed
(Continued)

(51) Int. Cl.
*G01N 21/05* (2006.01)
*G01N 21/69* (2006.01)
(Continued)

(52) U.S. Cl.
CPC ............ *G01N 21/05* (2013.01); *B01L 3/5027* (2013.01); *G01F 23/02* (2013.01); *G01F 23/292* (2013.01);
(Continued)

(58) Field of Classification Search
CPC ....... G01N 2021/0346; G01N 21/0303; G01N 21/05; B01L 2200/10; B01L 2300/0816;
(Continued)

(56) References Cited

U.S. PATENT DOCUMENTS 5,425,921 A *  6/1995  Coakley et al. .............. 422/547
7,497,997 B2    3/2009  Glezer et al.
(Continued)

FOREIGN PATENT DOCUMENTS

FR    2690740 A1    11/1993
GB    2206967 A     1/1989
(Continued)

OTHER PUBLICATIONS

International Search Report and Written Opinion issued in connection with corresponding International Application No. PCT/US2010/058913 dated Jul. 8, 2011.
(Continued)

*Primary Examiner* — Dean Kwak
(74) *Attorney, Agent, or Firm* — The H.T. Than Law Group

(57) ABSTRACT

Assay cartridges are described that have a detection chamber, preferably having integrated electrodes, and other fluidic components which may include sample chambers, waste chambers, conduits, vents, bubble traps, reagent chambers, dry reagent pill zones and the like. In certain embodiments, these cartridges are adapted to receive and analyze a sample collected on an applicator stick. Also described are kits including such cartridges and a cartridge reader configured to analyze an assay conducted using an assay cartridge.

19 Claims, 69 Drawing Sheets

Related U.S. Application Data on Dec. 10, 2009, provisional application No. 61/284,276, filed on Dec. 16, 2009.

(51) Int. Cl.

| | | |
|---|---|---|
| *G01N 21/76* | (2006.01) | |
| *G01N 21/03* | (2006.01) | |
| *G01F 23/02* | (2006.01) | |
| *G01F 23/292* | (2006.01) | |
| B01L 3/00 | (2006.01) | |
| *B01L 7/00* | (2006.01) | |
| *B01L 9/00* | (2006.01) | |

(52) U.S. Cl.
CPC ......... *G01N 21/03* (2013.01); *G01N 21/0303* (2013.01); *G01N 21/69* (2013.01); *G01N 21/76* (2013.01); *B01L 3/502723* (2013.01); *B01L 3/502746* (2013.01); *B01L 3/502784* (2013.01); *B01L 7/00* (2013.01); *B01L 9/527* (2013.01); *B01L 2200/025* (2013.01); *B01L 2200/04* (2013.01); *B01L 2200/0605* (2013.01); *B01L 2200/0684* (2013.01); *B01L 2200/0689* (2013.01); *B01L 2200/12* (2013.01); *B01L 2200/141* (2013.01); *B01L 2200/147* (2013.01); *B01L 2200/16* (2013.01); *B01L 2300/021* (2013.01); *B01L 2300/024* (2013.01); *B01L 2300/027* (2013.01); *B01L 2300/044* (2013.01); *B01L 2300/0645* (2013.01); *B01L 2300/0654* (2013.01); *B01L 2300/0809* (2013.01); *B01L 2300/0874* (2013.01); *B01L 2300/0877* (2013.01); *B01L 2300/0887* (2013.01); *B01L 2300/126* (2013.01); *B01L 2300/161* (2013.01); *B01L 2400/0487* (2013.01); *B01L 2400/0672* (2013.01); *B01L 2400/0683* (2013.01); *B01L 2400/0688* (2013.01); *G01N 2021/0346* (2013.01); *Y10T 137/0396* (2015.04); *Y10T 137/8593* (2015.04)

(58) Field of Classification Search
CPC ..... B01L 2300/0867; B01L 2400/0688; B01L 3/5027; B01L 2200/0684; B01L 2300/0681; B01L 2300/0887; B01L 2400/049; B01L 3/502715; B01L 3/5029; B01L 9/527; B01L 2200/027; B01L 2200/0605; B01L 2200/0621; B01L 2200/0631; B01L 2200/16; B01L 2300/0864; B01L 2300/087; B01L 2300/0883; B01L 2400/0487; B01L 2400/0694; B01L 7/525
USPC ..................................... 422/554, 82.05, 400
See application file for complete search history.

(56) References Cited

U.S. PATENT DOCUMENTS

| | | |
|---|---|---|
| 2002/0000120 A1 | 1/2002 | Dillon |
| 2003/0155538 A1 | 8/2003 | Siepmann |
| 2004/0189311 A1* | 9/2004 | Glezer et al. ................. 324/444 |
| 2004/0259237 A1* | 12/2004 | Kellogg et al. ............ 435/287.1 |
| 2005/0136541 A1* | 6/2005 | De Haan ................. B01L 3/502 436/8 |
| 2006/0099111 A1* | 5/2006 | Kikuchi et al. .............. 422/68.1 |
| 2006/0110292 A1 | 5/2006 | Deverse et al. |
| 2006/0228259 A1 | 10/2006 | Samsoondar |
| 2007/0264629 A1 | 11/2007 | Holmes et al. |
| 2008/0242553 A1* | 10/2008 | Kayyem ............... B01L 3/5027 506/9 |
| 2010/0173394 A1* | 7/2010 | Colston, Jr. ........... B01F 3/0807 435/287.2 |
| 2016/0139164 A1* | 5/2016 | Brueckner ......... G01N 35/1002 436/501 |

FOREIGN PATENT DOCUMENTS

| | | |
|---|---|---|
| JP | S55103408 A | 8/1980 |
| JP | 2004009488 A | 1/2004 |
| JP | 2008292364 A | 12/2008 |

OTHER PUBLICATIONS

European Search Report issued in connection with corresponding European Patent Application No. 10 836 455 dated Aug. 27, 2013.

* cited by examiner

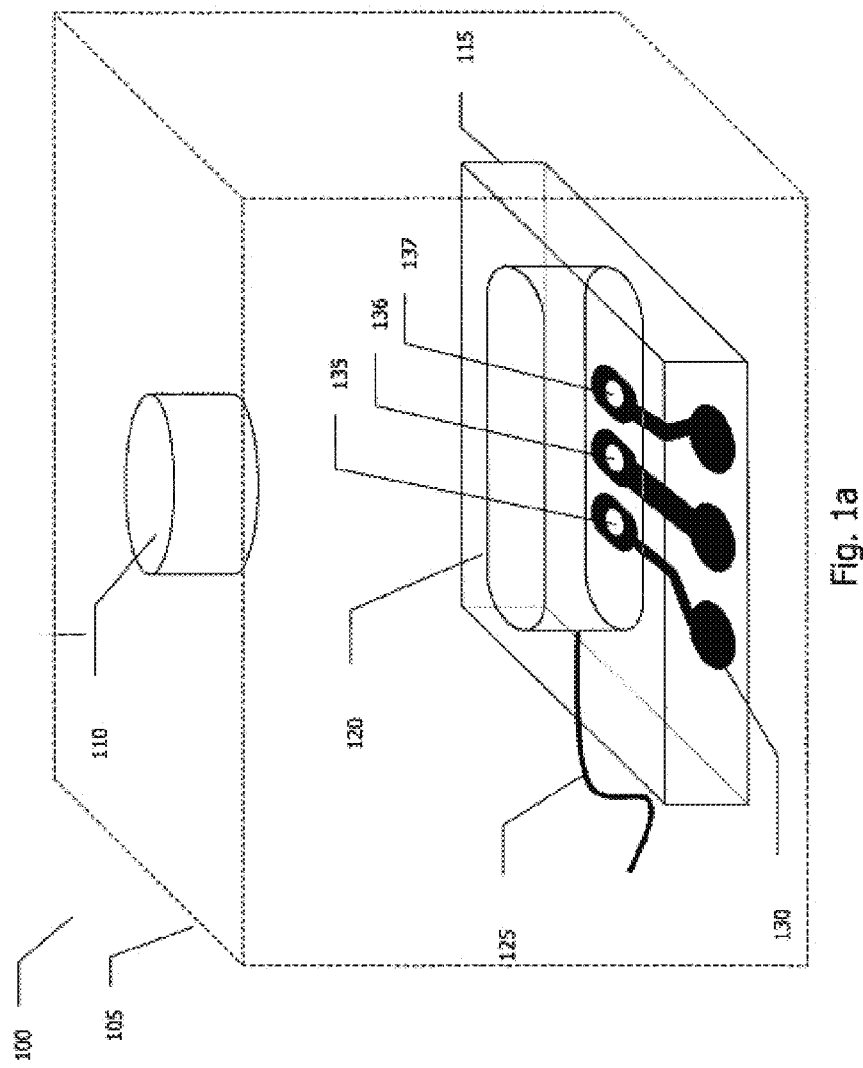

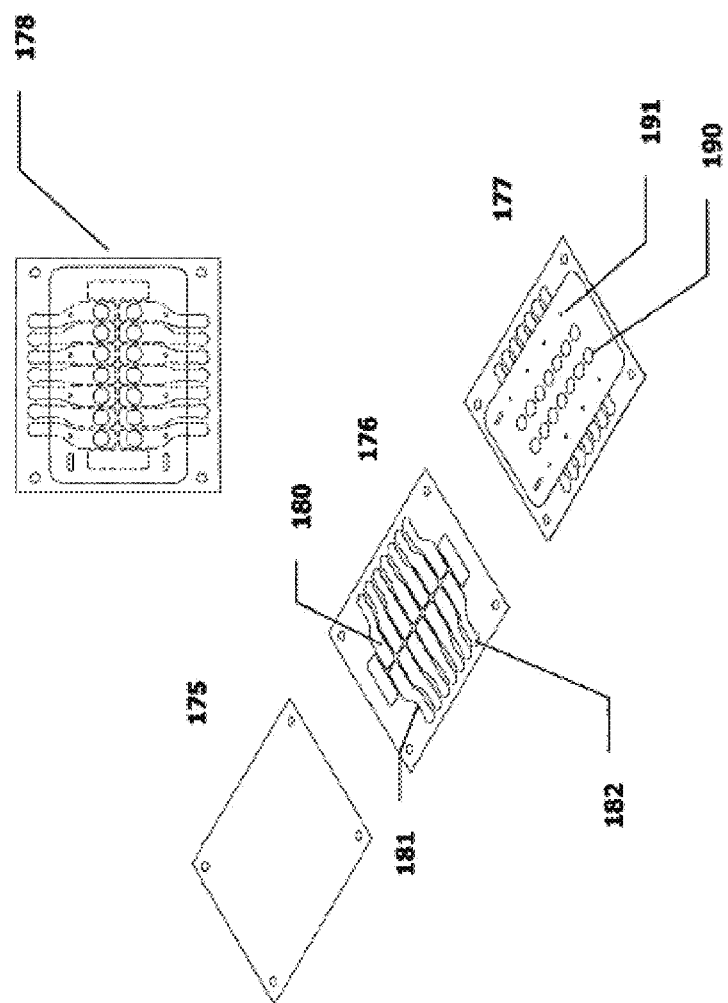

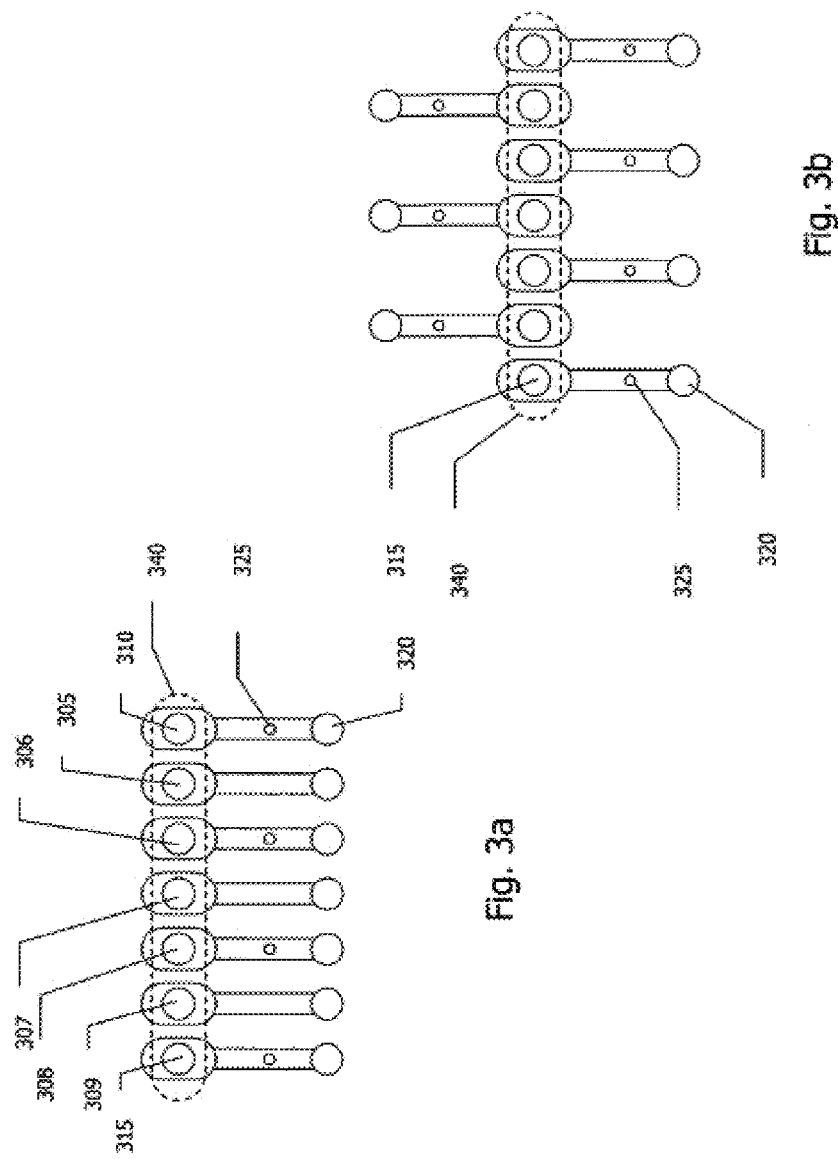

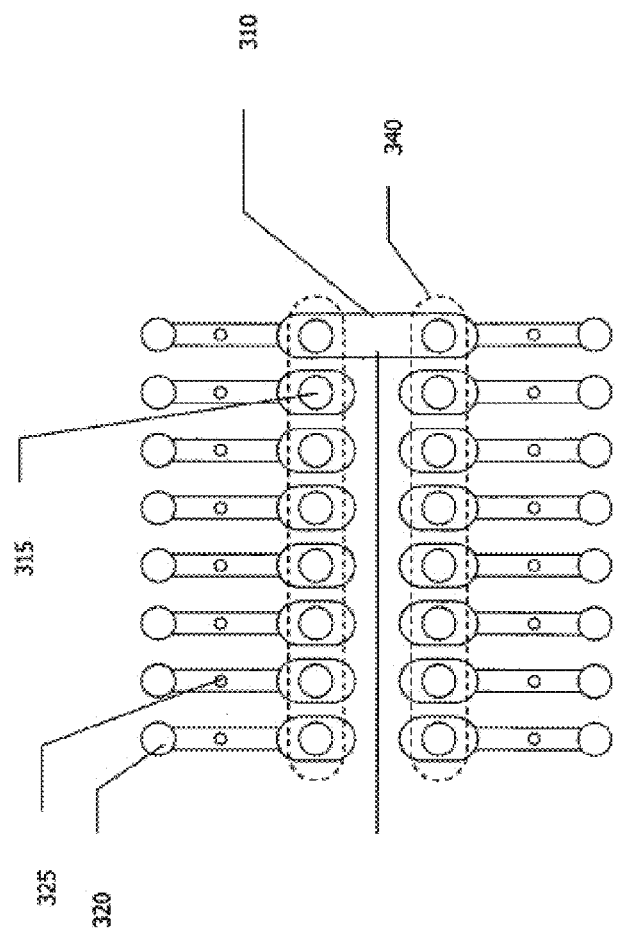

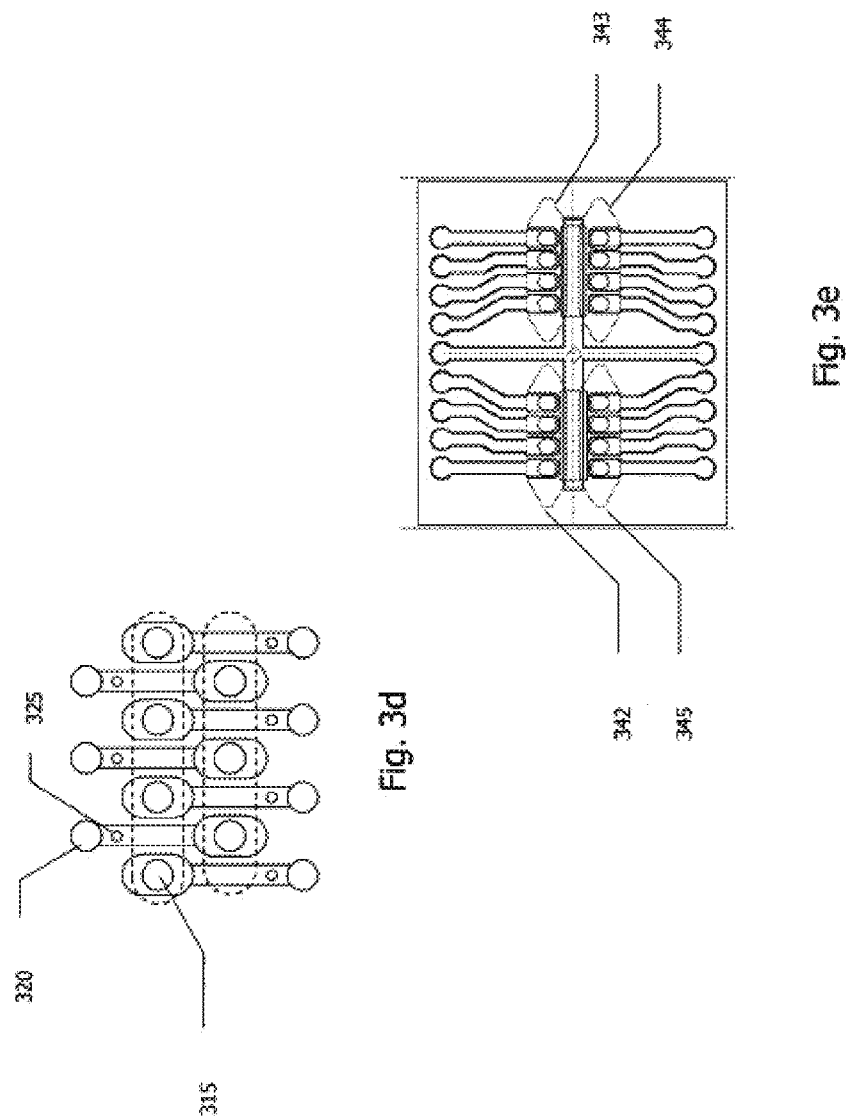

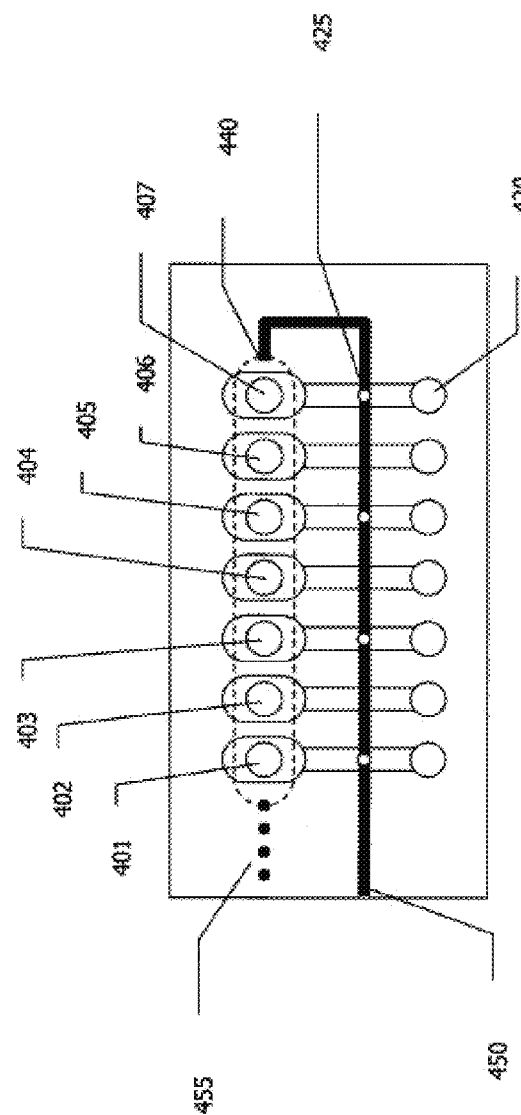

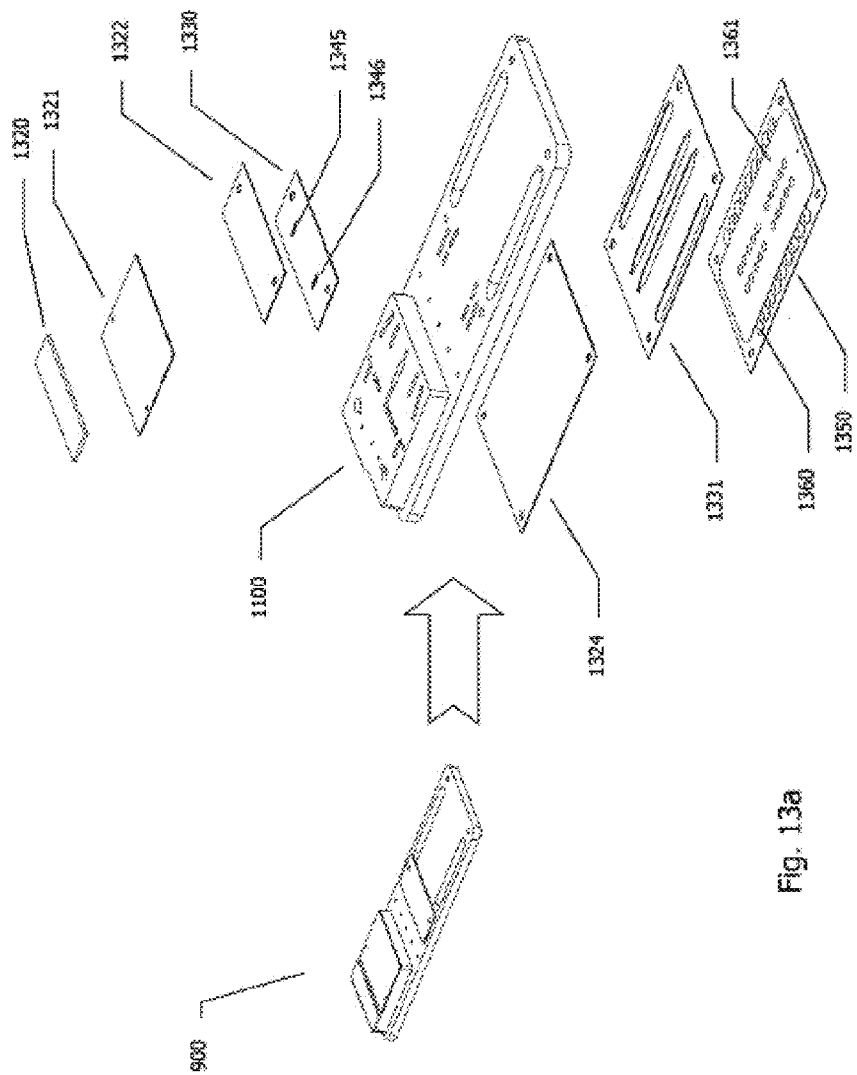

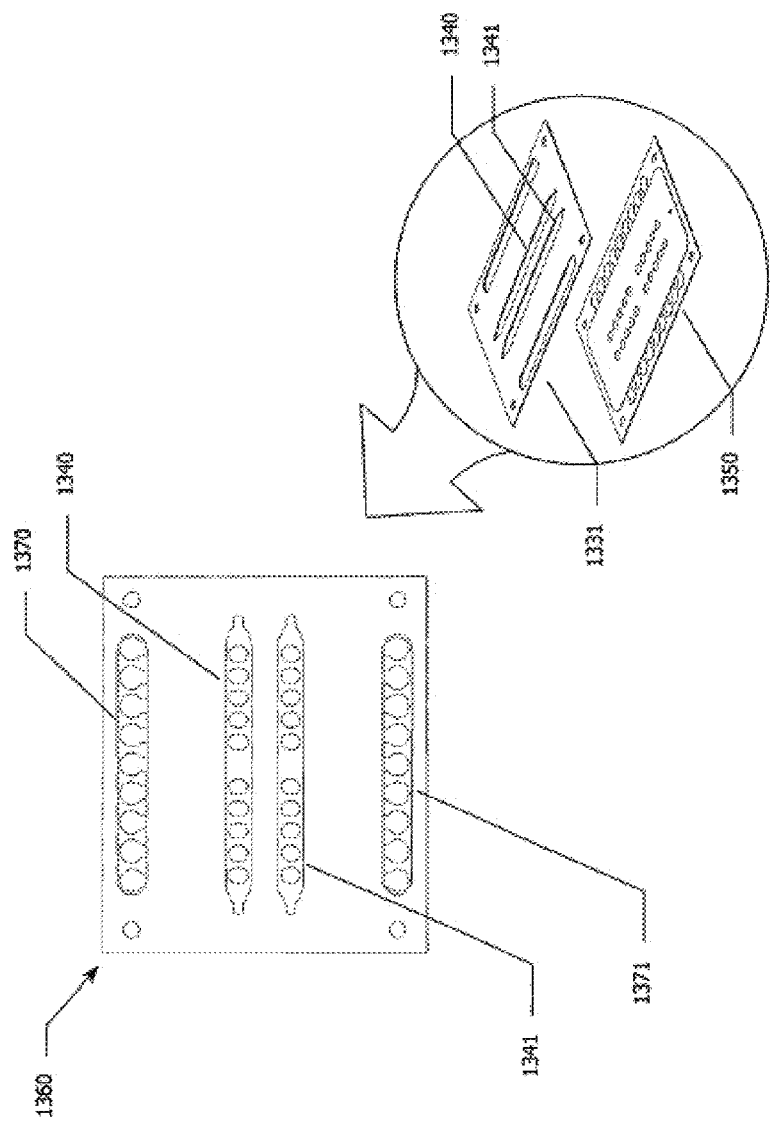

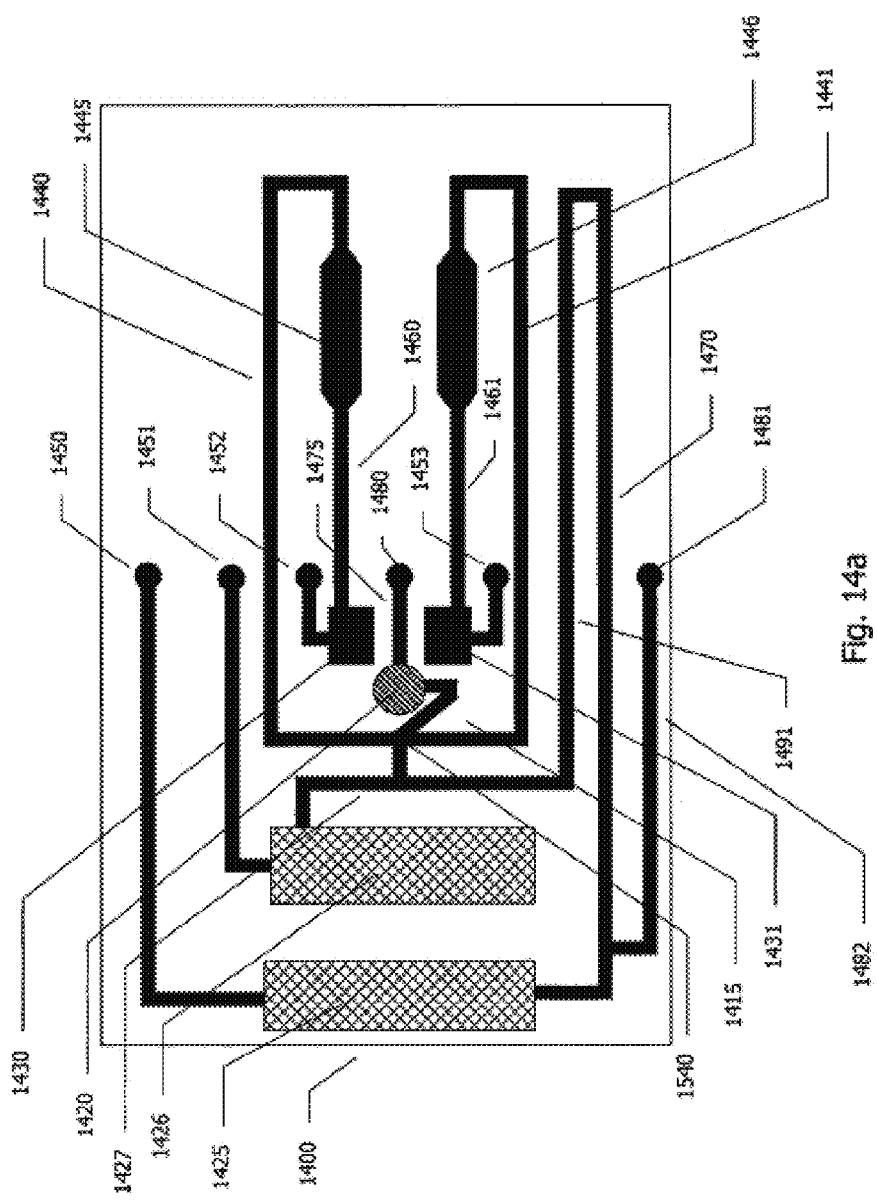

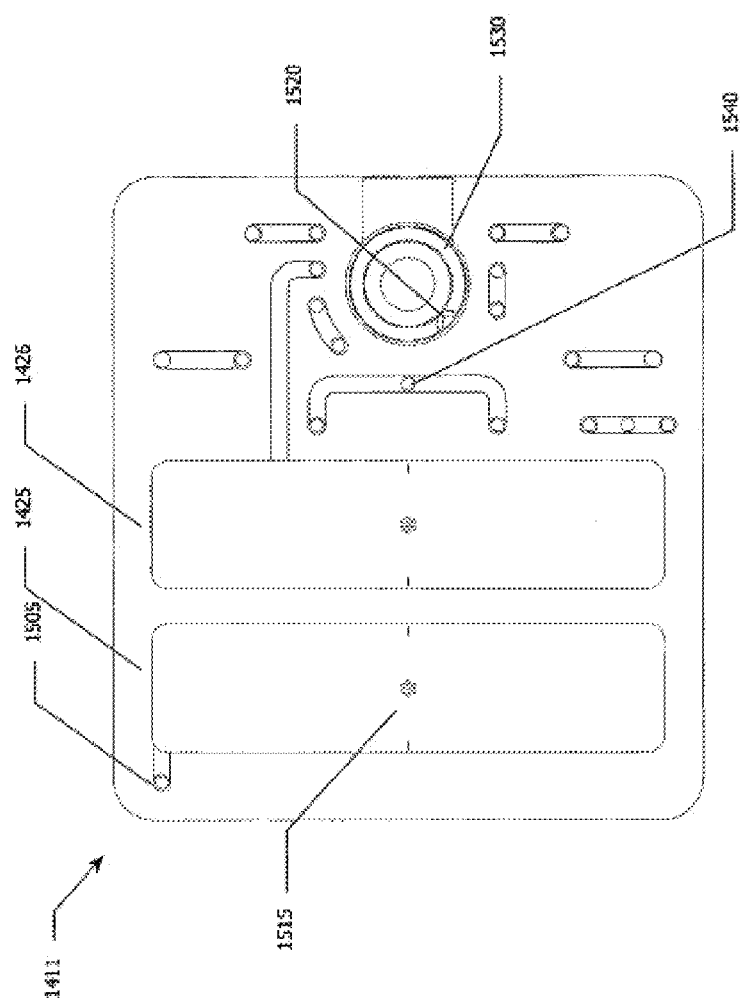

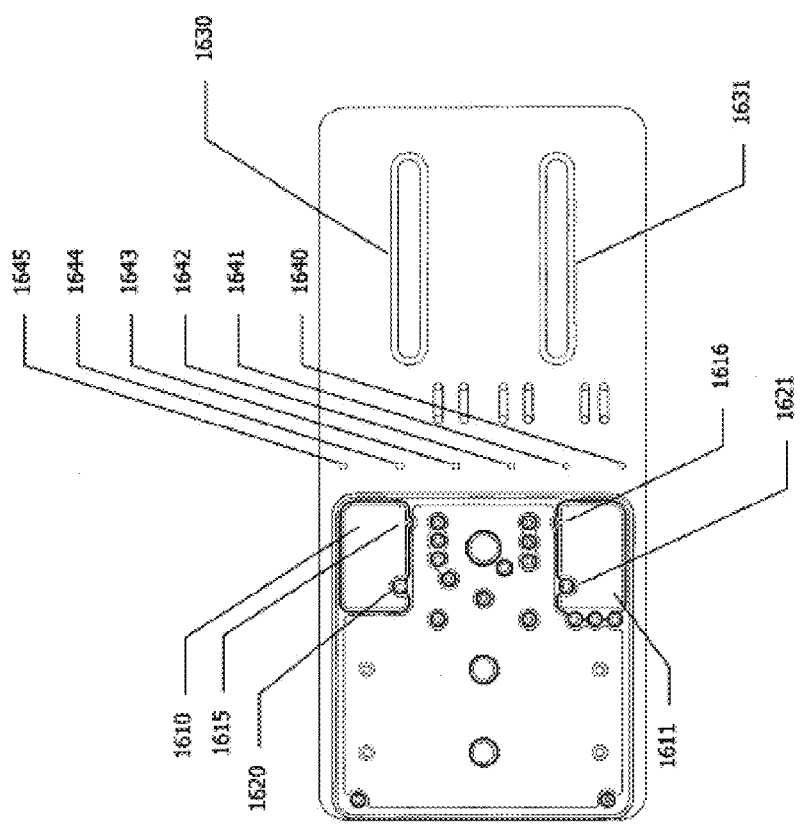

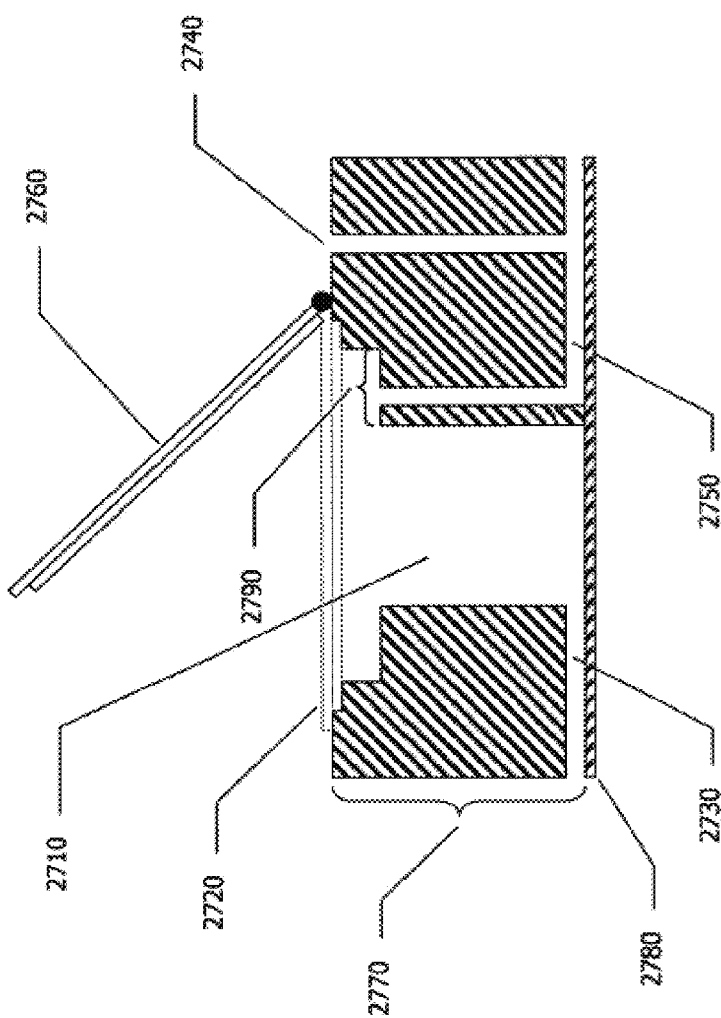

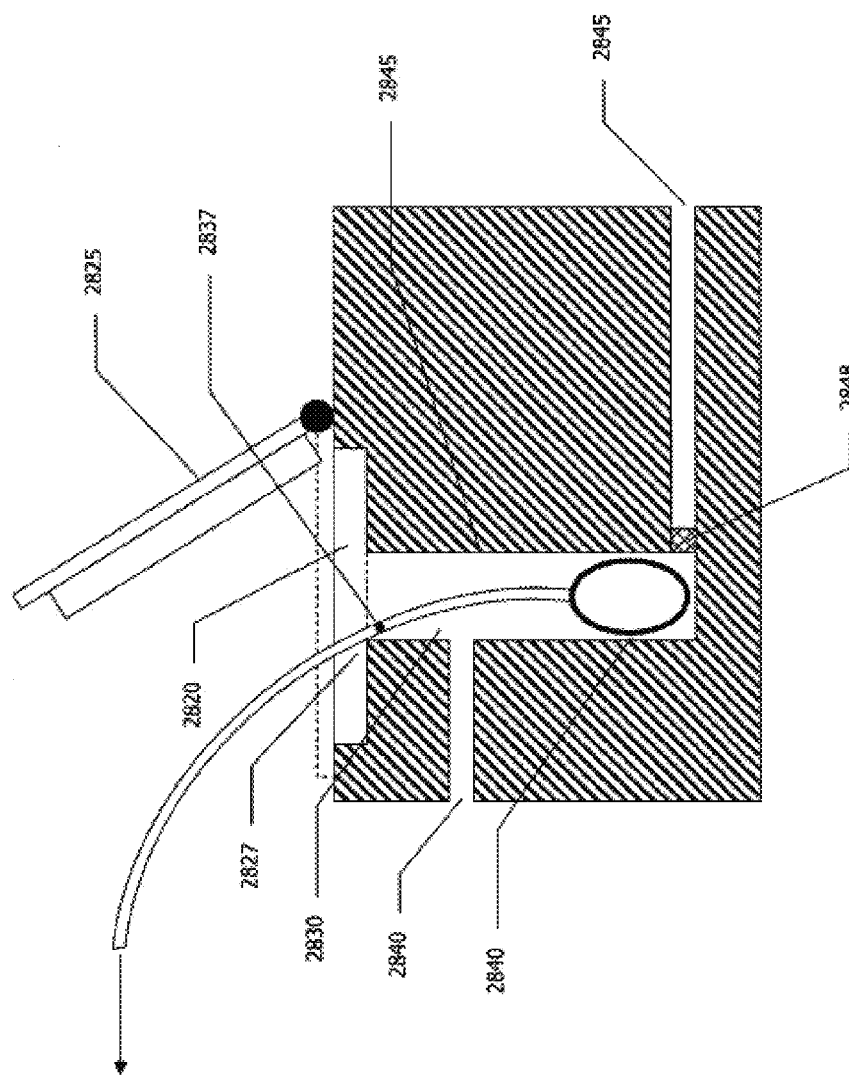

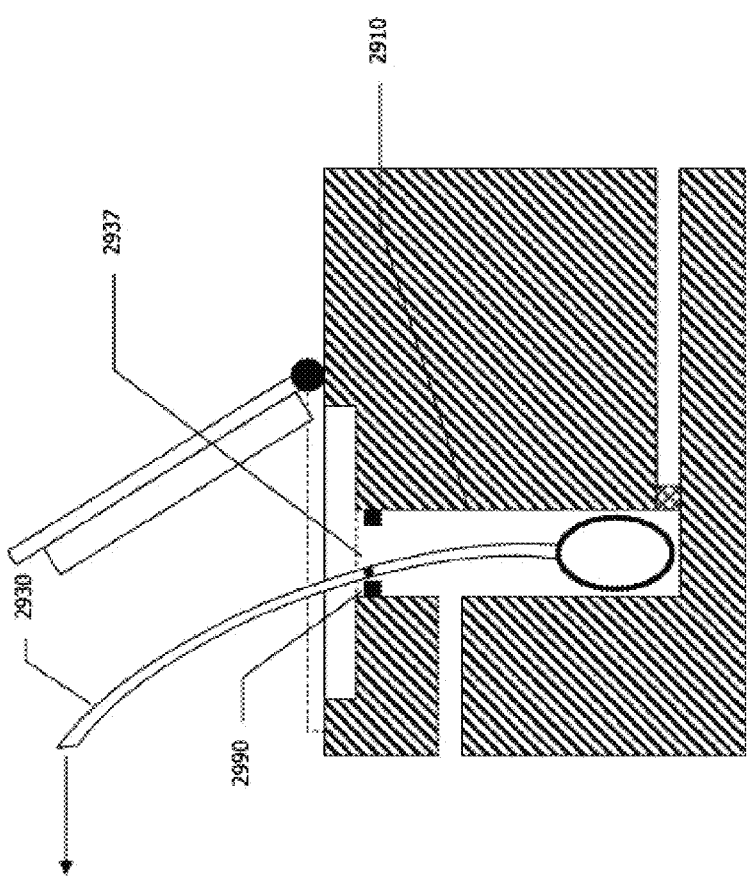

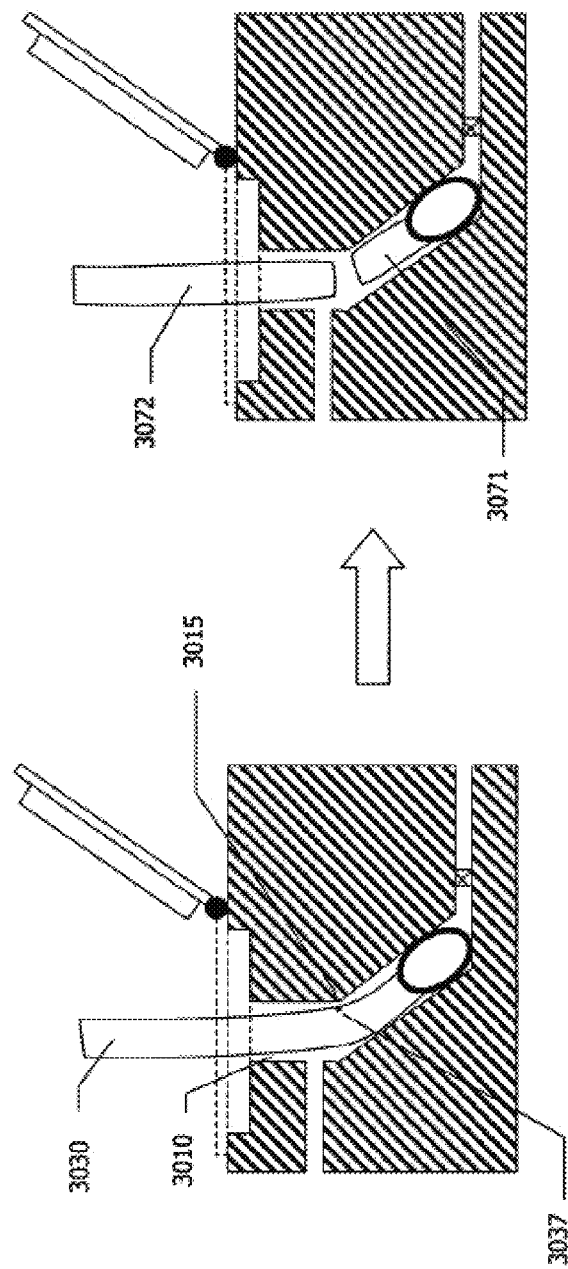

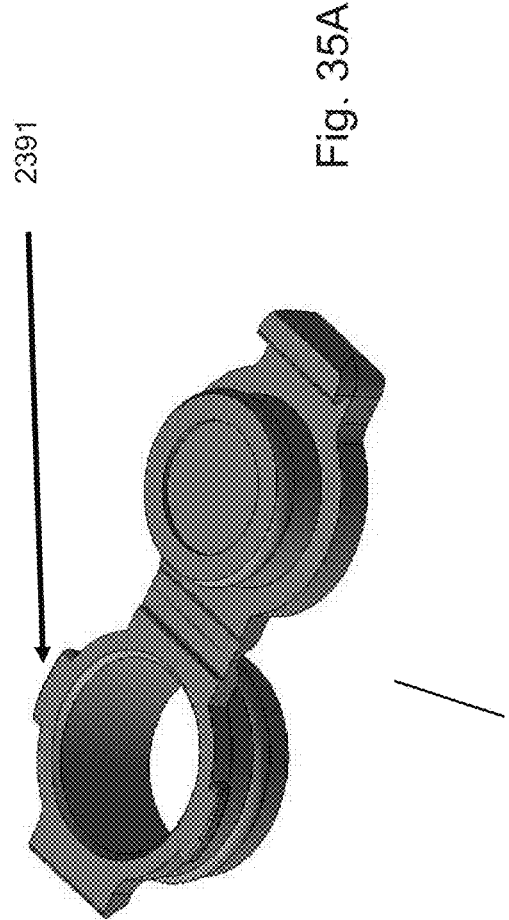
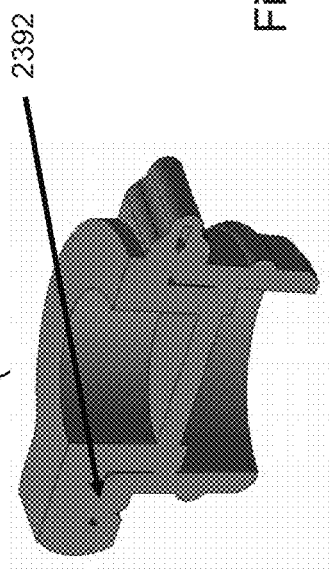

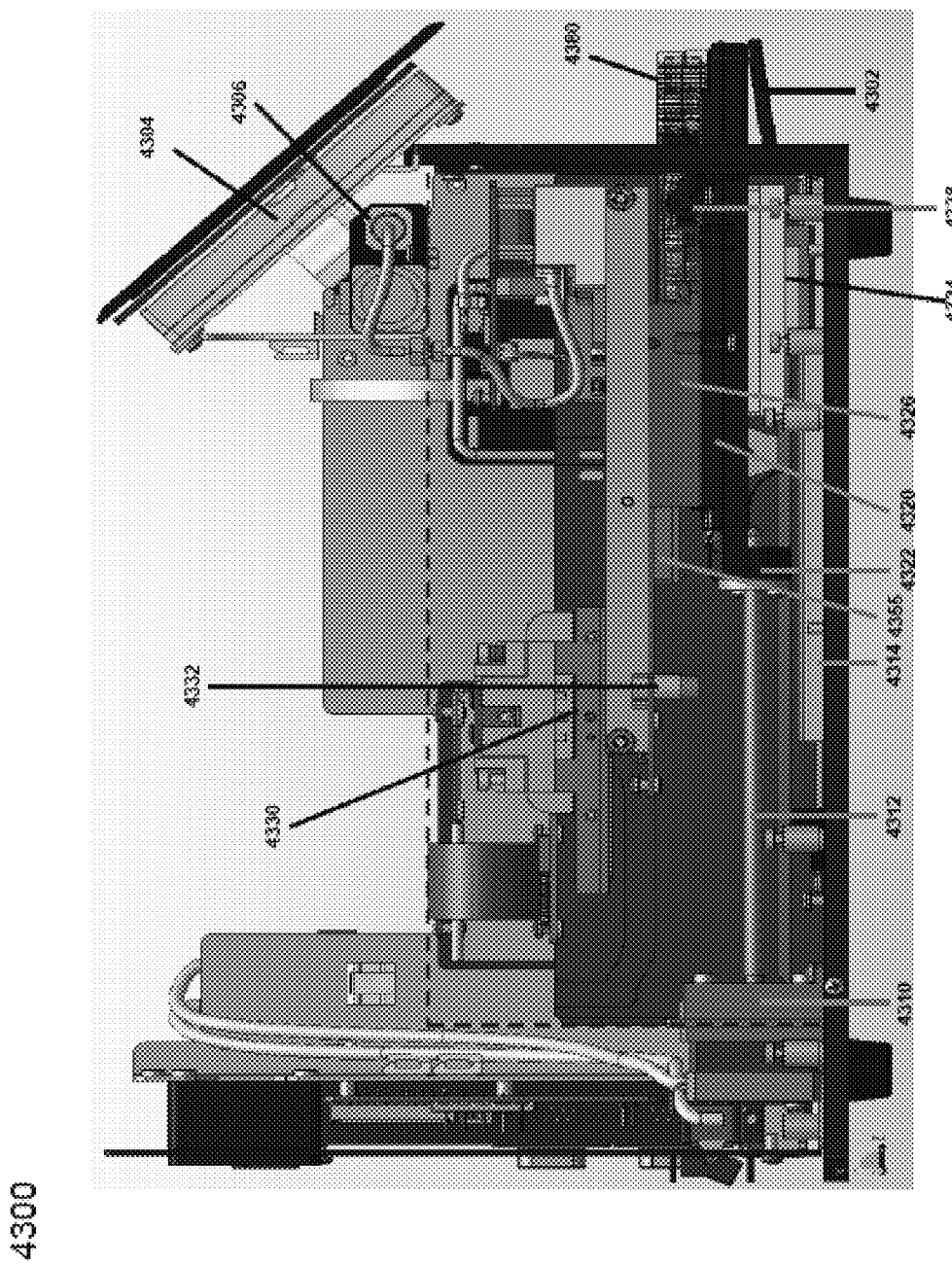

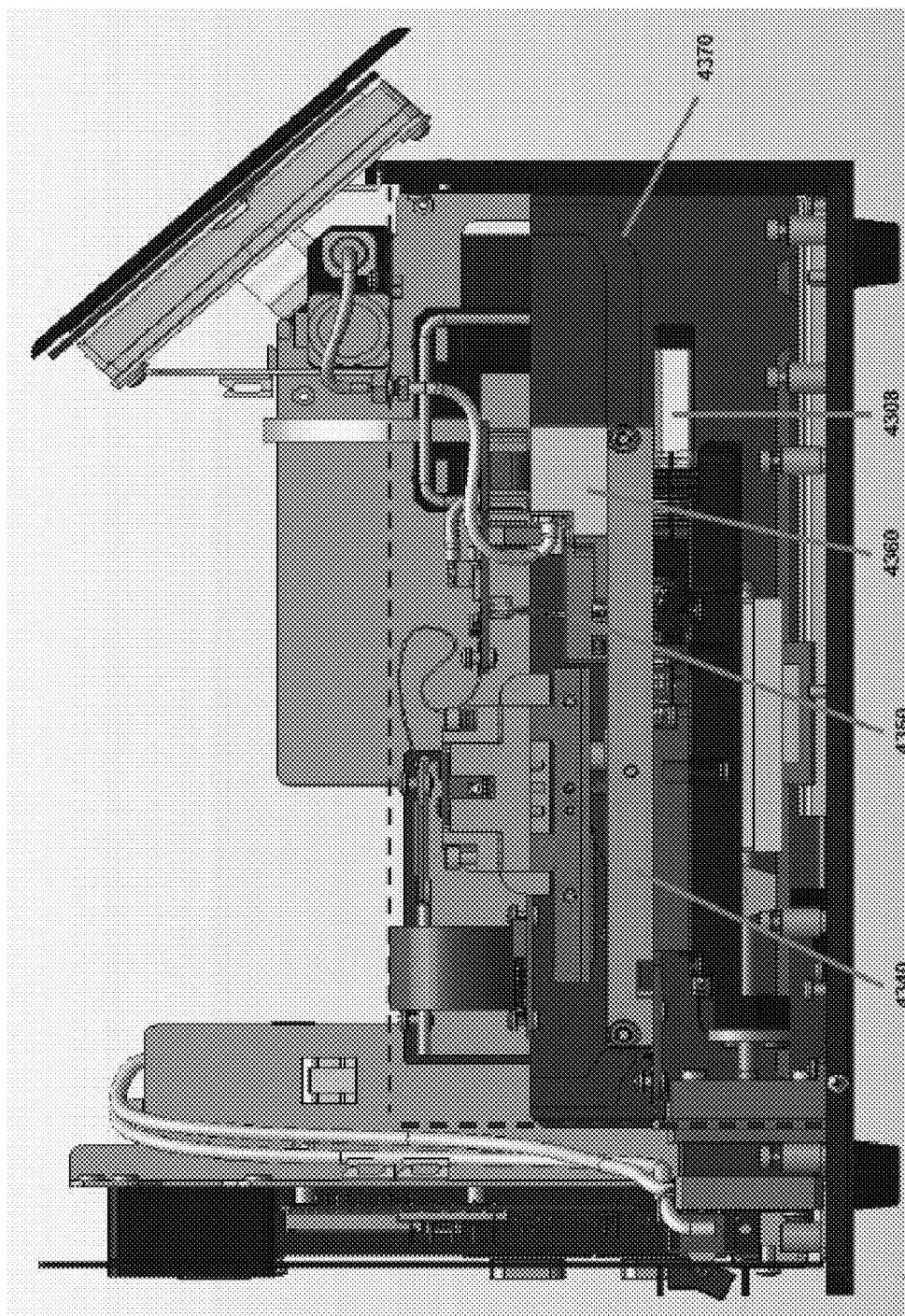

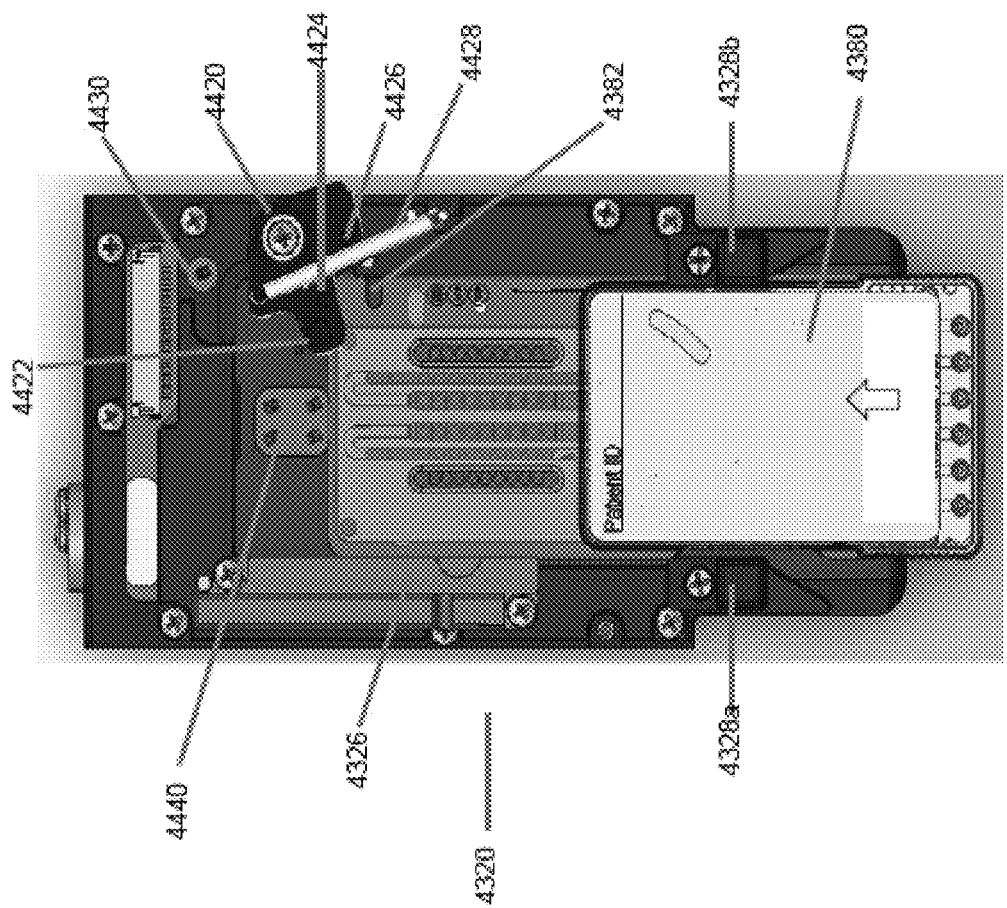

ASSAY CARTRIDGES AND METHOD OF USING THE SAME

CROSS-REFERENCE TO RELATED APPLICATION

Reference is made to application Ser. No. 10/744,726, filed Dec. 23, 2003, now U.S. Pat. No. 7,497,997 B2, and U.S. Provisional application Ser. No. 60/136,569, filed Dec. 26, 2002. The disclosures of each of these applications are incorporated herein by reference.

This utility application claims priority to U.S. Provisional application Ser. Nos. 61/283,677, filed on Dec. 7, 2009, 61/283,927, filed on Dec. 10, 2009, and 61/284,276, filed on Dec. 16, 2009. The disclosures of each of these applications are incorporated herein by reference.

STATEMENT REGARDING FEDERALLY-SPONSORED RESEARCH

This invention was made with federal support under HHS 200-2007-19346 awarded by the Department of Health and Human Services. The U.S. government has certain rights in the invention.

FIELD OF THE INVENTION

This application relates to apparatuses, systems, kits and methods for conducting chemical, biochemical and/or biological assays on a sample. These apparatuses include assay cartridges and cartridge readers for conducting these assays. The application also describes electrode arrays for use in assays, methods of preparing and using these electrode arrays and diagnostic devices comprising the arrays. These electrode arrays may be incorporated into the cartridges and apparatuses of the invention.

BACKGROUND OF THE INVENTION

Clinical measurements have been traditionally carried out in central clinical labs using large clinical analyzers that can handle large numbers of samples in batch mode. These laboratories are staffed by trained personnel that are capable of maintaining and running these complex analyzers. There is a growing desire to move clinical measurements from the central lab to the "point of care", e.g., the emergency room, hospital bedside, physicians office, home, etc. Point of care measurements allow a care provider or patient to quickly make decisions based on diagnostic information, as opposed to having to wait hours or days to receive laboratory results from a clinical lab. The difficulty in developing point of care diagnostic systems has been making them small enough and easy enough to use so that they can be used by unskilled operators in decentralized clinical settings, but at the same time maintaining the low cost, diverse assay menu, and/or high performance of tests carried out on traditional clinical analyzers in central laboratories.

SUMMARY OF THE INVENTION

Therefore, the present invention provides an assay cartridge that may be used to conduct a biological assay in a cartridge reader. The assay cartridge and accompanying reader include numerous features to facilitate sample collection and assay processing.

In one embodiment, the invention provides an assay cartridge including an indicator window to facilitate sample collection and processing in the assay cartridge. The assay cartridge includes a sample chamber, a sample indicator window and an optical path from a reflecting surface to said indicator window, wherein the reflecting surface reflects a sample level in the sample chamber to the indicator window. Alternatively, the assay cartridge may include a sample chamber, a sample indicator window, a reflecting surface, and an optical path connecting the sample chamber, the sample indicator window and the reflecting surface. The sample indicator window may include an indicating feature, e.g., an indicating line that indicates a fluid level within the sample chamber, wherein the level is selected from the group consisting of a sample minimum, a sample maximum, a target level and a combination thereof. Alternatively, the indicating feature is a boundary of the indicator window.

The reflecting surface may be a mirrored surface and in one embodiment, the cartridge comprises a cartridge body and the reflecting surface is provided by total internal reflection at an angled surface in the cartridge body. The angled surface may be configured such that an angle of incidence along the optical path is greater than a critical angle for total internal reflection at the reflecting surface. In one embodiment, the angled surface is provided by a surface of a cavity within the cartridge body such that light traveling through the cartridge body along the optical path intersects an air-body interface at the cavity surface and is reflected along the optical path to the indicator window. For example, the angle of incidence may be greater than or equal to about 43 degrees. In one specific embodiment, the angle of incidence is about 45 degrees. The cartridge body may comprise a material with a refractive index greater than or equal to 1.46 and may include a cartridge top, a cartridge bottom and a cover layer mated to the cartridge bottom and the optical path may be provided by the cartridge top. The sample chamber in the assay cartridge may be connected to an overflow chamber via a sample overflow conduit, wherein the overflow chamber is connected to a sample vent port via a vent conduit, optionally positioned at or near the top of the overflow chamber.

The invention also provides a method of determining a fluid level in an assay cartridge that includes a sample indicator window. That method includes the steps of (a) adding a volume of fluid to the sample chamber, wherein the fluid level is reflected via the optical path to the indicator window; (b) viewing the fluid level in the sample indicator window; and (c) comparing the fluid level relative to an indicating feature on the sample indicator window.

The invention also provides an assay cartridge including a sample chamber configured to receive and process a sample deposited on an applicator stick. Such an assay cartridge may be used to analyze a sample collected with an applicator stick comprising a shaft and a sample collection head (e.g., a swab), the cartridge comprising a sample chamber having an elongated cavity that has a first region and a second region, wherein the first and second regions are oriented at an angle with respect to each other and the angle is selected to bend the shaft upon insertion of the applicator stick into the sample chamber and promote fracture of the shaft, wherein the sample chamber comprises a sample head retention feature. The retention feature may be selected from the group consisting of a barb, a shelf, and combinations thereof. In one embodiment, the retention feature is barb and the barb is angled to allow for insertion of the shaft into the sample chamber and to prevent removal of the collection head from the sample chamber. The sample chamber may include a sample collection head extraction location at or near the terminus of the cavity and the barb is positioned in the cavity so as to retain the collection head in the extraction location. The retention feature may be is a shelf, wherein the shelf is a stepped discontinuity in an internal surface of the sample chamber. The sample chamber may be curved and the radius of curvature of the internal surface, as a function of increasing depth in the elongated cavity, steps from a first value to a second higher value at the discontinuity. In one embodiment, the shelf is positioned in the cavity so as to engage a shaft fragment linked to the head after the shaft fractures and to retain the collection head in the extraction location. In this embodiment, the shelf may be configured to retain a swab head contacted with the shelf within the extraction location.

The invention also provides a method of using an assay cartridge with a sample chamber configured as described, above. This method includes the steps of (a) inserting the applicator stick into the sample chamber; (b) fracturing the shaft of the applicator stick into a head fragment linked to the sample collection head and a handle fragment that has been separated from the sample collection head; and (c) removing the handle fragment. In this method the sample collection head retention feature(s) engage the sample collection head and retain the head during removal of the handle fragment.

The assay cartridge described above may include an integrated filter element in the second region, and the assay cartridge further comprises an extraction buffer chamber connected to an extraction buffer vent port and an extraction buffer conduit connected to the sample chamber, wherein the sample chamber is connected to a collection chamber via a sample chamber conduit. The extraction buffer conduit may comprise a Z-transition. In one embodiment, the sample chamber comprises a sample introduction port and the first region is proximate to the sample introduction port and the second region is distal to the sample introduction port. The sample chamber may also include an internal terminus and the integrated filter element is positioned at or near the terminus. Still further, the extraction buffer conduit may be positioned at or near the internal terminus of the sample chamber, e.g., within about 1 to 2 centimeters of the sample chamber base.

In one embodiment, the collection component of the assay cartridge may include a collection chamber and a sensing chamber, wherein the collection chamber is connected to (i) an input conduit connected, to the top of the collection chamber, wherein the input conduit is positioned proximal to a wall of the collection chamber; (ii) an output conduit connected to the bottom of the collection chamber; and (iii) a sensing conduit comprising a tube that extends down from the top of the collection chamber to pre-defined height in the collection chamber, wherein the sensing chamber connects to the sensing conduit at the top of the sensing chamber and proximal to a wall of the sensing chamber and to a sensing chamber vent. The collection component may further comprise (a) a baffle positioned at the top of the collection chamber and adjacent to the input conduit, and/or (b) an optical sensor adapted to detect the presence of liquid in the sensing chamber.

The assay cartridge described herein may be adapted to perform any number of assays for an analyte of interest. In one embodiment, the cartridge is configured to conduct influenza assays. In this embodiment, the assay cartridge includes a first detection chamber and a second detection chamber. The first detection chamber includes a first set of assay reagents and the second detection chamber includes a second set of assay reagents. The first and second detection chambers may be configured to conduct duplicate or different measurements of an analyte of interest. In one embodiment, the first set of assay reagents are configured to conduct a first measurement of a first analyte and the second set of assay reagents are configured to conduct a second measurement of a second analyte. The first detection chamber may configured for detection and typing of influenza virus. In this embodiment, the first set of assay reagents comprise an antibody directed to a target selected from the group consisting of influenza A nucleoprotein, influenza B nucleoprotein, and combinations thereof, and optionally, the first set of assay reagents further comprise an element selected from the group consisting of a positive control, a negative control, and combinations thereof. Still further, the first set of assay reagents may further include an antibody directed to an additional target selected from the group consisting of influenza C, adenovirus, parainfluenza, human metapneumovirus, and combinations thereof. The second set of assay reagents may include antibodies directed to at least two different hemagglutinin (HA) antigen subtypes. The different HA antigen subtypes may be selected from the group consisting of H1, H3, H1 from swine origin influenza virus (SOIV), atypical hemagglutinin subtype, pandemic hemagglutinin subtype, H2, H5, H7, H9, and combinations thereof. In one specific embodiment, the first detection chamber includes a first plurality of working electrodes having the first set of assay reagents immobilized thereon, the first plurality of working electrodes being arranged in a first one-dimensional array within the first detection chamber; and (ii) the second detection chamber comprises a second plurality of working electrodes having the second set of assay reagents immobilized thereon, the second plurality of working electrodes being arranged in a second one-dimensional array within the second detection chamber. The assay cartridge may also include an additional component selected from the group consisting of an extraction buffer chamber, a wash buffer chamber, and combinations thereof. In one embodiment, the extraction buffer is acidic, e.g., the extraction buffer comprises a buffering agent selected from the group consisting of carboxylic acids, polycarboxylic acids, quaternary ammonium buffers, and combinations thereof. The buffering agent may include a carboxylic acid selected from the group consisting of acetic acid, lactic acid, and combinations thereof. In one embodiment, the buffering agent comprises polycarboxylic acid selected from the group consisting of citric acid, glutaric acid and combinations thereof. The extraction buffer may also comprise an additional agent selected from the group consisting of anti-foam agent, a surfactant, and combinations thereof, e.g., an anti-foam agent selected from the group consisting of SE-15, Antifoam 204, Antifoam A, Antifoam B, Antifoam C, Antifoam Y-30, and combinations thereof; a non-ionic surfactant selected from the group consisting of Tween 20, Thesit, Triton X-100 and combinations thereof; and/or an ionic surfactant selected from deoxycholic acid, CHAPS and combinations thereof.

The invention also contemplates a kit including an assay cartridge as described herein. Such a kit may also include an applicator stick. The applicator stick may include a shaft segment and a head segment, wherein the shaft segment comprises a weak point configured to break the applicator stick at the weak point upon application of a force upon the applicator stick. The invention also provides a method of analyzing a sample collected with an applicator stick comprising a shaft and a sample collection head, wherein the cartridge includes (a) a sample chamber having an elongated cavity that has a first region and a second region, the regions oriented at an angle with respect to each other and the angle is selected to bend the shaft upon insertion of the applicator stick into the sample chamber and promote fracture of the shaft, wherein the sample chamber further comprises a sample collection head retention feature; (b) an extraction buffer chamber connected to an extraction buffer vent port through an integrated filter element to an extraction buffer conduit; (c) a waste chamber; (d) a first detection chamber connected to the sample chamber via a sample conduit comprising a first sample conduit branch, the first detection chamber is connected to the waste chamber via a waste conduit; (e) a second detection chamber connected to the sample chamber via a sample conduit comprising a second sample conduit branch, the second detection chamber is connected to the waste chamber via the waste conduit; and (f) a reagent chamber containing a volume of a liquid reagent, the reagent chamber being connected to the sample conduit through a reagent conduit; wherein the method comprises the steps of (i) inserting the applicator stick into the sample chamber such that the swab head contacts the retention feature, (ii) breaking the swab head within the sample chamber; (iii) extracting the sample from the swab head; (iv) moving the extracted sample from the sample chamber into the first and second sample conduit branches; (v) moving a slug of the extracted sample having a predetermined volume into the first and second detection chambers and (vi) moving the extracted sample in the first and second detection chambers into the first waste chamber; (vii) moving the first liquid reagent into the first and second detection chambers; and (viii) measuring a signal from the first and second detection chambers. The sample conduit may include a dry reagent, in which case the method includes reconstituting the dry reagent in the sample conduit prior to the extracting step (iii).

In a specific embodiment, the first detection chamber comprises a first set of assay reagents and the second detection chamber comprises a second set of assay reagents, and the measuring step (viii) comprises conducting duplicate or different measurements of an analyte of interest in the first and second detection chambers. In one embodiment, the measuring step (viii) comprises conducting a first measurement of a first analyte and conducting a second measurement of a second analyte. The first detection chamber may be configured for detection and typing of influenza virus and the measuring step (viii) comprises measuring a signal that indicates the presence or absence of a type of influenza virus in the sample. For example, the first set of assay reagents comprise an antibody directed to a target selected from the group consisting of influenza A nucleoprotein, influenza B nucleoprotein, and combinations thereof, and the measuring step (viii) comprises measuring a signal that indicates the presence or absence of the target in the sample. The first set of assay reagents may further comprise an antibody directed to an additional target selected from the group consisting of influenza C, adenovirus, parainfluenza, human metapneumovirus, and combinations thereof, and the measuring step (viii) further comprises measuring a signal that indicates the presence or absence of the additional target in sample. Moreover, the second set of assay reagents comprise antibodies directed to at least two different hemagglutinin (HA) antigen subtypes and the measuring step (viii) further comprises measuring a signal that indicates the presence or absence of the at least two different HA antigen subtypes. The two different HA antigen subtypes may be selected from the group consisting of H1, H3, H1 from swine origin influenza virus (SOIV), atypical hemagglutinin subtype, pandemic hemagglutinin subtype, H2, H5, H7, H9, and combinations thereof.

The invention also provides an assay cartridge comprising a cartridge body including a reagent chamber adapted to receive a cylindrical ampoule, wherein the reagent chamber comprises side walls and a plurality of support brackets protruding from the side walls, wherein the support brackets are configured to provide a multi-point cradle support for the cylindrical ampoule. The side walls may be sloped such that the width of the reagent chamber at the base of the reagent chamber is narrow relative to the width of the reagent chamber at the top of the reagent chamber. The plurality of support brackets may be sloped inward such that the width of the width of the cradle support is narrower at the bottom of the reagent chamber than at the top.

Further, the invention contemplates an assay cartridge comprising a sample chamber connected to a collection component via a collection conduit, the collection component comprising a collection chamber and a sensing chamber, wherein the collection chamber is connected to (i) the collection conduit, wherein the collection conduit is connected to the top of the collection chamber and is positioned proximal to a wall of the collection chamber, (ii) an output conduit connected to the bottom of the collection chamber; and (iii) a sensing conduit comprising a tube that extends down from the top of the collection chamber to a pre-defined height in the collection chamber, wherein the sensing chamber connects to the sensing conduit at the top of the sensing chamber and proximal to a wall of the sensing chamber and the sensing chamber also connects to a sensing chamber vent. The collection chamber may further include a baffle positioned at the top of the collection chamber, adjacent to the collection conduit and between the collection and sensing conduits. Moreover, the collection component further comprises an optical sensor adapted to detect the presence of liquid in the sensing chamber. The invention further provides a method of collecting a liquid in an assay cartridge as described herein, wherein the method comprises (i) introducing liquid into the collection chamber via the collection conduit until a liquid level reaches the pre-defined height in the collection chamber; (ii) introducing additional liquid into the collection chamber via the collection conduit such that the additional liquid is transferred through the sensing conduit into the sensing chamber; (iii) detecting liquid in the sensing chamber via the optical sensor; and (iv) transferring liquid from the collection chamber through the outlet conduit. The liquid introduced into the collection chamber may contain bubbles and the liquid transferred through the outlet conduit is substantially free of bubbles, and optionally, the method removes bubbles from the liquid. The collection chamber may include a baffle positioned at the top of the collection chamber and adjacent to the input conduit, and the method further comprises contacting the liquid with the baffle and the wall of the collection chamber to constrain bubbles within the liquid.

The assay cartridge may include a detection chamber and a distribution conduit interconnected, to a plurality of fluid conduits comprising the outlet conduit, a detection chamber conduit connected to the detection chamber and, optionally, one or more fluid conduits connected to one or more cartridge components selected from the group consisting of a wash buffer chamber, an air vent, a waste chamber, and combinations thereof. A connection between the distribution conduit and one of the plurality of fluid conduits may include a Z-transition. The cartridge may include an air vent and the one or more fluid conduits include an air vent conduit connected to the air vent, wherein the detection chamber conduit is distal from the air vent conduit. Moreover, the cartridge may include a wash buffer chamber and the one or more fluid conduits comprise a wash buffer chamber conduit connected to the wash buffer chamber, wherein the wash buffer chamber conduit is proximal to the air vent conduit and distal to the detection chamber conduit.

The assay cartridge described herein may also include a sample introduction port comprising a sealable closure including a sealing/capping mechanism comprising (a) a flexible hinge; (b) a latching mechanism; and (c) a retention component comprising a retention ring or tab. In one embodiment, the sealing/capping mechanism is a modular detachable insert comprising a cap for sealing the sample chamber.

The invention also provides a fluid flow path comprising: (a) a first resistance region; (b) a connecting region proximal to the first resistance region; and (c) matching resistance region proximal to the connecting region and distal to the first resistance region, wherein the hydrodynamic resistance of the matching resistance region is substantially equivalent to the hydrodynamic resistance of the first resistance region and is substantially greater than the hydrodynamic resistance of the connecting region. The flow path may also include an additional region selected from the group consisting of: (d) an inlet region proximal to the first resistance region and distal to the connecting region; (e) an outlet region proximal to the matching resistance region and distal to the connecting region; and (f) combinations thereof. In one embodiment, the connecting region is provided, in the same plane as the first resistance region. Alternatively, the connecting region is provided in a different plane relative to the first resistance region and the matching resistance region. The connecting region may include a Z-transition between the first resistance region and the matching resistance region. The connecting region may be positioned at an exit orifice of the first resistance region and/or the matching, resistance region may be positioned at an exit orifice of the connecting region.

The invention further provides a fluidic network comprising the fluid flow path described herein. The fluidic network may further comprise a metering component linked to the fluid flow path and configured to meter a fluid slug through the first resistance region, the connecting region and the matching resistance region. The metering component may be configured to meter the fluid slug through an additional region of the fluid flow path selected from the group consisting of: (d) an inlet region proximal to the first resistance region and distal to the connecting region; (e) an outlet region proximal to the matching resistance region and distal to the connecting region; and (f) combinations thereof. In one embodiment, the metered volume is approximately equal to the sum of the volumes of the first resistance region and the connecting regions. The sum of the volumes of the first resistance region and the connecting region is about 75-125%, e.g., about 85-115%, 95-105%, or 100% of the metered volume. Alternatively, the sum of the volume of the first resistance region and the connecting region is about 100-125% of the metered volume, e.g., about 100-115%, or 100-105% of the metered volume. The volume of the fluid slug may be less than about 200 uL, e.g., less than about 50 uL, or less than about 10 uL.

The volume of the fluid slug may be between about 20 and about 50 uL. Still further, the volume of the first resistance region relative to the volume of the fluid slug varies over a range of about 10-90%, e.g., about 20-80%, or 30-70%. In one embodiment, the combined volume of the first resistance region and the connection region relative to the volume of the fluid slug varies over a range of about 10-90%, e.g., about 20-80%, or 30-70%.

The fluid flow path described herein may include a fan region in the first resistance region. The first resistance region may be a high aspect ratio flow cell. In one specific embodiment, the first resistance region is configured as a detection chamber. The first resistance region may be about 5 mils×120 mils and the matching resistance region may be about 10 mil×80 mil. In one embodiment, the height of the first resistance region is about half the height of the matching resistance region. Still further, the inlet region comprises a throw region and the inlet region is positioned between two sensing sites, wherein the volume of the connecting region is greater than or equal to the volume of the throw region.

The invention also provides a method for moving fluid in a fluidic network comprising: (a) introducing a fluid slug into a hydrodynamic resistance matched fluid flow path within the fluidic network, wherein the flow path comprises the following components: (i) a first resistance region; (ii) a connecting region proximal to the first resistance region; and (iii) a matching resistance region proximal to the connecting region and distal to the first resistance region; and (b) using air pressure to move the fluid slug through the flow path. The flow path may be configured such that (i) the hydrodynamic resistance of the matching resistance region is substantially equivalent to the hydrodynamic resistance of the first resistance region and is substantially greater than the hydrodynamic resistance of the connection region; and (ii) the volume of the fluid slug is greater than the volume of the first resistance region and less than the combined volume of the first resistance region, the connecting region and the matching resistance region. The method may further comprise metering the fluid slug prior to introducing the fluid slug into the flow path (step (a)). The method may also include following steps: (a) introducing the fluid slug into the inlet region (with a throw region), the first resistance region and the connecting region; (b) moving the fluid slug under air pressure until the trailing edge of the fluid slug passes the second sensing site; (c) moving the fluid slug under air pressure in the reverse direction until the leading edge of the fluid slug passes first sensing site; (d) repeating steps (b) and (c) a plurality of times to achieve a back-and-forth mixing action. In addition, the method may also include (d) clearing the fluid slug from the first resistance region through the matching resistance region, and optionally, maintaining a constant flow rate as the fluid slug is cleared from the flow path.

Also provided is a cartridge reader configured to analyze an assay conducted in an assay cartridge, the cartridge reader comprising (a) an enclosure; (b) a cartridge tray for holding a cartridge during analysis in the cartridge reader; (c) a rail in the enclosure, wherein the cartridge tray is mounted on the rail the tray and can move in and out of the enclosure by moving along the rail; (d) an actuator to move the cartridge tray along the rail; (e) a mounting frame in the enclosure, the mounting frame configured to align the cartridge with one or more reader components; and (f) an alignment guide attached to the cartridge tray that is configured to engage with and control movement of the mounting frame. The assay cartridge may include a flow cell having a sample chamber, a detection chamber and an outlet, wherein the sample chamber, the detection chamber, and the outlet define a flow path through the flow cell, the detection chamber comprising a plurality of electrodes. The actuator may include a motor and a lead screw cooperating with a lead screw nut affixed to the cartridge tray, wherein the motor is configured to turn the lead screw to translate the lead screw nut, to move the cartridge tray along the rail. The one or more reader components are selected from the group consisting of (i) a photodiode assembly comprising at least one photodiode; (ii) an ampoule breaking mechanism; (iii) electrode contact pin assembly; (iv) a fluidic manifold configured to drive fluid motion within the flow path; and (v) a bar code reader. The enclosure may be a light-tight enclosure and the enclosure further comprises a door to seal the light-tight enclosure. In one embodiment, the one or more reader components include the ampoule breaking mechanism and the ampoule breaking mechanism is affixed to the mounting frame. Still further, the one or more reader components may include the electrode contact pin assembly and the electrode contact pin assembly is affixed to the mounting frame and supports conductive pins configured to make electrical contact to the plurality of electrodes on the assay cartridge. The one or more reader components may further include the fluidic manifold and the fluidic manifold is affixed to the mounting frame and comprises an additional element selected from the group consisting of fluidic connectors to mate with a vent port in the assay cartridge, an air cylinder pump, a plurality of valves, and combinations thereof.

The alignment guide may include a vertical tab and the mounting frame comprises an engagement pin and rollers, wherein the enclosure further comprises tracks on each side of the mounting frame, wherein the rollers are received by the tracks and the vertical tab contacts the engagement pin during movement of the cartridge tray, causing the mounting frame to translate along the tracks in coordination with the cartridge tray. Still further, the tracks comprise at least one downward sloping region and a flat region, and (i) movement within the sloping region causes the mounting frame to be lowered relative to the cartridge tray for cartridge processing; and (ii) movement within the flat region causes the mounting frame to move along with the cartridge tray while remaining in vertical and horizontal alignment for cartridge processing. In one embodiment, the rollers move within the downward sloping regions, the engagement pin is received in a notch defined on the alignment guide. The mounting frame may include two rollers on each side of the mounting frame and the rollers are each received in tracks. Still further, the alignment guide comprises a notch adjacent to the vertical tab and configured to receive the pin, the pin engaging the notch to releasably hold the mounting frame into horizontal alignment. Moreover, the cartridge tray may include vertical guides configured to engage the mounting frame, wherein the vertical guides define the vertical height of the mounting frame relative to the cartridge tray. The track may comprise an elevated shelf region on which the rollers rest when the mounting frame is not engaged by the alignment guide, wherein the elevated shelf region is connected to the downward sloping region. In one embodiment, the elevated shelf region is connected to the downward sloping region at the apex of the downward sloping region.

The cartridge reader of the present invention may include a cartridge tray with a locking mechanism. In one embodiment, the assay cartridge comprises a skirt and the cartridge tray comprises a slot sized to receive the skirt. The slot may be positioned on an exterior surface of the assay cartridge. In addition, the locking mechanism comprises a spring loaded rotating latch, a first pin configured to engage with the assay cartridge, a second pin configured to engage with a notch on the assay cartridge, wherein movement of the assay cartridge onto the cartridge tray contacts the first pin causing the latch to rotate and the second pin to engage with the notch. The spring loaded rotating latch may include a spring to resist the rotation of the latch, and optionally, the resistance of spring is reduced as the second pin engages with the notch. The latch may also include a tab and the locking mechanism further comprises an optical sensor, wherein the tab is configured to cover the optical sensor when the locking mechanism is engaged. The tab may include a pin extending down toward the optical sensor.

The one or more reader components may include the photodiode assembly and the photodiode assembly comprises a traveler block including positioning pins extending from the traveler block, the positioning pins being configured to couple motion of the mounting frame to the lateral motion of the traveler block. Moreover, the enclosure further comprises a cartridge tray positioning optical sensor, and optionally, an additional optical sensor to control the movement of a fluid slug in the assay cartridge.

The cartridge tray may further comprise an integrated heater and/or a coating including a water-resistant seal. The seal may include a polymeric film and it may transmit infra-red light. In one embodiment, the seal does not transmit visible light.

The photodiode assembly may also include an alignment component to align the photodiode with a region on the assay cartridge. The at least one photodiode may be mated to an optical coupler, and optionally, the at least one photodiode is mated to a light guide. In one embodiment, the optical coupler is surrounded by a conductive shield. The at least one photodiode may be mounted to the traveler block, the traveler block being configured to move side-to-side along at least one guide cylinder mounted in the photodiode assembly. The traveler block may be spring loaded and is movable when a force sufficient to overcome the spring force is applied. The cartridge reader may be configured to analyze an assay conducted in an assay cartridge comprising an ampoule, the cartridge reader comprising an ampoule breaking mechanism comprising a hammer element. The hammer element may be coupled to an active drive element selected from the group consisting of a motor, a solenoid, and a spring. In one embodiment, the hammer element is coupled to a spring and the hammer is held under a spring force. The hammer element may include a lever arm including a striking face, e.g., a protruding striking face, which is optionally pointed. The hammer element may be configured to be raised and lowered relative to the assay cartridge by rotation of the hammer element around a hammer axle, and optionally, the hammer element further comprises a control surface in coordination with a cam affixed to a rotating control axle, wherein the rotation of the control axle raises and lowers the striking face relative to the assay cartridge. The cam may include a mechanical stop positioned on a surface of the cam, and optionally, the cam is in coordination with a mechanical step positioned on an additional element of the ampoule breaking mechanism, e.g., a frame positioned on the ampoule breaking mechanism. The surface of the cam may be circular and comprises a tab protruding from the surface.

In one embodiment, the assay cartridge comprises two ampoules and the ampoule breaking mechanism is configured to break the two ampoules serially or in parallel. The ampoule breaking mechanism may be configured to break the two ampoules serially or in parallel. The ampoule breaking mechanism may include a plurality of ampoule release mechanisms, each ampoule breaking mechanism comprises a first ampoule release mechanism and a second ampoule release mechanism, wherein the first ampoule release mechanism comprises a first hammer element in coordination with a first cam on a control axle and the second ampoule release mechanism comprises a second hammer element in coordination with a second cam on the control axle. The first and second cams may be located in different relative rotational positions in the ampoule breaking mechanism, and the first and second cams are configured to engage the first and second hammer elements at different times during the rotation of the control axle. Alternatively, the first and second cams are located in approximately the same relative rotational positions in the ampoule breaking mechanism, and the first and second cams are configured to engage the first and second hammer elements at approximately the same time during the rotation of the control axle.

The invention also provides a method of using a cartridge reader configured to analyze an assay conducted in an assay cartridge, the cartridge reader comprising (a) a enclosure comprising a mounting frame configured to align the cartridge with one or more reader components located within the enclosure; (b) a cartridge tray mounted to a rail configured to move the tray in and out of the enclosure, wherein the cartridge tray comprises an alignment guide configured to selectively control movement of the mounting frame; and (c) an actuator to move the cartridge tray along the rail, the method comprising the steps of: (i) inserting the assay cartridge into the cartridge tray; (ii) moving the cartridge tray into the enclosure; (iii) moving the cartridge tray within the enclosure to cause the mounting frame to be lowered relative to the cartridge tray for cartridge processing; (iv) moving the cartridge tray within the enclosure to cause the mounting frame to move along with the cartridge tray, wherein the cartridge tray and the mounting frame remain in vertical and horizontal alignment for cartridge processing by the one or more reader components. The mounting frame may include an engagement pin and rollers, wherein the rollers are received by tracks on each side of the mounting frame, and the alignment guide comprises a vertical tab and the vertical tab contacts the engagement pin during movement of the cartridge tray, and the moving steps (iii) further comprises contacting the vertical tab and the engagement pin to cause the mounting frame to translate along the tracks in coordination with the cartridge tray. In one embodiment, the tracks comprise at least one downward sloping region and a flat region and the moving step (iii) comprises moving the cartridge tray within the sloping region, and the moving step (iv) comprises moving the cartridge tray within the flat region. The alignment guide may include a vertical tab configured to engage with (a) a groove in the mounting frame, (b) the engagement pin in the mounting frame, and (c) a notch in the alignment guide, the notch positioned adjacent to the vertical tab, such that the method further comprises the step of coordinating the translation of the mounting frame and the cartridge tray prior to step (iii).

The cartridge reader may further include a locking mechanism comprising a spring loaded rotating latch, a first pin configured to engage with the assay cartridge, and a second pin configured to engage with a notch on the assay cartridge, wherein the inserting step (i) comprises moving the assay cartridge into the cartridge tray to contact the first pin, causing the latch to rotate and the second pin to engage with the notch. In one embodiment, the spring loaded rotating latch comprises a spring and the inserting step (i) further comprises causing the spring to resist the rotation of the latch. Still further, the inserting step (i) further comprises reducing the resistance of the spring as the second pin engages with the notch. The latch may further include a tab and the locking mechanism further comprises an optical sensor, wherein the tab is configured to cover the optical sensor when the locking mechanism is engaged and the inserting step (i) further comprises detecting an optical signal from the optical sensor to confirm that the assay cartridge is engaged by the locking mechanism.

The one or more reader components may include the photodiode assembly and the photodiode assembly comprises a traveler block including positioning pins extending from the traveler block, the positioning pins being configured to couple motion of the mounting frame to the lateral motion of the traveler block, wherein one or more of the moving steps (iii) and (iv) further comprise moving the mounting frame in coordination with the traveler block. The one or more of the moving steps (iii) and (iv) may further comprise coupling motion of the mounting frame to the lateral motion of the traveler block. The photodiode assembly may also comprise an alignment component to align at least one photodiode with a region on the assay cartridge and one or more of the moving steps (iii) and (iv) further comprise aligning the at least one photodiode with a region of the assay cartridge. The at least one photodiode may be mounted to the traveler block, the traveler block being configured to horizontally translate along a guide cylinder mounted in the photodiode assembly and the moving step (iv) further comprises translating, horizontally, along the guide cylinder to align the at least one photodiode with the region of the assay cartridge.

Moreover, the one or more reader components may comprise an ampoule breaking mechanism configured to break an ampoule within the assay cartridge and the method further comprises (v) breaking the ampoule within the assay cartridge. The ampoule breaking mechanism may include a hammer element coupled to a spring and the hammer is held under a spring force, the hammer, the breaking step (v) comprises (i) rotating the hammer around a hammer axle, and (ii) raising and lowering the hammer relative to the assay cartridge. The ampoule breaking mechanism may include a plurality of ampoule breaking mechanisms and the assay cartridge comprises a plurality of ampoules, wherein the breaking step (v) comprises breaking the plurality of ampoules in series or in parallel. The plurality of ampoule breaking mechanisms may include a plurality of hammer elements. In one embodiment, the plurality of ampoule breaking mechanisms comprises a first ampoule breaking mechanism and a second ampoule breaking mechanism, wherein the first ampoule breaking mechanism comprises a first hammer element in communication with a first cam on a control axle and the second ampoule breaking mechanism comprises a second hammer element in communication with a second cam on the control axle. The first and second cams may be located in different relative rotational positions in the ampoule breaking mechanism, and the first and second cams are configured to engage the first and second hammer elements at different times during the rotation of the control axle, wherein the breaking step (v) comprises breaking the plurality of ampoules in series. Alternatively, the first and second cams are located in approximately the same relative rotational positions in the ampoule breaking mechanism, and the first and second cants are configured to engage the first and second hammer elements at approximately the same time during the rotation of the control axle, wherein the breaking step (v) comprises breaking the plurality of ampoules in parallel.

BRIEF DESCRIPTION OF THE DRAWINGS

FIG. 1a depicts a simplified pictorial representation of a cartridge-based assay module.

FIG. 1c illustrates an exploded assembly of one embodiment of an electrode array.

FIGS. 3a-3e illustrate various configurations of an electrodes array for use with a pair-wise firing schemes.

FIG. 4 depicts the electrode array of FIG. 3a in one embodiment of an assay cartridge.

FIG. 7b is a cross-sectional view of the localized washing apparatus depicted in FIG. 7a.

FIG. 11a illustrates the fluidic networks formed on one side of the cartridge, FIG. 11b illustrates the fluidic network formed on the other side of the cartridge and FIG. 11c provides an isometric view with phantom lines to illustrate the entire cartridge fluidic network as seen within the cartridge body.

FIG. 13a is an exploded assembly drawing illustrating the laminar assemblage for the assay cartridge depicted in FIG. 9.

FIG. 13b is a detail drawing of the gasket and electrode array cover layer depicted in FIG. 13a.

FIG. 14a is a schematic representation of another embodiment of an assay cartridge illustrating various fluidic components.

FIG. 14b is an exploded, assembly drawing illustrating the laminar assemblage for the two-piece assay cartridge depicted in FIG. 14a.

FIG. 15a is a top view of the upper cartridge component of the assay cartridge depicted in FIG. 14b.

FIGS. 16a and 16b are top and bottom views, respectively, of the lower cartridge component of the assay cartridge depicted in FIG. 14b.

FIGS. 18a and 18h are top and bottom isometric views, respectively, depicting the fluidic network in accordance with the schematic representation of FIG. 14a.

FIG. 24 illustrates one preferred valve configuration for the assay cartridge depicted in FIG. 14a.

FIG. 27 is a cross-sectional view of a sample chamber having an integral vent port within the chamber itself.

FIG. 28 is a cross-sectional view of one embodiment of a sample chamber for extracting analyte from a solid or solid-containing matrix.

FIG. 29 is a cross-section view of an alternative embodiment of a sample chamber for extracting analyte from a solid or solid-containing matrix incorporating force focusing elements.

FIG. 30 is a cross-section view of another embodiment of a sample chamber for extracting analyte from a solid or solid-containing matrix incorporating a two-region, or compound, sample chamber.

FIGS. 35(a)-(b) show one embodiment of a cap for a cartridge sample chamber.

FIGS. 43(c)-(e) show schematic representations of the mechanisms for inserting and properly positioning the cartridge tray within this reader design. FIGS. 43(f) and (g) are black and white depictions of FIGS. 43(a) and (b).

FIGS. 44(a)-(d) show top views of one embodiment of a cartridge tray for holding a cartridge in a cartridge reader. Views are provided showing (a) a cartridge partially inserted in the tray and (b) a cartridge fully seated in the tray. FIGS. 44(c) and (d) are black and white depictions of FIGS. 44(a) and (b).

DETAILED DESCRIPTION

Figure 1B:
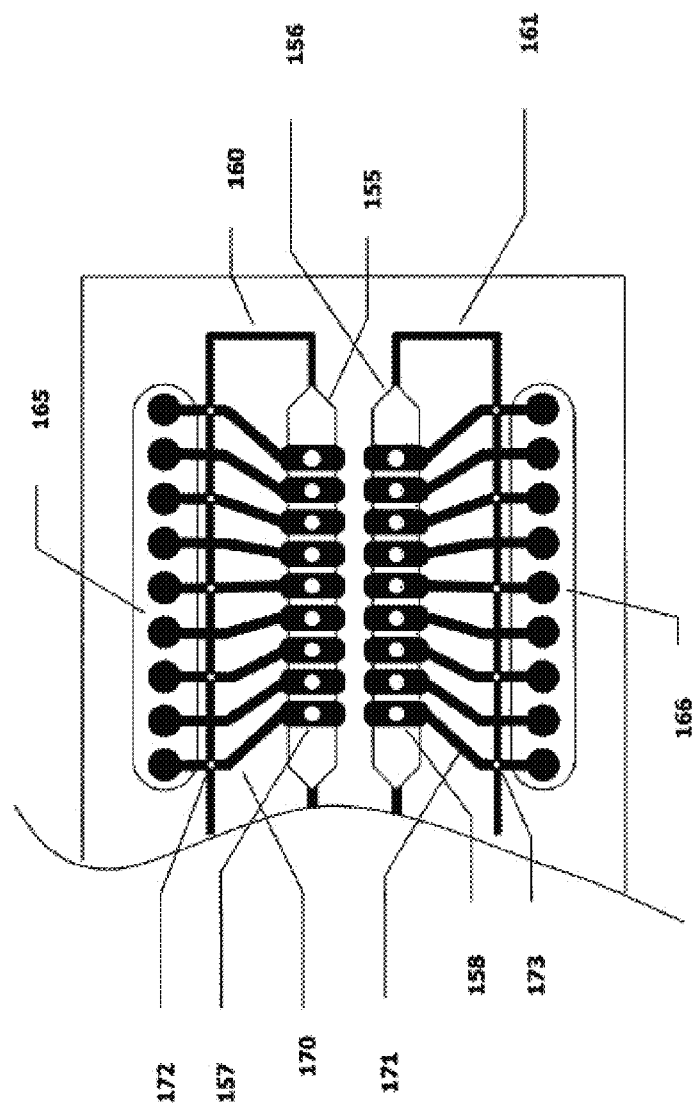
FIG. 1b depicts one embodiment of an assay cartridge having two detection chambers and two banks of individually addressable electrodes.

The invention, as well as additional objects, features and advantages thereof, will be understood more frilly from the following detailed description of certain preferred embodiments. Where the terms "measure" or "measurement" are used herein, they are understood to encompass quantitative and qualitative measurement, and encompasses measurements carried out for a variety of purposes including, but not limited to, detecting the presence of a thing or property, measuring the amount of a thing or property, and/or identifying a thing or property in a sample. Unless otherwise defined herein, scientific and technical terms used in connection with the present invention shall have the meanings that are commonly understood by those of ordinary skill in the art. Further, unless otherwise required by context, singular terms shall include pluralities and plural terms shall include the singular. The articles "a" and "an" are used herein to refer to one or to more than one (i.e., to at least one) of the grammatical object of the article. By way of example, "an element" means one element or more than one element.

The present invention includes apparatuses, electrodes, electrode arrays, systems, system components, kits, reagents and methods for performing one or more assays on a sample. The invention includes assay modules (e.g., assay cartridges, assay plates, etc.) having one or more assay cells wells, compartments, chambers, conduits, flow cells, etc.) that may comprise one or more assay domains (e.g., discrete locations on a assay cell surface where an assay reaction occurs and/or where an assay dependent signal, such as an electrochemical or preferably an electrode induced luminescence signal is induced) for carrying out a plurality of assay measurements.

In certain preferred embodiments, assay domains are supported on assay electrodes (preferably, an array of assay electrodes, most preferably a one dimensional array of assay electrodes) so as to permit the conduct of assays based on electrochemical or electrode induced luminescence measurements. The assay domains are, optionally, defined by a dielectric layer deposited on the electrodes. The assay modules, preferably, have one or more attributes that make them suitable for use in "point of care" clinical measurements, e.g., small size, low cost, disposability, multiplexed detection, ease of use, etc. The methods and apparatuses of the invention, allow these benefits to be achieved while maintaining the performance of traditional batch processing instruments of the type typically used in the central clinical lab.

The assay module may comprise the necessary electronic components and/or active mechanical components for carrying out an assay measurement, e.g., one or more sources of electrical energy, ammeters, potentiometers, light detectors, temperature monitors or controllers, pumps, valves, etc. Preferably, some or all of the electronic and/or active mechanical components are arranged within a separate assay module reader. The reader would also have the appropriate electrical, fluidic and/or optical connections to the assay module for carrying out an assay on the assay module. Using such an arrangement, the assay module can be designed to be low cost and disposable while the reader (which holds the more expensive and complex components is reusable. A preferred assay procedure using an assay module and assay reader would comprise inserting the cartridge in the reader, making the appropriate electrical, fluidic and/or optical connections to the cartridge (making use of electrical, fluidic and/or optical connectors on the cartridge and reader), and conducting an assay in the cartridge. The sample is preferably introduced into the cartridge prior to inserting the cartridge in the reader. The assay may also involve adding one or more assay reagents to the cartridge; preferably, one or more assay reagents are stored in the cartridge in a dry and/or wet form.

The invention also includes methods of preparing the assay modules including methods for preparing electrode arrays and forming assay domains on these electrode arrays. The invention also includes methods for washing assay domains to remove unbound reagents without a allowing these reagents to interact with other surfaces in the assay module.

One preferred embodiment of the invention comprises an assay cartridge comprising one or more assay flow cells. The assay flow cell comprises a chamber having a fluid inlet and fluid outlet and a flow path between the inlet and outlet. An array of electrodes is patterned on an internal surface of the chamber. When used in electrode induced luminescence assays, the internal chamber surface opposing the electrode array, is, preferably, light-transmissive so as to allow for the detection of light generated at the electrodes. One or more of the electrodes comprise assay reagents immobilized on the electrode. These assay domains are used to carry out assay reactions which are detected by using the electrode to induce an assay dependent signal such as an electrochemical or, more preferably, an electrode induced luminescence signal and detecting the signal. Preferably, these assay reagents are arranged in one or more assay domains defined by apertures in a dielectric layer deposited on the electrode. Optionally, the fluid inlet comprises a fluid inlet line that has sensors for detecting the presence of fluid in the fluid inlet line.

Preferably, the electrodes in the assay cartridge are patterned in a one dimensional array along the fluid path. The array and or fluid path are, preferably, in a linear arrangement, although other shapes (e.g., arcs, curves, zig-zags, etc. may also be used). In such a configuration, it is advantageous for the active area of the electrodes and aspect ratio of the flow path be selected to ensure that assay domains on the electrode efficiently sample analytes in fluids passing through the flow cell. Most preferably, the length of the flow path along the direction of flow is greater than the width perpendicular to the direction of flow, the active area of the electrode takes up a significant portion of the width of the flow path (preferably greater than 60%, more preferably greater than 80%), and/or the height of the flow path above the electrodes is small compared to the width of the flow path. Surprisingly, it has been found that the surface area of dedicated counter electrodes in the flow cell can be reduced significantly without affecting assay performance by reusing electrodes used as working electrodes (e.g., working electrodes having binding domains used for electrode induced luminescence assays), these electrodes being reused as counter electrodes for measuring an assay dependent signal from another, preferably adjacent, working electrode. In an especially preferred embodiment, the electrodes are activated in a pair-wise fashion along the path of the flow cell, the interior electrodes in the one-dimensional electrode array being used as working electrodes for inducing an assay dependent signal and subsequently as counter electrodes for inducing an assay dependent signal at an adjacent electrode.

The assay cartridges of the invention may comprise a plurality of flow cells or detection chambers. In certain preferred embodiments the flow cell may comprise the same assay domains or, at least, have at least some assay domains that share specificity for the same analytes of interest. In these embodiments, the plurality of flow cells may be used to analyze a plurality of different samples or to compare samples that have been pre-treated in different ways. Alternatively, one of the flow cells may be a control flow cell used to analyze a control sample and another of the flow cells may be a test flow cell used to analyze a test sample. The control sample may be a completely pre-defined control sample or may be a mixture comprising the test sample but spiked with added analytes of interest so as to allow for calibration of the assays by the method of standard addition. In an alternative embodiment, the assay cartridge has at least two flow cells that have assay domains for two different assay panels. Advantageously, such a cartridge may be used to separately perform assay reactions that are incompatible with each other.

FIG. 1a depicts a simplified schematic of a cartridge-based biochemical detection system 100 in accordance with one embodiment of the invention. Preferably a system housing, e.g., cartridge reader 105, would include an optical detector 110 and would be adapted and configured to receive and position cartridge 115 and/or optical detector 110 for processing. The system would preferably contain support subsystems (not shown) that may include one or more of the following: storage subsystem for storing assay reagents/consumables and/or waste; sample acquisition/preprocessing/storage subsystem for sample handling; fluidic handling subsystem for handling the reagents, sample, waste, etc. and for providing fluids to the detection chamber 120 via a fluid inlet line 125; electrical subsystem for electrically contacting the cartridge's electrical contacts 130 and supplying electrical energy to the electrodes 135,136,137; and a control subsystem for controlling and coordinating operation of the system and subsystems and for acquiring, processing and storing the optical detection signal.

As illustrated, one preferred embodiment would use an electrode array that preferably has at least one dedicated counter electrode 135, one dual-role electrode 136 and one dedicated working electrode 137. Such a preferred configuration would use a pair-wise firing scheme (discussed in detail below) wherein the dual-role electrode can be reused. FIG. 1b depicts in greater detail one possible embodiment for the detection portion of a cartridge-based device 150. As depicted, two detection chambers 155,156 each contain a bank of nine individually addressable electrodes 157,158. There are two fluid input lines depicted 160,161 for introducing sample, reagents and/or wash solutions into the detection chambers and two banks of electrical contacts 165,166 with corresponding electrical leads 170,171 to the electrodes 157,158. Also depicted in this preferred embodiment are two banks of impedance sensors 172,173 that may be used fluid detection (e.g., sample, reagents, wash, buffer, etc.) and/or fluid discrimination (e.g., discriminating between sample, reagents, wash, buffer, etc. and/or sample type such as whole blood, plasma, mucous, etc.).

FIG. 1c is an assembly schematic for one preferred embodiment illustrating the assembly of cartridge component 178 comprising an electrode array 176. According to one embodiment, electrode array 176 (preferably, comprised of carbon ink) is applied to the substrate layer 175 forming the electrode 180, electrical lead 181 and electrical contact 182 portions. A dielectric layer 177 is preferably applied over the electrode layer to define the assay domains 190 and the impedance sensors 191. Alternately, electrical contacts 182 could be printed on the opposing side of the substrate and connected to electrodes 180 or electrical leads 181 via conductive through-holes through the substrate. Methods for applying the carbon and dielectric layers as well as various alternative materials are discussed below in greater detail.

Cartridge component 178 is, preferably, mated with a second cartridge component. The second cartridge component has channels or apertures arranged on the mating surface so that when mated to cartridge component 178 it acts to form detection chambers over the electrode arrays (e.g., as illustrated, by detection chambers 155 and 156 in FIG. 1b and detection chamber 120 in FIG. 1a). Preferably, the second cartridge component has channels on the mating surface that form flow cells over the electrodes when mated to component 178 (the flow cells having one surface defined by component 178 and, an opposing surface and wells defined by the second component. The channels may also be used to form other fluidic paths such as fluidic inlet and outlet lines to the flow cell. These channels may, e.g., be molded or cut into the second component. Alternatively, the walls of the flow cell or other fluidic paths may be defined by a gasket material (preferably, double sided adhesive tape) applied between component 178 and the second cartridge component, Alternatively, the second component has apertures in the mating surface that form wells when mated to component 178.

In a preferred embodiment of the invention, an assay cartridge has minimal or no active mechanical or electronic components. When carrying out an assay, such an assay cartridge may be introduced into a cartridge reader which provides these functions. For example, a reader may have electronic circuitry for applying electrical energy to the assay electrodes and for measuring the resulting potentials or currents at assay electrodes. The reader may have one or more light detectors for measuring luminescence generated at assay electrodes. Light detectors that may be used include, but are not limited to photomultiplier tubes, avalanche photodiodes, photodiodes, photodiode arrays, CCD chips, CMOS chips, film. The light detector may be comprised within an optical detection system that also comprise lenses, filters, shutters, apertures, fiber optics, light guides, etc. The reader may also have pumps, valves, heaters, sensors, etc. for providing fluids to the cartridge, verifying the presence of fluids and/or maintaining the fluids at an appropriate controlled temperature. The reader may be used to store and provide assay reagents, either onboard the reader itself or from separate assay reagent bottles or an assay reagent storage device. The reader may also have cartridge handling systems such as motion controllers for moving the cartridge in and out of the reader. The reader may have a microprocessor for controlling the mechanical and/or electronic subsystems, analyzing the acquired data and/or providing a graphical user interface (GUI). The cartridge reader may also comprise electrical, mechanical and/or optical connectors for connecting to the cartridge.

One aspect of the invention relates to the assay modules employing electrodes, the immobilization of assay reagents on these electrodes, and their use in assays, preferably electrode-induced luminescence assays. Co-pending U.S. patent application Ser. No. 10/185,274, filed Jun. 28, 2002, hereby incorporated by reference, provides a number of examples of electrode and dielectric materials, electrode patterns and patterning techniques and immobilization techniques that are adapted for use in electrode-induced luminescence assays and suitable for use with the assay modules of the invention. Electrodes in the present invention are preferably comprised of a conductive material. The electrode may comprise a metal such as gold, silver, platinum, nickel, steel, iridium, copper, aluminum, a conductive alloy, or the like. They may also comprise oxide coated metals (e.g. aluminum oxide coated aluminum). Electrodes may comprise non-metallic conductors such as conductive forms of molecular carbon. Electrodes may also be comprised of semiconducting materials (e.g. silicon, germanium) or semiconducting films such as indium tin oxide (ITO), antimony tin oxide (ATO) and the like. Electrodes may also be comprised of mixtures of materials containing conductive composites, inks, pastes, polymer blends, metal/non-metal composites and the like. Such mixtures may include conductive or semi-conductive materials mixed with non-conductive materials. Preferably, electrode materials are substantially free of silicone-based materials.

Electrodes (in particular working electrodes) used in assay modules of the invention are advantageously able to induce luminescence from luminescent species. Preferable materials for working electrodes are materials able to induce electrochemiluminescence from ruthenium-tris-bipyridine in the presence of tertiary alkyl amines (such as tripropyl amine). Examples of such preferred materials include platinum, gold, ITO, carbon, carbon-polymer composites, and conductive polymers.

Preferably, electrodes are comprised of carbon-based materials such as carbon, carbon black, graphitic carbon, carbon nanotubes, carbon fibrils, graphite, carbon fibers and mixtures thereof. Advantageously, they may be comprised of conductive carbon-polymer composites, conductive particles dispersed in a matrix (e.g. carbon inks, carbon pastes, metal inks), and/or conductive polymers. One preferred embodiment of the invention is an assay module, preferably an assay cartridge, having electrodes (e.g., working and/or counter electrodes) that comprise carbon, preferably carbon layers, more preferably screen-printed, layers of carbon inks. Some useful carbon inks include materials produced by Acheson Colloids Co, e.g., Acheson 440B, 423ss, PF407A, PF407C, PM-003A, 30D071, 435A, Electrodag 505SS, and Aquadag™), E.I. Du Pont de Nemours and Co. Dupont 7105, 7101, 7102, 7103, 7144, 7082, 7861D, E100735 62B and CB050), Advanced Conductive Materials (e.g., PTF 20), Gwen Electronics Materials (e.g., C2000802D2) and Conductive Compounds Inc (e.g., C-100), and Ercon Inc. (e.g., G-451, G-449 and 150401).

In another preferred embodiment, the electrodes of the invention comprise carbon fibrils. The terms "carbon fibrils", "carbon nanotubes", single nanotubes (SWNT), multiwall nanotubes (MWNT), "graphitic nanotubes", "graphitic fibrils", "carbon tubules", "fibrils" and "buckeytubes", all of which terms may be used to describe a broad class of carbon materials (see Dresselhaus, M. S.; Dresselhaus, G.; Eklund, P. C.; "Science of Fullerenes and Carbon Nanotubes", Academic Press, San Diego, Calif., 1996, and references cited therein). The terms "fibrils" and "carbon fibrils" are used throughout this application to include this broad class of carbon-based materials. Individual carbon fibrils as disclosed in U.S. Pat. Nos. 4,663,230; 5,165,909; and 5,171,560 are particularly advantageous. They may have diameters that range from about 3.5 nm to 70 nm, and length greater than $10^2$ times the diameter, an outer region of multiple, essentially continuous, layers of ordered carbon atoms and a distinct inner core region. Simply for illustrative purposes, a typical diameter for a carbon fibril may be approximately between about 7 and 25 nm, and a typical range of lengths may be 1.000 nm to 10,000 nm. Carbon fibrils may also have a single layer of carbon atoms and diameters in the range of 1 nm-2 nm. Electrodes of the invention may comprise one or more carbon fibrils, e.g., in the form of a fibril mat, a fibril aggregate, a fibril ink, a fibril composite (e.g., a conductive composite comprising fibrils dispersed in an oil, paste, ceramic, polymer, etc.).

Electrodes may be formed into patterns by a molding process (i.e., during fabrication of the electrodes), by patterned deposition, by patterned printing, by selective etching, through a cutting process such as die cutting or laser drilling, and/or by techniques known in the art of electronics microfabrication. Electrodes may be self supporting or may be supported on another material, e.g. on films, plastic sheets, adhesive films, paper, backings, meshes, felts, fibrous materials, gels, solids (e.g. metals, ceramics, glasses), elastomers, liquids, tapes, adhesives, other electrodes, dielectric materials and the like. The support, or substrate, may be rigid or flexible, flat or deformed, transparent, translucent, opaque or reflective. Preferably, the support comprises a flat sheet of plastic such as acetate or polystyrene. Electrode materials may be applied to a support by a variety of coating and deposition processes known in the art such as painting, spray-coating, screen-printing, ink-jet printing, laser printing, spin-coating, evaporative coating, chemical vapor deposition, etc. Supported electrodes may be patterned using photolithographic techniques (e.g., established techniques in the microfabrication of electronics), by selective etching, and/or by selective deposition (e.g., by evaporative or CVD processes carried out through a mask). In a preferred embodiment, electrodes are comprised of extruded films of conducting carbon/polymer composites. In another preferred embodiment, electrodes are comprised of a screen printed conducting ink deposited on a substrate. Electrodes may be supported by another conducting material, in some applications, screen printed carbon ink electrodes are printed over a conducting metal ink (e.g., silver ink) layer so as to improve the conductivity of the electrodes. Preferably, in assay cartridges, a miniaturized design allows the use of electrodes having short printed electrode leads (preferably less than 1.5 cm, more preferably less than 1.0 cm) that are relatively similar in length. By keeping the leads short, it is possible to use screen printed carbon electrodes without an underlying conductive metal layer such as a silver layer.

According to one preferred embodiment of the invention, the electrode surface (preferably a working electrode surface of an assay module or assay plate) is bounded by a dielectric surface, the dielectric surface being raised or lowered (preferably, raised) and/or of different hydrophobicity (preferably, more hydrophobic) than the electrode surface. Preferably, the dielectric boundary is higher, relative to the electrode surface, by 0.5-100 micrometers, or more preferably by 2-30 micrometers, or most preferably by 8-12 micrometers. Even more preferably, the dielectric boundary has a sharply defined edge (i.e., providing a steep boundary wall and/or a sharp angle at the interface between the electrode and the dielectric boundary).

Preferably, the first electrode surface has an advancing contact angle for water 10 degrees less than the dielectric surface, preferably 15 degrees less, more preferably 20 degrees less, more preferably 30 degrees less, even more preferably 40 degrees less, and most preferred 50 degrees less. One advantage of having a dielectric surface that is raised and/or more hydrophobic than the electrode surface is in the reagent deposition process where the dielectric boundary may be used to confine a reagent within the boundary of the electrode surface. In particular, having a sharply defined edge with a steep boundary wall and/or a sharp angle at the interface between the electrode and dielectric boundary is especially useful for "pinning" drops of solution and confining them to the electrode surface. In an especially preferred embodiment of the invention, the dielectric boundary is formed by printing a patterned dielectric ink on and/or around the electrode, the pattern designed so as to expose one or more assay domains on the electrode.

Electrodes may be modified by chemical or mechanical treatment to improve the immobilization of reagents. The surface may be treated to introduce functional groups for immobilization of reagents or to enhance its adsorptive properties. Surface treatment may also be used to influence properties of the electrode surface, e.g., the spreading of water on the surface or the kinetics of electrochemical processes at the surface of the electrode. Techniques that may be used include exposure to electromagnetic radiation, ionizing radiation, plasmas or chemical reagents such as oxidizing agents, electrophiles, nucleophiles, reducing agents, strong acids, strong bases and/or combinations thereof. Treatments that etch one or more components of the electrodes may be particularly beneficial by increasing the roughness and therefore the surface area of the electrodes. In the case of composite electrodes having conductive particles or fibers (e.g., carbon particles or fibrils) in a polymeric matrix or binder, selective etching of the polymer may be used to expose the conductive particles or fibers.

One particularly useful embodiment is the modification of the electrode, and more broadly a material incorporated into the present invention by treatment with a plasma, specifically a low temperature plasma, also termed glow-discharge. The treatment is carried out in order to alter the surface characteristics of the electrode, which come in contact with the plasma during treatment. Plasma treatment may change, for example, the physical properties, chemical composition, or surface-chemical properties of the electrode. These changes may, for example, aid in the immobilization of reagents, reduce contaminants, improve adhesion to other materials, alter the wettability of the surface, facilitate deposition of materials, create patterns, and/or improve uniformity. Examples of useful plasmas include oxygen, nitrogen, argon, ammonia, hydrogen, fluorocarbons, water and combinations thereof. Oxygen plasmas are especially preferred for exposing carbon particles in carbon-polymer composite materials. Oxygen plasmas may also be used to introduce carboxylic acids or other oxidized carbon functionality into carbon or organic materials (these may be activated, e.g., as active esters or acyl chlorides) so as to allow for the coupling of reagents. Similarly, ammonia-containing plasmas may be used to introduce amino groups for use in coupling to assay reagents.

Treatment of electrode surfaces may be advantageous so as to improve or facilitate immobilization, change the wetting properties of the electrode, increase surface area, increase the binding capacity for the immobilization of reagents (e.g., lipid, protein or lipid/protein layers) or the binding of analytes, and/or alter the kinetics of electrochemical reactions at the electrode. In some applications, however, it may be preferable to use untreated electrodes. For example, we have found that it is advantageous to etch carbon ink electrodes prior to immobilization when the application calls for a large dynamic range and therefore a high binding capacity per area of electrode. We have discovered that oxidative etching (e.g., by oxygen plasma) has additional advantages in that the potential for oxidation of tripropyl amine (TPA) and the contact angle for water are both reduced relative to the unetched ink. The low contact angle for water allows reagents to be adsorbed on the electrode by application of the reagents in a small volume of aqueous buffer and allowing the small volume to spread evenly over the electrode surface. Surprisingly, we have found that excellent assays may also be carried out on unetched carbon ink electrodes despite the presence of polymeric binders in the ink. In fact, in some applications requiring high sensitivity or low-non specific binding it is preferred to use unetched carbon ink electrodes so as to minimize the surface area of exposed carbon and therefore minimize background signals and loss of reagents from non-specific binding of reagents to the exposed carbon. Depending on the ink used and the process used to apply the ink, the electrode surface may not be easily wettable by aqueous solutions. We have found that we can compensate for the low wettability of the electrodes during the adsorption of reagents by adding low concentrations of non-ionic detergents to the reagent solutions so as to facilitate the spreading of the solutions over the electrode surface. Even spreading is especially important during the localized immobilization of a reagent from a small volume of solution. For example, we have found that the addition of 0.005-0.04% Triton X-100® allows for the spreading of protein solutions over unetched carbon ink surfaces without affecting the adsorption of the protein to the electrode and without disrupting the ability of a dielectric film applied on or adjacent to the electrode (preferably, a printed dielectric film with a thickness of 0.5-100 micrometers, or more preferably 2-30 micrometers, or most preferably 8-12 micrometers and having a sharply defined edge) to confine fluids to the electrode surface. Preferably, when non-ionic detergents such as Triton X-100® are used to facilitate spreading of reagents (e.g., capture reagents) onto unetched screen-printed electrodes (i.e., so as to allow the immobilization of the reagents), the solutions containing the reagents are allowed to dry onto the electrode surface. It has been found that this drying step greatly improves the efficiency and reproducibility of the immobilization process.

The efficiency of the immobilization of reagents on carbon ink electrodes, especially unetched carbon ink electrodes, may exhibit some variability due to different levels of contamination of the electrodes surface. This effect is particularly pronounced when certain dielectric inks are used to form assay domains on the electrodes. We have found that we can improve the immobilization efficiencies and lower the variability by pre-washing the electrode surfaces, preferably with a surfactant solution.

The contamination of carbon ink electrodes by certain dielectric inks was observed by quantitatively assessing the surface wetting properties of the electrodes by measuring the contact diameter, where the larger, the contact diameter, the better the wetting. A comparison of three alternative carbon surfaces with different dielectric layers is depicted in Table 1. As shown by the data in Table 1, washing the electrode surfaces can significantly increase the wetting properties (contact diameter) of carbon surfaces contacting the 451 dielectric (presumably by removing contamination of the electrode surface associated with the printing of the 451 dielectric, e.g., by migration of components of the dielectric ink on to the electrode surface).

TABLE 1

Comparision of Contact Diameters on Carbon Electrode Surfaces for Three Different Dielectric Materials (Mean 50 nL water drop diameter at 400 μs open time)

| Surface | Contact Diameter, inches* |
| --- | --- |
| No pre-treatment: | |
| Carbon with 451 dielectric | 0.0366 |
| Carbon with Nazdar dielectric | 0.0461 |
| Carbon with PD039A dielectric | 0.0457 |
| Pre-treated: | |
| Carbon with 451 dielectric | 0.0438 |
| Carbon with Nazdar dielectric | 0.0463 |
| Carbon with PD039A dielectric | 0.0448 |

In one embodiment, a method of decontaminating the carbon electrode surfaces may be employed wherein the electrode surfaces are soaked in an aqueous 0.5% Triton X-100 solution for several hours, subsequently rinsed with deionized water, then soaked in deionized water for approximately one hour and finally dried. The Triton solution preferably removes the contaminants from the surface and the deionized water removes the adsorbed surfactant. This method of decontamination is an effective cleaning procedure that enhances the differences between the retreating contact angles on the carbon and the dielectric inks.

Figure 6A:
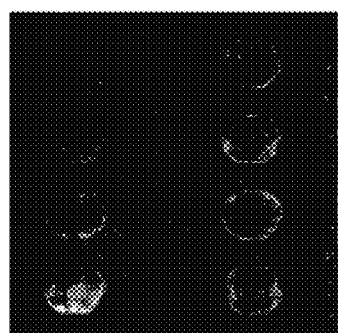
FIGS. 6a and 6b are images of electrochemiluminescence from electrode arrays that are untreated (FIG. 6a) or that have been pre-washed with a surfactant (FIG. 6b).
Figure 6B:
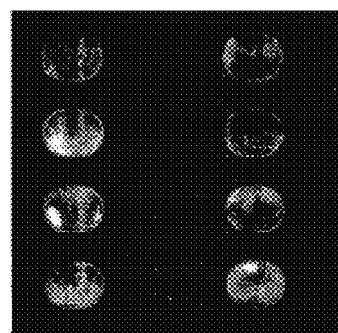

FIG. 6 demonstrates the results of the decontamination procedure. Specifically, FIG. 6 depicts images of ECL from ECL label over carbon ink electrodes, the exposed areas of the electrode being defined by a dielectric film. FIG. 6a is the ECL image without decontamination and FIG. 6b is the ECL image after decontamination with Triton X-100 in accordance with the present embodiment. These ECL images show that the treatment process greatly reduces the variation in ECL intensity over the surface of the electrode, the patchiness of ECL on the untreated electrode presumably being caused by patches of contamination on the surface.

Electrodes can be derivatized with chemical functional groups that can be used to attach other materials to them. Materials may be attached covalently to these functional groups, or they may be adsorbed non-covalently to derivatized or underivatized electrodes. Electrodes may be prepared with chemical functional groups attached covalently to their surface. These chemical functional groups include but are not limited to COOH, OH, $NH_2$, activated carboxyls N-hydroxy succinimide (NHS)-esters), poly-(ethylene glycols), thiols, alkyl $((CH_2)_n)$ groups, and/or combinations thereof). Certain chemical functional groups (e.g., COOH, OH, $NH_2$, SH, activated carboxyls) may be used to couple reagents to electrodes. For further reference to useful immobilization and bioconjugation techniques see G. Hermanson, A. Mania and P. Smith, *Immobilized Affinity Ligand Techniques* (Academic Press, San Diego, 1992) and G. Hermanson, *Bioconjugate Techniques* (Academic Press, San Diego, 1996).

In preferred embodiments, NHS-ester groups are used to attach other molecules or materials bearing a nucleophilic chemical functional group (e.g., an amine). In a preferred embodiment, the nucleophilic chemical functional group is present on and/or in a biomolecule, either naturally and/or by chemical derivatization. Examples of suitable biomolecules include, hut are not limited to, amino acids, proteins and functional fragments thereof, antibodies, binding fragments of antibodies, enzymes, nucleic acids, and combinations thereof. This is one of many such possible techniques and is generally applicable to the examples given here and many other analogous materials and/or biomolecules. In a preferred embodiment, reagents that may be used for ECL may be attached to the electrode via NHS-ester groups.

It may be desirable to control the extent of non-specific binding of materials to electrodes. Simply by way of non-limiting examples, it may be desirable to reduce or prevent the non-specific adsorption of proteins, antibodies, fragments of antibodies, cells, subcellular particles, viruses, serum and/or one or more of its components, ECL labels (e.g., $Ru^{II}(bpy)_3$ and $Ru^{III}(bpy)_3$ derivatives), oxalates, trialkylamines, antigens, analytes, and/or combinations thereof). In another example, it may be desirable to enhance the binding of biomolecules.

One or more chemical moieties that reduce or prevent non-specific binding (also known as blocking groups) may be present in, on, or in proximity to an electrode. Such moieties, e.g., PEG moieties and/or charged residues (e.g., phosphates, ammonium ions), may be attached to or coated on the electrode. Examples of useful blocking reagents include proteins (e.g., serum albumins and immunoglobins), nucleic acids, polyethylene oxides, polypropylene oxides, block copolymers of polyethylene oxide and polypropylene oxide, polyethylene imines and detergents or surfactants (e.g., classes of non-ionic detergents/surfactants known by the trade names of Brij, Triton, Tween, Thesit, Lubrol, Genapol, Pluronic (e.g., F108), Tetronic, Tergitol, and Span).

Materials used in electrodes may be treated with surfactants to reduce non-specific binding. For example, electrodes may be treated with surfactants and/or detergents that are well known to one of ordinary skill in the art (for example, the Tween, Triton, Pluronics (e.g., F1.08), Span, and Brij series of detergents). Solutions of PEGs and/or molecules which behave in similar fashion to PEG (e.g., oligo- or polysaccharides, other hydrophilic oligomers or polymers) ("Polyethylene glycol chemistry: Biotechnical and Biomedical Applications", Harris, J. M. Editor, 1992, Plenum Press) may be used instead of and/or in conjunction with surfactants and/or detergents. Undesirable non-specific adsorption of certain entities such as those listed above may be blocked by competitive non-specific adsorption of a blocking agent, e.g., by a protein such as bovine serum albumin (BSA), casein or immunoglobulin G (IgG). One may adsorb or covalently attach an assay reagent on an electrode and subsequently treat the electrode with a blocking agent so as to block remaining unoccupied sites on the surface.

In preferred embodiments, it may be desirable to immobilize (by either covalent or non-covalent means) biomolecules or other assay reagents to carbon-containing materials, e.g., carbon inks, carbon black, fibrils, and/or carbon dispersed in another material. One may attach antibodies, fragments of antibodies, proteins, enzymes, enzyme substrates, inhibitors, cofactors, antigens, haptens, lipoproteins, liposaccharides, cells, sub-cellular components, cell receptors, viruses, nucleic acids, antigens, lipids, glycoproteins, carbohydrates, peptides, amino acids, hormones, protein-binding ligands, pharmacological agents, and/or combinations thereof. It may also be desirable to attach non-biological entities such as, but not limited to polymers, elastomers, gels, coatings, ECL tags, redox active species (e.g., tripropylamine, oxalates), inorganic materials, chelating agents, linkers, etc. A plurality of species may be co-adsorbed to form a mixed layer on the surface of an electrode. Most preferably, biological materials (e.g., proteins) are immobilized on carbon-containing electrodes by passive adsorption. Surprisingly, biological membranes (e.g., cells, cell membranes, membrane fragments, membrane vesicles, liposomes, organelles, viruses, bacteria, etc.) may be directly adsorbed on carbon without destroying the activity of membrane components or their accessibility to binding reagents (see, e.g., copending U.S. patent application Ser. No. 10/208,526 (entitled "Assay Electrodes Having Immobilized Lipid/Protein Layers, Methods Of Making The Same And Methods Of Using The Same For Luminescence Test Measurements"), filed on Jul. 29, 2002, hereby incorporated by reference.

Electrodes used in the assay modules are, preferably, non-porous, however, in some applications it is advantageous to use porous electrodes (e.g., mats of carbon fibers or fibrils, sintered metals, and metals films deposited on filtration membranes, papers or other porous substrates. These applications include those that employ filtration of solutions through the electrode so as to: i) increase mass transport to the electrode surface to increase the kinetics of binding of molecules in solution to molecules on the electrode surface); ii) capture particles on the electrode surface; and/or iii) remove liquid from the well.

Preferred assay modules may use dielectric inks, films or other electrically insulating materials (hereinafter referred to as dielectrics). Dielectrics in the present invention may be used to prevent electrical connectivity between electrodes, to define patterned regions, to adhere materials together (i.e., as adhesives), to support materials, to define assay domains, as masks, as indicia and/or to contain assay reagents and other fluids. Dielectrics are non-conducting and advantageously non-porous (i.e., do not permit transmission of materials) and resistant to dissolving or degrading in the presence of media encountered in an electrode induced luminescence measurement. The dielectrics in the present invention may be liquids, gels, solids or materials dispersed in a matrix. They may be deposited in uncured form and cured to become solid. They may be inks, solid films, tapes or sheets. Materials used for dielectrics include polymers, photoresists, plastics, adhesives, gels, glasses, non-conducting inks, non-conducting pastes, ceramics, papers, elastomers, silicones, thermoplastics. Preferably, dielectric materials of the invention are substantially free of silicones. Examples of non-conducting inks include UV curable dielectrics such as materials produced by Acheson Colloids Co. (e.g., Acheson 451SS, 452SS, PF-455, PD039A, PF-021, ML25251, ML25240, ML25265, and Electrodag 38DJB16 clear), Nazdar (e.g., Nazdar GS2081 3400SPL) and E.I. du Pont de Nemours and Co, Dupont: 5018, 3571, and 5017).

Dielectrics in accordance with certain preferred embodiments, may be applied by a variety of means, for example, printing, spraying, laminating, or may be affixed with adhesives, glues, solvents or by use of mechanical fasteners. Patterns and/or holes in dielectric layers may be formed by molding processes (i.e., during fabrication of the layer), by selective etching and/or by a cutting process such as die cutting or laser drilling. Dielectrics may be deposited and/or etched in patterns through the use of established photolithographic techniques (e.g., techniques used in the semiconductor electronics industry) and/or by patterned deposition using an evaporative or CVD process (e.g., by deposition through a mask). In a preferred embodiment, a dielectric ink is deposited on a substrate by printing (e.g., ink jet printing, laser printing or, more preferably, screen printing) and, optionally, UV cured. Preferably, the screen printed dielectric is UV curable allowing for improved edge definition than solvent based dielectrics. In another preferred embodiment, a non-conducting polymeric film is affixed to a support using an adhesive.

When using a dielectric ink printed on, or adjacent to, an electrode to confine fluids to regions of the electrode surface, the dielectric film preferably has a thickness of 0.5-100 micrometers, or more preferably 2-30 micrometers, or most preferably 8-12 micrometers and also, preferably, has a sharply defined edge with steep walls.

Figure 3F:
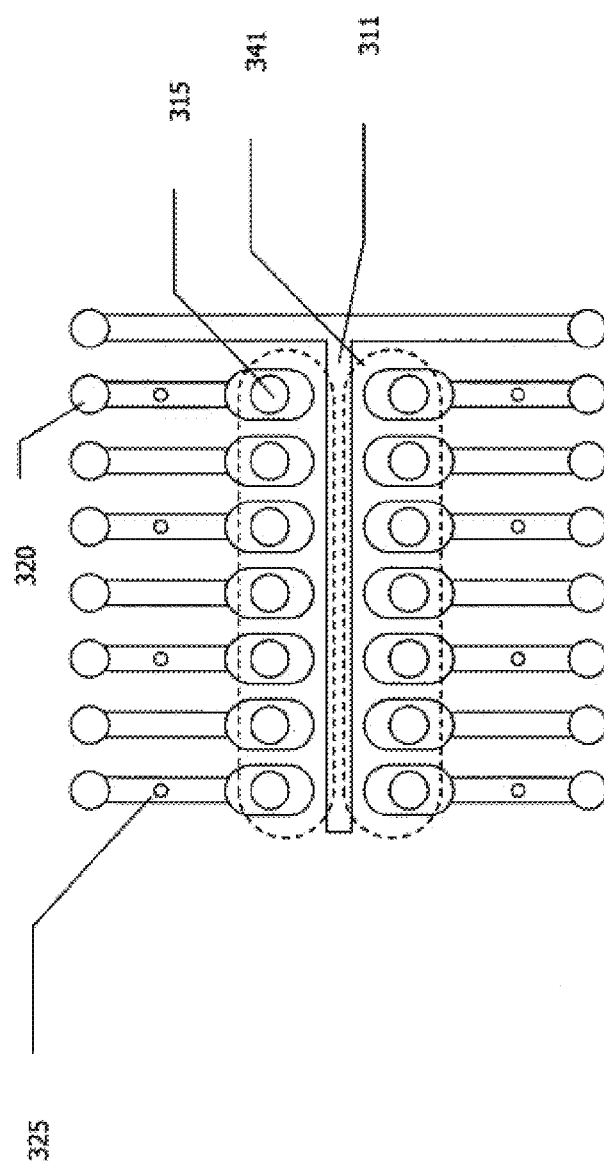
FIGS. 3f-3g illustrate two possible configurations of an electrode array employing a single, common counter electrode.
Figure 3G:
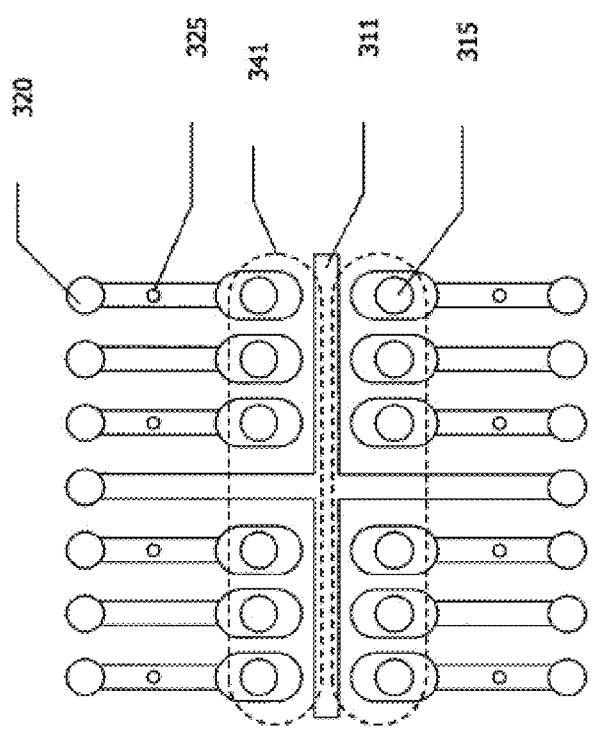

Miniaturization of various components and processes required to support ECL-based assays can also benefit from novel approaches to induce ECL. When inducing ECL, the working electrode and a counter electrode are, preferably, spaced relatively close to one another to minimize the effect of voltage drops in solution on the intensity and spatial distribution of ECL signals. When multiple ECL measurements are to be made in the same solution volume, each measurement, preferably, uses a closely spaced working electrode (where electrochemiluminescence is induced) and a counter electrode (to complete the electrochemical circuit). One possible configuration is for each measurement to have its own pair of electrodes; however, this configuration would require the largest volume, space, and number of electrical contacts on the device. An alternative configuration is for each measurement to share a common counter electrode that is reused. FIGS. 3*f* and 3*g* illustrate possible alternative approaches for using common counter electrodes. As can be seen, the detection chambers (e.g., detection chamber 341) for such configurations would still require a large space in order to accommodate both the working electrodes (e.g., working electrode 315) and the single, common counter electrode 311. Moreover, the relative size and spacing of each working electrode-counter electrode pair will affect the relative performance of each pair. Therefore, as depicted in FIGS. 3*f* and 3*g* configurations employing a single, common counter electrode would preferably ensure that the relative size and spacing of each working-counter electrode pair is approximately equal. Preferably, the working electrodes are arranged in a one dimensional array, the array being preferably arranged along the flow path of a flow cell. The common counter electrode is also, preferably aligned with the flow path to one side of the array so as to maintain approximate equal spacing to each of the working electrodes. Preferably, no working electrode is located in the shortest path between the counter electrode and a different working electrode; application of a large potential between the counter electrode and a first working electrode can under some conditions generate high enough potentials in the intervening solution to trigger an undesired emission of ECL at a second working electrode located in the shortest path between the first working electrode and the counter electrode. Optionally, the electrode surface area in contact with the detection chamber is defined by an aperture in a dielectric film deposited on the electrode layer (shown as circles on the electrode layer).

In one preferred embodiment, an electrode pair-wise firing scheme can be employed in order to miniaturize the cartridge to the largest extent practicable, and therefore greatly reduce the volume and space required. This preferred pair-wise firing scheme, or electrode-pairing scheme, would preferably employ a sacrificial, or dedicated counter electrode for the first measurement and thereafter allow the reuse of a previously fired (where fired describes the state of the surface after the application of a working electrode potential, e.g., a potential sufficient to generate electrochemiluminescence at a working electrode) working electrode as the next counter electrode for the next measurement. Surprisingly, as discussed below, it was observed that neither having a protein coating on the electrode being used as the counter electrode nor the fact that the electrode was already fired once as a working electrode affected the performance of that electrode for use as a counter electrode, thus allowing the use of electrodes in a dual-role as both working and counter electrodes.

FIGS. 3a-3e depict possible alternative configurations for electrode arrays employing the pair-wise firing scheme. FIG. 3a illustrates a single bank of electrodes that can be used in one or more detection chambers (a single detection chamber 340 is indicated here by the dotted line). The electrodes are preferably arranged in a one dimensional array. Optionally, the electrode surface area in contact with the detection chamber is defined by an aperture in a dielectric film deposited on the electrode layer (shown as circles on the electrode layer). In one embodiment, electrode 310 may be configured as the dedicated counter electrode, electrodes 305-309 may be configured as the dual-role electrodes and electrode 315 may be configured as the dedicated working electrode. The electrode bank has impedance sensors 325 on leads to the electrodes which can be arranged to contact fluid in input or outlet lines to the detection chamber. Preferably, the impedance sensors are defined by apertures in a dielectric layer deposited on the electrode layer. The electrode array of FIG. 3a utilizes a configuration wherein the electrical contacts and leads are located to one side of the electrodes allowing for simplified mating with the control unit. FIG. 3b depicts an alternative configuration wherein the electrical contacts and leads are alternately placed on either side of the electrodes. Such an alternating configuration can allow for the impedance sensors to be placed on each of the electrical leads so as to allow interrogation of the fluids during both ingress and egress from the detection chamber (e.g., by arranging the fluid inlet line and fluid outlet line so that they, respectively, contact impedance sensors on alternate sides of the electrodes).

FIGS. 3c-3e illustrate configurations employing multiple detection chambers. In particular, FIGS. 3c and 3d depict two detection chambers employing two banks of electrodes. FIG. 3d illustrates a configuration wherein the electrodes for one set of contacts/leads are within the oppositely placed detection chamber. Such a configuration may provide added benefits such as a more densely packed electrode array and the ability to place impedance sensors on each lead. Impedance sensors may be placed on each lead since each detection chamber can be alternately processed; i.e., fluid is first directed to on detection chamber and all assays are performed and then fluid is directed to the other detection chamber for processing of the remaining assays.

FIG. 3e depicts an embodiment utilizing four detection chambers. It should be noted that while FIG. 3e depicts an electrode array employing a single, common counter electrode in each detection chamber, such a configuration can also be employed using the pair-wise firing scheme discussed above.

Preferably, the electrode arrays depicted in FIGS. 3a-3g are supported on a support such as a plastic film or sheet. The detection chambers are, preferably, formed by mating the support to a second cartridge component having channels or apertures defined thereon (optionally, these features being at least partially defined by a gasket between the electrode support and the second cartridge component); see the discussion of FIG. 1c.

Since it was believed that using the electrode-pairing scheme might result in the assay on a previously used working electrode affecting its function as the counter electrode for the next working electrode, an experiment was devised wherein three different protein coatings were used to determine their effect. The effects of three protein coatings were measured: avidin, CK-MB capture antibody, and Bovine IgG. The ECL of a 10 nM ruthenium-tris-bipyridine solution in a tripropylamine-containing buffer was measured on non-coated electrodes with various counter electrodes (coated, non-coated, fired, and virgin); these results are listed in Table 2. In this table $ECL_{fired\ CE}$ denotes the ECL from the working electrode when paired with a counter electrode that has been previously fired as a working electrode and $ECL_{virgin\ CE}$ is for ECL from the working electrode when paired with a counter electrode that has not been previously fired as a working electrode. The observed ECL signals were all within experimental error of one another demonstrating the unexpected result that neither the presence of protein on the surface nor the prior use as a working electrode had any affect on the performance of that surface as a counter electrode.

TABLE 2

Effects of Protein Coating and Application of Oxidative Potentials to Electrodes Previously Used as a Counter Electrode in Free TAG ECL Generation

| Protein on C.E. | $ECL_{fired\ CE}$ | $ECL_{virgin\ CE}$ |
|---|---|---|
| anti-CK-MB | 199 | 207 |
| Blank | 199 | 197 |
| Avidin | 181 | 205 |
| IgG | 203 | 214 |

With reference to FIG. 4, and by way of example only, operation of a simplified, electrode array employing the pair-wise firing scheme within a single detection chamber will be described. For purposes of this operational example, introduction of sample, assay reagent(s), wash solution(s) and/or buffer(s) through the fluid input line 450 will not be discussed; it is to be understood that each of the necessary constituents for performing the assay are present in the detection chamber for this example. At least one of the electrodes will operate as a dedicated counter electrode, e.g., 401, and will therefore not have any assay reagents immobilized thereon. Electrodes 402-407 will have assay reagents immobilized thereon; electrodes 402-406 are to be used as dual-role electrodes and electrode 407 is to be used as a dedicated working electrode. As pictured in the figure, the electrodes are preferably arranged in one dimensional arrays (most preferably, linear arrays) along the fluid path in the detection chamber. The dedicated counter electrode 401 will be used first in conjunction with the adjacent dual-role electrode 402, wherein the dual-role electrode will be operated as a working electrode to perform the desired assay at dual-role electrode 402. Thereafter, dual-role electrode 402 will be operated as a counter electrode and will be pair-wise fired with dual-role electrode 403, wherein dual-role electrode 403 will be operated as a working electrode to perform the desired assay at dual-role electrode 403. This pair-wise firing is continued, for the remaining electrodes until electrode pair 406 and 407. This last remaining pair will operate dual-role electrode 406 as a counter electrode and dedicated working electrode 407 as a working electrode to perform the desired assay at dedicated working electrode 407. Preferably, the electrode pairs used, in a specific firing are adjacent each other (i.e., there are no other electrodes located between them) to avoid the undesired emission of ECL from an electrode located in the intervening space.

The use of patterned electrodes in cartridges may impose certain unique design and/or performance constraints. In particular, the use of patterned electrode leads may lead to problems associated with voltage drops along the leads, especially in applications like electrochemiluminescence that often require relatively high currents. The problems are often greatest when using electrodes comprising thin layers of only moderately conductive materials such as carbon inks. The problem may be partially mitigated by use of multi-layer patterned electrodes (where the conductivity of an exposed moderately conductive material such as a carbon ink is increased by printing over a more conductive material such as a silver ink) although this approach introduces additional manufacturing steps. Alternatively, the problem may be partially mitigated in systems having multiple assay electrodes by keeping the leads short (preferably, so that the resistance between the electrode and the electrical contact is less than 500 ohms, more preferably less than 300 ohms, most preferably less than 100 ohms) to minimize the voltage drop and by keeping the leads about the same length to make the voltage drop consistent from electrode to electrode.

In an assay module comprising multiple working electrodes, the variability from electrode to electrode in the voltage drop across the electrode leads is preferably smaller than the potential applied during the course of an assay measurement so that this variability has minimal effect on the variability of the measurements. In especially preferred embodiments, the variability in voltage drop across the leads is less than 20% of the potential applied during the course of an assay measurement, more preferably less than 10% or most preferably less than 2%. Alternatively, the uniformity in leads can be described in terms of the variation in resistance across the leads which is preferably less than 50 ohms, more preferably less than 10 ohms, most preferably less than 1 ohm.

Where the arrangement of the electrodes and/or contacts makes it difficult to keep the leads a uniform length, the matching of lead resistances can be accomplished by geometrically matching the length-to-width ratio of each electrode lead (assuming consistent print thickness). This length-to-width ratio is referred to hereinafter as the "number of squares". Typically, for a preferred cartridge-based configuration using screen printed carbon inks, the electrode leads are on the order of 4 to 5 squares. Commercially available inks typically have ink resistances that are specified in resistance per square per thickness (e.g., ohms/square/mil) and can vary widely depending on the ink selected. In a particularly preferred embodiment, a carbon ink is used that possesses an ink resistance that measures approximately 15 ohms/square/mil. The total resistance measured from end-to-end across a lead for one preferred embodiment is typically on the order of 450 ohms for a configuration utilizing a 5 squares lead.

Figure 2:
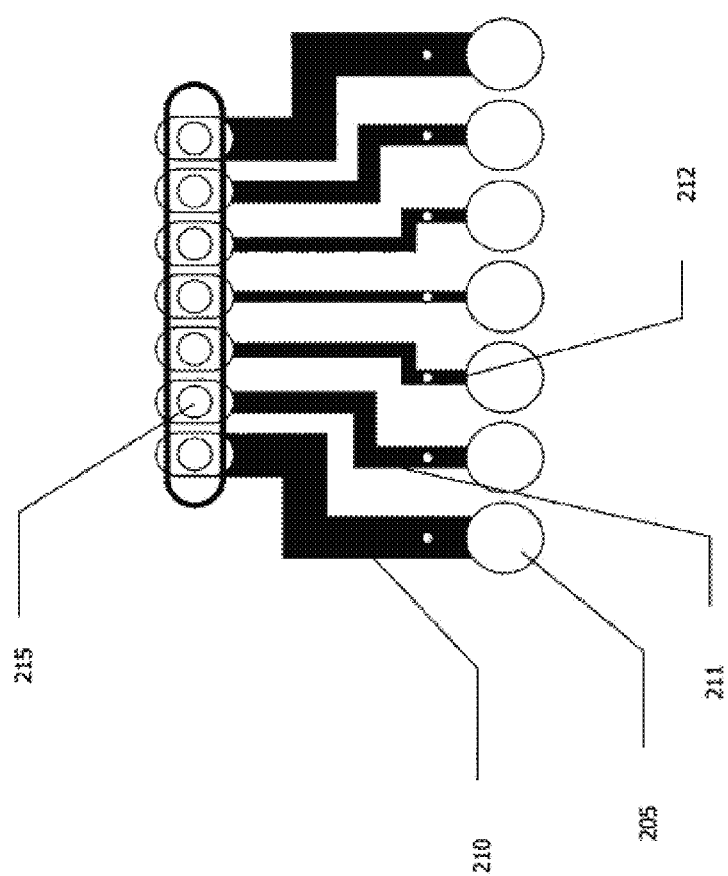
FIG. 2 is a pictorial representation of an electrode array having matched electrical lead resistances.

FIG. 2 depicts one preferred embodiment of an addressable electrode array for generating ECL that can be incorporated into a cartridge-based form factor having the requisite provisioning for sample/reagent mixing/delivery. As illustrated, contacts 205 and leads 210 are used to allow electrodes 215 in the addressable electrode array to be controlled by a control unit (not shown) adapted to contact, or mate, with the cartridge. Since the resistance across leads 210 represents a large fraction of the total cell resistance during an assay measurement, it is preferable to match the resistance across each lead as closely as possible. As shown in the figure, the length of the leads varies according to the positioning of the electrodes and contacts, however, the width is varied so that the length to width ratio of the leads is kept constant so as to provide a uniform lead resistance (the widths in the figure are not to scale and have been exaggerated for emphasis).

Utilization of the electrode array for multiple purposes contributes to a miniaturized cartridge-based device since the need for additional components is obviated. According to another aspect of the present invention, the electrode array may advantageously also be used for detecting the presence of fluid, for the detection of trapped air and/or for the identification of sample type. Preferably, an impedance measurement may be used to monitor the state of the cell during the cartridge routine. The measurement may assess whether there is trapped air on or above an electrode during incubation and after the wash step. Additionally, the impedance measurement may also allow usage of the electrode array to distinguish different sample types drawn into the cartridge, e.g., differentiate between samples of urine, saliva, serum, plasma, or whole blood, and make any necessary adjustments that may be needed.

The advantages associated with utilizing the electrode array to monitor cartridge operations by performing impedance measurements can be many fold. In particular, use of the electrode array in this manner affords a non-destructive measurement to be made since application of low voltage DC or, preferably, AC waveforms can be carried out with no effect on the subsequent ECL measurement. Also, the impedance measurement performed by the electrode array is relatively fast compared to other cartridge operations. Still further, the impedance measurement performed by the electrode array is very precise and can preferably be used in conjunction with other sensors; e.g., pressure, optical, etc.

At low voltages, the electrodes located in the region where detection is to be made, i.e. the read chamber, behave like a series RC circuit. This has proven to be a suitable model for the development of a fail safe mechanism to ascertain the presence of fluid, the presence of an unwanted bubble or to discriminate between sample specimen in types in the read chamber. In practice, it has been observed that trapped air may reside either on the electrode surface or in the solution bulk. According to the present invention, the location of the air with respect to the electrodes is important. According to one embodiment, a resistance measurement can be utilized to provide an indicator that is sensitive to air trapped in the bulk solution and at the electrode/solution interface. According to another embodiment, a capacitance measurement can be employed to provide an indicator that is primarily sensitive to air trapped at the interface. In yet another alternative embodiment, the electrochemical current during an ECL measurement (e.g., the TPA oxidation current during ECL) may be used to detect trapped air during the ECL measurement, however, this measurement would not provide information related to trapped air during the sample entry and incubation phases and would not allow corrective steps to be taken before the ECL measurement.

With respect to using a capacitance measurement, the pertinent capacitance is the double layer capacitance. Since the parallel plate capacitance is insignificant at frequencies below about 1 MHz, it is preferably ignored. Each electrode has a double layer capacitance. It is noted that the double layer capacitance is not a true capacitor, as it does exhibit a small frequency dependence. Advantageously the capacitance is primarily affected by changes at the interface (e.g., changes in the effective area of an electrode due to the trapping of an air bubble on the electrode surface), and not by the bulk; the capacitance is therefore preferably used to detect air bubbles at the electrode/solution interfaces. Preferably, the capacitance measurement uses an AC voltage input with a frequency between 10-40,000 Hz, more preferably between 20-2000 Hz, more preferably between 50-100 Hz, most preferably around 200 Hz. Other factors besides trapped air, e.g., errors in the printing of the electrodes, may change the effective area of an electrode and thus the measured capacitance. The measurement of capacitance can be used to check for these factors as well as for bubbles and can be used to trigger error flags if the capacitance values fall out of an acceptable range or, alternatively, to allow for normalization of the reported ECL signal to compensate for the actual electrode area.

With respect to using a resistance measurement, the pertinent resistances are the solution and lead resistances. It has been observed that the solution resistance will have a small frequency dependence. The resistance is affected by changes in the bulk solution (e.g., by bubbles interfering with the flow of current through bulk solution) and changes at the electrode/solution interface (e.g., trapped air at the interface has the affect of reducing the effective electrode area and therefore increasing the resistance). The solution resistance can also be expected to be very sensitive to the nature of the solution in contact with the electrodes and can also be used to identify the sample.

The resistive (in-phase) and capacitive (out-of phase) components of the impedance may be measured simultaneously using conventional impedance analyzing circuitry, preferably using a voltage waveform having a frequency at which both components have a significant effect on the impedance and/or a voltage waveform having a plurality of frequencies comprising at least one frequency where the resistance is a significant component of the impedance and at least one frequency where the capacitance is a significant component of the impedance. Alternatively, the resistive and capacitive components may be measured separately, preferably at frequencies that maximize the effect of the component being measured. For example, at high frequencies the effect of surface capacitance is minimized and the impedance is primarily due to solution resistance. In one embodiment of the invention, the solution resistance is measured by applying a voltage waveform having a frequency greater than 2000 Hz, more preferably between 2,000 and 100,000 Hz, most preferably around 20,000 Hz.

Sample matrix identification can be very important since certain biochemical assays may have varied steps or different post-processing requirements (e.g., the blood samples may be treated different than plasma samples). Tables 3 and 4 list resistance and capacitance values acquired for five different matrices by applying low voltage AC excitation to electrodes within an experimental cartridge. The electrode array comprised screen printed carbon ink electrodes, the exposed surface of which were defined by a patterned dielectric layer printed over the carbon ink. The impedance measurements were taken at 25 degrees C. using an excitation voltage equal to 0.010 V rms at the frequencies indicated in the tables. For capacitance measurements, since it is desirable to use a frequency where all (or nearly all) of the voltage drop occurs across the capacitive element, a frequency of 200 Hz was utilized as this was found to result in greater than 95% of the voltage drop to occur across the double layer capacitance; the solution losses were almost negligible. Resistance and capacitance were calculated using a series RC model.

As can be seen in Tables 3 and 4, the capacitance varied little between the different sample matrices, however, the resistances showed much greater variation among the matrices.

TABLE 3

Sample Discrimination Using Capacitance Measurements (phase angles 76 to 82 degrees).

| Matrix | Capacitance, uF at 200 Hz |
| --- | --- |
| Assay buffer | 0.023 |
| Saline | 0.021 |
| Serum | 0.019 |
| Plasma | 0.018 |
| Blood | 0.020 |

TABLE 4

Sample Discrimination Using Resistance Measurements (includes 700 ohms of lead resistance; phase angles 12 to 16 degrees)

| Matrix | Resistance, ohms at 20,000 Hz |
| --- | --- |
| Assay buffer | 2516 |
| Saline | 3722 |
| Serum | 3996 |
| Plasma | 4158 |
| Blood | 7039 |

Figure 5:
FIG. 5 is an image of electrochemiluminescence emitted from an electrode array where one of the electrodes has an air bubble on the electrode surface.

In certain preferred embodiments the electrochemical current measured during the induction of ECL, may be used to detect the presence of trapped air over an electrode since trapped air may cause a significant decrease in the electrochemical current (e.g., current from TPA oxidation during ECL). FIG. 5 depicts an image of ECL emitted from an electrode array. One of the electrodes has a small dark spot 500 due the presence of a small air bubble on the electrode surface. Even such a small bubble gave a detectable change in the electrochemical current measured at that electrode during the ECL experiment; the current in the presence of the air bubble (178 uA) was significantly different (by 5%) than the average of the current at the other electrodes (187 uA). Other factors besides trapped air, e.g., errors in the printing of the electrodes, may change the effective area of an electrode and thus the measured current. The measurement of current during ECL can be used to check for these factors as well as for bubbles and can be used to trigger error flags if the current values fall out of an acceptable range or, alternatively, to allow for normalization of the reported ECL signal to compensate for the actual electrode area.

The bubble detection methods described above can also be employed to detect the presence of fluids, the presence of bubbles in fluids and/or identify classes of samples in compartments in an assay cartridge outside the detection flow cells. For example, certain preferred embodiments of assay cartridges comprise fluid inlet and/or outlet lines for introducing and removing fluids from the cartridge flow cells, wherein these inlet and/or outlet lines comprise fluid detection electrodes for detecting the presence of fluid, the presence of air bubbles in fluids and/or for identifying samples. These fluid detection electrodes may have independent electrode leads and contacts. So as to reduce the number of electrical contacts to the cartridge, these fluid detection electrodes, preferably, comprise exposed surfaces of the leads to assay electrodes (e.g., assay electrodes in the assay cartridge flow cells). In this arrangement, it is further preferred that the exposed leads in a given fluid volume (e.g., an inlet line or outlet line) do not comprise leads from two electrodes that will be tired together in an assay measurement (e.g., used as a working electrode counter electrode pair in an ECL measurement). In this fashion it is ensured that the assay measurements are not affected by low resistance current paths between exposed leads.

With reference to the simplified embodiment depicted in FIG. 4, use of the impedance sensors 425 for detection of fluid presence and/or discrimination within the fluid input line 450 will now be discussed. Impedance sensors 425 are regions of electrically conductive surfaces on the electrode leads between electrodes 401-407 and electrode contacts 420. The electrically, conductive surfaces are, preferably, exposed via apertures in a patterned dielectric layer that is patterned over the electrode leads. As fluid is directed into and through the fluid input line 450 (e.g., by use of pumps, valves, capillary flow, and the like), the impedance sensors 425 may be activated by a controller (not shown) that applies interrogation potentials between sensor pairs to detect and/or discriminate the fluid (the interrogation potentials being preferably lower than those required to induce ECL at the assay electrodes). The position of bubbles or fluids in the input line can be determined by sequentially measuring the impedance between different sensor pairs and comparing the values, The sensors are on alternating electrode leads so that when adjacent electrodes are fired during, e.g., an ECL measurement, the potential across the assay electrodes is not short circuited by current between sensors.

According to another aspect of the present invention, the electrode surfaces are coated with assay reagents such as antibodies or other specific binding reagents by dispensing solutions comprising the reagents to one or more appropriate locations on the electrode array, i.e., the capture surfaces. Preferably, the assay reagents collect on the surface (e.g., via the formation of covalent bonds, non-specific adsorption or specific binding interactions) to form an immobilized layer on the electrode. In a preferred embodiment, accurate volume delivery to a specified location results in complete coverage of only the desired electrode surface and/or a desired portion thereof. Accurate volume delivery to a specified location can be readily accomplished with commercially available dispensing equipment; e.g., commercially available equipment from BioDot.

Attaining complete coverage of a pre-defined region on a surface (e.g., an assay electrode) via localized deposition of a liquid (e.g., an assay reagent or a liquid comprising an assay reagent can be difficult to achieve if the advancing contact angle of the liquid, on the surface is high, thereby inhibiting spreading of the liquid on the surface (as has been observed for surfactant-free aqueous solutions on untreated carbon ink electrodes). Spreading can be accelerated by chemically modifying the surface to make it more wettable or by adding surfactants to the liquid, however, in many circumstances it is undesirable to change the physical properties of the surface or liquid. Alternatively, we have found that excellent and well controlled spreading of liquids can be achieved on surfaces, such as carbon ink electrodes, having high contact angle hysteresis (i.e., large differences in the advancing and retreating contact angle of the liquid on the surface, preferably differences greater than 10 degrees, more preferably greater than 30 degrees, more preferably greater than 50 degrees, most preferably greater than 70 degrees) by using impact-driven fluid spreading. Such results can be achieved without surface modification or the use of surfactants. Fluid is deposited (preferably, using a fluid micro-dispenser such as a micro-pipette, microsyringe, solenoid valve controlled micro-dispenser, piezo-driven dispenser, ink-jet printer, bubble jet printer, etc.) on the surface at high velocity (preferably greater than 200 cm/s, more preferably greater than 500 cm/s, most preferably greater than 800 cm/s) so as to drive spreading of the liquid over the surface, despite the high advancing contact angle, to a size dictated by the volume and velocity of the dispensed fluid. The low retreating contact angle prevents significant retraction of the fluid once it has spread. Using the impact-driven spreading technique, it is possible to coat, with a predetermined volume of liquid, regions of a surface that are considerably larger (preferably, by at least a factor of 1.2, more preferably by at least a factor of two, even more preferably by at least a factor of 5) than the steady state spreading area of the predetermined volume of liquid on the surface (i.e., the area over which a drop having that volume spreads when touched to the surface at a velocity approaching zero).

Preferably, the region to be coated is defined by a physical boundary that acts as a barrier to confine the deposited fluid to the pre-defined region (e.g., a surrounding ledge or depression, a boundary formed of patterned materials deposited or printed on the surface, and/or a boundary formed via an interface with a surrounding region that varies in a physical property such as wettability). More preferably, the liquid has a higher receding contact angle on the surrounding region than on the pre-defined region (preferably, the difference is greater than 10 degree, more preferably greater than 30 degrees, most preferably greater than 50 degrees). Even more preferably, the surrounding region also exhibits a low contact angle hysteresis for the liquid (preferably, less than 20 degrees, most preferably, less than 10 degrees). By using a surrounding region having high receding contact angle and/or low hysteresis, the tolerance for imprecision in deposition velocity or spreading rate becomes much improved. In a preferred deposition method, a small volume of reagent is dispensed onto the pre-defined region with sufficient velocity to spread across the pre-defined region and slightly onto the surrounding region, the liquid then retracts off the surrounding region (due to its high receding contact angle) but does not retract smaller than the size of the pre-defined area (due to its low receding contact angle). In especially preferred embodiments of the invention the pre-defined area is an exposed area of an electrode (preferably, a carbon ink electrode) and the surrounding region is provided by a dielectric ink patterned on the electrode.

Figure 8:
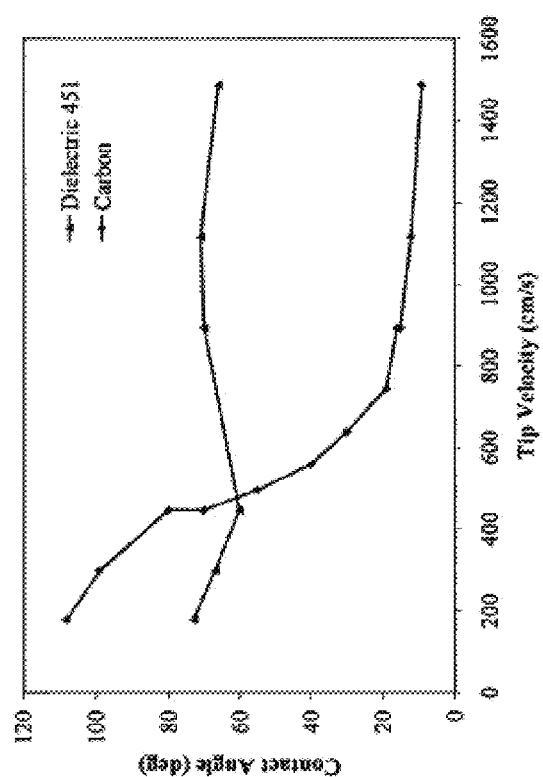
FIG. 8 plots the contact angle of drops of fluid on carbon ink and dielectric ink surfaces as a function of the dispensing velocity.

FIG. 8 illustrates typical observed contacts angles of 250 nL drops of water deposited using a solenoid valve-controlled micro-dispenser (Bio-Dot Microdispensor, Bio-Dot Inc.) on a preferred dielectric ink and a preferred carbon ink. The figure plots the contact angle as a function of the velocity of fluid as it leaves the tip of the dispenser. At low velocity, the observed contact angle is close to the advancing contact angle of water on the surface. As the velocity increases, impact-driven spreading causes the liquid to spread over a greater area and the observed contact angle decreases. At the high velocities, the observed contact angle becomes relatively independent of velocity as it approaches the receding contact angle of the liquid on the surface, the receding contact angle being the lowest contact angle the liquid can have on the surface (a lower contact angle would cause the drop to recede till it achieves the receding contact angle).

As described above, assay reagents such as antibodies or other specific binding reagents may be patterned by depositing (e.g., via impact driven spreading) solutions comprising the reagents on pre-defined locations on a surface (e.g., an electrode surface, preferably a carbon ink electrode surface) and allowing the reagents to become immobilized on the surface (e.g., via covalent bonds, non-specific interactions and/or specific binding interactions). Preferably, the region to be coated is defined by a physical boundary that acts as a barrier to confine the deposited fluid to the pre-defined region (e.g., a surrounding ledge or depression, a boundary formed of patterned materials deposited or printed on the surface, and/or a boundary formed via an interface with a surrounding region that varies in a physical property such as wettability) so as to form a fluid containment region.

In certain preferred embodiments, antibodies or other binding reagents (preferably proteinaceous binding reagents) are immobilized on carbon ink electrodes by non-specific adsorption. It may be advantageous to allow the assay reagent solution to dry on the electrode during the immobilization procedure. Preferably, the immobilization procedure further comprises blocking un-coated sites on the surface with a blocking agent such as a protein solution solutions of BSA or casein), washing the surface with a wash solution (preferably a buffered solution comprising surfactants, blocking agents, and/or protein stabilizers such as sugars) and/or drying the surface.

In a preferred immobilization procedure of the invention, imprecision due to variations in the ability of different assay reagents to adsorb on a surface such as a carbon ink electrode are reduced by immobilizing via a specific binding interaction involving a first and second binding partner. Such an immobilization technique is less likely to be affected by small variations in the properties of the surface. By way of example, antibodies may be patterned by patterned deposition of antibody solutions (the first binding partner) on a surface coated with an antibody binding reagent (the second binding partner, e.g., an anti-species antibody, protein A, protein G, protein L, etc.). Alternatively, assay reagents labeled with the first binding partner (preferably, biotin) may be patterned by patterned deposition of the assay reagents on a surface coated with the second binding partner (preferably, anti-biotin, streptavidin, or, more preferably, avidin). Most preferably, the second binding partner is deposited in the same pattern as the assay reagents. By analogy, the method can be adapted to use any of a variety of known first binding partner—second binding partner pairs including, but not limited to, hapten-antibody, nucleic acid—complementary nucleic acid, receptor-ligand, metal-metal ligand, sugar-lectin, boronic acid—diol, etc.

Accordingly, one embodiment of an immobilization method of the invention comprises forming an assay domain comprising an assay reagent by: i) treating a predefined region of a surface (preferably, a carbon ink electrode surface) with a solution comprising a second binding partner no as to form an adsorbed capture layer (or, alternatively, a covalently bound layer) of said second binding partner (preferably, avidin) within the predefined region of said surface; (ii) treating the capture layer in the pre-defined region with a solution comprising the assay reagent, wherein the assay reagent is linked to or comprises a first binding partner (preferably, an assay reagent that is labeled with biotin) that binds the second binding partner. Preferably, a micro-dispensing technique is used to pattern the second binding partner and/or the assay reagent into the pre-defined region (more preferably both are patterned). More preferably, the pre-defined region is defined by a boundary (preferably defined, by a dielectric layer patterned on the surface) adapted to confine small volumes of fluid to the pre-defined region.

The treating steps may comprise allowing the solutions to dry on the pre-determined regions. Between binding the second binding partner and binding the assay reagent, it may be advantageous to wash the surface with one or more wash solutions to remove excess unbound second binding partner. The wash solutions, preferably, comprise surfactant and/or blocking agents. After immobilizing the assay reagent, it may be advantageous to wash the surface with one or more wash solutions to remove unbound assay reagent. The wash solutions, preferably, comprise surfactants, blocking agents and/or protein stabilizers such as sugars. Useful blocking agents include standard blocking agents of the art (BSA, casein, etc.) but also include blocking reagents comprising the first binding partner (for example, free biotin) no as to block free binding sites on the immobilized layer of the second binding reagent. The wash steps may employ the wash techniques of the invention that employ concentric tubes for adding and removing wash solution. The surfaces are optionally dried after preparation for long term storage.

Preferably, the amounts of the second binding reagent and assay reagent applied to the pre-defined region are equal to or less than that required to saturate the surface. By choosing amounts roughly equal to the amounts required to saturate the surface, it may be possible to minimize both the amount of excess unbound reagent and the amount of unbound sites and thus avoid the need for washing or blocking steps. In an alternative embodiment, the amount of the assay reagent is kept below the amount of available binding sites in the capture layer to ensure that the binding capacity is determined by the amount of assay reagent added and not by amount of immobilized second binding partner (thus reducing the effect of variability in the efficiency of, e.g., the adsorption of the second binding partner).

The method may be applied to forming a plurality of assay domains comprising assay reagents immobilized in a plurality of pre-defined regions. In this case, the method is simply repeated for each of the pre-defined regions. Preferably, at least two of the assay domains comprise assay reagents that differ in selectivity for analytes of interest. When forming a plurality of assay domains, it is particularly advantageous to block the final product with a blocking reagent comprising the first binding partner (but not the analyte specific components of the assay reagent) to block excess binding sites on immobilized second binding partners; this procedure prevents assay cross-talk due to excess assay reagent on one pre-defined region diffusing and binding, via first binding partner-second binding partner interactions, to a different assay domain. For example, after using the two step procedure of binding avidin and then a biotin-labeled antibody, the surface may be blocked with free biotin. Alternatively, after using a two step procedure of binding Protein A (or other Fc binding receptor) and then an antibody against an analyte of interest, the surface may be blocked by using a different antibody or, more preferably, an Fc fragment of an antibody.

It has been observed that in some cases assay reagents adsorbed on a surface such as a carbon ink may, over time, slowly dissociate from the surface. This dissociation leads to the presence of free assay reagents that may interfere with assays that employ the adsorbed assay reagents. This dissociation may be greatly slowed by cross-linking the adsorbed assay reagents so that the immobilized species are greater molecular weight and have more points of contact with the surface. Accordingly, in the immobilization methods described above, the second binding partner is, preferably, cross-linked to minimize dissociation of the reagent during surface preparation and/or storage. The cross-linking may be carried out via covalent cross-linking using standard chemical cross-linking agents. Alternatively, the cross-linking is carried out using specific binding interactions. In a preferred embodiment of the invention, the second binding partner is polyvalent (i.e., has multiple binding sites for the first binding partner) and is cross-linked by combining it with a cross-linking reagent that is either a polyvalent first binding partner or a molecule which comprises multiple first binding partners. In this embodiment, the amount of the cross-linking agent is selected so as to provide a beneficial amount of cross-links without saturating all the available binding sites on the second binding partners. The cross-links may be formed after the second binding partner is immobilized but are, preferably, formed in solution prior to immobilization. Advantageously, we have found that this cross-linking procedure not only acts to thrill a more stable surface but also increases the number of available binding sites on the surface (i.e., the binding capacity of the surface) by allowing the immobilization of more than a packed monolayer of the second binding partner (e.g., by extension of the polymerized second binding partner into solution).

By way of example, avidin (a tetrameric binding protein having four binding sites for biotin) is cross-linked to form poly-avidin by the addition of a small quantity of biotin-labeled cross-linking agent (for example, a protein such as BSA) having multiple biotin labels per protein molecule. Poly-avidin is then immobilized and used as a capture surface for immobilizing a biotin-labeled assay reagent, e.g., using the immobilization methods described above. The amount of biotin-protein is selected to allow cross-linking while leaving sufficient biotin binding sites available so that the immobilized poly-avidin can be used to capture a biotin-labeled first binding reagent a biotin-labeled antibody). Preferably, the biotin-labeled cross-linking agent comprises at least two, more preferably, at least four, or more preferably, at least eight biotins per molecule. Preferably, the number of molar equivalents of cross-linking agent per mole of avidin is between 0.01 and 4, more preferably, between 0.01 and 1, even more preferably between 0.01 and 0.25, even more preferably between 0.05 and 0.25 and most preferably between 0.05 and 0.10. The concentration of avidin used for immobilization was preferably between 50-1000 ug/mL, more preferably between 100-800 ug/mL and most preferably around 400 ug/mL. By analogy, avidin may be replaced in these methods by other poly-valent biotin-specific receptors such as streptavidin.

Experiments were conducted to demonstrate the benefit of using poly-avidin capture layers on carbon ink electrodes and/or the two-step immobilization procedures of the invention. These experiments used screen printed carbon ink electrodes that were patterned on a plastic substrate. The working electrodes had an exposed circular area of about 3 mm$^2$ that was defined by a patterned dielectric layer that was screen printed over the carbon ink electrodes. The substrate also comprised at least one additional carbon ink electrode for use as a counter electrode. Reagents were immobilized by depositing (using a Bio-Dot dispenser) small volumes (200-300 nL) of a solution comprising the reagent onto the exposed electrode area (the solution being confined to the exposed electrode area by the dielectric layer) and allowing the solution to dry on the electrode. Poly-avidin was prepared by combining the appropriate amounts of avidin and biotin-BSA and incubating for 15 minutes. After the immobilization and/or washing steps (as described below), the substrate was either mated with a multi-well plate top so as to form the bottom surface of a well of multi-well plate or it was mated using a gasket made of double stick tape to a plastic sheet so as to form the bottom surface of a flow cell of an assay cartridge. The electrode surfaces were contacted with a buffered solution comprising tripropylamine (MSD Assay Buffer, MSD) by adding the buffer to a well of a multi-well plate or by introducing the buffer into the flow cell, ECL was induced by applying a voltage between the working and counter electrode (a ramp of 2-5 V over 3 seconds), ECL was measured by taking an image of the substrate using a cooled CCD camera.

Electrodes were coated with either avidin (by treating with 200 mL of a 75 ug/mL solution of avidin) or with poly-avidin (by treating with 200 mL of a solution containing 75 ug/mL avidin and 3.1 ug/mL biotin-labeled BSA and allowing the solutions to dry overnight; the BSA being labeled with a 4-fold excess of biotin-LC-sulfo NHS ester and having an expected ratio of biotins per BSA of roughly 2-3). The substrates were washed with water and the electrodes were then treated with 300 nL of a solution containing 100 ug/mL of an biotin-labeled anti-TSH antibody. The electrodes were washed with water, assembled into a cartridge into which was introduced a solution containing 20 uIU/mL of TSH and 12 ug/mL of an anti-TSH antibody that was labeled with a Sulfo-TAG NHS ester (MSD), an electrochemiluminescent label. The cartridge was incubated for 8 minutes to allow the binding reactions to occur, the substrate was then washed by passing MSD Assay Buffer into the flow cell and ECL was measured. The average emitted electrochemiluminescence intensity from the poly-avidin treated electrode (1652 units) was approximately three times that from the avidin treated electrode (602 units). Without being bound by theory, it is believed that the higher signal on the poly-avidin electrode represents an increased number of binding sites on the poly-avidin treated electrode and/or a reduction in the amount of avidin that washes off the poly-avidin electrode and adsorbs on other surfaces of the cartridge (thus competing with binding sites on the electrode).

In a similar experiment, the direct adsorption of anti-TSH antibody (by treatment of the electrode with a 100 ug/mL solution of an anti-TSH antibody) was compared to immobilization via a poly-avidin layer (as described above except that the poly-avidin solution contained 400 ug/mL avidin and 25 ug/mL biotin-BSA and the biotin-labeled anti-TSH was at a concentration of 100 ug/mL). The results showed that signal obtained using immobilization via poly-avidin (2207) was roughly twice that obtained using direct adsorption (1264). In addition, two step immobilization protocol was found to provide more precise results; the coefficients of variation (CVs) were three times lower when the two step method was employed.

The poly-avidin layers were further characterized by using avidin that was labeled with an electrochemiluminescent label (on average 0.3 Sulfo-TAG NHS labels per protein). The electrodes were treated with one of three solutions: (i) 75 ug/mL avidin, (ii) 75 ug/mL avidin and 25 ug/mL BSA or (iii) 75 ug/mL, avidin and 25 ug/mL biotin-BSA. All the solutions contained 0.0035% Triton X-100. The electrodes were washed with water, immersed in MSD Assay Buffer and ECL was measured. The electrode treated with all the components of poly-avidin (avidin and biotin-BSA) gave an ECL signal (150981) that was roughly twice that observed for avidin alone (85235) or avidin with unlabeled BSA (65570), demonstrating that cross-linking was required for the improved performance of poly-avidin. It was also observed that the intensity of ECL was much more evenly distributed across the electrode for the poly-avidin electrodes than for the other electrodes.

In a different experiment the labeled and immobilized avidin or poly-avidin layers were i) not washed or ii) exposed to a solution containing BSA for 2 hours and then extensively washed with phosphate buffered saline. In this experiment, the avidin concentration was 0.5 mg/mL, the ratio of avidin to biotin-BSA was 16:1 and the labeled avidin was mixed with unlabeled avidin (at a 1:100 ratio) to reduce the overall signals. The experiment was carried out on both non-treated electrodes and electrodes that were treated with an oxygen plasma. Table 5, below, shows that the use of poly-avidin substantially reduced the loss of avidin from the surface after extensive washes and exposure to protein-containing solutions.

assay electrode. It should be understood, however that the invention is not limited to a single concentric tube device but can, preferably, employ an array of concentric tubes, preferably, arranged in the same pattern and spacing as the assay domains. Preferably, wash fluid is dispensed through inner tube 705 and aspirated through outer tube 710. In operation, as the fluid transitions from the inner tube to the outer, it preferably passes over the assay domain surface, washing the assay domain in an area confined by the diameter of the outer tube. The figure shows the concentric tube being used to wash a carbon ink electrode 720 patterned on substrate 730, the exposed surface of electrode 720 being defined by patterned dielectric layer 725 which acts as a boundary to form a fluid containment region on electrode 720. By analogy, the concentric tubes may be used to wash assay domains on a variety of other surfaces, the assay domains being preferably but not necessarily defined by a fluid boundary. The tubes are preferably configured so that the outer tube removes fluid with a high enough efficiency so as to prevent the spread of fluid to regions outside the domain being washed. In alternate embodiments, the functions of the

TABLE 5

| | Unmodified Electrodes | | | Plasma-Treated Electrodes | | | |
|---|---|---|---|---|---|---|---|
| | Avidin | | Poly-Avidin | | Avidin | | Poly-Avidin |
| | Signal | % Left | Signal | % Left | Signal | % Left | Signal | % Left |
| No Wash | 21,107 | | 26,618 | | 10,871 | | 18,512 | |
| Wash | 9,545 | 45 | 18,845 | 71 | 3,332 | 31 | 14,024 | 76 |

After immobilizing assay reagents on surfaces for use in solid phase assays (e.g., by applying solutions comprising the assay reagents to the surfaces, most preferably, by patterned depositions of these solutions to form an array of assay domains comprising the assay reagents), assay performance is often improved by washing the assay electrodes to remove unbound assay reagents. This washing step is particularly important when unbound assay reagent may interfere with an assay (e.g., unbound antibodies may interfere by competing with the capture of analytes to antibodies on the surface). Preferably, this washing step is carried out using a procedure that minimizes the ability of unbound reagents to adsorb in other undesirable locations. For example, after immobilization of an antibody on an assay domain on an electrode in an assay module, the washing step will preferably minimize the adsorption of unbound antibody to non-electrode surface (antibody adsorbed on non-electrode surfaces interfering with binding assays by competing for the binding of analyte with antibody immobilized on the electrode). Even more importantly, in array type measurements involving a plurality of assay domains specific for different analytes of interest, the washing step should minimize the diffusion of an unbound assay reagent from one assay domain and its adsorption on a different assay domain (this process leading to assay cross-talk).

Figure 7A:
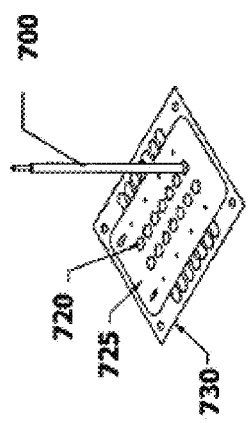
FIG. 7a illustrates the use of a localized washing apparatus having concentric tubes.
Figure 7B:
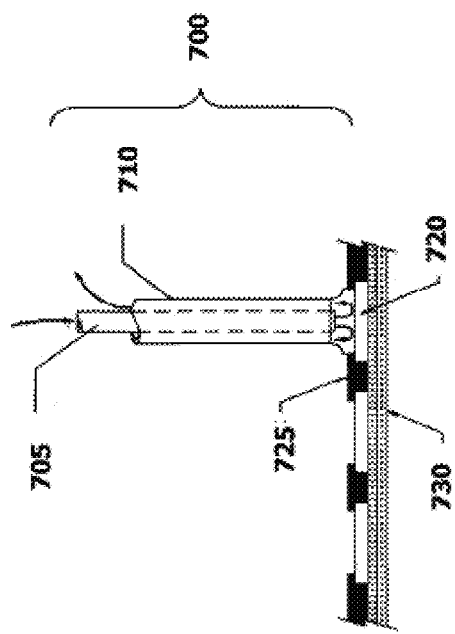

We have found that we can prevent the undesired adsorption of assay reagents outside pre-defined locations by localized washing of assay domains using a concentric tube dispense/aspirate fixture. FIGS. 7*a* and 7*b* depict one embodiment wherein a washing fixture was constructed that consists of a single concentric tube structure which may be used to wash a single assay domain in an assay module or to sequentially wash multiple assays domains in an assay module by positioned the concentric tube structure over each inner and outer tubes may also be reversed such that the wash fluid is dispensed through the outer tube, and aspirated up the center via the inner tube. These arrangements of tubes prevent unbound assay reagents on the assay domains from contacting other surfaces of the assay module.

In another alternate embodiment, a tube structure having three concentric tubes is used to pattern and wash assay reagents on assay domains. A first tube (preferably the inner tube) is used to microdispense assay reagents on an assay domain. This tube is preferably linked to a low volume fluid dispensing controller such as a microsyringe (optionally, having a solenoid valve flow controller) or piezoelectric dispenser. The second tube (preferably the middle tube) is used to dispense bulk washing reagents on the assay domain. The third tube (preferably the outer tube) is used to aspirate excess assay reagent and/or to wash reagents from the assay domain. Using this arrangement, a single device may be used to dispense assay reagents onto an assay domain (e.g., so as to cause localized immobilization of the assay reagent on the assay domain) and to wash excess assay reagent from the assay domain, these operations occurring without contamination of adjacent surfaces with the assay reagent. Optionally, an array of these devices is used to pattern and wash an array of assay domains.

The invention relates in part to assay cartridges. An assay cartridge of the invention incorporates one or more fluidic components such as compartments, wells, chambers, fluidic conduits, fluid ports/vents, valves, and the like and/or one or more detection components such as electrodes, electrode contacts, sensors (e.g., electrochemical sensors, fluid sensors, mass sensors, optical sensors, capacitive sensors, impedance sensors, optical waveguides, etc.), detection windows (e.g., windows configured to allow optical measurements on samples in the cartridge such as measurements of absorbance, light scattering, light refraction, light reflection, fluorescence, phosphorescence, chemiluminescence, electrochemiluminescence, etc), and the like. A cartridge may also comprise reagents for carrying out an assay such as binding reagents, detectable labels, sample processing reagents, wash solutions, buffers, etc. The reagents may be present in liquid form, solid form and/or immobilized on the surface of solid phase supports present in the cartridge. Certain preferred embodiments of the invention, comprise detection chambers having the electrode arrays and/or binding domains as described above (e.g., the electrode arrays described in FIGS. 1-4).

The fluidic components are preferably designed and incorporated into the cartridge body to form the fluidic network using certain predefined design guidelines. The design guidelines for each component can be dependent upon one or more factors such as, e.g., cartridge body design (i.e., single-piece body, multiple piece body, modular body, single read chamber, multiple read chamber, and the like), manufacturing process (e.g., injection molding, blow molding, hot stamping, casting, machining, etc.), materials (e.g., acrylic, PVDF, PET, polystyrene, polypropylene and the like), assay, requirements (e.g., binding assay, competitive binding assay, single step assay, two-step assay, etc.), functional requirements (e.g., sample size, assay reagent volumes, detection technology, time-to-result, incubation, heating, mixing/agitating), safety/handling requirements (e.g., self-containment, regulatory approval, ease of use, etc.), and/or the like.

The skilled practitioner will be able to readily select materials suitable for the fabrication of the cartridges of the invention. Suitable materials include glass, ceramics, metals and/or plastics such as acrylic polymers such as Lucite), acetal resins (such as Delrin), polyvinylidene fluoride (PVDF), polyethylene terephthalate (PET), polytetrafluoroethylene (e.g., Teflon), polystyrene, polypropylene, ABS, PEEK and the like. Preferably, the materials are inert to any solutions/reagents that will contact them during use or storage of the cartridge. In certain preferred embodiments, at least some portion of the cartridge is fabricated from transparent and/or translucent materials such as glass or acrylic polymer to provide windows that allow optical interrogation of fluids or surfaces inside the cartridge, e.g., for analysis of compositions within detection chambers of the cartridge or for monitoring and controlling the movement of liquids through the fluidic networks defined within the cartridge.

One preferred embodiment of the invention is a cartridge that includes one or more sample chambers, one or more detection chambers (preferably, detection chambers adapted for use in ECL measurements as described above) and one or more waste chambers. The chambers are connected in series by fluid conduits so that a sample introduced, into a sample chamber can be delivered into one or more detection chambers for analysis and then passed into one or more waste chambers for disposal. Preferably, this cartridge also includes one or more reagent chambers for storing liquid reagents, the reagent chambers connected via conduits to the other components so as to allow the introduction of the liquid reagents into specified sample or detection chambers. The cartridge may also include vent ports in fluidic communication with the sample, detection and/or waste chambers (directly or through vent conduits) so as to allow the equilibration of fluid in the chambers with the atmosphere or to allow for the directed movement of fluid into or out of a specified chamber by the application of positive or negative pressure.

In an alternative embodiment, a sample chamber and a waste chamber are both arranged upstream from a detection chamber having first and second inlet/outlet conduits (preferably, a detection chamber having an elongated shape, the inlet/outlet conduits being arranged at or near the opposite ends of the elongated dimension). The cartridge is configured to allow the introduction of sample into the detection chamber via the first inlet/outlet conduit and then the reversal of flow to direct the sample fluid back out the first inlet/outlet conduit and to the waste chamber. Preferably, a reagent chamber is located downstream of the detection chamber and the cartridge is configured to allow introduction of the reagent to the detection chamber via the second inlet/outlet conduit (i.e., in "reverse flow" relative to the introduction of sample). This arrangement is particularly well suited to measurements that suffer from strong sample interference, the reverse flow being especially efficient at washing residual sample from the detection chamber. This embodiment is especially useful in ECL-based assays for markers (e.g., cell wall markers of gram positive bacteria) in samples containing a nitrous acid-containing extraction buffer (see, e.g., the extraction methods and reagents disclosed in U.S. Provisional Patent Application 60/436,591, filed Dec. 26, 2002, entitled Methods Compositions and Kits for Biomarker Extraction, hereby incorporated by reference). One preferred embodiment of the invention uses a cartridge configured with a reverse flow wash to conduct an ECL binding assay for a panel of upper respiratory pathogens including streptococcal species and optionally other pathogens such as influenza A and B and RSV (preferably by employing an array of antibodies against markers of the pathogens, the array preferably being formed on one or more electrodes, most preferably an electrode array as described above and in FIGS. 1-4).

The reverse flow wash significantly reduces the detrimental effects of nitrous acid on ECL measurements. In preferred embodiments, the washing efficiency is such that the fraction of sample (or reagent) left in a detection chamber after a wash is less than $1/1000$; more preferably less than $1/10,000$, even more preferably less than $1/100,000$ The sample chamber is a chamber defined within a cartridge that is adapted for receiving a sample to be analyzed in the cartridge. The sample chamber includes a sample introduction port for introducing sample into the chamber. The port is preferably an opening in the cartridge that provides access to the sample chamber. Alternatively, the port may be a membrane or septa through which a sample may be injected into the sample chamber, e.g., through the use of a needle or cannula. Preferably, the cartridge also includes a sealable closure for sealing the sample introduction port and preventing leakage of the sample and possible exposure of the user and/or associated instruments to biohazards. Preferably the sealing/capping mechanism utilizes a hinged configuration so that the sample chamber is easily accessed and sealed. In particularly preferred embodiments the sealing/capping mechanism incorporates a flexible hinge, e.g., rubber, plastic or the like. Most preferably, the sample chamber is adapted and configured to receive a modular detachable insert that includes a cap for sealing the sample chamber. Use of a modular detachable insert within the sample chamber also allows for independent selection of materials for the main cartridge body. In an alternative embodiment, sealing of the sample introduction port is achieved by applying an adhesive tape to the port. The sample chamber may contain dry reagents used in carrying out the assay that reconstitute on addition of a liquid sample. Optionally, the sample chamber contains an anti-foam agent to prevent foaming of the sample in the cartridge.

In one embodiment, the sealing/capping mechanism further comprises a latching mechanism to prevent the sealing/capping mechanism from opening during use. Still further, the sealing/capping mechanism may comprise a retention component to prevent the mechanism from being dislodged from the cartridge. For example, the mechanism may include a retaining ring or retaining tabs affixed or molded to the body of the mechanism to secure the mechanism within the port. Optionally, the port has ledges that secure the retaining components in place once the cap is inserted into the cartridge body. An example of the sealing/capping mechanism is shown in FIGS. 35a-b. As shown for cap 3500 in FIG. 35a, the sealing/capping mechanism is optionally fabricated as a single unit, e.g., molded from a thermoplastic elastomer material. FIG. 35a illustrates one embodiment of the retention component, 2391, comprising two retaining tabs molded to the body of the sealing/capping mechanism. FIG. 35b illustrates a latching mechanism, 2392, that may be used in the sealing/capping mechanism.

Figure 9:
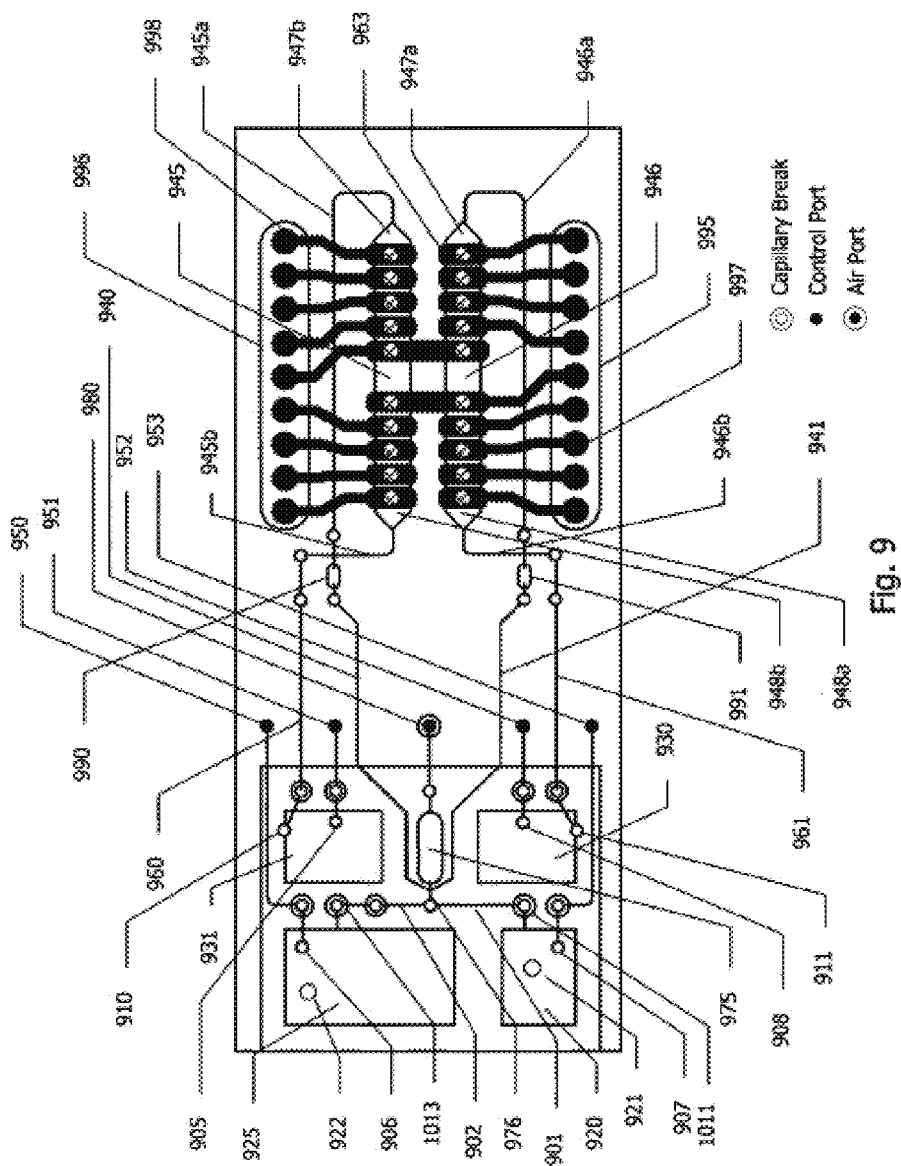
FIG. 9 is a schematic representation of one embodiment of an assay cartridge illustrating various fluidic components.
Figure 20:
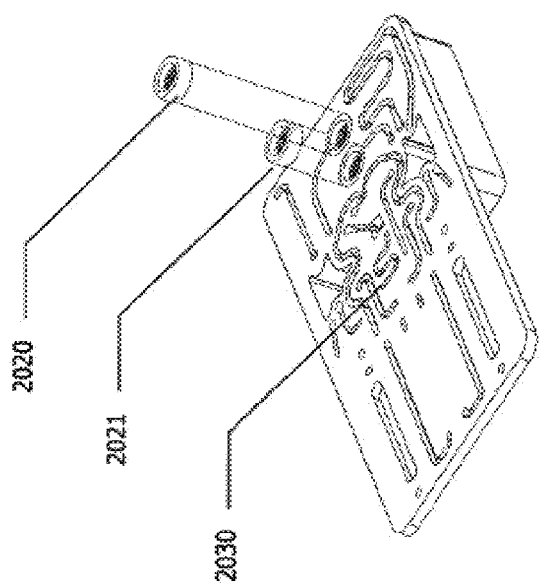
FIG. 20 is a bottom isometric view of an alternative assay cartridge embodiment illustrating filter inserts.

The sample chamber is connected to a sample conduit for transferring fluids from the sample chamber to other fluidic components in the cartridge. The sample chamber may also be connected to a vent port and/or a reagent chamber (e.g., through fluidic conduits). In a preferred configuration for receiving liquid samples, the sample chamber is connected to a sample conduit and a vent port. A cross-sectional view of a preferred embodiment is shown in FIG. 27. Sample chamber 2710 has sample introduction port 2720 and is linked to sample conduit 2730 and sample vent port 2740 (through vent conduit 2750). Sample conduit 2730 is advantageously arranged to intersect sample chamber 2710 at or near the bottom of the chamber (relative to the orientation of the cartridge during operation) so as to allow for efficient transfer of a large fraction of the sample volume without the introduction of bubbles. Vent conduit 2750 is advantageously arranged to intersect sample chamber 2710 above sample conduit 2730 and at a height that is greater than the anticipated sample fill level height to avoid possible contamination of the instrument and/or escape of the sample fluid. Preferably, vent conduit 2750 has sufficient volume in the fluidic conduit so that a small amount of sample fluid, e.g. as may be observed if the sample is foamy or has bubbles, may enter the conduit without being pulled all the way to vent port 2740. In one embodiment, as depicted in FIG. 9, a well/trap 975 may be arranged within the fluidic conduit. In another embodiment, as depicted in FIG. 20, the fluidic conduit may be extended/lengthened, e.g., utilizing a serpentine configuration 2030.

Cap 2760 can be used to seal sample introduction port 2720 without preventing the flow of air through vent conduit 2750. In FIG. 27, the fluidic compartments and conduits are formed by recesses (e.g., channels) or holes in cartridge body 2770 and by cover layer 2780 which is sealed against cartridge body 2770. Sample chamber 2710 has internal ledge 2790. Vent conduit 2750 includes a vertical hole from the bottom of cartridge body 2770 to the top face of ledge 2790. This arrangement provides for a simplified manufacturing process that is amenable to injection molding or machining of the cartridge body; other arrangements of the vent conduit will be readily apparent to the skilled artisan.

FIGS. 47(a)-(c) illustrates an alternate embodiment of a sample chamber that includes a feature for preventing overfilling of the chamber and a feature to provide the user with a visual indication of the liquid level in the chamber. In one embodiment, the assay cartridge includes a sample chamber, a sample indicator window, a reflecting surface, and an optical path connecting the sample chamber, sample indicator window and the reflecting surface. The figure shows the sample chamber from the top (FIG. 47(a)) and as a cross-sectional slice (FIG. 47(b)). Sample chamber 4700 includes a sample well 4720 with a sample introduction port with a sealable cap 4722, which may have locking features as described for cap 3500 above. The sample chamber 4700 is linked to a sample conduit 4730, which is used to transfer sample from the sample chamber to other sample processing fluidic components of a cartridge (e.g., as described for cartridges 900, 1400, 2500, 3200 and 3700). The sample conduit is arranged to intersect the sample chamber below the expected sample height and, preferably, at or near the bottom of the chamber. The sample conduit may include a Z-transition, other capillary break or valve element (not shown).

Sample chamber 4700 is also linked to sample overflow conduit 4740, which intersects the chamber above the level of the volume of sample required by the cartridge and which connects the sample chamber to overflow chamber 4742. Overflow chamber 4742 vents through vent conduit 4750 (which, preferably, connects at or near the top of the overflow chamber) to the sample vent port (not shown). If during sample addition the user accidently adds too much sample, the excess sample will drain into the overflow chamber instead of overfilling the sample chamber and contaminating the top of the cartridge.

Figure 47:
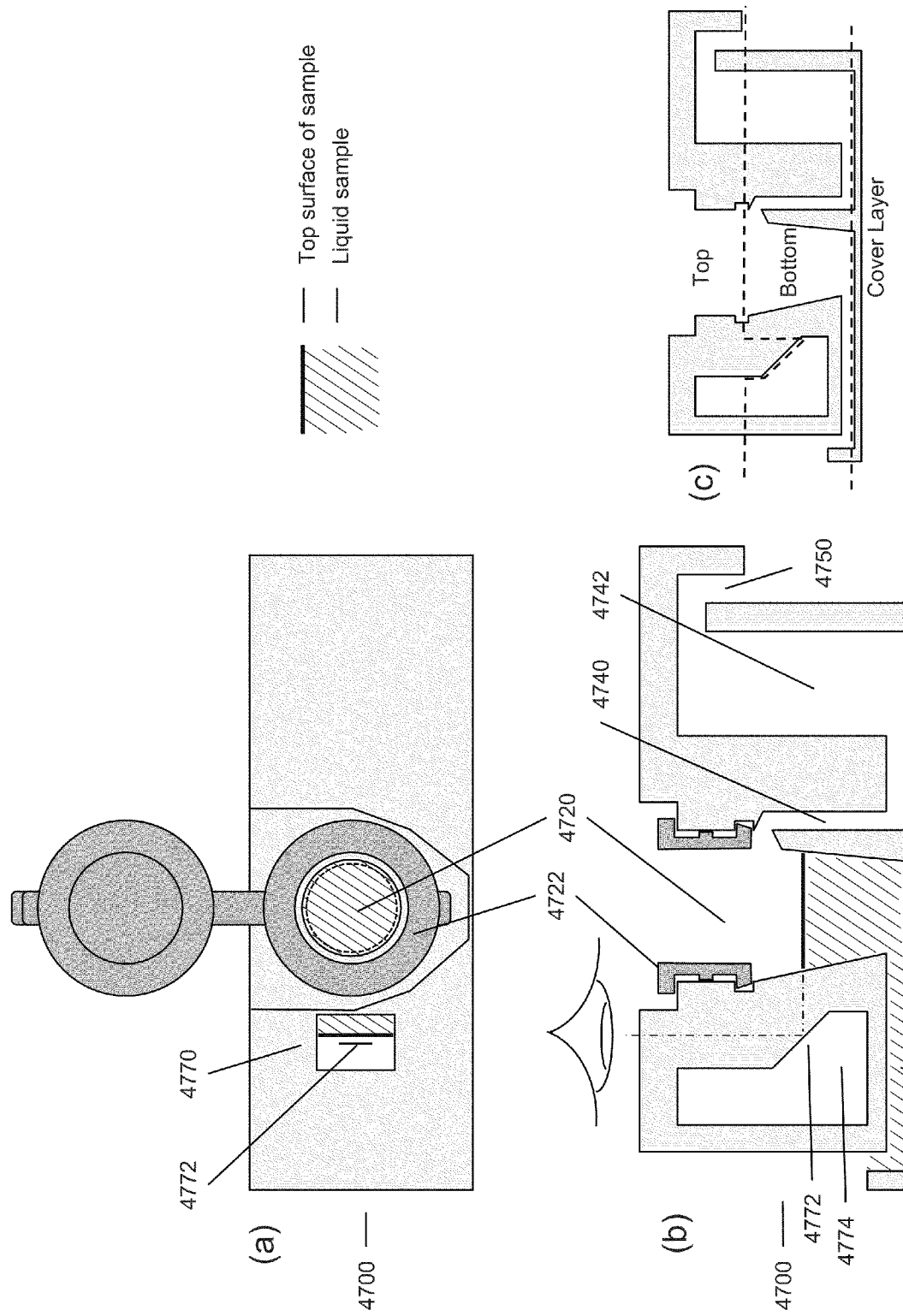
FIGS. 47(a)-(c) illustrate one embodiment of a sample chamber that includes a sample overflow chamber and a sample volume indicator window.

Sample chamber 4700 also provides sample indicator window 4770 to allow a user to view the level of a liquid sample in the sample chamber. A reflecting surface, e.g., mirrored surface, 4772 in the cartridge body is positioned such that it reflects a side view of the chamber (showing the height of the sample in the chamber) onto the indicator window. FIG. 47 shows a volume of sample in the sample chamber (the sample is represented as hatched lines and the top of the sample volume is represented, in side view, as a dark black line) and also shows the liquid level as it would be observed by a user looking at the indicator window from the top of the cartridge. The viewer window may have indicating features, such as indicating line 4772, that indicate minimum, maximum or target sample levels. For example, the indicator window may include one or more indicating lines that reflect a fluid level within the sample chamber, e.g., a sample minimum, a sample maximum, a target or desired level, and combinations thereof. The indicator window may have one or more indicating lines. Alternatively, the targeted minimum and/or maximum sample volumes may be indicated by the defined boundaries of the indicator window (e.g., the user may be instructed to add sample until the top of the sample is seen in the indicator window).

Therefore, using an assay cartridge including an indicator window allows the user to determine an appropriate fluid level in the assay cartridge. Briefly, the user would add a volume of fluid to the sample chamber. The fluid level is reflected via the optical path to the indicator window. The user may view the fluid level in the sample indicator window and compare the fluid level viewed in the window to an indicating feature on the window. In one embodiment, the window includes a line indicating a sample minimum, sample maximum, and/or a target fluid level and the user may view the actual fluid level in the sample chamber relative to the indicating feature on the window.

As shown by the dotted line in FIG. 47b, a cartridge comprising sample chamber 4700 has an optical path from the sample in the sample well to mirror surface 4772 to the indicator window. The optical path should be transparent to at least a portion of the visible light spectrum and is, preferably, transparent to visible light. Mirror surface 4772 may be any reflecting surface. In one embodiment of sample chamber 4700, mirror 4772 is provided by total internal reflection at an angled surface in the cartridge body, the angle being set such that the incident angle along the optical path is greater than the critical angle for total internal reflection at the interface. As shown in the figure, a totally internally reflective surface may be provided by incorporating a cavity in the cartridge body with a surface angled relative to the optical path (e.g., cavity 4774) such that light traveling in the cartridge body hits the air-body interface at the surface of the cavity and is reflected. One of ordinary skill in the art will be able to select appropriate angles of incidence for specific materials. In certain embodiments, the angle of incidence is selected to be greater than or equal to 43°, a value which will provide total internal reflection at an air interface for a wide variety of transparent engineering materials with refractive indices greater than or equal to 1.46 including many silica glasses and plastics used in injection molding (such as polystyrene and polymethylmethacrylate). Preferably, the angle of incidence is selected to be 45° to provide for reflection at a right angle (as shown in the figure).

In one non-limiting embodiment of sample chamber 4700, the sample chamber is included within a multi-part injection molded cartridge, using a design approach analogous to the one shown for cartridge 1400 in FIG. 14. One suitable multi-part design is illustrated in FIG. 47c and comprises a cartridge top, a cartridge bottom and a cover layer mated to the cartridge bottom (dashed lines in the figure being used to show, conceptually, one way to divide the design into its components). Optionally, the optical path from the mirror to the window is provided by a single injection molded part, e.g., the cartridge top in FIG. 47c. It should be noted that, while FIGS. 47b and 47c show the optical path and conduits 4720 and 4740 as being in the same plane, this arrangement is not a requirement and, e.g., some or all of these components may be angled into or out of the plane of the diagram.

In one embodiment of the sample chamber, a separate vent port and vent conduit are omitted and the sample introduction port also provides a vent port, e.g., the sample introduction port aperture also acts as a vent port. The vent port may also be provided through the top of the sealing/capping mechanism by, e.g., incorporating a vent hole in the top surface of the sealing/capping mechanism. An alternative embodiment may employ a scheme whereby the cartridge reader itself can include a piercing/venting mechanism that is adapted and configured to pierce through the top surface of the flexible sealing/capping mechanism. In a particularly preferred embodiment, the sealing/capping mechanism is adapted and configured to be self-sealing upon withdrawal/removal of the piercing/venting mechanism, e.g., via the use of a septum preferably comprising an elastomeric material. The advantage of a self-sealing cap mechanism is that the sample cannot escape from the sample chamber once the piercing/venting mechanism has been removed.

The sample chamber may also include a filter for, e.g., removing particulate matter that may be present within the sample itself or that may be present as a result of using a swab or the like to introduce sample into the sample chamber. A preferable embodiment may employ a filter that not only removes any particulate matter but that is also designed to separate red blood cells (RBC) from blood plasma; e.g., where the particular assay/assay format requires blood plasma as the sample. Such a filter can be an integral cross-flow filter, in-line filter or the like. Preferably, the filter is arranged at or near the entrance of the sample conduit.

In a preferred embodiment for extracting analytes from a solid matrix or a matrix that comprises solids (e.g., for extracting analytes from an absorbent material (e.g., a cotton ball, piece of filter paper, etc.), an applicator stick, dirt, food, sludge, feces, tissue, etc.) the sample chamber is connected to a reagent chamber (e.g., via a reagent conduit) comprising an extraction reagent, e.g., an extraction reagent disclosed in U.S. Provisional Patent Application 60/436,591, filed Dec. 26, 2002, entitled Methods Compositions and Kits for Biomarker Extraction, hereby incorporated by reference. Applicator stick is used herein to refer to a sample collection device comprising an elongated handle (preferably a rod or rectangular prism) and a sample collection head (preferably comprising an absorbant material or, alternatively, a scraping blade) configured to collect sample from a surface or biological tissue) and includes sample collection swabs and tissue scrapers. The reagent conduit and sample conduit are, preferably, arranged to intersect the sample chamber at or near opposing ends of the chamber so that reagent introduced through the reagent conduit is drawn through the sample before passing into the sample conduit. More preferably, the sample chamber has an elongated shape with the two conduits being arranged to intersect at or near the opposing ends of the length. The sample chamber may also include a filter, as described above, for removing solid material. Extraction of analytes from solid materials and, in particular, porous meshes such as may be found in swab heads may lead to the introduction of bubbles and air gaps into the resulting fluid stream. Preferably, the sample chamber or the downstream fluidic components (e.g., the sample conduit) include a bubble trap to remove air introduced during an extraction step.

FIG. 28 shows a cross-sectional view of one exemplary embodiment of a sample chamber for extracting analyte from a solid or solid-containing matrix. Elongated sample chamber 2810 has a sample introduction port 2820 equipped with a sealable closure as described above. The sample chamber is shown holding an applicator stick, specifically swab 2830 having absorbent swab head 2835. Reagent conduit 2840 and sample conduit 2845 are arranged to intersect sample chamber 2810 on opposing sides of swab head 2835 so that extraction reagent introduced through reagent conduit 2840 passes through swab head 2835 before entering sample conduit 2845. Optionally, a filter element 2848, may be included to remove particulates from the extracted sample. Preferably, the width of sample chamber 2810 in the region that surrounds the head of an inserted applicator stick is less than two times (more preferably less than 1.5 times, even more preferably less than 1.2 times, most preferably equal to or less than 1.0 times) the width of the widest region of the applicator stick that needs to pass through that region during insertion of the applicator stick. Alternatively, the cross-sectional area of sample chamber 2810 in the region that surrounds the head of an inserted applicator stick is less than four times (more preferably, less than two time, most preferably less than or equal to 1.0 times the cross-sectional area of the widest region of the applicator stick that needs to pass through that region. When used to extract sample from porous compressible materials (e.g., a swab having a porous compressible head), the width of the sample chamber is selected so that the width is narrow enough around the applicator stick head so that the material fills most or all the width of the chamber (ensuring the most efficient flow of extraction buffer through the material) but wide enough so that material can be easily inserted without the need for excessive force and without causing leakage of fluid in the material onto the outside surfaces of the cartridge (optionally, both properties may be achieved by use of a chamber that, with respect to a seated applicator stick is narrower in the region that surrounds the head than in the region that surrounds the shaft). Advantageously, sealing sample port 2820 prevents the release of air from that end of sample chamber 2810 and prevents the wasteful flow of extraction reagent away from sample conduit 2845. Optionally, swab 2830 and/or chamber 2810 are designed so that swab 2830 fits completely into chamber 2810. Alternatively (as shown), an applicator stick is too long to fit in chamber 2810 (e.g., the length of swab necessary to collect a mucous sample from the throat or nasal cavity may be too long to fit within the desired form factor of a cartridge) but is cleaved (e.g., broken, fractured, cut or otherwise detached) prior to or, preferably, after its introduction into chamber 2810 so as to produce a shortened stick fragment comprising the sample collection head. The shortened fragment is short enough to fit in chamber 2810 and allow closure 2825 to be sealed. In certain embodiments, the swab is designed to allow for easy detachment by having, e.g., a reversibly detachable head or by including a weak point in the shaft that allows for facile fracture of the shaft.

One method of introducing an applicator stick such as swab 2830 to sample chamber 2810 comprises i) introducing it into chamber 2810; ii) cleaving the swab shaft to form a head segment (comprising the head) and a shaft segment and iii) sealing the head segment in chamber 2810 by sealing closure 2825. The method may further comprise iv) introducing an extraction reagent through reagent conduit 2840; v) extracting analyte from swab head 2830 by passing extraction reagent through swab head 2835 and vi) removing the extracted analyte through sample conduit 2845. The extracted analyte may then be directed to a detection chamber for analysis. In one preferred embodiment, the shaft is cleaved by applying a force to the exposed end of the shaft of swab 2830 in a direction perpendicular to the length of chamber 2810 so as to break the shaft at an edge 2827 of chamber 2810 and allow removal of the part of the shaft that extends out of the chamber. Preferably, swab head 2830 is seated against the opposing end of chamber 2810 prior to cleaving the shaft.

In an especially preferred embodiment, the shaft of swab 2830 is constructed to have weak point (shown as weak point 2837) so that application of a force causes swab 2830 to reproducibly break at the weak point. Preferably, the swab shaft includes a stress/strain concentration feature (notch, score, or the like), e.g., the weak point is introduced by making the swab shaft narrower at the weak point or by "scoring" the shaft (i.e., cutting or etching one or more notches into the shaft at the weak point). Preferably the notch forms a circuit around the shaft so that the shaft may be broken in any direction. Such a notch may be made by cutting a groove in the shaft (e.g., with a tool or a laser) while turning the applicator stick on a lathe. Most preferably, the weak point is located no that when the shaft is inserted into chamber 2810 it is sufficiently near to edge 2827 so that a sufficient force can be applied to break the shaft, but sufficiently close to head 2835 so that the closure 2825 can be sealed. Optionally, the assay cartridge includes a window through which the user may view the inserted swab head on the applicator stick to verify that it is properly inserted into the sample chamber.

The sample chamber may also include additional passive and/or active features to promote a facile and reproducible break of a swab within the sample chamber. Passive features may include one or more of, e.g., geometrical configuration/arrangement of the sample chamber itself (e.g., curvature or angles along the length of the sample chamber), force focusing elements (e.g., protrusions from the internal walls of the sample chamber), and the like. Active features may include one or more actuatable mechanisms arranged and configured within the sample chamber for cleaving the swab, e.g., a "guillotine" device similar to a cigar cutter that can be actuated by a user exerting a force upon the device.

FIG. 29 shows sample chamber 2910, an adaptation of sample chamber 2810. Sample chamber 2910 has a constriction defined by protrusions 2990 that project inward from the walls of the chamber to form force focusing elements within the chamber. As illustrated in the figure, applying a lateral force to swab 2930 that is seated in sample chamber 2910 causes the swab shaft to contact one or more protrusions 2990. The lateral force is thereby focused on one location on the swab, promoting breakage of the swab at that location. Preferably, the swab and sample chamber are designed/selected so that the swab has a weak point (shown as weak point 2937) at the same location (preferably, the swab is scored at that location).

In an especially preferred embodiment, the sample chamber is configured to cause an applicator stick to bend upon insertion thus promoting fracture of the shaft. FIG. 30 shows sample chamber 3010, an especially preferred adaptation of sample chamber 2810 that has a bend or angle 3015 along its length such that the sample chamber has a first elongated region (on one side of the bend or angle) oriented in one direction and a second elongated region (on the other side of the bend or angle) oriented in second direction, the two regions being oriented at an angle relative to each other. As shown in the FIG. 30, insertion of swab 3030 leads to contact between a location on the shaft of the swab and a site on the inner surface of the angle or bend. This contact focuses force on that location and promotes breakage of the shaft at that location (to form head segment 3071 and shaft segment 3072). Preferably, the width of the sample chamber is designed to fit the swab head snugly but not so tightly that insertion of the swab requires excessive force. Most preferably, the swab and sample chamber are designed/selected so that the swab has a weak point (shown as weak point 3037) at or near the location of contact (preferably, the swab is scored at that location). Applicants have found that this arrangement allows for concurrent insertion and breaking of the swab in one simple operation. Advantageously, the breakage is reproducible and occurs without any violent motion that can lead to expulsion of sample from the cartridge. Preferred angles or degrees of curvature are 20-90 degrees, more preferably 30-70 degrees, even more preferably 40-50 degrees, most preferably 45 degrees. While FIGS. 28, 29 and 30 illustrate embodiments employing swabs, the techniques are applicable to other types of application sticks.

The sample chamber is connected to a sample conduit for transferring fluids from the sample chamber to other fluidic components in the cartridge. The sample chamber may also be connected to a vent port and/or a reagent chamber (e.g., through fluidic conduits). In a preferred configuration for receiving liquid samples, the sample chamber is connected to a sample conduit and a vent port. A cross-sectional view of a preferred embodiment is shown in FIG. 27. Sample chamber 2710 has sample introduction port 2720 and is linked to sample conduit 2730 and sample vent port 2740

(through vent conduit 2750). Sample conduit 2730 is advantageously arranged to intersect sample chamber 2710 at or near the bottom of the chamber (relative to the orientation of the cartridge during operation) so as to allow for efficient transfer of a large fraction of the sample volume without the introduction of bubbles. Vent conduit 2750 is advantageously arranged to intersect sample chamber 2710 above sample conduit 2730 and at a height that is greater than the anticipated sample fill level height to avoid possible contamination of the instrument and/or escape of the sample fluid. Preferably, vent conduit 2750 has sufficient volume in the fluidic conduit so that a small amount of sample fluid, e.g., as may be observed if the sample is foamy or has bubbles, may enter the conduit without being pulled all the way to vent port 2740. In one embodiment, as depicted in FIG. 9, a well/trap 975 may be arranged within the fluidic conduit. In another embodiment, as depicted in FIG. 20, the fluidic conduit may be extended/lengthened, e.g., utilizing a serpentine configuration 2030.

Cap 2760 can be used to seal sample introduction port 2720 without preventing the flow of air through vent conduit 2750. In FIG. 27, the fluidic compartments and conduits are formed by recesses (e.g., channels) or holes in cartridge body 2770 and by cover layer 2780 which is sealed against cartridge body 2770. Sample chamber 2710 has internal ledge 2790. Vent conduit 2750 includes a vertical hole from the bottom of cartridge body 2770 to the top face of ledge 2790. This arrangement provides for a simplified manufacturing process that is amenable to injection molding or machining of the cartridge body; other arrangements of the vent conduit will be readily apparent to the skilled artisan.

The reagent chambers are chambers adapted to hold liquid reagents used during the course of assays carried out in a cartridge. The reagent chamber design considerations for preferred embodiments of a cartridge depend, in part, upon the particular assay(s) to be performed by the cartridge. For example, a cartridge may have one, two or more reagent chambers depending on the number of reagents required by the assay format. Liquid reagents that may be held in a reagent chamber include buffers, assay diluents, solutions containing binding reagents proteins, receptors, ligands, haptens, antibodies, antigens, nucleic acids and the like), solutions containing enzymes and/or enzyme substrates, solutions containing control reagents, ECL read buffers containing ECL coreactants (e.g., tertiary amines such as piperazine-N,N'-bis(2-ethanesulfonic acid) and tripropylamine), wash solutions, anti-foam agents, extraction reagents (e.g., solutions containing detergents, acids, bases, nitrous acid, nitrate salts, etc.) and the like. A cartridge may have one, two or more reagent chambers depending, e.g., on the number of reagents required by the assay format. The reagent chamber design considerations for preferred embodiments of a cartridge depend, in part, upon the particular assay(s) to be performed by the cartridge. The reagent chamber is connected to a reagent conduit for transferring reagent from the chamber to other fluidic components in the cartridge. The reagent chamber is, preferably, also connected to a reagent vent port (optionally, through a reagent vent conduit). The arrangement of the conduit connections to the chamber falls under similar design considerations as those described for the sample chamber, sample conduit and sample port; preferably, the reagent conduit intersects the chamber at or near the bottom and the reagent vent/vent conduit intersects the chamber at or near the top (relative to the orientation of the cartridge during use). Optionally, a filter element is placed before or in the reagent conduit, e.g., if the reagent solution is expected to contain particles that may clog the cartridge fluidics or otherwise negatively affect assay performance.

In one embodiment of the invention, a cartridge has one or more reagent compartments that are empty or contain only dried reagents. Prior to conducting an assay, the user or cartridge reader dispenses liquid reagents into these chambers (e.g., through reagent vent ports or through reagent introduction ports similar to the sample introduction port described above) which, optionally, reconstitute any dried reagent present in the chambers; the reagents are thus prepared for use in the assay. Sealable closures may be used to prevent leakage of the reagents after their addition.

Preferably, where an assay requires the use of liquid reagents, some or all of these liquid reagents are stored in liquid form in reagent chambers so as to minimize the number and complexity of the operations that must be carried out by a user or cartridge reader. In one preferred embodiment the reagent chamber(s) can be filled with the requisite assay reagent(s) at the time of cartridge manufacture and subsequently sealed. When used to store liquid reagents, the reagent chambers should be designed so as to prevent leakage and or evaporative loss of the reagents from the chambers during storage. In a particularly preferred embodiment the assay reagents are incorporated into assay reagent modules that can be assembled into the cartridge's assay reagent chambers during manufacture. By designing the assay modules to have desired properties such as resistance to leakage and evaporative loss, the design and manufacture of the rest of the cartridge is greatly simplified. In such a preferred embodiment, an assay reagent release mechanism would preferably be incorporated within the cartridge reader for releasing the assay reagent from the reagent module. The assay reagent release mechanism is preferably adapted and configured to engage the reagent module and release/recover its contents.

Figure 19:
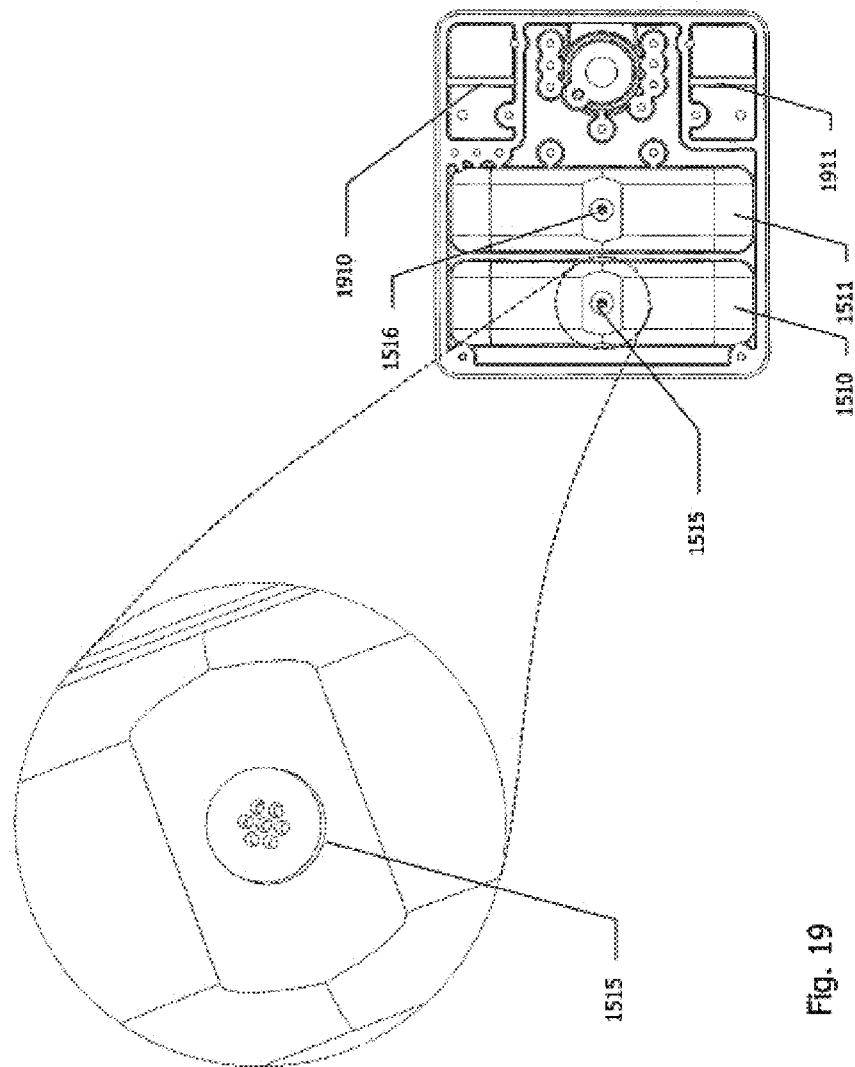
FIG. 19 is a bottom view of the upper cartridge component of the assay cartridge depicted in FIG. 14b illustrating one embodiment of integral filters.

The reagent module is a container such as an ampoule e.g., glass, plastic, or the like), a pouch (e.g., plastic, metal foil, plastic/metal foil laminates, robber, or the like), a blister pack, a syringe, or the like, or any other container that can be filled with fluid, sealed and dropped into the cartridge for subsequent fluid delivery. Preferred materials include glass, plastics with good water vapor barrier properties (e.g., cyclic olefin copolymers such as copolymers of ethylene and norbornene, nylon 6, polyethylene naphthalate, polyvinylidene chloride and polychlorotrifluoroethylene) and metal foil/plastic laminates because of their chemical inertness and their resistance to evaporative losses, other suitable materials will be apparent to the skilled practitioner. Ampoules, preferably, comprise a material that can be made to shatter or break on impact such as glass or hard plastic. Embodiments incorporating breakable ampoules preferably also include filters to ensure that substantially all of the fragments that may result upon rupturing the ampoules are not permitted to enter the fluidic network and possibly obstruct/block fluid flow. FIG. 19 depicts a cutaway top view of a cartridge showing filters 1515, 1516 at the bottom of chambers 1510 and 1511. These filters may be integrally molded/machined, etched/etc. into the corresponding chambers. Alternatively, as illustrated in FIG. 20 depicting a bottom view of a cartridge body, the filters 2020, 2021 may be separate components that are incorporated into the corresponding chambers during the manufacturing/assembly process; e.g., filter inserts that can be insert/snapped into a receptacle within the chamber that is arranged and configured to engagingly receive the filter insert.

Figure 21:
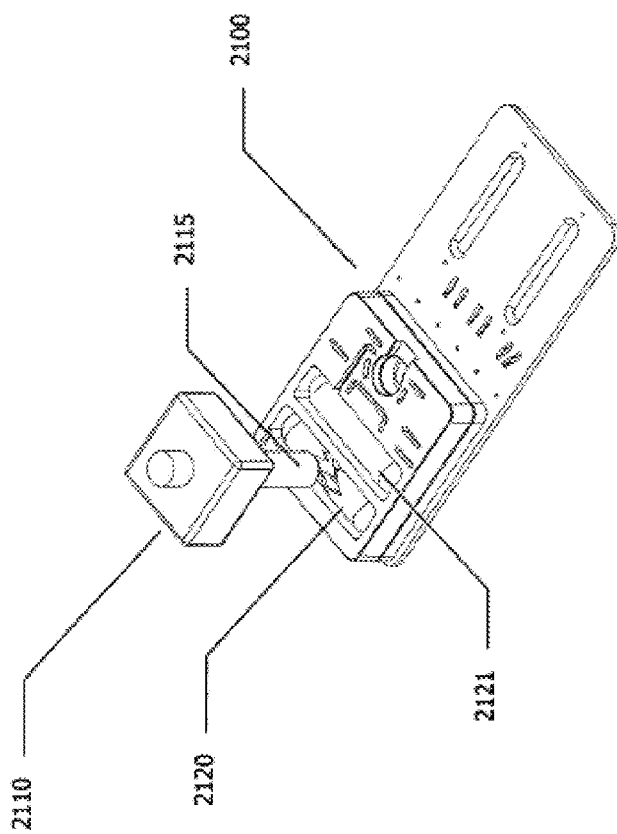
FIG. 21 is an isometric view of the assay cartridge depicted in FIG. 14b having assay reagent ampoules inserted therein, illustrating one embodiment for an assay reagent release mechanism.

The assay reagent release mechanism for releasing the contents of a breakable ampoule may be a simple mechanical device that is actuated to exert a force onto the ampoule; e.g., deliver a sharp blow to the ampoule thereby rupturing it and releasing its contents into the assay reagent chamber. FIG. 21 depicts one preferred embodiment of a reagent chamber employing assay reagent ampoules 2120, 2121. Preferably, a cover layer (not shown), most preferably made from a flexible material, is sealed to the top of the cartridge body so that liquid does not leak from the cartridge after the ampoules are ruptured (see, e.g., cover layer 1401 in FIG. 14). FIG. 21 also shows ampoule (not: assay) release mechanism 2110 (preferably, a component of a cartridge reader) which can be actuated so that hammer element 2115 strikes an ampoule, preferably by striking a flexible cover layer that then transfers the impact force to the ampoule (while, preferably, remaining intact so that it confines the released liquid to the reagent chamber). It has been observed that striking the ampoule quickly with an adequate impulsive force produces a more complete rupturing of the ampoule and thereby more effectively releases the assay reagent, whereas a slowly applied force increasing in magnitude until ultimately the ampoule fractures results in less complete rupture and less effective assay reagent release.

The ampoules may be broken serially (one at a time) or in parallel (simultaneously or substantially simultaneously). In one embodiment, an assay cartridge contains two ampoules with two different reagents (for example, a sample extraction buffer and a wash buffer). A cartridge reader for use with this cartridge can be configured to break both ampoules in parallel, releasing each ampoule's contents into their respective reagent chambers. Alternatively, the reader can be configured to break the ampoules serially. The second approach has advantages when the reagents are used at different times in the assay process, allowing each reagent to be released when it is needed, and reducing the risk that a reagent may leak out of a reagent chamber prematurely.

A variety of different approaches are available for driving a hammer element to break an ampoule including directly coupling the hammer to a motor, solenoid or other active drive element for striking the ampoule with the hammer or, alternatively, by releasing a hammer held under a spring force (in which case an active drive element may be used to load a spring). One embodiment of an assay reagent release mechanism is assay reagent release mechanism 4200 shown in FIG. 42. Hammer element 4210 is an elongated lever arm with a protruding striking face 4212, which preferably has pointed striking surface (e.g., the striking face may be triangular in cross-section). Striking face 4212 is raised and lowered relative to an inserted cartridge by rotation of hammer element 4210 around hammer axle 4214. Hammer element 4210 also comprises a control surface 4216 that rides on cam 4220 which is affixed to rotating control axle 4222, thus raising and lowering striking face 4212. Control surface 4216 may be, but is not required to be, at one end of the elongated lever arm; optionally, control surface 4216 and hammer axle 4214 are at opposite ends of the elongated lever arm. A force is applied to hammer element 4210, pushing it against the cam and/or down towards the cartridge. This force may be supplied by a spring (e.g., spring element 4218 between hammer element 4210 and assay reagent release mechanism frame 4230).

Cam 4220 has an asymmetric design that, on rotation of the cam (e.g., in response to a motor driving control axle 4222), smoothly raises the hammer element, but on continued rotation, quickly releases the hammer allowing it to fall rapidly (preferably, unimpeded by the cam) under the spring force such that it strikes and breaks an ampoule in the cartridge. The extent of the travel of the hammer may be restricted and defined by a mechanical stop that can be provided by the cam surface itself or by a separate mechanical stop such as a different stopping surface, e.g., a surface of assay reagent release mechanism frame 4230, as shown in the figure. A variety of suitable cam shapes are available that can achieve this effect. One suitable cam shape has (as illustrated by cam 4220 in FIG. 42) a roughly circular cross-section except for a rounded tab that protrudes from the circle. The leading edge of the tab (assuming the cam is turning counter-clockwise in the figure) provides for gradual lifting of the hammer element (and is, preferably, roughly aligned with a diameter of the circle). The trailing edge of the tab is tangential to the circle, so that the hammer is released and fills unimpeded by the cam. As the cam continues to turn, the control surface of the hammer element will eventually reach the leading edge of the tab and the hammer element will once again be lifted.

Figure 42:
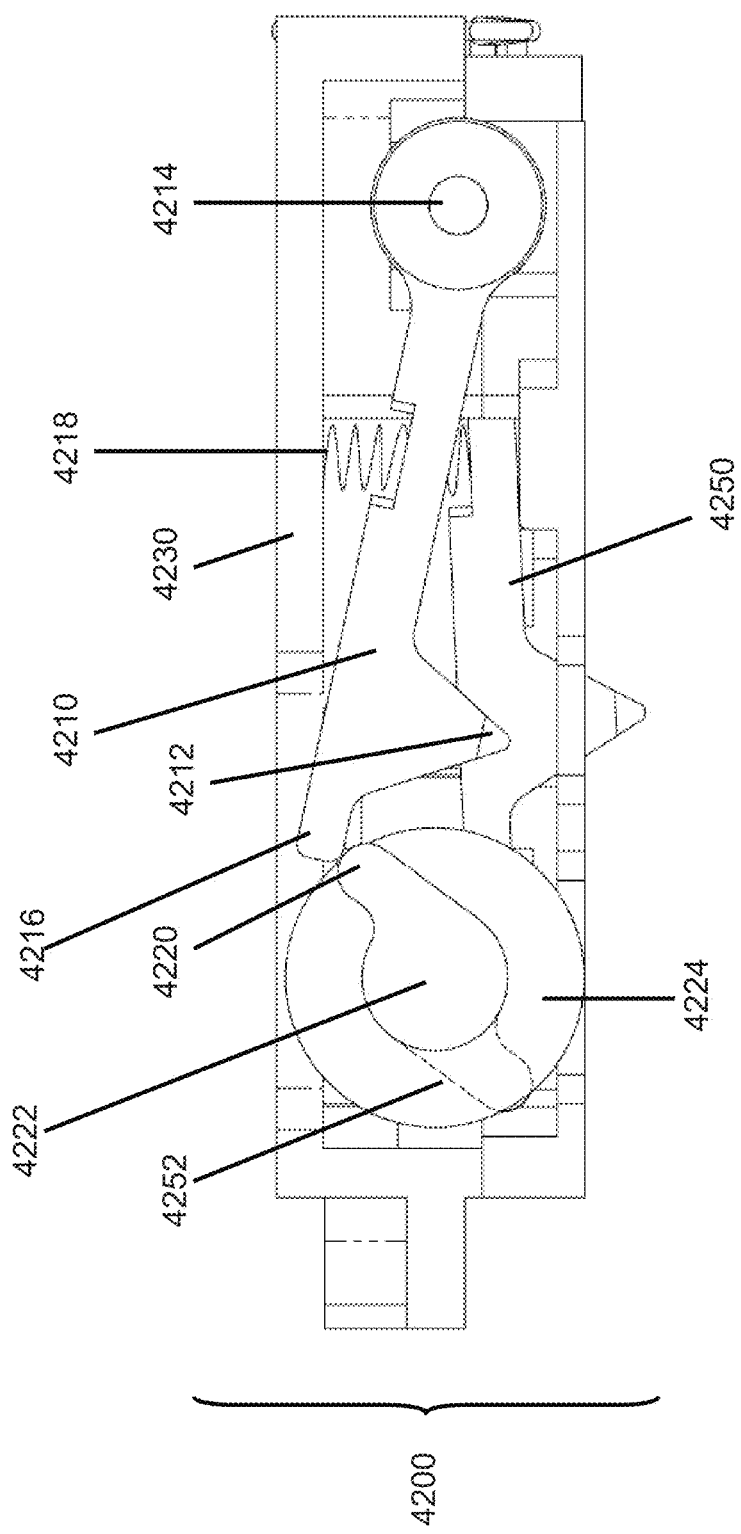
FIG. 42 shows one embodiment of an ampoule breaking mechanism for rupturing glass ampoules in a cartridge.

Multiple ampoules may be broken in series or in parallel by using multiple ampoule breaking mechanisms as described, above. In one alternate embodiment, a single motor may be used to control multiple hammer elements by coupling the motor to multiple cams. FIG. 42 shows a second hammer element 4250 (similar to hammer element 4210) that is controlled by a second cam 4252 on control axle 4222 (the second cam is not hidden in the figure by optional spacer ring 4224 between the cams; for illustrative purposes, the relative rotation location of the tab on second cam 4252 is shown as a dotted line; the spacer ring may be used to define the distance between the hammer elements, which may be matched to the distance between the ampoules). As shown in the figure, the two cams are in different relative rotational positions, such that they engage their respective hammer elements at different times during the rotation of control axle 4222. The figure shows the first hammer element at its highest position. Turning the control axle slightly counter clock-wise (e.g., by operating a motor driving the control axle) will release the first hammer element and break only one ampoule. When it is time to release the reagent in a second ampoule, the motor is turned on and the control axle is driven counter-clockwise until the second, cam tab engages the second hammer element, lifting it and releasing it to break a second ampoule. By placing the two cams in the same relative rotational positions, the same basic design can also be used to break two ampoules in parallel. It will be readily apparent that the same basic design can be used to break more than two ampoules serially and/or in parallel by introducing additional hammer elements and cams.

Figure 36:
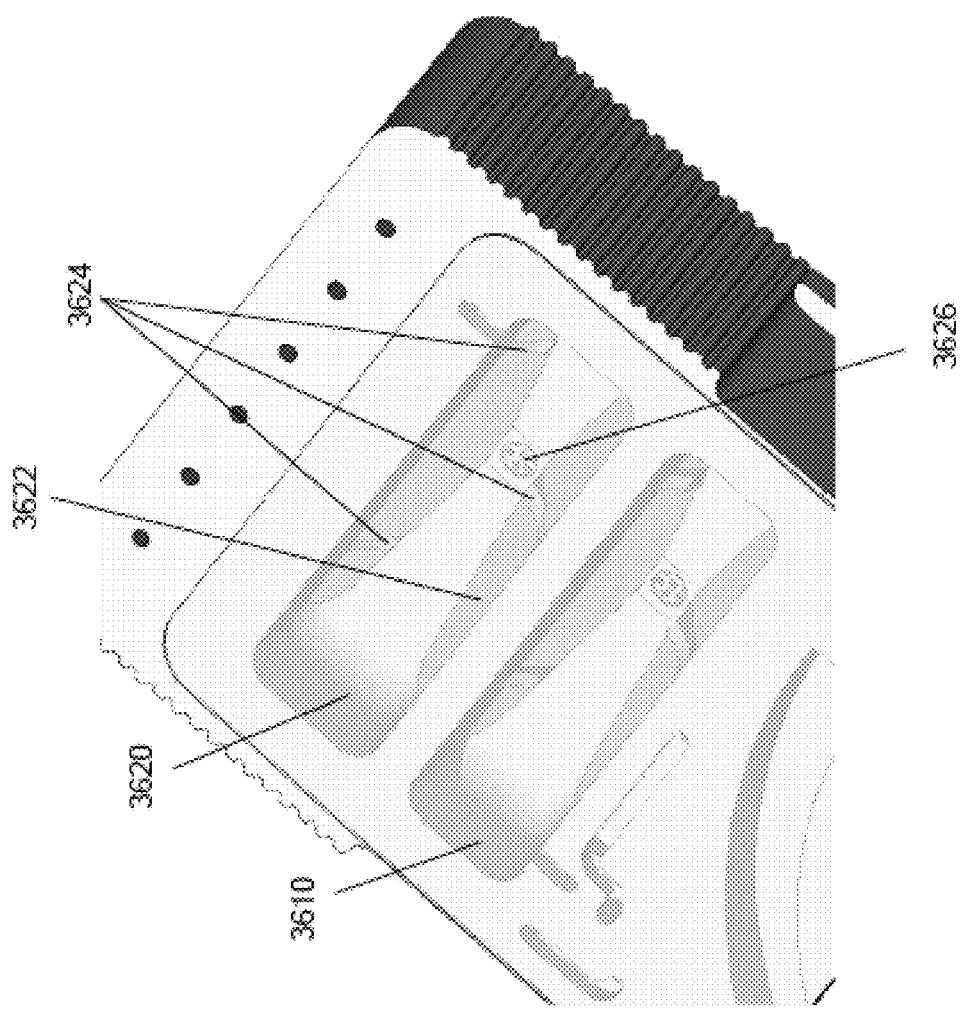
FIG. 36 shows a 3-point cradle design for holding ampoules in a cartridge.

FIG. 36 shows one embodiment of a cartridge having a cartridge body with two reagent chambers 3610 and 3620 defined therein, for holding reagent ampoules. The reagent chambers are wells within the cartridge body with outer openings that are roughly rectangular in shape and have lengths and widths greater than the length and width, respectively, of the roughly cylindrical ampoules they are designed to hold (see, e.g., ampoule 2121 in FIG. 21, which is a cylindrical ampoule with rounded ends). As described above, a cover layer (not shown) may be sealed to the openings to prevent leakage of assay reagents after an ampoule is opened within a reagent chamber. Side walls 3622 of reagent chamber 3620 (i.e., the walls along the length of the chambers) are sloped such that the width of the chamber at the bottom is less than the width at the top. The width at the bottom of the well is selected, based on the width of the reagent ampoules, such that the ampoules rest on the sloping walls of the chamber.

Optionally, the ampoules rest in an ampoule cradle adapted to receive a cylindrical ampoule. The ampoule cradle, i.e., a reagent chamber, includes side walls and a plurality of support brackets protruding from the side walls, and the support brackets are configured to provide a multi-point cradle support for a cylindrical ampoule. The reagent chamber may include three, four or more support brackets (e.g., brackets 3624), protruding from the side walls, at least one bracket being present on each side of the chamber. The brackets are, preferably, sloped inward such that the width of the reagent chamber becomes narrower with increased depth in the well (in which case, the side walls themselves do not need to be sloped). The brackets provide a multi-point cradle support for the ampoules (e.g., a three or four point cradle design) that allows for significant tolerance in the width and length of the ampoules. The surface of the supports that contact and support the ampoule may be slanted (as shown) or flat. The width of the brackets (i.e., the dimension along the length of the chamber) may be selected to be narrow (e.g., <5 mm or less than 2 mm) to focus forces on relatively small regions of the ampoule during ampoule breaking.

The reagent chambers include an outlet port (or drain), e.g., outlet 3626, for transferring reagent out of the reagent chamber. As shown, the outlet may include a filter element for preventing glass shards from entering the cartridge fluidics. Also as shown, the bottom of the chamber may be sloped such that the outlet is at the lowest point in the chamber.

Figure 22:
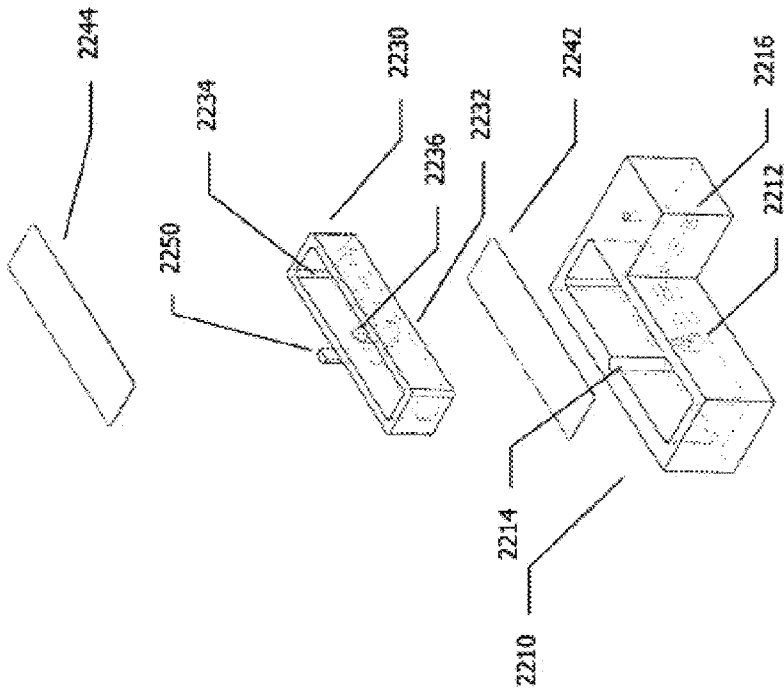
FIG. 22 illustrates one embodiment for a drop-in assay reagent blister pack assembly and integrated assay reagent release (piercing) mechanism.

In an alternative embodiment, a pierceable container such as a pouch or blister pack may be employed. Preferably, the pierceable container has a pierceable made from a plastic film, a metal foil, or most preferably, a metal foil/plastic film laminate. In such an embodiment the assay reagent release mechanism could employ a piercing scheme. FIG. 22 shows an exploded view of one preferred embodiment of a reagent chamber for holding a pierceable container. Reagent chamber 2210 has piercing tip 2212 located at the bottom of the chamber. Chamber 2210 is connected to reagent conduit 2216 and, optionally, a vent conduit (not shown). Reagent module 2220 comprises module body 2230, preferably made of injected molded plastic, that defines the walls of a fluid compartment, having a first opening 2232 and a second opening 2234. Fluid is sealed in the compartment by first opening cover 2242 and second opening cover 2244, the covers preferably made of a plastic-metal laminate (most preferably and aluminum coated mylar film) Module 2220 also, preferably, has tongue 2250 that fits in chamber groove 2214 so as to properly align module 2240 in chamber 2210 and hold module in an elevated position above piercing element 2212. Chamber 2210 also, preferably, has a chamber cover layer that prevents leakage of reagent from the chamber after rupture of module 2220. On application of a threshold downward force to module 2220, preferably through a flexible chamber cover layer, module 2220 is pushed against tip 2212, piercing first opening cover 2242 and releasing the reagent into the chamber. Module 2220 also, preferably, comprises a second piercing tip 2236 that is attached to the module walls via a cantilever (the second piercing element and cantilever are preferably integral to the module body; such a component is readily manufacturable, e.g., by injection molding). When piercing tip 2212 pierces first opening cover 2242 in a module with a second tip element 2236, piercing tip 2212 pushes second piercing tip 2236 until it pierces second opening cover 2234 making a second opening in module 2220 and facilitating extraction of the fluid from the pouch; i.e., venting the pouch itself.

In another alternate embodiment, liquid reagents are stored in a syringe comprising a syringe chamber and a plunger. The chamber may be an integral component of the cartridge, a module that is inserted into the cartridge or a separate component that is attached (e.g., via a luer lock connection) to the cartridge prior to use. Actuation of the plunger may be used to release the contents of the syringe into a reagent chamber or, alternately, to transfer the contents directly into other fluidic components of the cartridge.

An important consideration for cartridge based assay systems relates to long term storage of the cartridge prior to use; i.e., "shelf life" of the cartridge. Certain assay reagents (especially biological reagents and/or binding reagents such as enzymes, enzyme substrates, antibodies, proteins, receptors, ligands, haptens, antigens, nucleic acids and the like), when dissolved in a liquid medium require special handling and storage in order to improve their shelf life. In certain instances, even if the assay reagents dissolved in liquid media are handled and stored in strict compliance with the special handling and storage requirements their shelf life is impractically short. Furthermore, the need to observe special handling and storage requirements adds to the complexity and cost of the cartridge based system employing such reagents. The special handling and storage requirements can be substantially reduced, if not eliminated, and the complexity and cost of the system can be minimized by using more stable dry, or dehydrated, forms of the assay reagents. The use of dry reagents can also simplify mixing operations and reduce the volume and weight of a cartridge. Reagents that may be included in dry form include biological reagents, binding reagents, pH buffers, detergents, anti-foam agents, extraction reagents, blocking agents, and the like. The dry reagent may also include excipients used to stabilize the dry reagents such as sugars sucrose or trehalose). For assays that may employ acidic or basic samples (e.g., samples that are inherently acidic/basic and/or samples that are extracted or otherwise treated with an acidic/basic reagent), a dry reagent may include a neutralizing reagent (e.g., an acid, base of a pH buffer). In especially preferred embodiment that involve extraction of samples with nitrous acid, the extracted sample is passed over a dry reagent comprising abuse or, more preferably, the base form of a buffering agent (e.g., Tris, Hepes, phosphate, PIPES, etc.), A sufficient amount of the base or buffering agent is included to bring the pH of the extracted sample to a value that is compatible with subsequent assay reactions carried out on the sample (e.g., binding reactions with binding reagents).

Dry reagents may be employed in a cartridge based assay system in a number of ways. As described above, dry reagents may be stored in a reagent chamber that is filled prior to use by a user or by a cartridge reader apparatus. Similarly, dry reagents may be stored in other fluidic components such as within fluidic conduits or chambers, most preferably within a fluidic conduit connecting the sample and detection chambers. Introduction or passage of liquid (e.g., a liquid sample or a liquid reagent) through the conduit or chamber results in dissolution of the dry reagent. Dry reagents may be inserted during the manufacture of a cartridge by depositing the dry reagents in the appropriate fluidic component, e.g., by depositing the reagent in the form of a powder or pellet or by incorporating the dry reagent in a screen printed ink. Alternatively, the reagents may be inserted in solution and then dried to remove the solvent. In one preferred embodiment dried reagents may be formed upon a substrate by depositing solutions containing the reagents in one or more predefined locations and subsequently drying the reagents to form a dried reagent pill under conditions such that on addition of a liquid sample or an appropriate solvent, the dry reagent dissolves into solution. The term "pill" is used herein to refer generally to an amount of a dry, but redissolvable, reagent on a substrate and not to connote any specific three dimensional shape. The location of a pill on a substrate is referred to herein as a "pill zone". The substrate is preferably a component of the cartridge, e.g., cartridge body, chamber, cover layer, electrode array, etc. Suitable locations for the pill zone include the sample chamber, reagent chamber, sample conduits, and reagent conduits so that liquid reagents and samples pick up the dry reagent prior to their introduction to the detection chambers. Alternatively, the reagent pills may be located within the detection chambers themselves. In the preferred embodiment depicted in FIG. 13a, the dried reagent pills are formed upon the cover layer 1322 in two predefined pill zones, in another preferred embodiment, a reagent chamber holds a liquid reagent in an ampoule and a dry reagent pill, so that the dry reagent is reconstituted upon rupture of the ampoule. This arrangement is useful for preparing a reagent containing a reactive component. In one example, the ampoule contains an acid such as acetic acid and the dry reagent is a nitrate salt so that rupture of the ampoule results in the preparation of nitrous acid.

A pill zone in which dried reagents are deposited may be prescribed by a boundary which confines the volume of a deposited solution (and, therefore, the dried reagent left after allowing the solution to dry) to a specific region of a substrate. According to one preferred embodiment of the invention, a cartridge comprises a pill zone that is bounded by a boundary surface, the boundary surface being raised or lowered (preferably, raised) and/or of different hydrophobicity (preferably, more hydrophobic) than the pill zone. Preferably, the boundary surface is higher, relative to the substrate surface within the pill zone, by 0.5-200 micrometers, or more preferably by 2-30 micrometers, or most preferably by 8-12 micrometers. Even more preferably, the boundary surface has a sharply defined edge (i.e., providing a steep boundary wall and/or a sharp angle at the interface between the pill zone and the boundary). Preferably, the pill zone surface has a contact angle for water 10 degrees less than the boundary surface, preferably 15 degrees less, more preferably 20 degrees less, more preferably 30 degrees less, even more preferably 40 degrees less, and most preferred 50 degrees less.

In one preferred embodiment the pill zone is defined by a depression cut or molded into the substrate. In another embodiment, the boundary surface around a pill zone is defined by a boundary material applied on the substrate. In one example, the pill zone is defined by a cutout in a film or gasket applied to the substrate, preferably a cutout in a film of adhesive tape. In another preferred embodiment the boundary can be physically defined by applying a coating in a manner which defines the boundary of the pill zone using, e.g., established techniques for forming patterned coatings such as photolithography, patterned deposition, screen printing, etc. In one example, a patterned dielectric coating can be screen-printed onto the surface of a substrate material, the pattern including apertures, the boundaries of which define the pill zone. The reagent can then be dispensed onto the substrate within the pill zone boundary and thereafter dried to form the dried reagent pill.

The waste chambers are chambers adapted to hold excess or waste liquid. In certain embodiments, the detection chamber may also act as a waste chamber. In certain embodiments, however, it is beneficial to have a separate waste chamber, e.g., when carrying out assay formats that involve passing samples through the detection chamber having a volume greater than the volume of the detection chamber or when carrying out assay formats that involve wash steps to remove sample from the detection chamber. Sizing of the waste chambers is preferably done in accordance to the anticipated volumes of sample and liquid reagents that will be used in the assay. Another sizing related factor for the waste chambers that is preferably taken into account relates to the potential for waste fluids, as they enter the waste chamber to foam or bubble. In such instances, where foaming or bubbling is anticipated, the waste chamber volume could be increased sufficiently to avoid any issues that can arise from such foaming or bubbling.

Figure 10:
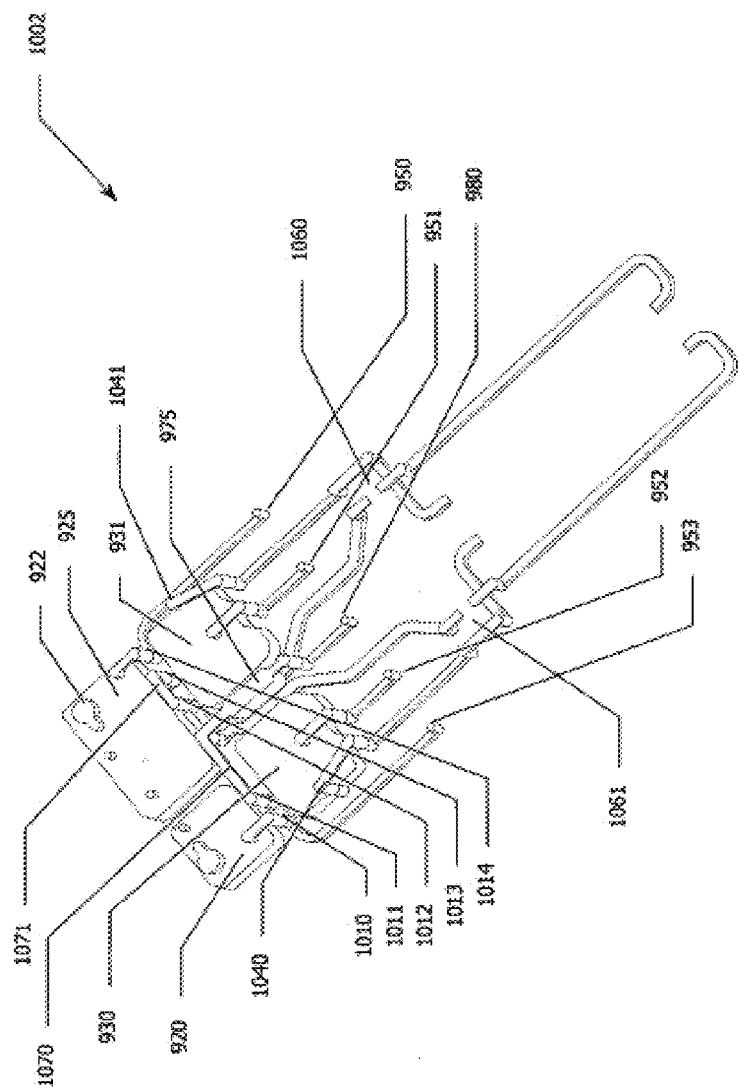
FIG. 10 depicts the fluidic network in accordance with the schematic representation of FIG. 9.

Waste chambers are linked to a waste chamber conduit and, preferably, to a vent port (e.g., through a vent conduit). The waste chamber is configured to allow liquid, waste to be delivered to the waste chamber through the waste chamber conduit and, preferably, for air that is included in the waste stream to escape through a waste chamber vent port. Optionally, the waste chambers contain a water absorbing material, such as a sponge, that retains waste fluid and prevents leakage of the waste fluid on disposal of a cartridge. A factor that is preferably considered when designing the configuration and arrangement of the waste chambers relates to eliminating or substantially reducing the possibility that fluid from the waste chamber can flow back ("back-flow") into the cartridge's fluidic network. In particularly preferred embodiments, as illustrated in FIG. 10, the waste chamber conduits are arranged/routed such that they are fluidically connected to the waste chambers at points 1040, 1041 that are above the anticipated fill levels/lines (i.e., the fill level/line is defined by the volume of waste fluid that resides within the waste chamber at the conclusion of the assay). This preferred configuration substantially reduces or eliminates the possibility that fluid from the waste chamber can flow back ("back-flow") into the cartridge's fluid network.

The issue of back-flow may also arise in the context of bubbling/foaming of the waste fluids. The vent port is preferably linked via a conduit with a lame enough volume to allow a small amount of liquid to enter the conduit (e.g., because of foam in the waste chamber) without this liquid reaching the vent port (as described for above for the sample chamber). Furthermore, aerosol-prevention plugs or gas-selective membranes (i.e. materials that selectively allow the passage of gas but prevent the passage of liquids) may be included into the waste chamber vent conduits or vent ports to prevent release of liquid through these passages. Aerosol-prevention plugs are commonly used in pipette tips to prevent contamination of pipettors and include materials that allow the passage of air when dry but swell and seal up the passage when they come in contact with liquid (e.g., filter materials impregnated or coated with cellulose gum).

An additional measure for eliminating or substantially reducing foaming/bubbling of waste fluids as they are introduced into the waste chamber can be employed in particularly preferred embodiments. Such an additional anti-foaming/bubbling measure may include arranging/routing the waste chamber conduit such that it enters the waste chamber at a position that is located above the fill line and that intersects vertical wall of the waste chamber, as illustrated by conduit segments 910 and 911 entering waste chambers 930 and 931 in the embodiment depicted in FIGS. 9 and 10. Such a configuration allows the waste fluid to be introduced into the waste chamber in a manner so as to allow the fluid to ran along a vertical wall of the waste chamber. Advantageously, this substantially reduces or eliminates foaming/bubbling of the waste fluid as it is routed into the waste chamber.

Yet another anti-foaming/bubbling measure that may be employed in certain preferred embodiments comprises a vertical web, or partial wall, that can be included in the upper portion of the waste chamber. A particularly suitable embodiment for inclusion of such an anti-foaming/bubbling measure is the two-piece cartridge body design depicted in FIG. 16. The anti-foaming web/wall is preferably included in the upper portions of the waste chambers 1610, 1611 located in the upper cartridge component 1500. Preferably the anti-foaming web is arranged between the waste chamber vent and the waste chamber input. The height of the anti-foaming web preferably extends the full depth of the upper portion of the waste chamber but may be less than the full depth as well. Alternatively, the anti-foaming web can extend beyond the depth of the upper portion of the waste chamber so that it protrudes into the lower portion of the waste chamber. Preferably the height of the anti-foaming web is selected to achieve optimum anti-foaming by allowing the flow of liquid under the web/wall but blocking the flow of bubbles above the surface of the liquid in the waste chamber.

Yet another anti-foaming/bubbling measure is to include an anti-foam agent in the waste chamber or in another conduit or chamber of the cartridge so that liquid entering the waste chamber has less propensity to foam and/or form bubbles.

The detection chambers are adapted for carrying out a physical measurement on the sample. The detection chamber is connected to an inlet conduit. Preferably, the detection chamber is also connected to an outlet conduit and is arranged as a flow cell. If the measurement requires illumination or optical observation of the sample (e.g., as in measurements of light absorbance, photoluminescence, reflectance, chemiluminescence, electrochemiluminescence, light scattering and the like) the detection chamber should have at least one transparent wall arranged so as to allow the illumination and/or observation. When employed in solid phase binding assays, the detection chamber preferably comprises a surface (preferably, a wall of the chamber) that has one or more binding reagents (e.g., antibodies, proteins, receptors, ligands, haptens, nucleic acids, etc.) immobilized thereon (preferably, an array of immobilized binding reagents, most preferably an array of immobilized antibodies and/or nucleic acids). In an especially preferred embodiment, the detection chamber is an electrochemiluminescence detection chamber as described above, most preferably having one or binding reagents immobilized on one or more electrodes. In one preferred embodiment, the cartridge comprises a working electrode having an array of binding reagents immobilized thereon. In another preferred embodiment, the cartridge comprises an array of independently controllable working electrodes each having a binding reagent immobilized thereon. Preferably, in cartridges employing arrays of binding reagents, at least two elements of the array comprise binding reagents that differ in specificity for analytes of interest. Suitable detection chambers, electrode arrays and arrays of immobilized binding reagents for use in ECL-based cartridge systems are described in detail above and include embodiments shown in FIGS. 1-4.

The detection chamber is, preferably, arranged in an elongated flow cell design with inlet and outlets at or near opposing ends of the elongated dimension. Depending on the application, manufacturing approach, sample size, etc., the flow cell dimensions can range from nanometers to tens of centimeters and the volume from picoliters to milliliters. Certain preferred embodiment have widths that can range from 0.05-20 mm, more preferably, 1-5 mm and heights (preferably, less than or equal to the width so as to increase, for a given volume, the surface area of the bottom of the detection chamber, especially when this surface is used to immobilize binding reagents) that range from 0.01-20 mm, more preferably, 0.05-0.2 mm. Preferably, the height is less than or equal to the width. Preferably, the detection chamber is designed to accommodate sample volumes between 0.1-1000 uL, more preferably, 1-200 uL, more preferably, 2-50 uL, most preferably, 5-25 uL. In embodiments that are limited by sample volume (e.g., cartridges measuring blood from finger pricks), especially preferred detection chamber volumes are less than 10 uL, more preferably 0.5-10 uL, even more preferably 2-6 uL. The flow cell preferably has a width greater than or equal to the height.

A cartridge may comprise one or more detection chambers. Cartridges comprising multiple detection chambers may comprise separate fluidic systems for each detection chamber multiple sample chambers and/or reagent chambers and associated fluidic conduits) so that assays on multiple samples may be carried out in parallel. In certain preferred embodiments, multiple detection chambers are linked to a single sample chamber and may share the use of other fluidic components such as reagent chambers, waste chambers and the like. In these embodiments, the two detection chambers may be used to carry out different sets of assays, thus increasing the number of measurements that can be carried out on a sample relative to a cartridge with one detection chamber. Advantageously, the use of multiple detection chambers allows for carrying out in a single cartridge multiple incompatible measurements, that is measurements that can not be performed in a single reaction volume or benefit from being carried out in separate reaction volumes, e.g., measurements that have different requirements for pH or assay composition or otherwise negatively interfere with each other.

In an alternate embodiment employing a plurality of detection chambers, one or more of a plurality of detection chambers is used as control/calibration chamber for measuring assay control/calibration samples. In one such embodiment, a first and a second detection chamber are each configured to carry out a panel of one or more assays for one or more analytes. One detection chamber (the test chamber) is used to analyze a sample. The other detection chamber (the control chamber) is used to analyze a spiked sample having a predetermined additional amount of the one or more of the analytes of interest (this predetermined additional amount, preferably, being provided by passing the sample through a reagent pill zone comprising the additional amounts). The change in signal between the two chambers allows for the calculation of the responsiveness of the signal to changes in analyte and can be used to calibrate the system and/or to determine if the cartridge is functioning properly. In another embodiment employing a control chamber, the control chamber is not used to analyze the sample or a derivative thereof, but is used to measure analyte in a separate control or calibrator matrix. The signal in the control chamber may be used for determining background signals (by using a matrix with no analyte), for calibrating the instrument (by using a calibrator matrix with a predetermined amount of analyte to determine calibration parameters) or to determine if the cartridge is functioning properly (by using a control matrix with a predetermined amount of analyte and determining if the signal falls within a predetermined acceptable range).

Figure 31:
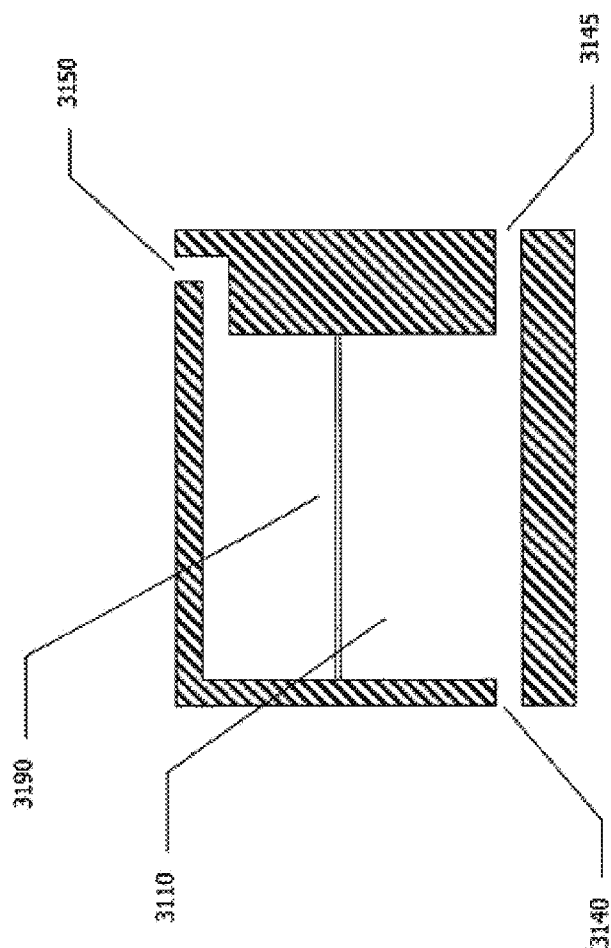
FIG. 31 is a cross-sectional view depicting one embodiment of a bubble trap chamber.

The cartridge fluidics may include bubble traps. The bubble trap is a chamber or conduit adapted for removing bubbles from fluid streams. Preferably, there is a bubble trap between the sample and detection chambers so that bubbles in the sample may be removed prior to introducing the sample into the detection chamber. FIG. 31 shows a cross-sectional view of one exemplary embodiment and shows bubble trap chamber 3110 connected to inlet conduit 3140 and outlet conduit 3145 (the inlet and outlet conduits being, preferably, located near the bottom of chamber 3110) and vent port 3150. Liquid is introduced into chamber 3110 via inlet 3140. Chamber 3110 is, preferably, wide enough so that bubbles in a liquid introduced to the chamber can rise to the top of the chamber and be expelled via vent port 3150. Bubble-free liquid is then expelled via outlet 3145. Optionally, outlet conduit 3115 is omitted; in this case a liquid, is admitted via inlet conduit 3140, bubbles are expelled via vent port 3150 and the liquid is then expelled back through inlet conduit 3140. Optionally, an air-permeable but water-impermeable membrane (e.g., a membrane made from Gor-tex material) is placed between inlet 3140 and vent port 3150. When a liquid passes through the conduit that contains bubbles or is present in a stream that is segmented by slugs of gas, the gas/bubbles will pass through the membrane and exit through vent port 3150 (preferably, the process is aided by applying suction at vent port 3150) to ensure that liquid is not expelled via vent port 3150 (the optional membrane is shown as membrane 3190).

The fluidic conduits can be located at any position within the cartridge and oriented at any angle. Advantageously, the fluidic channels are located, primarily, in planar networks, preferably located proximate to the outside surfaces (e.g., the top 901,902 or bottom 903 surfaces of the cartridge shown in FIGS. 11a-c) to allow for a multi-layered cartridge design that uses, e.g., machined, die-cut, laser-cut and/or molded cartridge body components. Preferred conduit geometries include conduits with cross-sections that are circular, oval, square or rectangular in cross-section. The width is, preferably, similar to the height so as to minimize the surface area for a particular cross-sectional area. Width and height can vary widely from nm to cm ranges depending on the application, sample volume and cartridge design. Preferred ranges for the width and height are 0.05 to 10 mm, more preferably, (15 to 3 mm, most preferably 1 to 2 mm. Cartridges adapted to low volume samples such as blood from finger pricks may have small conduits, preferably having height/widths <1 mm, preferably between 0.4 to 1.0 mm.

The fluidic channels preferably make use of "Z-transitions" that route the fluid flow path between planes. A conduit with such a Z-transition may comprise first, second, and third conduit segments arranged in sequence, the first and third conduit segments being located in different planar fluidic networks and the second conduit segment connecting the two fluidic networks and arranged at an angle to the other two segments. By way of example, "Z-transitions" (denoted in FIG. 9 as capillary breaks) route the fluid flow/path, in the cartridge shown in FIGS. 11a-c, from fluidic conduits near the upper surface 901, 902 to fluid conduits near the bottom 903 surface and vice a versa. Z-transitions are advantageous in that they provide capillary breaks (as described below) and allow for more complicated fluidic networks than would be possible if the fluidic conduits were confined to one plane. Selective use/placement of capillary breaks, preferably Z-transitions, may be used to control the passive flow of fluids and prevent mixing of fluid streams. Certain preferred embodiments of the invention employ "double Z-transitions", that is conduits that comprise a first Z-transition that directs fluid flow from a first planar network to a second planar network, a second Z-transition that redirects fluid flow back to the first planar network and a connecting segment in the second planar network that connects the two Z-transitions. Such a double Z-transition may comprise first, second, third, fourth and fifth conduit segments arranged in series, the first and fifth segments located in a first planar fluidic network, the third segment located in a second planar fluidic network, the second and fourth segments located so as to direct flow between the two planar networks.

The fluidic network may be formed within the cartridge in a number of different ways, dependent, in part, upon the materials chosen for the cartridge. Any known fabrication method appropriate to the cartridge body material may be employed including, but not limited to, stereolithography, chemical/laser etching, integral molding, machining, lamination, etc. Such fabrication methods may be used alone or in combination. In certain embodiments of the invention, the cartridge comprises a cartridge body and one or more cover layers mated to surfaces of the cartridge body so as to define one or more fluidic networks (preferably, planar fluidic networks) therebetween. Similarly, Z-transitions and/or ports can be selectively molded into, or machined out of, the cartridge body at predetermined locations to form the fluidic connections between the channels on the upper and lower surfaces.

One preferred embodiment of the cartridge may be fabricated using a "lamination" process whereby the cartridge body's functional surfaces are sealed using cover layers to form the fluidic network. For example, recesses (e.g., channels, grooves, wells, etc) in one or more surfaces of the cartridge body provide what is referred to herein as "functional surfaces". Sealing/mating of the functional surfaces to cover layers forms a fluidic network comprising fluidic components (e.g., conduits, chambers, etc.) at least some of which are defined in part by the recesses in the cartridge body and in part by a surface of a cover layer. The cover layers are preferably comprised of plastic film such as mylar film. The cover layer may be coated with an adhesive to seal the cover layer against the cartridge layer. Other methods for mating the cover layer to the cartridge body will be known to the skilled artisan, e.g., the seal may be achieved by heat sealing, ultrasonic welding, RF (radio frequency) welding, by solvent welding (applying a solvent between the components that softens or partially dissolves one or both surfaces), by use of an intervening adhesive layer (e.g., a double sided adhesive tape, etc.). Advantageously, cartridge features that are created by patterned deposition (e.g., patterned deposition of electrode or dielectric layers and/or patterned deposition of reagents to form dry reagent pills or to form binding domains with immobilized binding reagents) are created on cover layers so as to take advantage of automation available to process plastic film in large sheets or rolls.

Recesses may be, e.g., molded in, etched in or machined from the cartridge body. By analogy, fluidic components may also be defined, at least in part, by recesses in a cover layer that is mated to a cartridge body. Fluidic components may also be defined, at least in part, by regions cutout from gasket layers disposed between the cartridge body and cover layers. Apertures in the cartridge body and/or cover layers may be used to provide for access ports to the fluidic network, e.g., sample introduction ports, vent ports, reagent addition ports and the like. Vent ports, preferably, allow the equilibration of fluid in the chambers with the atmosphere or to allow for the directed movement of fluid into or out of a specified chamber by the application of positive or negative pressure. Vent ports, preferably, are designed to prevent the leakage of liquid samples or reagents through the ports and may include aerosol-resistance filters, membrane or filter materials that permit air flow but act as barriers to aqueous solutions (e.g., filter or membranes made from porous hydrophobic materials such as Gortex), and materials that are porous to air but seal when they come in contact with aqueous solutions (e.g., cellulose gum impregnated filters).

Preferred embodiments include a cartridge having a cartridge body with a first side and a second, preferably opposing, side and one or more cover layers mated to the first side to form a first fluidic network therebetween and one or more cover layers mated to the second side to form a second fluidic network therebetween. Through-holes through the cartridge body (which may be formed by molding, etching, machining, etc.) may be used to link the first and second fluidic networks and to provide Z-transitions. Additional fluidic complexity can be built into a cartridge by employing a laminated cartridge body having multiple cartridge body layers and additional fluidic networks between these layers; through-holes through the various cartridge body layers are used to link the different fluidic networks.

A high degree of control over the movement of liquids in the cartridges of the invention may be attained, without the introduction of active valve elements in the cartridge, through the use of fluidic networks comprising capillary breaks, "Capillary break", as used herein, refers to a region in a fluid conduit that acts as a barrier to liquid moving through the conduit under capillary action or under the driving force of a low pressure gradient below a threshold pressure. In preferred examples of capillary breaks, application of a pressure above the threshold pressure acts to push the fluid past the barrier. Capillary breaks may be designed into fluid conduits by introducing, e.g., i) a transition, on a surface of a conduit, from a wettable surface to a less wettable surface (e.g., as indicated by the contact uncle for water); ii) a transition in conduit width from a region of narrow width that promotes capillary flow to a region of wider width; iii) a transition, on a surface of a conduit, in roughness; iv) a sharp angle or change in direction and/or v) a change in cross-sectional geometry. In another embodiment, a fluid conduit has a flexible wall/diaphragm that impinges into the conduit and blocks flow driven by a pressure below a threshold pressure. Application of a higher pressure threes the flexible wall/diaphragm out of the flow path and lets fluid flow. Preferably, the diaphragm is made of a material (e.g., Gortex) that allows gas to pass through but prevents the flow of liquid up to a certain pressure. Preferred capillary breaks involve a sharp angle or change in direction in a fluid conduit, most preferably a "Z-transition" as described above.

In one embodiment of the invention, a liquid is introduced into a chamber comprising an outlet conduit that includes a capillary break (preferably a Z-transition). The liquid enters the outlet conduit but stops at the Z-transition. A pressure gradient is then applied (e.g., by applying positive pressure to the chamber or negative pressure to the other end of the conduit) which cause the liquid to flow past the Z-transition into the rest of the conduit.

The fluidic paths in the fluidic networks of a cartridge may include one or more regions of higher hydrodynamic resistance. In such embodiments of the invention, it may be advantageous to configure the fluid paths in the cartridge and/or certain fluidic operations using the cartridge so that fluid slugs moving in/out of a region of higher hydrodynamic resistance maintain a near constant velocity under a constant driving pressure. In one non-limiting embodiment of the invention, a cartridge includes a detection chamber with inlet and outlet conduits, where the chamber has a higher hydrodynamic resistance than the input and output conduits, e.g., because it has a higher cross-sectional aspect ratio and/or a smaller cross-sectional area. High aspect ratio detection chambers may be advantageous, in certain applications, by providing a large optical window into the chamber and/or by increasing the area of a sensing surface relative to the volume of the detection chamber. Other regions in a cartridge that may have high hydrodynamic resistances include, but are not limited to, regions filled with filtration or chromatography media.

In certain embodiments of the invention, maintaining a controlled liquid velocity through a higher hydrodynamic resistance region is addressed by incorporating a hydrodynamic resistance matched fluid flow path in the fluidic network of the cartridge. The fluid flow path includes several fluidic regions (which may be or include fluidic conduits or chambers), that are linked together to form the fluid flow path. In one embodiment, the fluid flow path includes, in sequence, a first resistance region, a low resistance connecting region, and a matching resistance region. The fluid flow path may, optionally, also include a low resistance inlet region that provides a fluidic inlet to the first resistance region and/or a low resistance outlet region that provides a fluidic outlet to the matching resistance regions. Low and matching resistance, as used herein, are relative to the hydrodynamic resistance of the first resistance region.

The connecting region may be provided in the same plane as the first resistance region or it may be in a different plane relative to the other components of the flow path. For example, the connecting region may provide Z-transition between the first resistance region and the matching resistance region. The connecting region is positioned at the exit orifice of the first resistance region. The matching resistance region, proximal to the connecting region and distal to the first resistance region, is located along the fluid flow path at the exit orifice of the connecting region.

The hydrodynamic resistance fluid flow path may be comprised within a fluidic network (e.g., a fluidic network within an assay cartridge) that comprises a metering component linked to the fluid flow path and configured to meter fluid slugs through the first resistance, connecting and matching resistance regions and optional inlet and/or outlet regions. The invention includes a method in which a slug of fluid is passed through the fluid flow path, preferably using air pressure or vacuum to drive the fluid movement. The fluid slug volume is greater than the volume of the first resistance region (Vr) and less than the combined volumes of the first resistance, connecting and matching regions (Vr+Vc+Vm). Thus, as the fluid moves through the fluid path, the loss of hydrodynamic resistance from movement of the trailing edge of the slug through the first resistance region is compensated by the increase in hydrodynamic resistance from movement of the leading edge of the slug into the matching region. The fluid therefore moves at a controlled velocity throughout the fluid flow path. In the absence of the matching region, a fluid slug being cleared from the first resistance region, under air pressure, will accelerate as the trailing edge moves through the region. Such acceleration could have detrimental effects on the performance of a fluidic network, e.g., by changing mass transport rates to surfaces in the fluid path and/or by preventing controlled de-wetting of surfaces at the trailing edge of a slug and, thereby, causing an increase in fluid left on the walls of the fluid path.

Therefore, the invention provides a hydrodynamic resistance matched fluid flow path, wherein the flow path comprises the following components:

(a) a first resistance region;

(b) a connecting region proximal to said first resistance region; and (c) a matching resistance region proximal to said connecting region and distal to said first resistance region, wherein the hydrodynamic resistance of said matching resistance region is substantially equivalent to the hydrodynamic resistance of said first resistance region and is substantially greater than the hydrodynamic resistance of the connecting region.

The flow path may further comprise d) an inlet region proximal to said first resistance region and distal to said connecting region and/or e) a outlet region proximal to said matching resistance region and distal to said connecting region. The flow path may be comprised within a fluidic network (which may be within an assay cartridge) which comprises a metering component for introducing a metered fluid slug volume into said fluid flow path.

The invention also provides a method for moving fluid in a fluidic network comprising:

(a) introducing a fluid slug into a hydrodynamic resistance matched fluid flow path within said fluidic network, wherein the flow path comprises the following components:

(i) a first resistance region;

(ii) a connecting region proximal to said first resistance region; and (iii) a matching resistance region proximal to said connecting region and distal to said first resistance region, and (b) using air pressure to move said fluid slug through said flow path.

In this method, the flow path is configured such that i) the hydrodynamic resistance of said matching resistance region is substantially equivalent to the hydrodynamic resistance of said first resistance region and is substantially greater than the hydrodynamic resistance of the connection region and ii) the volume of the slug is greater than the volume of the first resistance region and less than the combined volume of the first resistance region, connecting region and matching resistance region. The method may further comprise metering said fluid slug, prior to introducing said fluid slug into said flow path. Furthermore, the flow path may further comprise (c) an inlet region proximal to said first resistance region and distal to said connecting region and/or (d) a outlet region proximal to said matching resistance region and distal to said connection region.

In some embodiments of the resistance matched flow path and the methods for using same, the metered volume is approximately equal to the sum of the volumes of the first resistance region and the connecting regions. For example, the sum of the volumes of the first resistance region and the connecting region is about 75-125%, about 85-115%, or about 95-105% of the metered volume. In other embodiments, the sum of the volumes of the first resistance region and the connecting region is about 85-100% or about 95-100% of the metered volume. In other embodiments, the sum of the volume of the first resistance region and the connecting region may be about 100% of the metered volume. Alternatively, the sum of the volume of the first resistance region and the connecting region may be about 100-125%, e.g., about 100-115%, or about 100-105% of the metered volume.

The resistance matched fluid path may be used with low volume fluid slugs in a microfluidic network. Such fluid slug volumes may be, e.g., less than 200 uL, less than 50 uL or less than 10 uL. In one embodiment, a fluid slug of between 20 uL and 50 uL is passed through the resistance matched fluid path. Depending on the specific application and any design constraints on the fluidic network, the volume of the first resistance region relative to the volume of the fluid slug (or alternatively, relative to the combined volume of the first resistance and connecting regions) may vary over a wide range. Suitable ranges include 10-90%, 20-80% and 30-70%.

Figure 40:
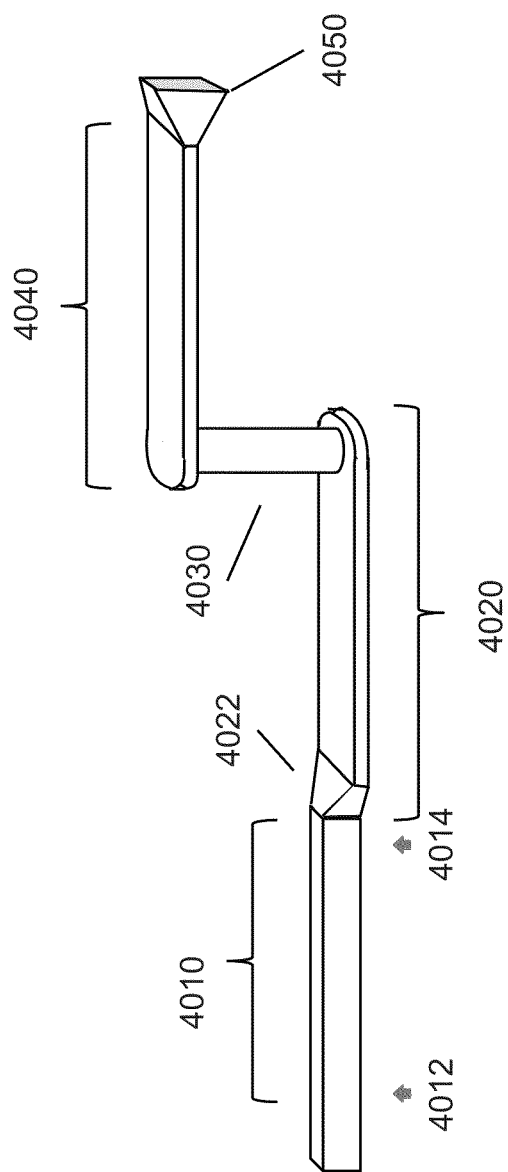
FIG. 40 shows a hydrodynamic resistance matched fluid flow path.

One example of a hydrodynamic resistance matched fluid flow path of the present invention is represented schematically by FIG. 40. The fluid flow path comprises an inlet region (4010), a first resistance region (4020), a connecting region (4030), a matching resistance region (4040) and an outlet region (4050), as described above. In this specific example, the first resistance region comprises a fan region (4022) to provide a smooth fluidic transition to the first resistance region from the lower resistance inlet region. The remainder of first resistance region 4020 is a high aspect ratio flow cell which may be configured as a detection chamber. Matched resistance region 4040 is designed to roughly match first resistance region 4020 in volume and hydrodynamic resistance.

One of ordinary skill in the art will be able to select geometries for the first and matching resistance regions that provide substantially equal hydrodynamic resistances (e.g., resistances that are within a factor of 2, within a factor of 1.4 or within a factor of 1.1). The geometries of the two regions may be, but are not required to be the same and cross-sectional areas may be, but are not required to be constant throughout the length of the regions. Hydrodynamic resistance (also sometimes referred to as hydraulic resistance) of a fluid flow path is proportional to the applied pressure drop ($\Delta P$) (generally measured in units of Pascals) divided by the flow rate (Q) (generally measured in units of microliters/second). This can be summarized in the formula: $R_h = \Delta P/Q$, wherein $R_h$ is the hydrodynamic resistance. Equations and software for calculating hydrodynamic resistance are available, e.g., *Viscous Fluid Flow*, 2d Ed. Frank M. White, McGraw-Hill (1991), which is incorporated herein by reference in its entirety. Equations for calculating the resistance of two simple channel geometries are provide below (an exact formula for rectangular cross-sections is provided on p. 120 of the *Viscous Fluid* Flow reference).

channel of circular cross-section (total length L, radius R):

$$R_h = \frac{8 \mu L}{\pi R^4}$$

rectangular cross-section (width w and height h, where h≪w)

$$R_h \approx \frac{12 \mu L}{wh^3 (1 - 0.630 \, h/w)}.$$

Figure 41A:
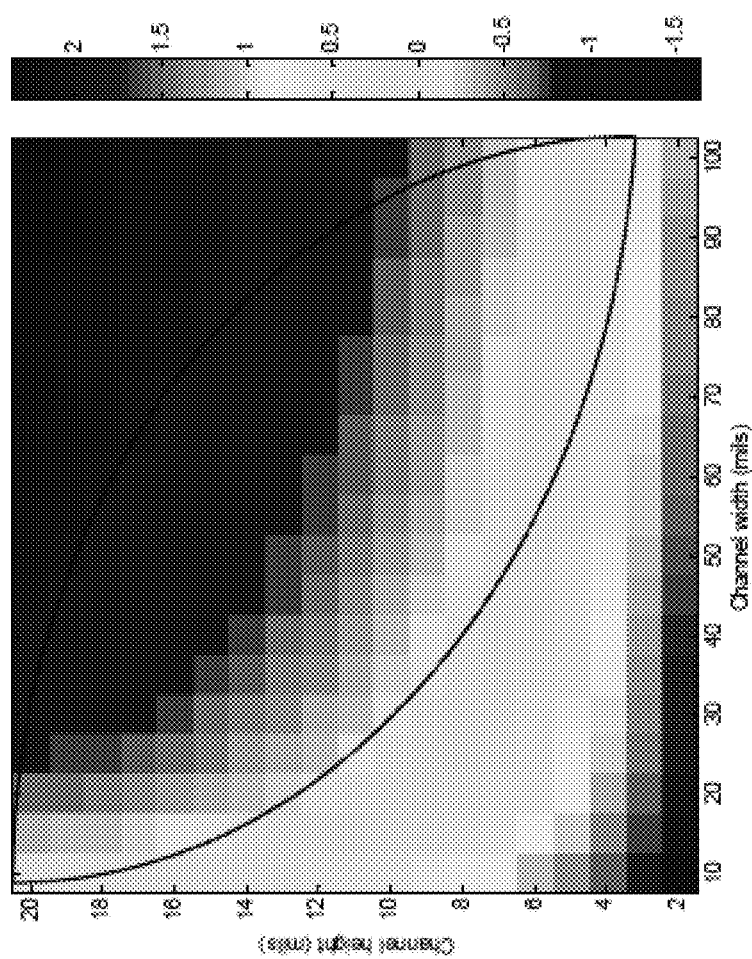
FIG. 41(a) is a color contour plot showing the effect of channel dimensions on hydrodynamic resistance.
Figure 41B:
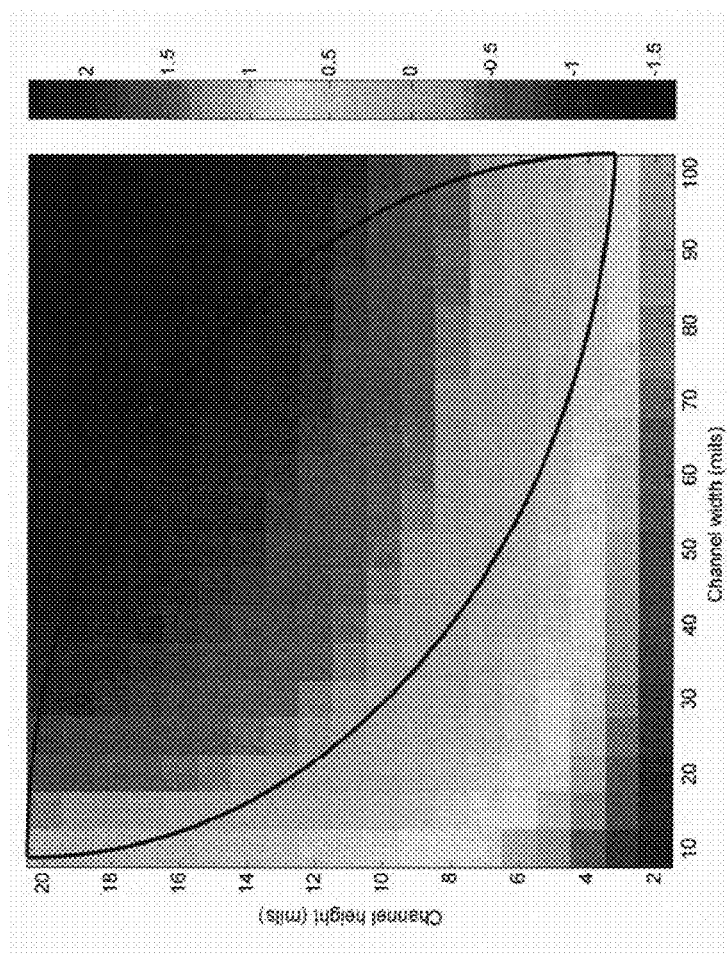
FIG. 41(b) is a black and, white version of the color plot depicted in FIG. 41(a).

In one embodiment, the first resistance region is approximately 5 mils×120 mils (wherein 1 mil=0.001 inches) and the matching resistance region is approximately 10 mil×80 mil. In an alternate embodiment, the height of the first resistance region may be approximately half that of the matching resistance region. FIG. 41 is a contour plot of the ratio of the matching region resistance to the read chamber resistance as a function of the matching region height and width (assuming a first resistance region height and width of 5 mils×120 mils). The ratio is shown on a log scale, so 2=100 times higher, 0=matched, and −1=10 times lower. An approximate design area is defined in the graph by lines A and B and this design area may be used to select combinations of heights and widths (for a rectangular cross-section channel) that provide a suitable hydrodynamic resistance.

As shown in the figure, low hydrodynamic resistance connecting region 4030 may provide a Z-transition between regions in two different planes of a fluidic network. The volume of connecting region 4030 is selected to be greater than or to be roughly equal the volume of a "throw" region in inlet 4010 between two fluid sensing sites (4012) and (4014) shown as block arrows in the figure (which may, for example, be located so that fluid entering or leaving the region may be sensed by cartridge reader or other fluid control instrumentation). This configuration provides for back and forth mixing of the fluid slug in first resistance region 4020 at a well controlled fluid flow rate under air pressure or vacuum when the fluid slug volume is substantially equal (e.g., within 20%, 10% or 1%) to the combined volumes of first resistance region 4020 and the volume of the fluid slug is less than the combined volumes of first resistance region 4020 and connecting region 4030. Preferably, the volume of the fluid slug is substantially equal (e.g., within 20%, 10% or 1%) of the combined volumes of the first resistance and connecting regions.

Accordingly, the invention includes a method of moving a fluid in a fluidic network comprising i) introducing a fluid slug into a fluid pathway comprising an inlet region (with a throw region), a first resistance region and a connecting region (where the fluid pathway and fluid slug are as described above), ii) moving the fluid slug under air pressure until the trailing edge passes sensing site 4014, iii) moving the fluid slug under air pressure in the reverse direction until the leading edge (i.e., the trailing edge in step ii) passes sensing site 4012 and iv) repeating steps ii and iii a plurality of times to achieve a back-and-forth mixing action. Using this method, first resistance region 4020 remains filled throughout the mixing process, thus providing a roughly constant hydrodynamic resistance during this time. The method may further comprise clearing the fluid slug from the first resistance region through a matching resistance region a described above.

The fluidic network may also comprise valves to control the flow of fluid through the cartridge. A variety of suitable valves (including mechanical valves, valves based on electrokinetic flow, valves based on differential heating, etc.) will be known to one of average skill in the art of assay cartridges or microfluidic devices. In preferred embodiments, however, at least one and more preferably all actively controlled valve elements are external to the cartridge. In one embodiment, a fluid conduit has a flexible wall/diaphragm that in the absence of external force allows fluid to pass through the conduit. Application of an external force on the wall/diaphragm (e.g., from a piston or via the application of gas or hydrostatic pressure) causes the diaphragm to impinge on the conduit, thus impeding the flow of fluid.

The fluidic network may include at least one viscosity measuring conduit, preferably linked to a sample chamber or sample conduit, having an inlet and an outlet. The conduit is adapted so that a liquid sample can be introduced into the conduit and the time it takes the liquid to move between two locations in the conduit can be timed (preferably using sensors such as impedance sensors or optical sensors in the cartridge or an associated cartridge reader). Such an arrangement can advantageously be used to measure clotting times of a blood or plasma sample. For measuring clotting times, the conduit or an upstream component preferably comprises a dry reagent necessary for the specific clotting measurement (e.g., activated clotting time, whole blood clotting time, prothrombin time, thrombin time partial thromboplastin time and the like).

Vent ports as described above are, preferably, apertures on the surface of the cartridge that are in fluidic communication with fluidic chambers or conduits within the cartridge. In a laminated cartridge construction, the vent ports may be provided, for example, by apertures in cover layers that seal against a cartridge body to define planar fluidic networks or alternatively, by through-holes exposed on one surface of the cartridge body that communicate with fluidic networks on the opposing side. The vent ports act as control ports that allow a cartridge reader to control the movement of fluid in the cartridge, e.g., by a combination of sealing one or more ports, opening one or more ports to atmospheric pressure, connecting one or more ports to a source of positive pressure and/or connecting one or more ports to a source of negative pressure. The vent ports may also be used to introduce air into liquid streams passing through the fluidic conduits of the invention, for example, to segment the fluid streams with slugs of air. The introduction of air may be used to prevent mixing of two liquid slugs passed sequentially through a conduit, to clear a liquid from a conduit and/or to enhance the efficiency of a wash step. Preferably, the vent ports are arranged in a single row at a common location along the cartridge body's width. Such an arrangement and configuration of the control points advantageously a lows the interface between the cartridge reader and the cartridge to be simplified. For example, using such a preferred configuration allows the cartridge reader to make use of a single fluidic mating device for placing the cartridge into fluidic communication with the cartridge reader. Such a configuration also allows the motion control subsystem(s) to be simplified in that a single motor or actuation device may be used to actuate the fluidic mating device and move it into sealing engagement with the cartridge body. FIG. 9 is a schematic representation of cartridge 900, one preferred embodiment of a cartridge of the invention that incorporates many of the fluidic features described above. This exemplary embodiment depicts a cartridge comprising an electrode array of the invention as described above. The skilled artisan, however, can readily adapt the fluidic components and design to cartridges employing other detection chamber designs and/or detection technologies. The cartridge schematic shown in FIG. 9 comprises various compartments including a sample chamber 920, assay reagent chamber 925, waste chambers 930 and 931 and detection chambers 945 and 946 comprising electrode arrays 949*a* and 949*b* and electrode contacts 997 and 998. Also depicted in FIG. 9 are fluid ports/vents 950-953 and 980 that may be utilized as fluidic control points, vents for allowing a chamber to equilibrate with atmospheric pressure, ports for introducing air bubbles or slugs into a fluid stream and/or as fluidic connections to a cartridge reader. FIG. 9 also depicts a number of fluidic conduits (shown as lines connecting the various chambers) that establish a fluidic network that connects the various compartments and/or fluid ports/vents. The fluidic conduits may comprise distribution points (e.g., branch points such as distribution point 976 that are adapted to distribute a fluid to two or more locations/compartments in a cartridge). Other fluidic features that are shown in FIG. 9 include pill chambers/zones 990, 991 for each of the read chambers. FIG. 10 depicts a three dimensional representation of the fluidic network formed by the various fluidic components employed in a preferred embodiment of FIG. 9.

Sample chamber 920 is a chamber defined within cartridge 900 that is adapted for receiving a sample, preferably a liquid sample, to be analyzed in the cartridge. Sample chamber 920 includes a sample introduction port 921, and is linked to vent port 953 through a vent conduit and detection chambers 945 and 946 through sample conduit 901 having sample conduit branches 940 and 941. Preferably, cartridge 900 also includes a sealable closure for sealing sample introduction port 921. Reagent chamber 925 is a chamber adapted to hold a liquid reagent and includes a vent conduit linked to vent port 950 and reagent conduit 902 linked to the sample conduit (preferably, between sample chamber 920 and distribution point 976). Also linked to the sample conduit is air chamber/trap 975 nuked to vent port 980. This arrangement allows for adding/removing air into/from the fluid stream(s) (e.g., to reagent or sample streams directed from reagent chamber 925 or sample chamber 920 towards detection chambers 945 or 946) in the fluidic pathway by applying positive pressure or suction to vent port 980. Pill chambers/zones 990 and 991 hold dry reagents and are positioned, respectively, in the fluidic pathway between sample port 920 and detection chambers 945 and 946 so that liquid passing through the chamber/zones will reconstitute the dried reagents and carry the resulting solutions into the detection chambers. Reagent chamber 925, air chamber trap 975, vent port 980 and/or pill chamber zones 990 and/or 991 may optionally be omitted.

Detection chambers 945 and 946 are adapted for carrying out a physical measurement on a sample, preferably an electrochemiluminescence measurement, most preferably a measurement employing an electrode array that is configured to be fired in a pair-wise fashion (as described above). Optionally, detection chamber 946 is omitted. As depicted in the preferred embodiment of FIG. 9, detection chambers 945 and 946 have different geometrical cross-sections than their respective input and output channels to which they are in fluidic communication. As such, it is preferable to incorporate transitional fluidic segments (947a,b and 948a,b) at the inputs and outputs of the read chambers such that fluid flow may be appropriately transitioned between the dissimilar regions. Preferably, the transition is designed to minimize the transition length; e.g., incorporating a diffusers/nozzles with as wide an angle as possible, while being gradual enough to prevent trapping of air bubbles. Detection chambers 945 and 946 are connected via waste conduits 960,961 to waste chambers 931 and 930. Waste chambers 930 and 931 are chambers configured to hold excess or waste fluids and are also connected, respectively, to vent port 952 via a vent conduit and vent port 951 via a vent conduit. The use of multiple waste chambers advantageously allows fluid flow through the multiple chambers to be controlled independently via the application of vacuum or pressure to the waste chamber vent ports. Alternatively, only one waste chamber is used (e.g., waste chamber 930 is omitted and detection chambers 945 and 946 are both connected to waste chamber 931).

In cartridges for conducting binding assays for analytes of interest, pill zones 990 and 991 preferably comprise labeled binding reagents (e.g., antibodies, nucleic acids, labeled analogs of analytes of interest, etc), detection chambers 945 and/or 946 comprise one or more immobilized binding reagents (preferably, an array of immobilized binding reagents, most preferably immobilized on electrodes for conducting ECL assays) and reagent chamber 925 comprises a wash reagent for removing sample solution and/or unbound labeled reagents from the detection chambers. In embodiments where one of the detection chambers is used for control assays or for assay calibration, the associated pill zone may comprise control reagents such as an added analyte (for example, to be used in spike recovery, calibration measurements or control assay measurements).

The fluidic network of cartridge 900 comprises Z-transitions that may act as capillary breaks and/or allow for the fluidic network to be extended to multiple planes of the cartridge. See, e.g., Z-transitions 1010-1014 in FIG. 10. Z-transition 1011 in the sample conduit and 1013 in the reagent conduit act as capillary breaks which confine sample liquids and reagent liquids to their corresponding chambers. Fluid can be moved from these chambers, in a controlled and reproducible manner, by application of an appropriate pressure gradient. Z-transitions 1060 and 1061 allows the waste conduits to cross sample conduit branches 940 and 941 by arranging them on different layers of the cartridge.

Figure 11:
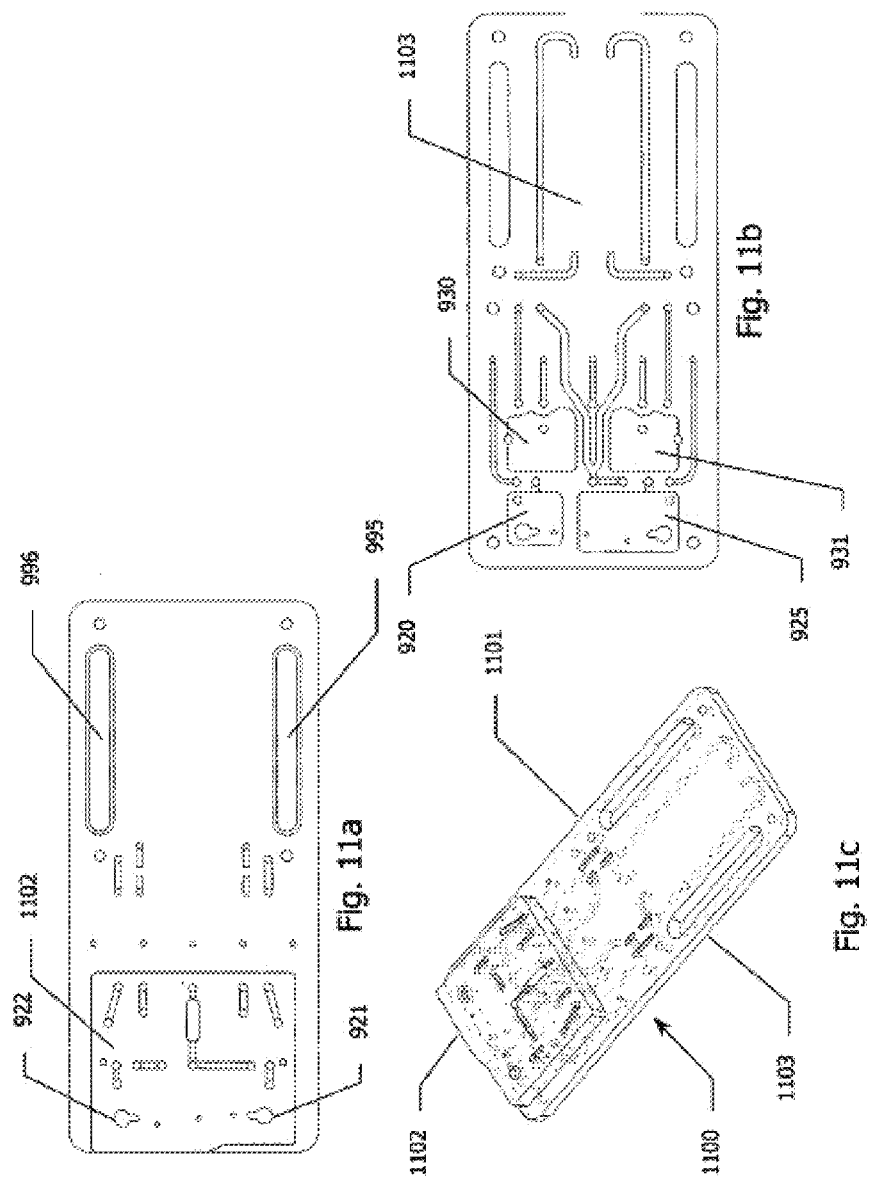
FIGS. 11a-11c are top, bottom and isometric views, respectively, of the assay cartridge of FIG. 9.

FIGS. 13a and 13b show exploded views of one embodiment of cartridge 900 that comprises cartridge body 1100 and cover layers 1324, 1350, 1320, 1321 and 1322 mated to the surfaces of cartridge body 1100. FIG. 11 shows top (FIG. 11a), bottom (FIG. 11b) and isometric (FIG. 11c) views of cartridge body 1100. The upper 1101,1102 and lower 1103 surfaces of the cartridge body 1100 incorporate (e.g., by molding, machining, etching, etc.) recessed features such as channels, grooves, wells, etc. The features are sealed to provide the chambers and conduits of the cartridge by applying the cover layers to the upper and lower portions of the cartridge body. To allow for adequate sample and/or reagent volumes, the cartridge body has thicker portion 902 which includes features (channels, grooves, wells, compartments, etc.) that define, in part, the sample, reagent and waste chambers. The remainder of the cartridge is, preferably, much thinner so as to minimize cartridge weight, volume and material costs and, in the case, of certain preferred cartridge designs, to allow optical detectors to as close as possible to the top surface of electrodes incorporated on a cover layer on the bottom of a cartridge.

Reagent chamber 925, sample chamber 920, waste chambers 930 and 931 and at least portions of the sample conduit, reagent conduit and waste conduits 960 and 961 are formed by sealing cover 1324 on cartridge body 1100. Detection chambers 945 and 946 are formed by sealing cover layer 1350 (having patterned conductive layer 1360 (which forms the patterned electrode array 963, shown in FIG. 9) and patterned dielectric overlayer 1365) to cartridge body 1100 through intervening gasket layer 1331 (preferably, made from double sided adhesive tape). The detection chamber's depth, length and width are defined by cutouts 1340 and 1341 within the gasket layer. Cover layer 1322 mates to cartridge body 1100 through gasket layer 1330 (preferably a double sided adhesive tape) to define conduit segments, such as 1060 shown in FIG. 10, that (via formation of double Z-transitions) act as bridge segments connecting the fluidic networks defined by cover layers 1324 and 1350. Advantageously, the use of a such a "bridge" cover layer allows cover layer 1350 having patterned electrodes (and, optionally, patterned binding reagents on the electrodes) to be only slightly larger than the patterned components. This arrangement decreases the cost of the patterned component. Alternatively, the bridge cover layer and associated double Z-transitions can be omitted and cover layers 1324 and 1350 can be combined into a single contiguous cover layer. Optionally, pill zones containing dry reagents pills are located on cover layer 1332 in the regions that are exposed by openings 1345 and 1346 in gasket 1330 so that they the reagents are reconstituted in liquids passing through the pill zones on the way to detection chambers 945 and 946. Cover layer 1321 seals air chamber/trap 976 and the top side conduit segments which include double Z-transition connecting segments 1070 and 1071. Cover layer 1320 seals sample introduction port 921 and reagent introduction port 922.

In the preferred embodiment shown in FIGS. 11 and 13, the cartridge body further includes electrical access regions 995 and 996 that, together with cutouts 1370 and 1371 in gasket layer 1331 allow electrical contact to be made with electrode contacts 997,998. Electrical access regions are cut-outs or holes in the cartridge body configured and arranged to be in alignment with the electrode contacts.

Figure 12:
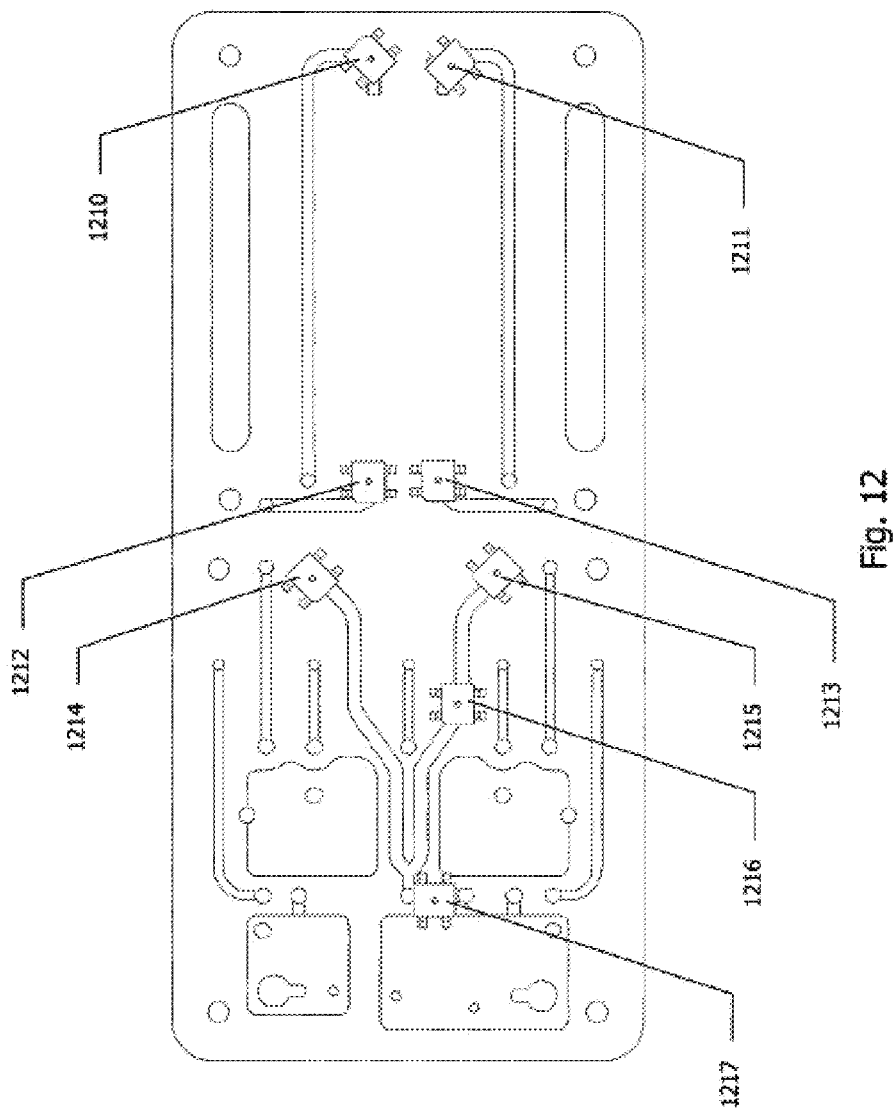
FIG. 12 is a bottom view of the assay cartridge of FIG. 9 illustrating one preferred layout for fluidic detectors to detect/monitor fluid movement.

At least a portion of cartridge body 1100 is adapted and configured to be an optical detection window and is arranged in optical registration with the electrodes to allow optical detection of luminescence generated by the electrode array. In one particularly preferred embodiment, the cartridge body and/or the cover layers are fabricated from a translucent material. The use of optically transparent materials has the further advantage that optical detectors, e.g. detectors arranged within a cartridge reader, can be used to detect the presence of liquids in the conduits. These optical detectors can be used to ensure that the cartridge is functioning properly and to provide feedback to the control systems controlling fluid movement in the cartridge. Alternatively, the cartridge body and/or cover layers may contain optical detection windows that are properly arranged locations that require optical detection of fluid presence and/or composition (e.g., detection of reflectance/transmittance from a light source). FIG. 12 depicts preferred locations for optical detection points 1210-1217 in cartridge 900.

Figure 14B:
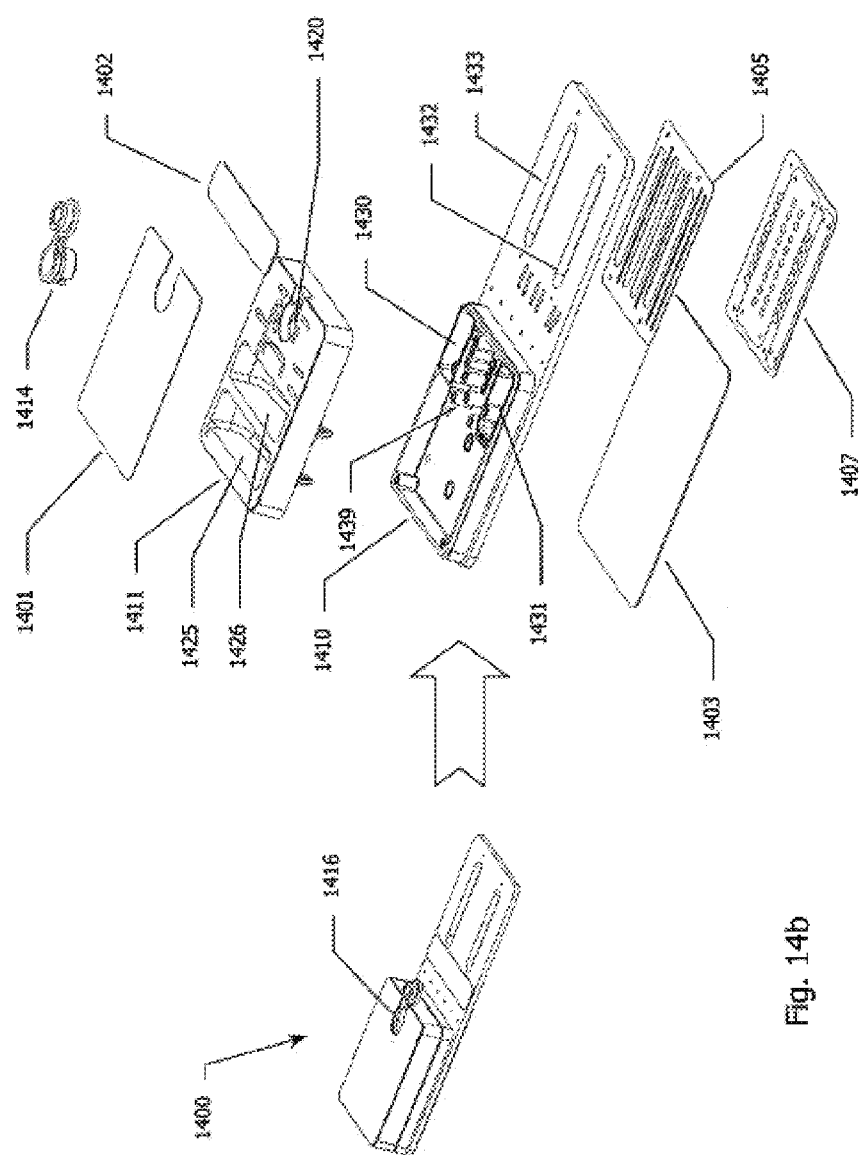
Figure 14C:
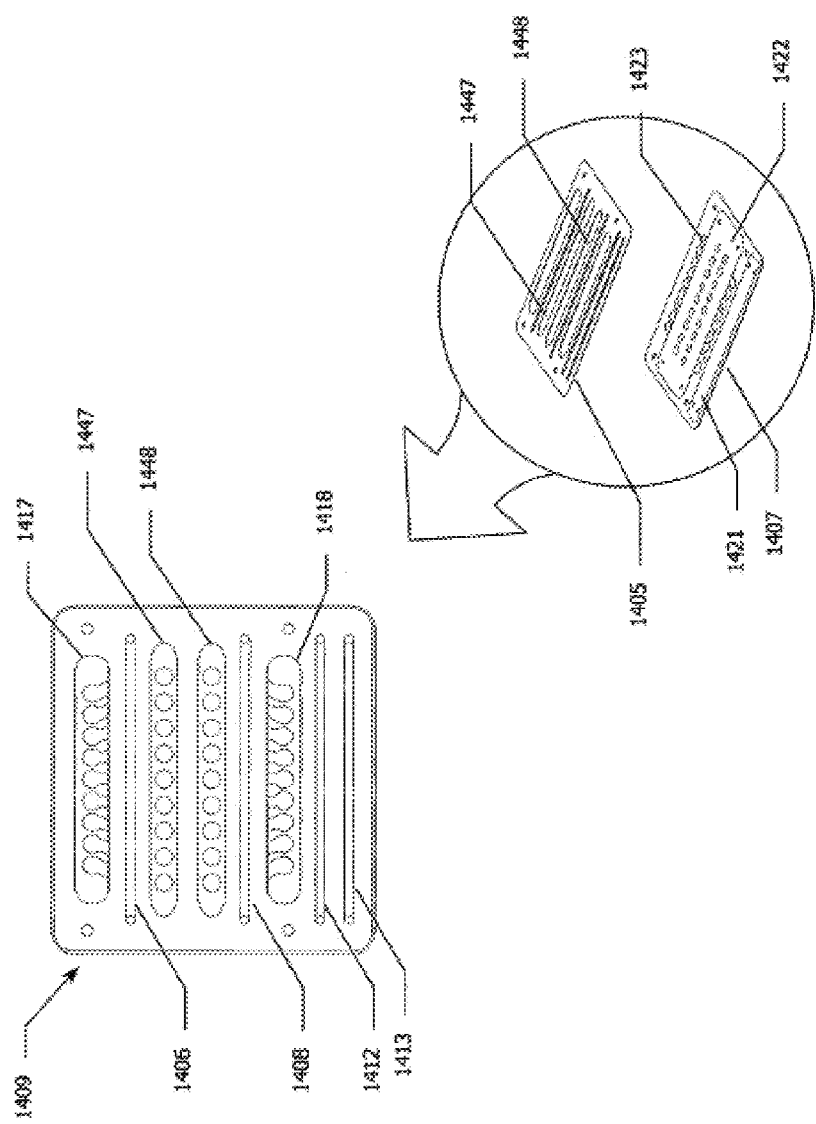
FIG. 14c is a detail drawing of the gasket and electrode array cover layer depicted in FIG. 14b.
Figure 18:
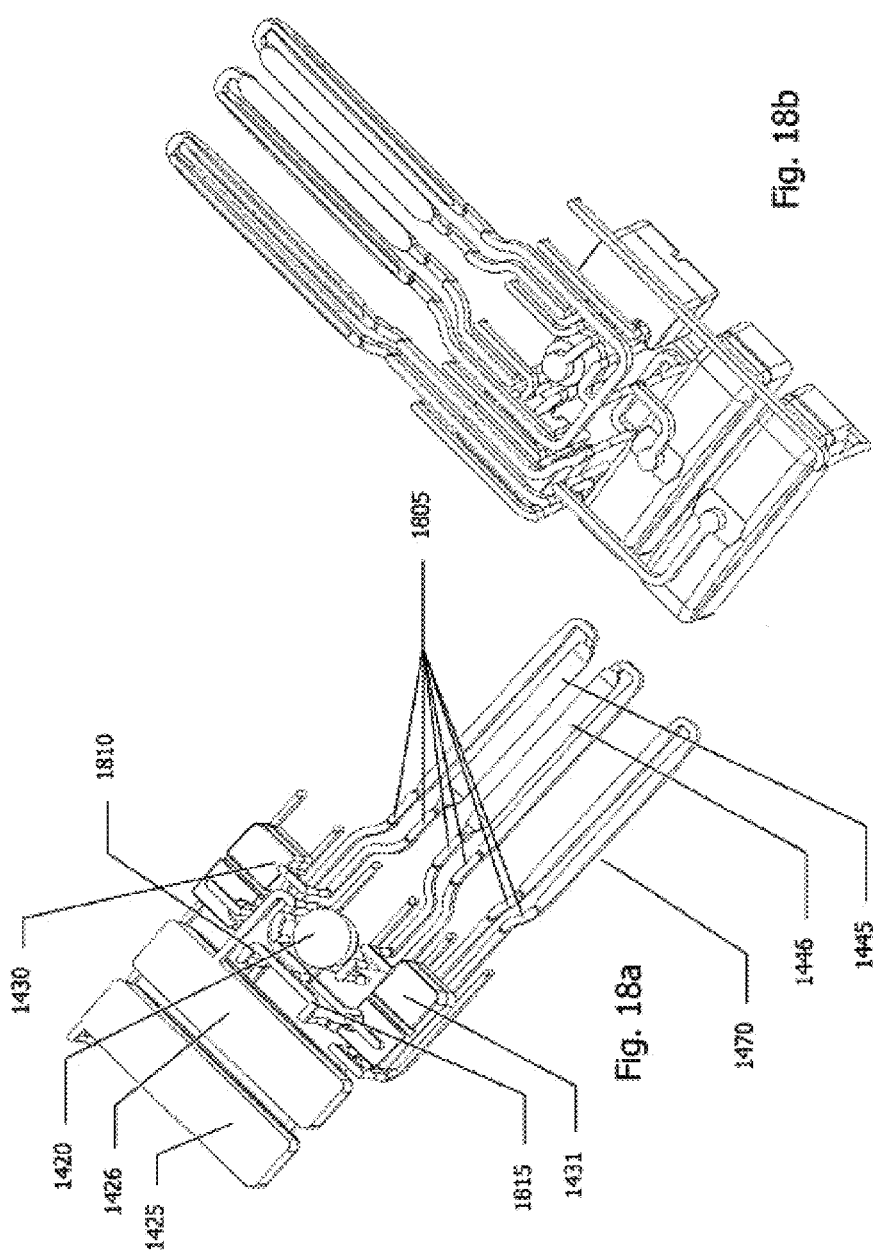

FIG. 14a is a schematic representation of the fluidic components of cartridge 1400, another preferred embodiment of the cartridge of the invention. FIGS. 14b and 14c show exploded views of one preferred design of cartridge 1400. FIG. 18 is a three dimensional representation of the fluidic network of this design. Cartridge 1400 comprises a sample chamber 1420, first and second reagent chambers 1425 and 1426, detection chambers 1445 and 1446, waste chambers 1430 and 1431. Sample chamber 1420 is preferably adapted to receive a liquid sample and is linked via vent conduit 1475 to vent port 1480 and via sample conduit 1415 (including sample conduit branches 1440 and 1441 that branch from distribution point 1540) to detection chambers 1445 and 1446. Vent conduit preferably has a serpentine shape to increase its length and prevent fluid from bubbles in sample chamber 1420 from back-flowing into vent port 1480. Sample conduit 1415 preferably comprises a Z-transition near the conduit connection to the sample chamber 1420 for preventing premature leakage of sample from sample chamber 1420. Sample chamber 1420 also has sample introduction port 1416 and cap insert 1414 for sealing the port. Optionally, sample conduit branches 1440 and/or 1441 comprise reagent pill zones.

Reagent chambers 1425 and 1426 are, preferably, adapted to hold reagent ampoules. Reagent chamber 1425 is connected via a reagent vent conduit to vent port 1450 and via reagent conduit 1470 to sample conduit 1415. Reagent conduit 1470 is further connected via vent conduit 1482 to vent port 1481 which may be used to introduce air into reagent conduit 1470 and downstream conduits such as sample conduit branches 1440 and 1441. Advantageously, reagent conduit 1470 has an extended segment between vent conduit 1482 and sample conduit 1415 which may be used as a staging area for a defined volume of liquid reagent. Preferably, this extended segment also comprises a reagent pill zone for introducing a dry reagent into the liquid reagent held, in reagent chamber 1425. Reagent chamber 1426 is connected, via a vent conduit to vent port 1451 and via reagent conduit 1427 to sample conduit 1415 (first intersecting with reagent conduit 1470 just downstream from sample conduit 1415). Reagent conduits 1427 and 1470 preferably comprise Z-transitions near to the connection of the conduits to their corresponding reagent chambers to prevent premature leakage of the reagent from the chambers. Detection chambers 1445 and 1446 preferably, comprise immobilized binding reagents for analytes of interest, preferably an array of binding reagents, preferably an array of binding reagents supported on electrode arrays for conducting ECL measurements, e.g., the electrode arrays of the invention as described above. Detection chambers 1445 and 1446 connect to sample conduit branches 1440 and 1441 and to waste conduits 1460 and 1461. Waste chambers 1430 and 1431 connect to waste conduits 1460 and 1461 and, via vent conduits to vent ports 1452 and 1453. Optionally, one detection chamber (and the associated fluidics and waste chamber) may be omitted.

Cartridge 1400 is adapted to carry out one and two step washed assays (assays that involve treating a detection chamber with one or two samples/reagents prior to conducting a wash step). A preferred embodiment of a one step washed assay comprises: i) introducing sample from sample chamber 1420 into detection chambers 1445 and/or 1446 via sample conduit branches 1440 and/or 1441 (optionally, the sample introduced into the detection chambers including reconstituted reagents such as labeled binding reagents and/or control/calibration reagents picked up in pill zones comprised in sample conduit branches 1440 and/or 1441) ii) washing detection chambers with a wash reagent contained in reagent chamber 1426 (the reagent preferably comprising an electrochemiluminescence coreactant and providing a suitable environment for an ECL measurement) and iii) interrogating the contents of the detection chamber (preferably, by conducting an ECL measurement). For cartridges carrying out such a one step protocol, reagent chamber 1425 may be omitted (in which case, vent port 1481 may be directly connected to reagent conduit 1427 or sample conduit 1415. A preferred embodiment of a two-step washed assay comprises: i) introducing sample from sample chamber 1420 into detection chambers 1445 and/or 1446 via sample conduit branches 1440 and/or 1441 (optionally, the sample introduced into the detection chambers including reconstituted reagents such as blocking agents, buffers, labeled binding reagents and/or control/calibration reagents picked up in pill zones comprised in sample conduit branches 1440 and/or 1441); ii) introducing a liquid reagent from reagent chamber 1425 into detection chambers 1445 and/or 1446 (optionally, the reagent introduced into the detection chambers including reconstituted reagents such as blocking agents, buffers, labeled binding reagents and/or control/calibration reagents picked up in pill zones comprised in reagent conduit 1470); iii) washing detection chambers with a wash reagent contained in reagent chamber 1426 (the reagent preferably comprising an electrochemiluminescence coreactant and providing a suitable environment for an ECL measurement) and iv) interrogating the contents of the detection chamber (preferably, by conducting an ECL measurement). Optionally, a wash step is included between steps (i) and (ii). Advantageously, the use of a two step format in binding assays allow analyte or other components in a sample to be bound to immobilized binding reagents in the detection chambers and washed out of the detection chamber prior to the introduction of labeled detection reagents (e.g., labeled binding reagents for use in sandwich binding assays or labeled analytes for use in competitive assays); carrying out assays in two steps may be advantageous in competitive assays and assays that suffer from large sample matrix effects or hook effects. Some assays may not require a wash step (e.g., non-washed ECL assays may be carried out by incorporating adding an ECL coreactant to the sample); for cartridges carrying out such non-washed assays (in one or two step formats), reagent chamber 1426 may be omitted.

A shown in FIG. 14*b*, a preferred embodiment of cartridge 1400 uses a laminar cartridge design employing a two part cartridge body (1410 and 1411) and cover layers 1401, 1402, 1403 and 1407. To allow for adequate sample and/or reagent volumes, the cartridge body has a thicker portion which includes features (channels, grooves, wells, compartments, etc.) that define, in part, the sample, reagent and waste chambers. The remainder of the cartridge is, preferably, much thinner so as to minimize cartridge weight, volume and material costs. The two part cartridge design is not required but is advantageous for producing the cartridge by low cost injection molding techniques by allowing the thicker regions of the cartridge body to be hollowed out thus reducing the amount of material needed to produce a cartridge, reducing the time required to cool the parts before ejection from an injection mold die and reducing the part deformation after release from the mold. In this hollowed out design, through-holes through the cartridge body can be provided for by tubes incorporated into body components 1410 and/or 1411 (see, e.g., tube 1439 in FIG. 14*b*). These tubes may be mated to tubes or holes in the other body component to form through-holes through the body. This mating can be accomplished by a variety of methods including tube mating methods known in the art. Preferred techniques include plastic welding techniques and/or the use of press fits (preferably, by mating a tapered tube with an outer diameter that decreases from $d_{max}$ to $d_{min}$ at its end with a tube that has an inner diameter between $d_{max}$ and $d_{min}$). In an alternate embodiment, a one part cartridge body is used.

At least portions of the sample, reagent and vent conduits are formed by sealing cover 1403 on lower cartridge body part 1410. Detection chambers 1445 and 1446, portions of sample conduit branches 1440 and 1441, and portions of elongated reagent conduit 1470 are formed by sealing cover layer 1407 (having patterned conductive layer 1423 (which forms a patterned electrode array analogous to the electrode array 963, shown in FIG. 9) and patterned dielectric overlayers 1421, 1422) to lower cartridge body part 1410 through intervening gasket layer 1405 (preferably, made from double sided adhesive tape). The detection chamber's depth, length and width are defined by cutouts 1447 and 1448 within the gasket layer. Cutouts 1406,1408,1412,1413 in the gasket layer expose regions of dielectric layers 1421 and 1422 to sample conduit branches 1440 and 1441 and elongated reagent conduit 1470. Advantageously, dry reagent pills comprised within these reagents are located on these regions. This choice of pill locations allows dry reagent pills and/or immobilized reagents within the detection chambers to be dispensed on a single substrate. Preferably, as shown in FIG. 14, sample conduit branches 1440 and 1441 have segments that are adjacent and/or substantially parallel to detection chambers 1445 and 1446 and a U-turn segment to allow connection to the detection chambers. This arrangement provides for conduit lengths that are long enough to allow for the introduction of a sample to the conduit and mixing of the sample with a pill in the conduit prior to introduction of the sample to the detection chamber. These lengths are achieved without adding to the length of the cartridge. Advantageously, this arrangement also allows the patterned electrode layer to be used to conduct capacitive or conductometric measurements of fluid within the sample conduits as described above. Similarly, elongated reagent conduit 1470 has entrance and return segments, connected via a U-turn segment that is parallel to detection chambers 1445 and 1446. Lower cartridge body component 1410 further includes electrical access regions 1432 and 1433 that, together with cutouts 1417 and 1418 in gasket layer 1405 allow electrical contact to be made with conductive layer 1423.

Cover layer 1402 mates to lower cartridge body component 1410 to define conduit segments 1805 (readily seen in FIG. 18*a*) that (by connecting two Z-transitions) act as bridge segments connecting the fluidic networks defined by cover layers 1403 and 1407. Optionally, pill zones formed on cover layer 1402 on surfaces of bridge segments comprised within the sample or reagent conduits may be used to introduce dry reagents to the sample or liquid reagents. Cover layer 1401 mates to upper cartridge body component 1411 and seals reagent chambers 1425 and 1426, preventing the release of fluid from ampoules within the chambers. Cover layer 1401 also seals top side conduit segments including double Z-transition connecting segments such as segments 1810 and 1815 readily seen in FIG. 18*a*.

Figure 16B:
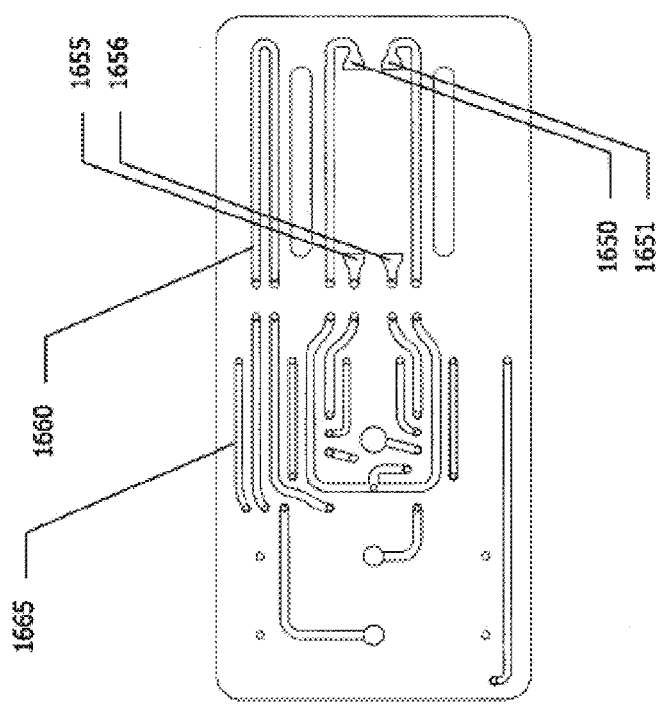

FIG. 15*a* shows a top view of upper body component 1411. FIGS. 16*a* and 16*b* show top and bottom views of lower body component 1410. As shown in FIG. 15*a*, the upper cartridge component 1411 preferably includes reagent chambers 1425, 1426 that are configured to hold reagent ampoules. Filters 1515, 1516 are preferably integrally molded into the upper cartridge component to ensure that substantially all of the glass fragments from the ruptured glass ampoules are not permitted to enter the fluidic network and possibly obstruct/block fluid flow. Alternatively, the filters may be separate components that are incorporated into the sample and/or assay reagent chambers during the manufacturing/assembly process; e.g., inserts that may preferably be snapped into place (see, e.g., inserts 2020 and 2021 in FIG. 20).

The two piece cartridge design also advantageously simplifies the employment of additional anti-foaming measures in the waste chambers. A vertical web, or partial wall, can be included in the upper portions of the waste chambers 1610, 1611 located in the upper cartridge component 1600, another embodiment of upper cartridge component 1411. Preferably the anti-foaming web is arranged between the waste chamber vent and the waste chamber input. The height of the anti-foaming web preferably extends the full depth of the upper portion of the waste chamber but may be less than the full depth as well. Alternatively, the anti-foaming web can extend beyond the depth of the upper portion of the waste chamber so that it protrudes into the lower portion of the waste chamber. Preferably the height of the anti-foaming web is selected to achieve optimum anti-foaming.

As discussed above, the input conduits of the waste chambers are preferably arranged so as to enter the waste chambers in a manner that allows the waste fluid to run down the wall of the waste chamber to minimize or eliminate foaming. As illustrated in FIG. 16*a*, the input conduits 1615, 1616 intersect one of the walls of the waste chambers. Additionally, the vents are configured and arranged to access the waste chambers at a point that will be above the anticipated fluid level. Locating the waste chamber vents at or near the top of the waste chamber also helps to ensure that any foaming that may occur within the chamber does not result in fluid entering the vent line and possibly contaminating the cartridge reader instrument.

Figure 32:
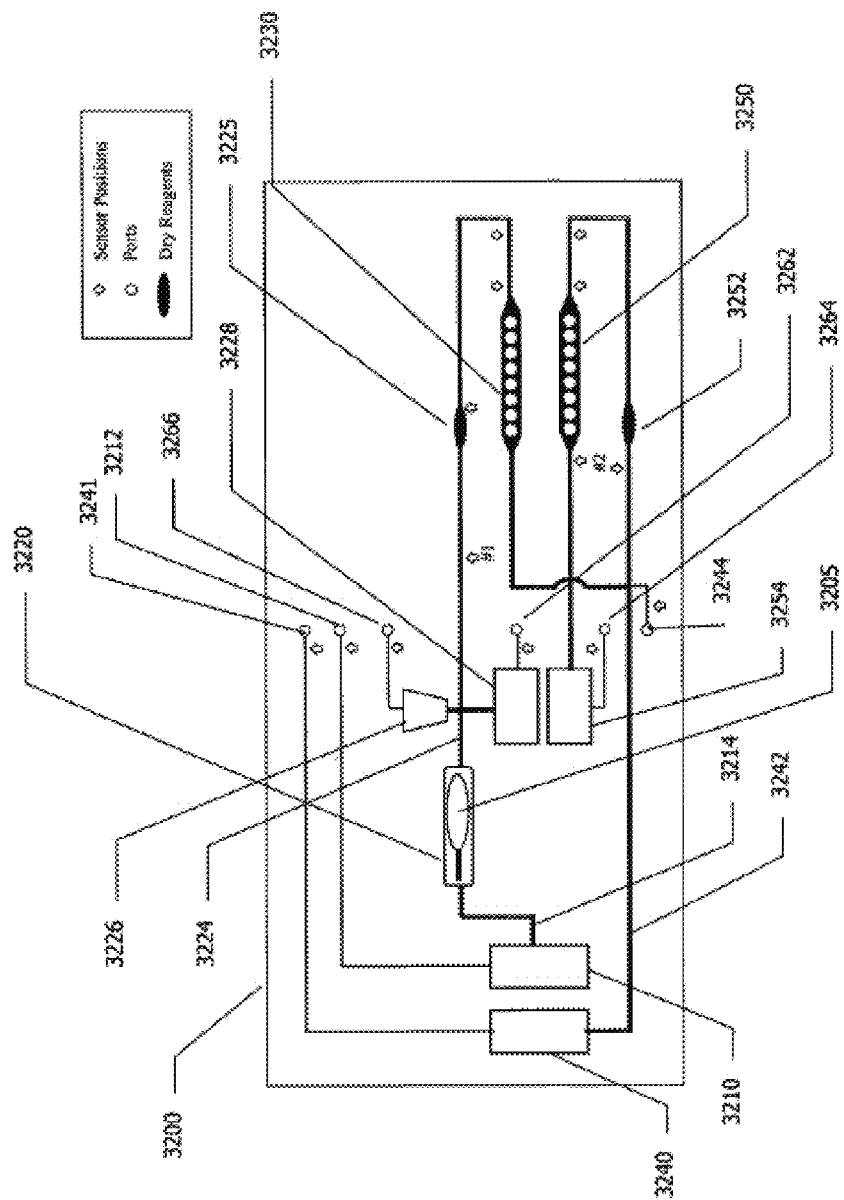
FIG. 32 is a schematic representation of another embodiment of an assay cartridge illustrating various fluidic components.
Figure 33:
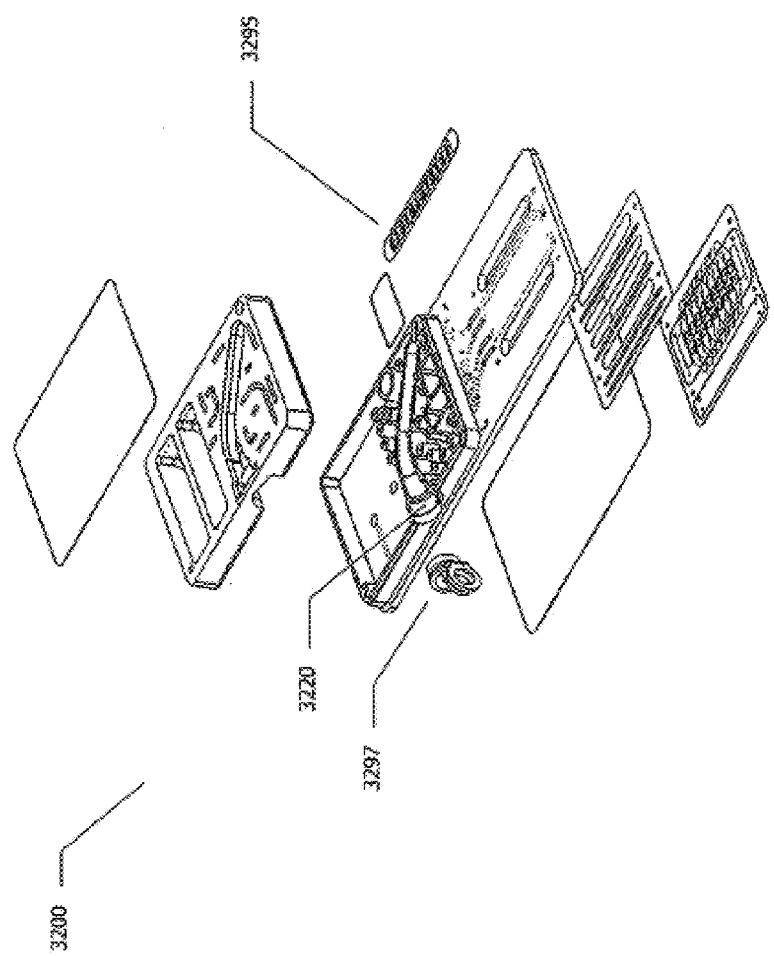
FIG. 33 is an exploded, assembly drawing illustrating the laminar assemblage for a two-piece, extraction assay cartridge in accordance with the schematic diagram given in FIG. 32.

FIG. 32 shows a schematic of the fluidic network of cartridge 3200, a preferred embodiment of the invention configured to extract analyte from a matrix, preferably from an applicator stick, most preferably from a swab. FIG. 33 shows an exploded view of a preferred design of cartridge 3200. Cartridge 3200 illustrates two preferred features of cartridges of the invention: a sample chamber for extracting analyte from a matrix and the use of a "reverse flow" wash. Cartridge 3200 has reagent chamber 3210 linked to vent port 3212 and extraction reagent conduit 3214 (preferably, comprising a Z-transition). Reagent chamber 3210 holds a liquid reagent suitable for extracting the analyte. Preferably, reagent chamber holds an ampoule of nitrous acid or, more preferably, an ampoule of an acid (preferably, acetic acid) and a dry nitrate salt outside of the ampoule so that rupturing the ampoule leads to the formation of nitrous acid. Nitrous acid is a particularly useful extraction reagent for extracting cell wall antigens from gram positive bacteria and may also be used to extract markers from other organisms in mucus containing samples such as upper respiratory samples (see, e.g., the extraction methods and reagents disclosed in U.S. Provisional Patent Application 60/436,591, filed Dec. 26, 2002, entitled Methods Compositions and Kits for Biomarker Extraction, hereby incorporated by reference).

Cartridge 3200 has an elongated sample chamber 3220 (a sample chamber configured for extracting samples such as those described above in connection with FIGS. 28-30) connected to extraction reagent conduit 3214 and sample conduit 3224 so as to allow the flow of extraction reagent through the sample (preferably, through swab head 3205). Preferably, as shown in FIG. 33, sample chamber 3220 is angled or curved along its elongated dimension so as to aid in breaking a scored swab inserted into the sample compartment. Sample conduit 3224 is connected to bubble trap 3226 (preferably connected to bubble trap vent port 3266) for removing air from the extracted sample and waste chamber 3228 (which is preferably connected to waste vent port 3262). Further downstream, sample conduit 3224 is connected to detection chamber 3230. Sample conduit 3224 comprises pill zone 3225 which may hold labeled binding reagents (e.g., labeled antibodies for use as detection reagents in sandwich immunoassays) and/or a neutralization reagent (e.g., a pH buffering component such as Tris, Hepes, phosphate and the like) for neutralizing an acidic extraction reagent in the sample (such as nitrous acid).

Detection chamber 3230, preferably, comprises immobilized binding reagents for analytes of interest, preferably an array of binding reagents, preferably an array of binding reagents supported on electrode arrays for conducting ECL measurements as described for other cartridge embodiments above. In an especially preferred embodiment the binding reagents are antibodies directed against markers of organisms (preferably including at least one gram positive bacteria, most preferably a *Streptococcus* species) that may be found in mucus-containing sample such as upper respiratory samples (see, e.g., the organisms described in U.S. Provisional Patent Application 60/436,591, filed Dec. 26, 2002, entitled Methods Compositions and Kits for Biomarker Extraction, hereby incorporated by reference). Detection chamber 3230 is connected to wash reagent chamber 3240 via wash reagent conduit 3242 (which, preferably, comprises a Z-transition). Vent port 3244 is arranged along wash reagent conduit 3242 between detection chamber 3230 and wash reagent chamber 3240. Wash reagent chamber 3240 is also connected to vent port 3241. Wash reagent chamber 3240 comprises a liquid wash reagent, preferably in an ampoule. The liquid was reagent, preferably, comprises an ECL coreactant and provides an appropriate chemical environment for an ECL measurement.

The fluidic arrangement of cartridge 3200 allows for forward flow of extracted sample through pill zone 3225 into detection chamber 3230 and reverse flow of sample into waste chamber 3228 and wash reagent from wash reagent chamber 3240 into detection chamber 3230.

Cartridge 3200 also has optional control detection chamber 3250 which is preferably configured like detection chamber 3230. The fluidic arrangement of the cartridge allows wash reagent from wash reagent chamber 3240 to pass through pill zone 3252 to detection chamber 3250. Pill zone 3252, preferably, comprises the same binding reagents as pill zone 3225 but also comprises control reagents (preferably, predetermined amount of the analytes measured in detection chamber 3230) so that reconstitution with wash reagent forms a control sample. The fluidic arrangement further allows the forward flow of control sample into waste chamber 3254 (which is preferably connected to waste vent port 3264) and wash reagent from wash reagent chamber 3240 into detection chamber 3250.

Figure 37A:
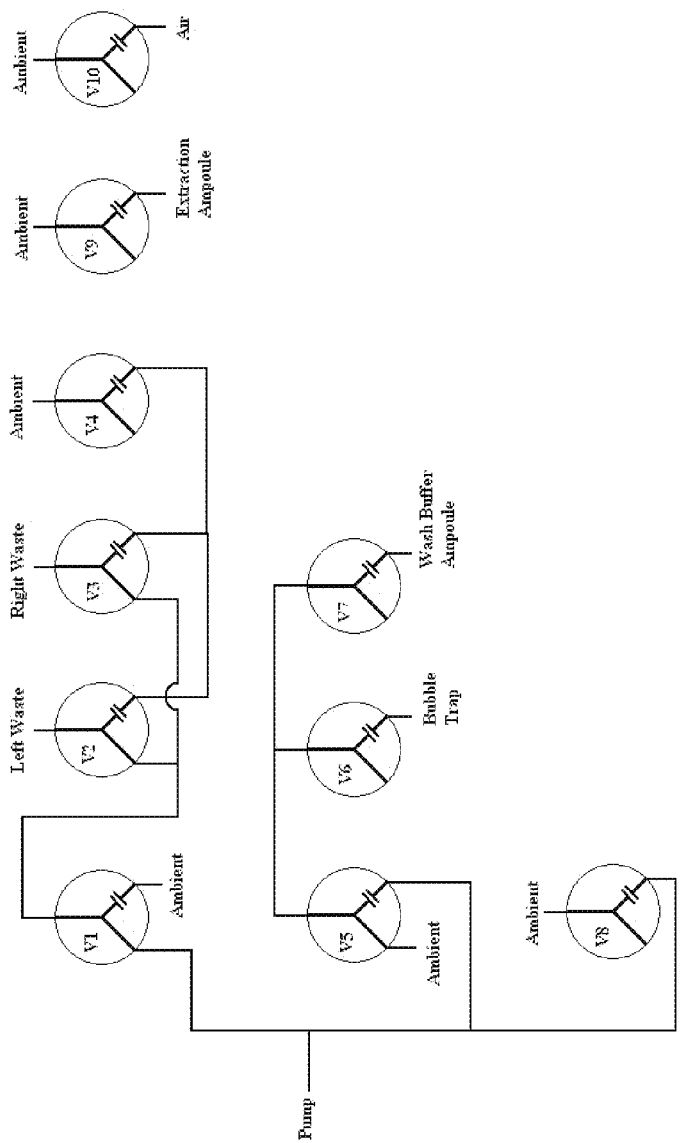
FIGS. 37(a)-(b) show a schematic representation of a fluidic design for one embodiment of a cartridge.

FIG. 37 shows a schematic of the fluidic network of cartridge 3700, an alternate embodiment of a cartridge configured to extract analyte from a matrix, preferably from an applicator stick, most preferably from a swab. Unlike cartridge 3200, cartridge 3700 is designed to split the extracted sample between two detection chambers. Cartridge 3700 also illustrates certain alternative approaches to fluidic features in a fluidic network including an alternative approach to collecting and removing bubbles from an extracted sample. Cartridge 3700 has an extraction buffer chamber 3710 linked to an extraction buffer vent port and, through an integrated filter element, to an extraction buffer conduit (preferably, comprising a Z-transition). Extraction buffer chamber 3710 holds a liquid extraction reagent (which may be in a reagent ampoule) for extracting analyte(s) of interest. Such extraction buffers may include buffers that are known in the art to be suitable for extracting the specific analyte(s) of interest that the cartridge is designed to measure and may also include anti-foam agents, including, without limitation, SE-15, Antifoam 204, Antifoam A, Antifoam B, Antifoam C, Antifoam Y-30, and combinations thereof (available from Sigma-Aldrich Corp., St. Louis, Mo., www.sigmaaldrich.com).

The invention includes cartridges and methods for carrying out assays for detecting influenza infections. In particular, applicants have discovered that the sensitivity of assays for detection of influenza and/or for determining influenza subtype by detection of influenza hemagglutinin proteins can be significantly enhanced by extraction of the samples under acidic conditions (pH 4.0 to 5.2 or 4.5 to 5.0). Suitable extraction reagents may achieve acidic pH through the inclusion of strong acids such as hydrochloric and sulfuric acid. Advantageously, the extraction reagent is a buffered solution at or near the desired pH that includes a buffering agent with buffering capacity in the appropriate pH range appropriate buffering agents include, but are not limited to, ones based on carboxylic acids such as acetic acid and lactic acid and, especially, polycarboxylic acids such as citric and glutaric acid and also include quaternary ammonium buffers such as MES). In one embodiment, the concentration of the buffer is between 10 to 500 mM or between 100 and 200 mM or around 117 mM and the pH of the buffer is between 4.0 to 5.2 or 4.5 to 5.0. In a specific embodiment, the buffer includes 30 mM glutaric acid. Alternatively, the buffer may include 15 mM citric acid. In addition, the buffer may include about 0.10 to 0.5 M NaCl, e.g., 0.15 M NaCl. The extraction reagent may also include an anti-foam agent and a surfactant (e.g., a non-ionic surfactant such as Tween 20, Thesit, Triton X-100 or an ionic surfactant such as deoxycholic acid or CHAPSO) preferably at a concentration near to or greater than the CMC. In one embodiment, the extraction reagent includes greater than 0.0296 Triton X-100 or greater than 0.05% Triton X-100 or about (1.1% Triton X-100. In one embodiment, the extraction reagent comprises glutarate buffer (or alternatively, citrate buffer) at a concentration of between 10 and 50 mM, a salt (e.g., sodium chloride) at a concentration between 100 and 200 mM, a non-ionic detergent (e.g., Triton X-100) at a concentration between 0.02 and 1% and an anti-foam agent (e.g., SE-15) at a concentration between 0.1 and 1% and has a pH between 4.2 and 5.2.

In one embodiment, the pH of the extracted sample is at least partially neutralized prior to or during analysis of the extracted sample by immunoassay. The method may therefore include treatment of the extracted sample with a reagent (e.g., a dry reagent pill within the cartridge fluidic network) that comprises a neutralization reagent that brings the pH to pH 6.0 or greater, pH 6.5 or greater or pH 7.0 or greater. The neutralization reagent may be a strong base such as sodium or potassium hydroxide or a buffering agent with buffering capacity in the appropriate pH range (e.g., HEPES, phosphate, Tris, etc.). In one embodiment, the concentration, after reconstitution in the extracted sample, is between 50-1000 mM or between 100 and 400 mM and the pH is between 6.0 to 8.5 or 6.5 to 8.0.

The sensitivity and specificity of an Influenza A test using the assay cartridge and methods of the present invention as calculated against a viral cell culture result is about 75% and about 100%, respectively, and in one embodiment, about 80% and about 100%, respectively. In a specific embodiment, the sensitivity of an Influenza A test as calculated against a viral cell culture result is about 82% and the specificity of an Influenza A test is about 99%. The sensitivity and specificity of an Influenza B test using the assay cartridge and methods of the present invention as calculated against a viral cell culture result is about 75% and about 100%, respectively, and in one embodiment, about 80% and about 100%, respectively. In a specific embodiment, the sensitivity of an Influenza B test as calculated against a viral cell culture result is about 81% and the specificity of an Influenza B test is about 100%. The sensitivity and specificity of Influenza A as calculated against viral cell culture and RT-PCR was about 75% and about 100%, respectively, and in one embodiment, about 80% and about 100%, respectively. In a specific embodiment, the sensitivity of Influenza A as calculated against viral cell culture and RT-PCR is about 88% and the specificity of Influenza A as calculated against viral cell culture and RT-PCR is about 100%. The sensitivity and specificity of Influenza B using the assay cartridge and methods of the present invention as calculated against viral cell culture and RT-PCR result was about 75% and about 1.00%, respectively. In a specific embodiment, the sensitivity of Influenza B as calculated against viral cell culture and RT-PCR is about 79% and the specificity of Influenza B as calculated against viral cell culture and RT-PCR is about 100%. The sensitivity and specificity of Influenza A/subtype, H1 as calculated against the viral cell culture and RT-PCR result is about 80% and about 100%, respectively.

Sample chamber 3720, however, includes additional features. Firstly, the integrated filter is located near the end of the sample chamber and the connection to the extraction reagent conduit is located 1 to 2 cm (roughly 1.5 cm) from the end of the chamber. The inlet and outlets from the sample chamber are located near the opposite ends of a typical nasal/throat swab head, when the swab head is fully inserted, providing for efficient extraction with the minimal volume of extraction buffer. Secondly, the sample chamber consists of a first region and a second region and these regions are oriented at an angle with respect to each other and that angle is selected to bend the shaft upon insertion of the applicator stick into the sample chamber, thereby promoting fracture of the shaft, and the sample chamber includes two sample collection head retention features: barb 3721a and shelf 3721b, both of which may be provided by the injection molded cartridge body. In one embodiment, the first region is proximate to a sample introduction port and the second region is distal to the sample introduction port. Barb 3721a is located near the end of the sample chamber adjacent to the location of a fully inserted swab head. In one embodiment, the second region of the sample chamber terminates in a sample chamber base and the barb is positioned at or near the sample chamber base. The barb is angled so as to allow for insertion of the swab head, but to also catch the swab head matrix and prevent removal or shifting of the swab head from the end of the chamber upon breaking and removal of the swab shaft. In one embodiment, the sample chamber includes a sample collection head extraction location at or near the terminus of the cavity of the sample chamber and the barb is position in the cavity so as to retain the collection head in the extraction location. The extraction location is a position within the sample chamber within which the collection head resides once the shaft is fractured. Shelf 3721b is located at roughly the location of the broken shaft end of a fully inserted swab head and also acts to prevent the swab head from being removed once the swab is fully inserted and broken. In one embodiment, the shelf is located at or near the sample chamber base in the second region, as defined. As shown, the shelf can be defined by a stepped discontinuity in an internal surface of the sample chamber where the radius of curvature transitions from a smaller to a larger radius. In one embodiment, the sample chamber is curved and the radius of curvature of the internal surface, as a function of increasing depth in the elongated cavity, steps from a first value to a second, higher value at the discontinuity. In another embodiment, the radius of curvature of the sample chamber in the first region is less than the radius of curvature of the sample chamber in the second region and the shelf is located on the longer of the curved surfaces defining the sample chamber such that when a swab shaft breaks in the chamber, the strain is released and the end of the swab fragment attached to the swab head is pushed against the longer curved surface and locked in place by the shelf. Therefore, the user inserts the applicator stick into the sample chamber and contacts the swab head of the applicator stick with the retention feature, i.e., the barb, the shelf or both, and the applicator stick is broken within the sample chamber. The swab head is retained within the second region of the sample chamber. The sample chamber also includes a recess to accommodate the swab handle protruding from the broken swab head.

Sample conduit 3224 is connected to collection component 3726 (which is shown in more detail in FIG. 37) where extraction buffer pulled through the sample chamber is collected and cleared of air bubbles. Further downstream, the collection component is connected through 4-channel fluidic junction 3728 and T-junction 3729 to conduits 3730*a* and 3730*b* leading to detection chambers 3731*a* and 3731*b*. Conduits 3730*a* and 3730*b* comprise dry reagent pill zones which may hold labeled binding reagents (e.g., labeled antibodies for use as detection reagents in sandwich immunoassays) and/or a neutralization reagent (e.g., a pH buffering component such as Tris, Hepes, phosphate and the like) as well as other assay reaction mixture components such as surfactants, salts, blocking agents, etc.

Detection chambers 3731*a* and 3731*b*, preferably, comprise immobilized binding reagents for analytes of interest, preferably an array of binding reagents, preferably an array of binding reagents supported on electrode arrays for conducting ECL measurements as described for other cartridge embodiments above. The two chambers may have the same arrays to allow for duplicate measurements to be carried out. Alternatively, the two channels have different arrays to expand the number of multiplexed assays that can be conducted and/or to segregate incompatible assays. In one embodiment, one detection channel may be processed and read prior to processing of the second detection channel.

In one embodiment, array elements in one channel are configured for detection and typing of influenza and includes array elements with antibodies against influenza A nucleoprotein, influenza B nucleoprotein and, optionally, negative and positive controls. The first channel may include additional array elements for other infectious agents including, but not limited to, influenza C, adenovirus, parainfluenza and human metapneumovirus. In this embodiment, the second channel is configured for subtyping of influenza A and includes array elements with antibodies for at least two different hemagglutinin subtypes (which may include common seasonal subtypes such as H1 and H3, H1 from swine origin influenza virus (SOIV), and subtypes from atypical, potentially pandemic, subtypes for humans such as H2, H5, H7 and H9). Accordingly, conduits 3730*a* and 3730*b* include dry reagent pills with the appropriate labeled detection antibodies for conducting measurements for the target analytes of the array elements in the corresponding detection chambers (3731*a* and 3731*b* respectively). Optionally, the extraction reagent is an acidic extract for optimal presentation of hemagglutinin antigens (as described above) and the dry reagent pills include a dry neutralization buffer.

Detection chambers 3731*a* and 3731*b* are linked to waste chambers 3734*a* and 3734*b* through conduits 3733*a* and 3733*b*. The detection chambers are high aspect ratio chambers with higher hydrodynamic resistances relative to conduits 3730*a* and 3730*b* and Z-transitions 3732*a* and 3732*b*. To enable well controlled clearing of liquids from the detection chambers, conduits 3733*a* and 3733*b* are configured as matching resistance regions that are matched to the hydrodynamic resistances of the detection chambers (as described in FIG. 40 and the accompanying text).

Cartridge 3700 also comprises a wash buffer chamber 3740 for holding a wash buffer (which may be provided in an ampoule). The liquid wash reagent, may comprise an ECL coreactant such as TPA and may be used to both wash excess sample/reagents from the detection chamber and to provide an appropriate chemical environment for an ECL measurement. Wash buffer chamber 3740 is linked to the detection channels through 4-channel junction 3728 and T-junction 3729. Air vents for controlling movement of fluids in the cartridge are provided to collection component 3726, extraction buffer chamber 3710, 4-channel junction 3728, waste chambers 3734*a* and 3734*b* and wash buffer chamber 3740.

Figure 39:
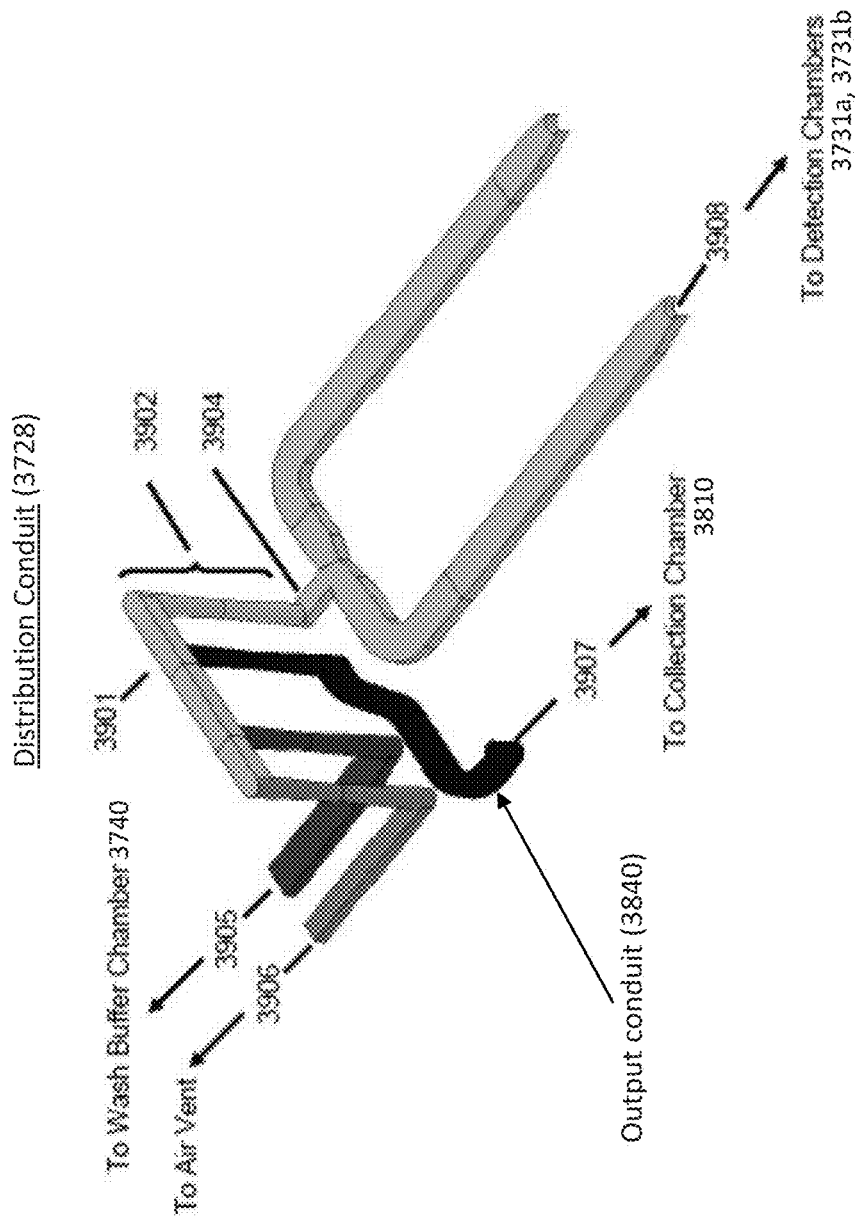
FIG. 39 shows one configuration of fluidic junctions, e.g., distribution conduit (3728) in the fluidics of a cartridge, e.g., cartridge 3700 shown in FIGS. 37(b) and 37(c).

FIG. 39 shows a detailed view of 4-channel junction 3728 and illustrates one approach to forming multi-conduit junctions. Four co-planar conduits (e.g., conduits formed by sealing channels on one surface of an injection molded cartridge) are linked by Z-transitions to a different plane on the cartridge (e.g., the opposite surface of an injection molded cartridge). A conduit formed on this opposite surface links the Z-transitions and provides the 4-channel junction.

In one embodiment, FIG. 39 shows a distribution conduit, such as distribution conduit 3728 of cartridge 3700 shown in FIGS. 37(*b*)-(*c*), interconnected to a plurality of fluid conduits comprising an outlet conduit, a detection chamber conduit connected to the detection chamber, and optionally one or more fluid conduits connected to one or more cartridge components selected from a wash buffer chamber, an air vent, detection chambers, and combinations thereof. In one embodiment, a connection between the distribution conduit and one of the plurality of fluid conduits comprises a Z-transition. In a specific embodiment, the cartridge includes an air vent and the one or more fluid conduits include an air vent conduit connected to the air vent, wherein the detection chamber conduit is distal from the air vent conduit. In another embodiment, the cartridge includes a wash buffer chamber and the one or more fluid conduits includes a wash buffer chamber conduit connected to the wash buffer chamber, wherein the wash buffer chamber conduit is proximal to the air vent conduit and distal to said detection chamber conduit. For example, the plurality of cartridge components includes an air vent and the plurality of fluid conduits include (a) a first fluid conduit connected to a detection chamber; (b) a second fluid conduit connected to a collection component; and (c) a third fluid conduit connected to the air vent, wherein the first fluid conduit is distal from the third fluid conduit. The plurality of cartridge components may also include a wash buffer chamber and the plurality of fluid conduits further includes an additional fluid conduit connected to the wash buffer chamber, wherein the additional fluid conduit is proximal to the third fluid conduit and distal to the first fluid conduit. Referring to FIG. 39, distribution conduit, 3901, is interconnected to a plurality of fluid conduits, 3902. The fluid conduits may include a T-junction, 3904. In the embodiment depicted in FIG. 39, the plurality of fluid conduits includes a first conduit (3906) that leads to an air vent and on the opposite side of the distribution conduit; there is a second conduit (3908) that leads to a detection chamber. The plurality of fluid conduits may also include a third fluid conduit (3905) that leads to a wash buffer chamber, e.g., wash buffer chamber 3740 show in FIGS. 38(*b*)-(*c*), and an additional conduit, 3907, which can be output conduit 3840, that leads to a collection chamber, such as collection chamber 3810 shown in FIGS. 38(*a*) and (*f*), wherein the third fluid conduit and the additional conduit are positioned in between the conduits leading to the detection chamber and the conduit leading to the air vent.

Figure 37B:
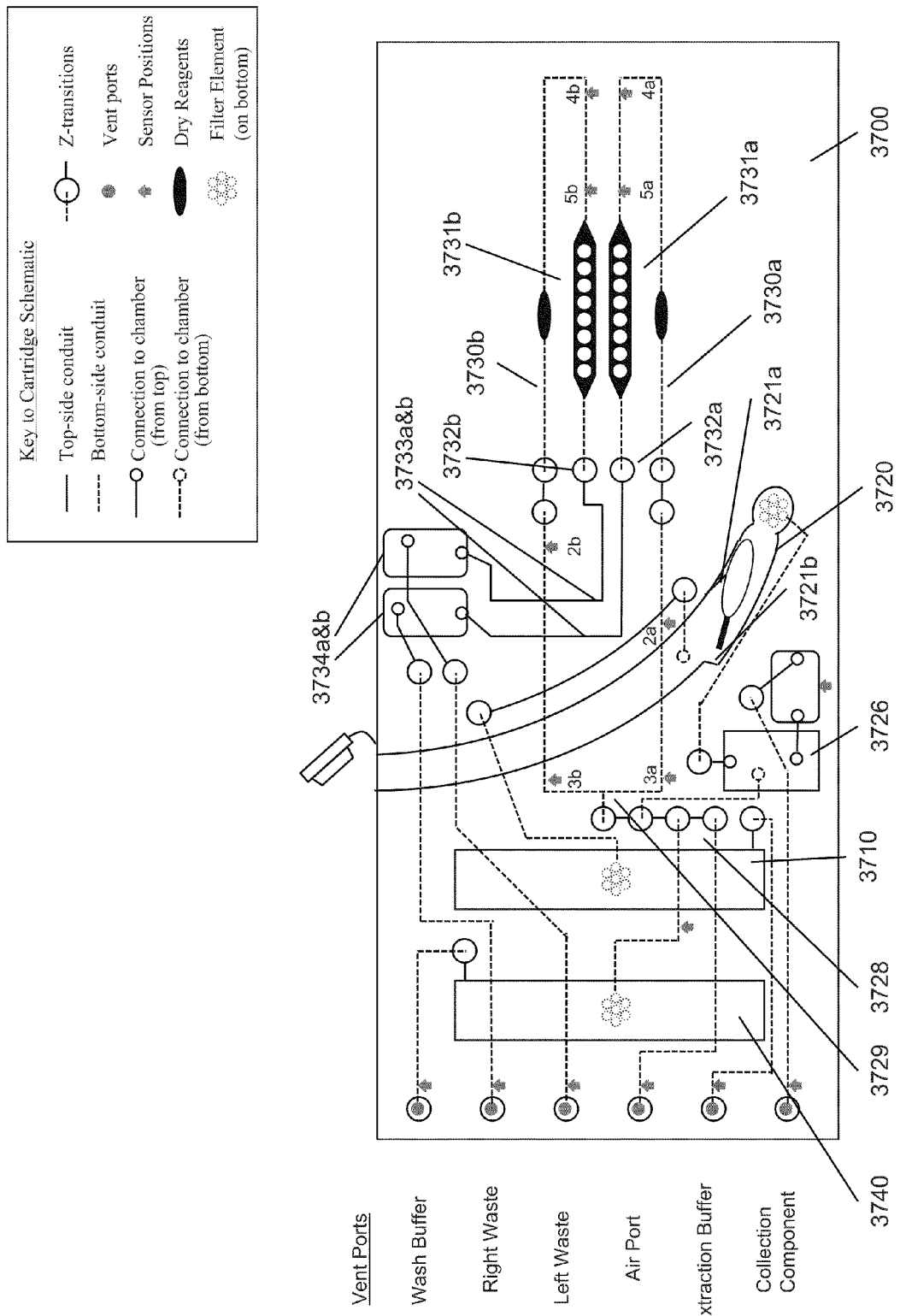
Figure 37C:
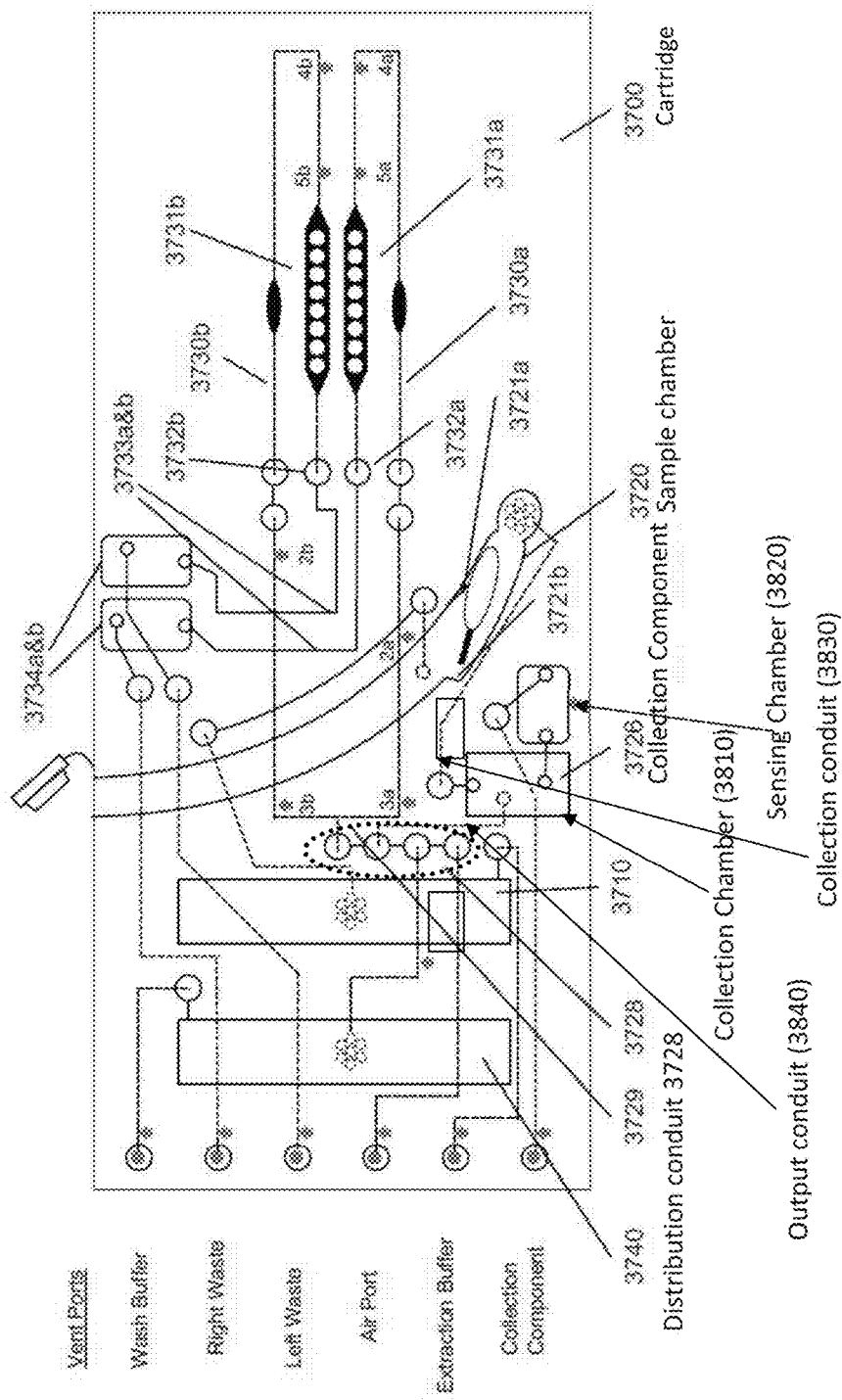
FIG. 37(c) is an annotated version of the cartridge shown in FIG. 37(b).
Figure 38:
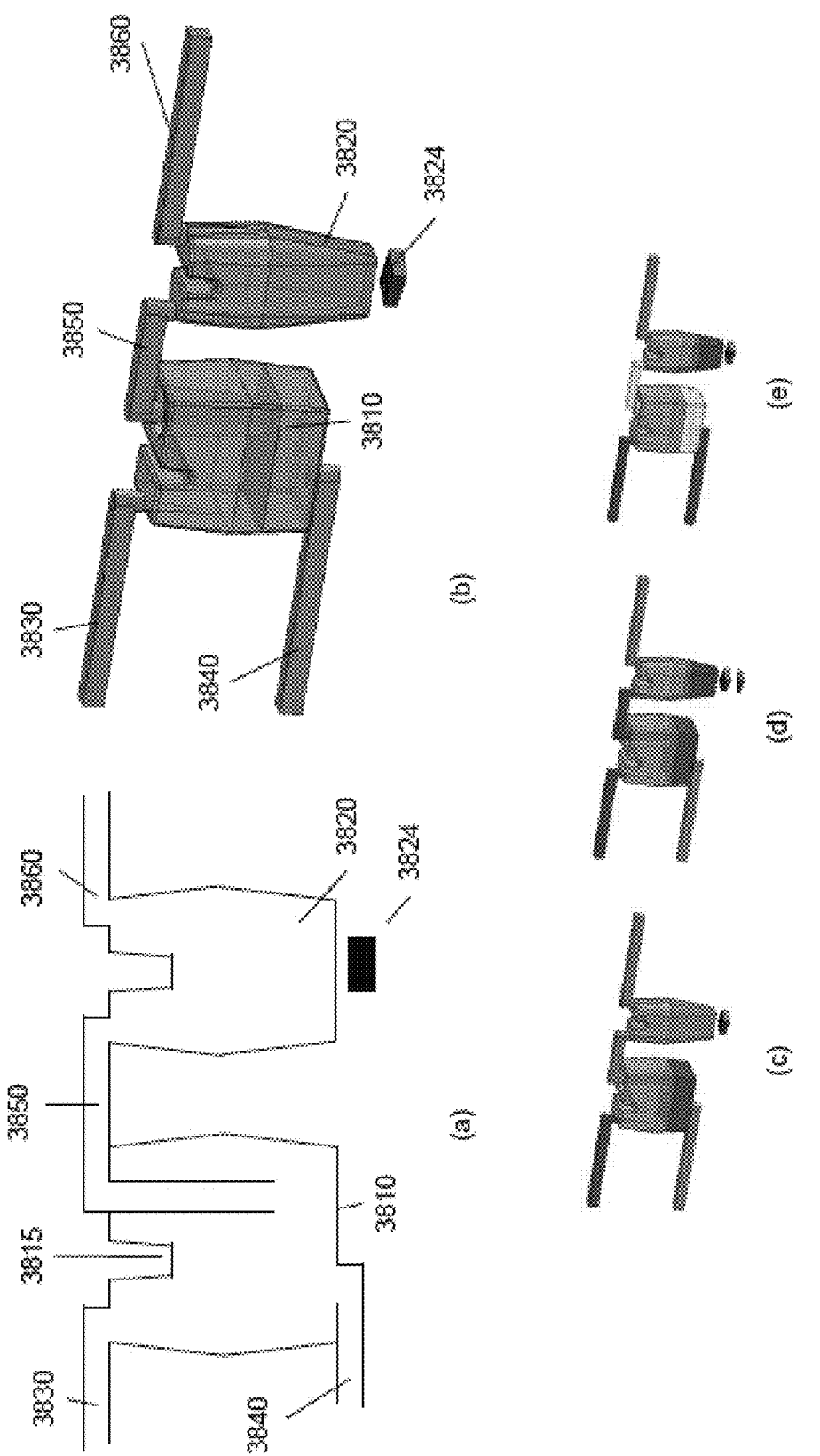
FIGS. 38(a)-(e) show one embodiment of a liquid collection chamber.
FIG. 38(f) is an annotated version of the liquid collection chamber shown in FIG. 38(a).
Figure 38F:
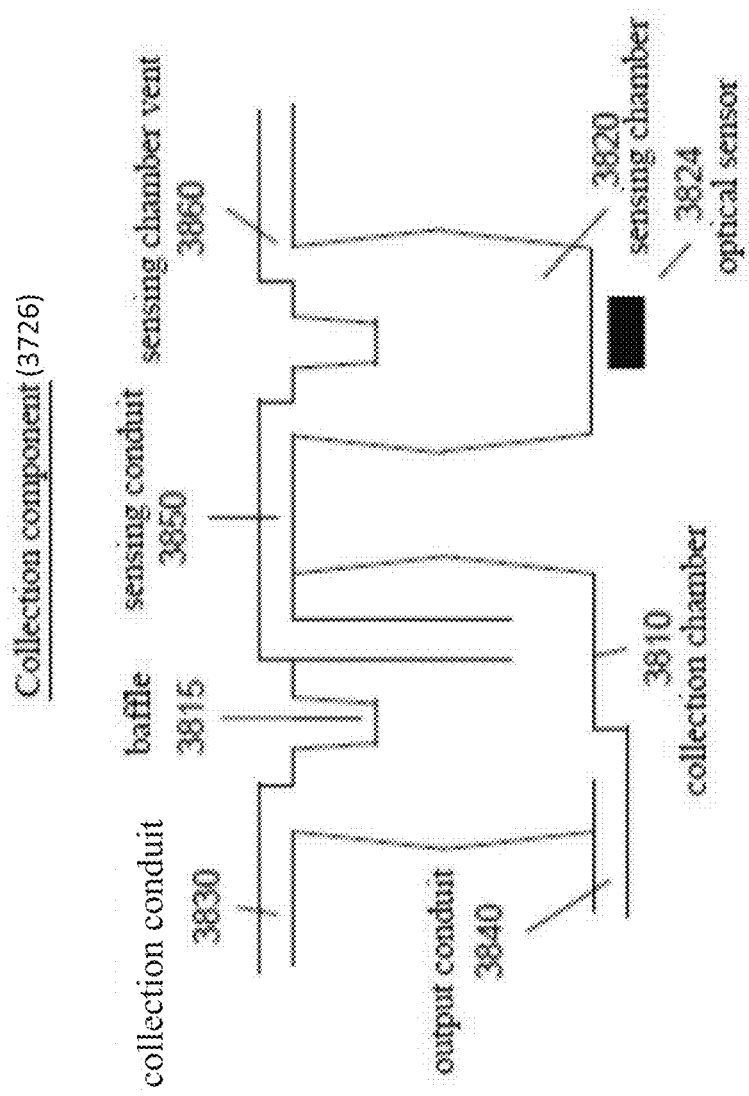

FIG. 38 shows detailed schematic (FIG. 38*a* and annotated FIG. 38*f*) and solid model (FIG. 38*b*) views of collection component 3726 and illustrates an approach to collecting small volume samples that may include bubbles, while ensuring that the bubbles are removed and that a defined volume of liquid is collected. The collection component includes a collection chamber, 3810 and a sensing chamber, 3820. The collection chamber connects to i) collection conduit 3830 that connects to the top of the collection chamber proximal to a wall of the chamber, ii) output conduit 3840 that connects to the bottom of the collection chamber and iii) sensing conduit 3850 which is a tube that extends down from the top of the collection chamber to a pre-defined height in the chamber. In one embodiment, fluid is introduced into the collection chamber via the input conduit and contacted with a baffle (3815) and the wall of the collection chamber to constrain bubbles within the liquid. The sensing chamber connects to the sensing conduit at the top of the sensing chamber proximal to a wall of the chamber and to a vent through conduit 3860 (which also connects to the top of the sensing chamber. The operation is illustrated in FIGS. 38 (*c*)-(*e*). Pulling vacuum on the collection component vent while opening the extraction buffer vent (see FIG. 37) pulls extraction buffer through the sample chamber (and a swab head in the sample chamber, if present), then through collection conduit 3830 and into the collection chamber where bubble-free liquid collects on the bottom of the chamber. When the liquid level reaches the sensing conduit any additional sample is then transferred through the sensing conduit to the sensing chamber. In one embodiment, the liquid volume in the collection chamber is about 125 uL and the air volume is about 250 uL, i.e., the approximate ratio of the liquid volume in the collection chamber to the air head space is about 1:2. An optical sensor 3824 (which may be in the cartridge reader processing the cartridge) is adapted to detect the presence of liquid in the sensing chamber and thereby to indicate that the collection chamber has a sufficient amount of sample. The collected sample may then be drawn from the collection chamber through output conduit 3840, e.g., by sealing the extraction buffer chamber air vent and pulling vacuum from one of the waste chamber vents while opening the collection component vent to the atmosphere (or, alternatively, by applying positive pressure to the collection component vent to drive fluid toward one of the waste chamber vents). In one embodiment, the waste chamber(s) included in the assay cartridge is configured as described above and depicted in FIG. 38. Accordingly, if liquid introduced into the collection chamber contains bubbles, the liquid transferred through the outlet conduit is substantially free of bubbles.

As shown in FIGS. 32, 33 and 37, cartridges 3200 and 3700, preferably, employ many of the same design features as preferred embodiments of cartridge 900 and/or 1400 such as use Z-transitions, laminar construction, electrode arrays, bridge segments, and the like. As shown in FIG. 33 for cartridge 3200, the cartridges preferably, have a two part design. Advantageously, this design allows the sample chamber to be constructed from two sections and simplifies the manufacture of the curved/angled elongated chamber. As shown in FIG. 33 for cartridge 3200, the cartridges 3200 may also comprises a bar code 3295 or other identifying feature that can, e.g., identify the assay panel carried out on the cartridge, the cartridge lot, the time of manufacture, the expiration date, cartridge specific calibration data, the sample source, etc.

Figure 23:
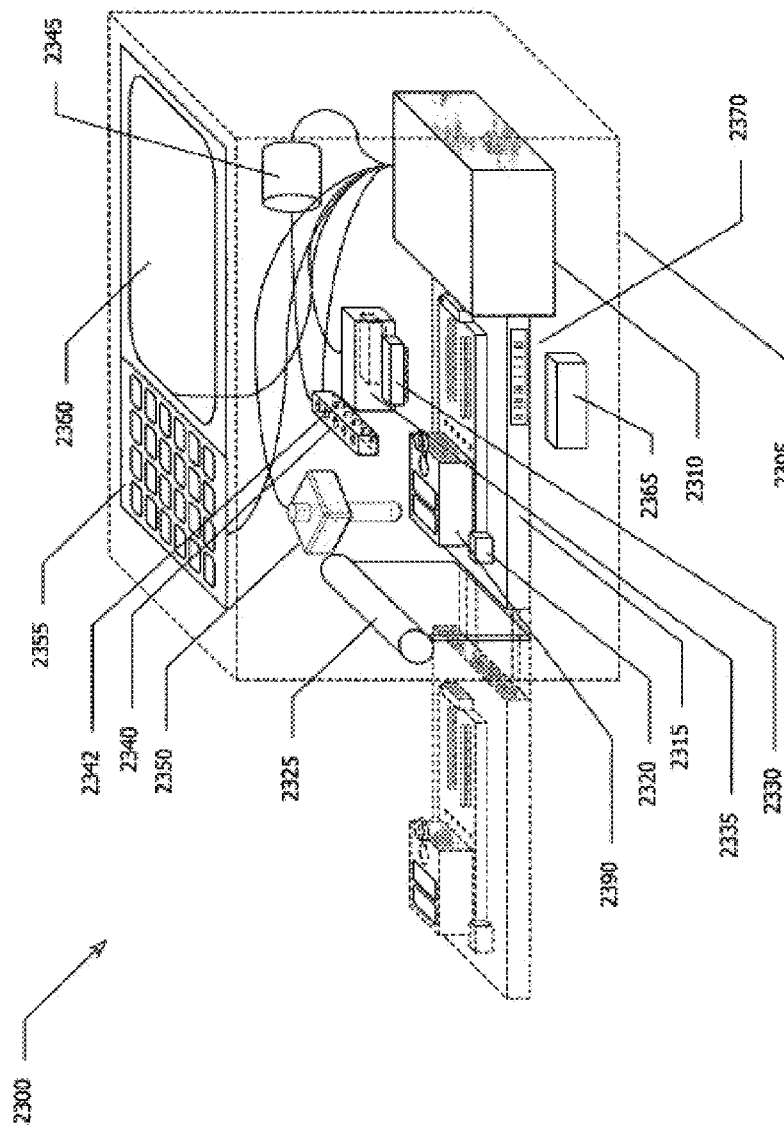
FIG. 23 illustrates one embodiment for a cartridge reader that incorporates various subsystems for performing a predetermined assay. The cartridge reader is depicted holding one embodiment of an assay cartridge.

The fluidic components are preferably adapted and configured to form a fluidic system that can be selectively controlled via a cartridge reader instrument. The cartridge reader 2300 is schematically depicted in FIG. 23 and preferably incorporates various subsystems for performing the predetermined assay. The cartridge reader is shown holding a cartridge 2390 which may be supplied separately. As depicted, the cartridge reader preferably includes the cartridge handler 2315, the fluidic handler 2340 and the assay electronics 2330 subsystems. Together these subsystems are preferably controlled by an electronic control system 2310 responsible, generally, for directing the cartridge handler subsystem to load and position the cartridge within the reader, for controlling/coordinating, the introduction/movement of fluids throughout the fluidic network and for directing the assay electronics to perform the assay measurement. The cartridge reader is preferably packaged as a single self-contained unit. In preferred embodiments employing luminescence based assays, a smaller light-tight region is incorporated within the overall cartridge reader housing. This allows the luminescence based assay to be performed within the light tight enclosure to ensure that the readings are not affected by ambient light. Preferably, electronic components and other heat-generating components are located outside of the light tight enclosure.

The cartridge handler subsystem preferably includes a motor to draw the cartridge into the cartridge housing and selectively position the cartridge within the cartridge reader; e.g., position the cartridge under a sensor/detector 2335. In one preferred embodiment, retraction of the cartridge within the cartridge reader housing may be mechanically coupled to one or more mechanisms within the cartridge reader for synchronized/coordinated operation of the linked mechanisms. For example, the retraction of the cartridge may be mechanically coupled to the mechanism for closing the door 2325 to the light tight enclosure after the cartridge has entered the chamber; the assay electronics subsystem (described in greater detail below) to allow the cartridge reader's electrical contacts 2330 to engage the cartridge's electrical contacts, i.e., be placed into electrical contact with the electrode array's electrode contacts; the fluidic handler subsystem's (described in greater detail below) fluidic manifold 2340 to engage the cartridge's fluid ports, i.e., be placed into fluidic communication with the cartridge's ports (e.g., establishing a pressure seal between the cartridge's fluidic ports and the fluid manifold); and/or the fluid handler subsystem's reagent module breaking mechanism 2350 to allow the reagent modules such as ampoule(s) to be broken during the cartridge retraction/positioning step.

In certain embodiments the measurement step may comprise reading the signal from each read chamber separately. While this may be accomplished by using a single suitable detector and optimal positioning of the cartridge's read chambers in relation to the single detector, successful measurement/detection may also be carried out by repositioning the desired read chamber in relation to the single detector or repositioning the detector in relation to the desired read chamber. For such an embodiment, the cartridge handler subsystem may include a separate motor to allow for positioning of the cartridge and/or the detector. In a particularly preferred embodiment, the cartridge handler subsystem is adapted and configured to precisely position the cartridge or the detector, or both, such that the detector is in registered alignment with the precise location where the measurement is being performed; e.g., the working electrode presently being stimulated to produce ECL.

In a preferred embodiment a barcode reader 2365 is incorporated on/within the cartridge reader to preferably automatically scan an identifying mark/label 2370 on the cartridge; e.g., as it is drawn into the reader. The label may contain encoded information relating to the specific assays that are to be performed, calibration parameters and/or any other information required to perform the assay. Further, a preferred embodiment may incorporate a heater within the cartridge reader to warm the cartridge to a predetermined temperature, e.g., 37° C., before proceeding.

Preferably, the reader does not come in contact with liquids contained within the cartridge. This feature may be accomplished by using pneumatic pressure applied at the vent ports to drive fluids in the cartridge. The fluidic handler subsystem preferably includes a pump 2345 (preferably a piston pump) to selectively apply positive and/or negative pressure (i.e. apply a vacuum) to one or more of the cartridge's fluidic components in order to selectively control movement of fluids within, and through, the cartridge and its various fluidic components. The fluidic handler subsystem is preferably adapted and configured to fluidically engage the cartridge at one or more fluidic control points; e.g., positive control ports, vent ports, and the like and includes fluidic connectors for providing these fluidic engagements. Selective application of pressure to the cartridge's fluidic components is preferably achieved by incorporating a fluid manifold 2340 housed within the cartridge reader to simplify and enhance the fluidic engagement function and to minimize the number and complexity of fluidic systems. Advantageously, the fluidic manifold 2340 can be adapted and configured to facilitate the use of a single pump; i.e., control valves 2342 can be incorporated within the fluidic manifold 2340 to selectively control fluid movement within and through the various fluidic components of the cartridge. The fluidic handler preferably includes a pressure sensor to facilitate precise/repeatable movement and/or positioning of fluids within the fluid network. The fluidic connectors, preferably, comprise aerosol-prevention plugs or gas-selective membranes (i.e., materials that selectively allow the passage of gas but prevent the passage of liquids) to prevent contamination of the reader fluidics with liquids in a cartridge. The components comprising these plugs or membranes are, preferably, easily removed and replaced if they become contaminated with liquid. Aerosol-prevention plugs are commonly used in pipette tips to prevent contamination of pipettors and include materials that allow the passage of air when dry but swell and seal up the passage when they come in contact with liquid (e.g., filter materials impregnated or coated with cellulose gum).

Figure 17:
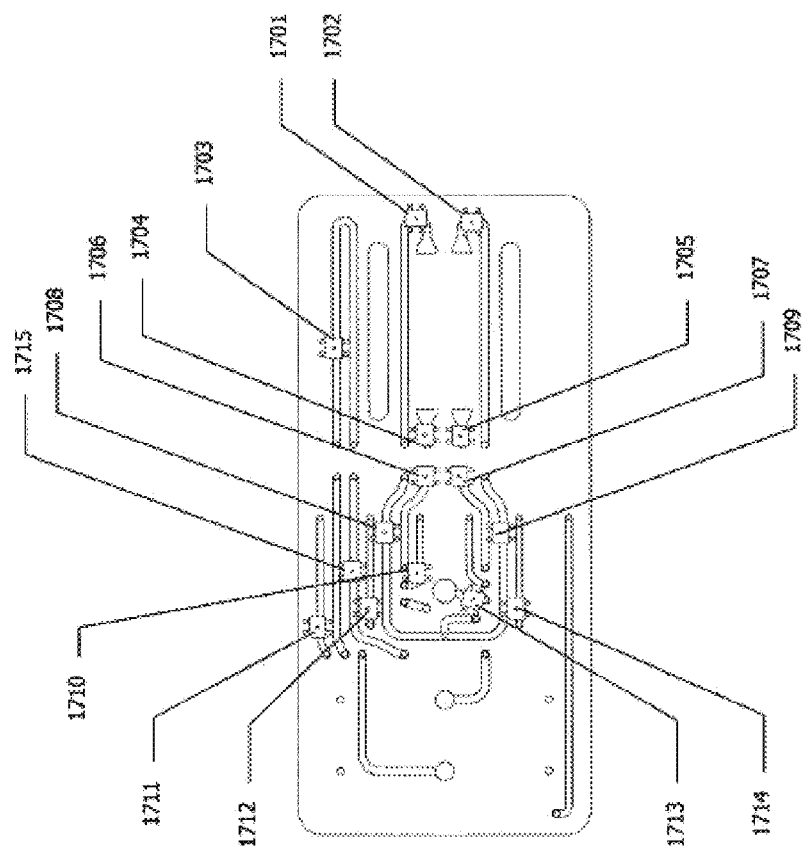
FIG. 17 is a bottom view of the assay cartridge of FIG. 14b illustrating one preferred layout for fluidic detectors to detect/monitor fluid movement.

The fluidic handler subsystem preferably employs fluid sensors (not readily seen in FIG. 23. FIGS. 12 and 17 illustrate alternative fluid sensor layouts in relative arrangement to the cartridge/fluidic network), e.g., reflective photo sensors, positioned at predetermined locations within the fluid network. In accordance with these preferred embodiments, the fluid sensors are positioned in registered alignment with the labeled optical detection points located on the cartridge body. Sensor signal data may be used to provide fluid positional information which may be used to control pump operational parameters such as pump speed, direction and the duration of a specific pump operation. In addition to precise control of fluid movement within and throughout the cartridge, fluid sensors may be used to control mixing of fluids (e.g., during the incubation period, and evacuation of sample from the read chambers during the wash and read cycle) by, e.g., defining the limits of the motion of slug fluid fronts during back and forth mixing motions and/or by measuring an optical property of the fluid such as absorbance or light scattering that is indicative of the state of a mixing operation. The fluid sensors may also be used to conduct viscosity measurements on a sample. In one embodiment, the reader pump is directed to move the fluid front of a sample through fluidic conduit from one optical sensor position to another by operating the pump at a predefined speed or under conditions designed to achieve a predefined pressure gradient. The time needed to move the fluid between the two positions is indicative of the viscosity. Such a viscosity measurement is optionally used to measure the coagulation time of a blood or plasma sample (e.g., whole blood clotting time, thrombin time, prothrombin time, partial thromboplastin time and/or activated clotting time). Such method may further comprise introducing one or more coagulation reagents (e.g., by passing the sample over a dry reagent comprising these reagents) prior to conducting the timing step. Suitable reagents for measuring thrombin time may include thrombin. Suitable reagents for measuring prothrombin time may include thromboplastin and/or calcium. Suitable reagents for measuring partial thromboplastin time may include cephalin and a negatively charge substance (preferably, diatomaceous earth, kaolin, glass particles and/or ellagic acid). Suitable reagents for measuring activated clotting time may include negatively charged substances such as diatomaceous earth, kaolin, glass particles and/or ellagic acid.

While the use of optical sensors to monitor fluid flow is advantageous, it is not required. In certain alternate embodiments, fluid movement operations are conducted by operating a pump for a predefined time at predefined speeds, or under conditions which have been determined through calibration of the pump) to result in a predetermined movement of a fluid slug.

The assay electronics subsystem preferably includes electrical contacts, sensors and electronic circuitry. The electrical contacts 2330 are preferably adapted and configured to be placed into electrical contact with the electrode array. In one preferred embodiment, the cartridge reader's electronic circuitry may include analog switching and trans-impedance amplification circuits to address a specific pair of electrodes pair-wise firing, discussed in greater detail above) and apply a predefined voltage waveform to the circuit formed by that electrode pair. The actual output voltage and current may be optionally measured for diagnostic purposes. Preferably the electronic circuitry is also capable of applying an AC waveform (e.g., 500 Hz or less) for capacitive or conductive measurements (as discussed above). Still further, the electronic circuitry may be configured to generate 20 kHz signals suitable for, e.g., hematocrit measurements of blood samples.

In one particularly preferred embodiment of the cartridge reader configured to perform luminescence based assays, the cartridge reader may employ an optical detector 2335, e.g., a photodiode (most preferably, a cooled photodiode), photomultiplier tube, CCD detector, CMOS detector or the like, to detect and/or measure light/luminescence emanating from the read chambers. If a cooled photodiode is employed, a thermo-electric cooler and temperature sensor can be integrated into the photodiode package itself providing for selective control by the electronic control system.

A computerized control system 2310 is preferably utilized to selectively control operation of the cartridge-based system. The computerized control system may be fully integrated within the cartridge reader, separated from the cartridge reader in an externally housed system and/or partially integrated within and partially separated from, the cartridge reader. For example, the cartridge reader can be configured with external communications ports (e.g., RS-232, parallel, USB, IEEE 1394, and the like) for connection to a general purpose computer system (not shown) that is preferably programmed to control the cartridge reader and/or its subsystems. In one preferred embodiment, a single embedded microprocessor may be used to control the electronics and to coordinate cartridge operations. Additionally, the microprocessor may also support an embedded operator interface, connectivity and data management operations. The embedded operator interface can preferably utilize an integrated display 2360 and/or integrated data entry device 2355 (e.g., keypad). The computerized control system may also preferably include non-volatile memory storage for storing cartridge results and instrument configuration parameters.

Figure 34:
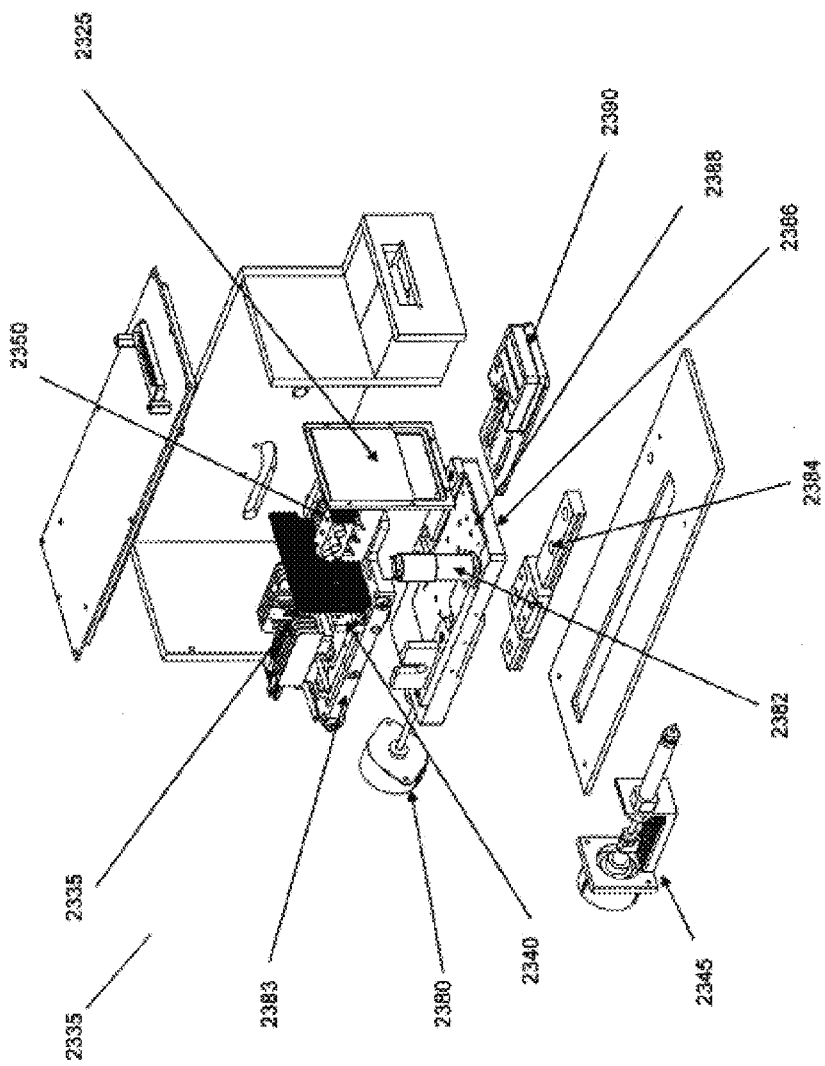
FIG. 34 depicts a cutaway exploded view of one preferred design for a cartridge reader.

FIG. 34 shows a cutaway exploded view of one preferred design for reader 2300 and also shows a cartridge drawer 2386 (preferably comprising an integrated cartridge heater) on linear guide 2384 and driven by motor 2380 for moving the cartridge in and out of the reader. FIG. 34 also shows fluid sensor array 2388 (holding sensors, preferably optical) for detecting fluid at selected positions in the cartridge and a motor 2382 for bringing the cartridge together with frame 2383 which supports the electrical connectors (not shown in this view), fluidic connectors (not shown in this view), ampoule breaking mechanism 2350 and light detector 2335.

Figure 24:
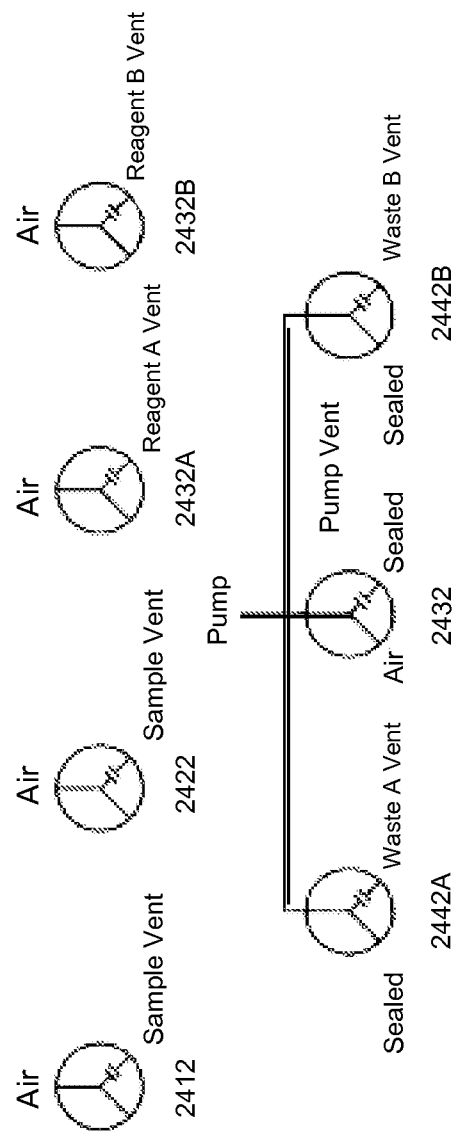
Figure 25:
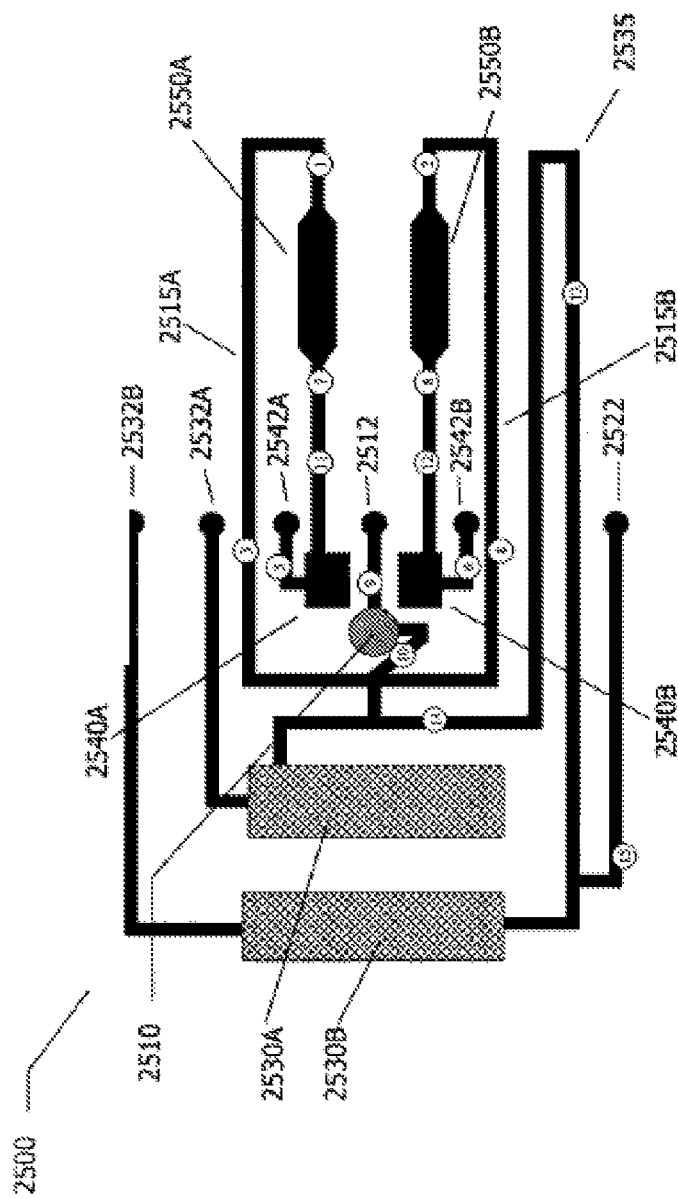
FIG. 25 is the schematic representation shown in FIG. 14a depicting the arrangement of fluidic components and locations of fluid detectors.

FIG. 24 illustrates a preferred configuration of valves in a cartridge reader fluidic handling sub-system configured for use with cartridge 2500 (analogous to cartridge 1400) shown in the fluidic diagram of FIG. 25 (along with preferred locations for cartridge reader fluid detection sensors 1-15). The sub-system comprises a pumping system that comprises a pneumatic pump (preferably, an air piston) linked to a pump manifold. The manifold is connected to control lines (comprising control valves 2412A and 2412B) that connect the pump to selected vent ports (preferably, the waste chamber A vent port 2512A and waste chamber B vent port 2512B) on a cartridge and allow the pump to be used to move fluid in the cartridge away or towards the selected vent ports.

The manifold is also connected to a pump vent line (comprising a pump vent line valve 2492) for venting the pump manifold. The control valves have a closed position that seals the control line and the associated cartridge vent port, an open position that connects the pump to the cartridge vent port and, optionally, a vent position that opens the cartridge vent port to ambient pressure. The pump vent line valve has a closed position that seals the pump vent port and an open position that exposes the pump manifold to ambient pressure and releases pressure/vacuum in the pump manifold. The fluidic handling sub-system further comprises vent lines (comprising vent valves 2412, 2422, 2432A and 2432B) that allow venting of vent ports (sample chamber vent port 2512, air port 2522, reagent chamber A vent port 2532A and reagent chamber B vent port 2532B, respectively) on a cartridge (preferably, the cartridge vent ports other than the waste cartridge ports). The vent valves have a closed position that seals the associated cartridge vent port and an open position that exposes the vent port to ambient pressure. The fluidic handling sub-system may also comprise a pressure sensor couple to the pump manifold for detecting pressure in the manifold. During fluidic control of a cartridge, the pressure in the manifold is, preferably, monitored to ensure that it falls within expected pressure ranges for specific operations and confirm that the fluidic handling system is operating properly. The specific preferred valve configuration shown in FIG. 24 is designed to move fluid primarily by aspirating it towards the valve chambers. Other valve configurations, e.g., configurations that drive fluids primarily by positive pressure, will be readily apparent to the skilled artisan and may valves that allow chambers other than the waste chambers to be connected to the pump and/or that allow the waste chambers to be directly vented to the atmosphere.

Figure 43:
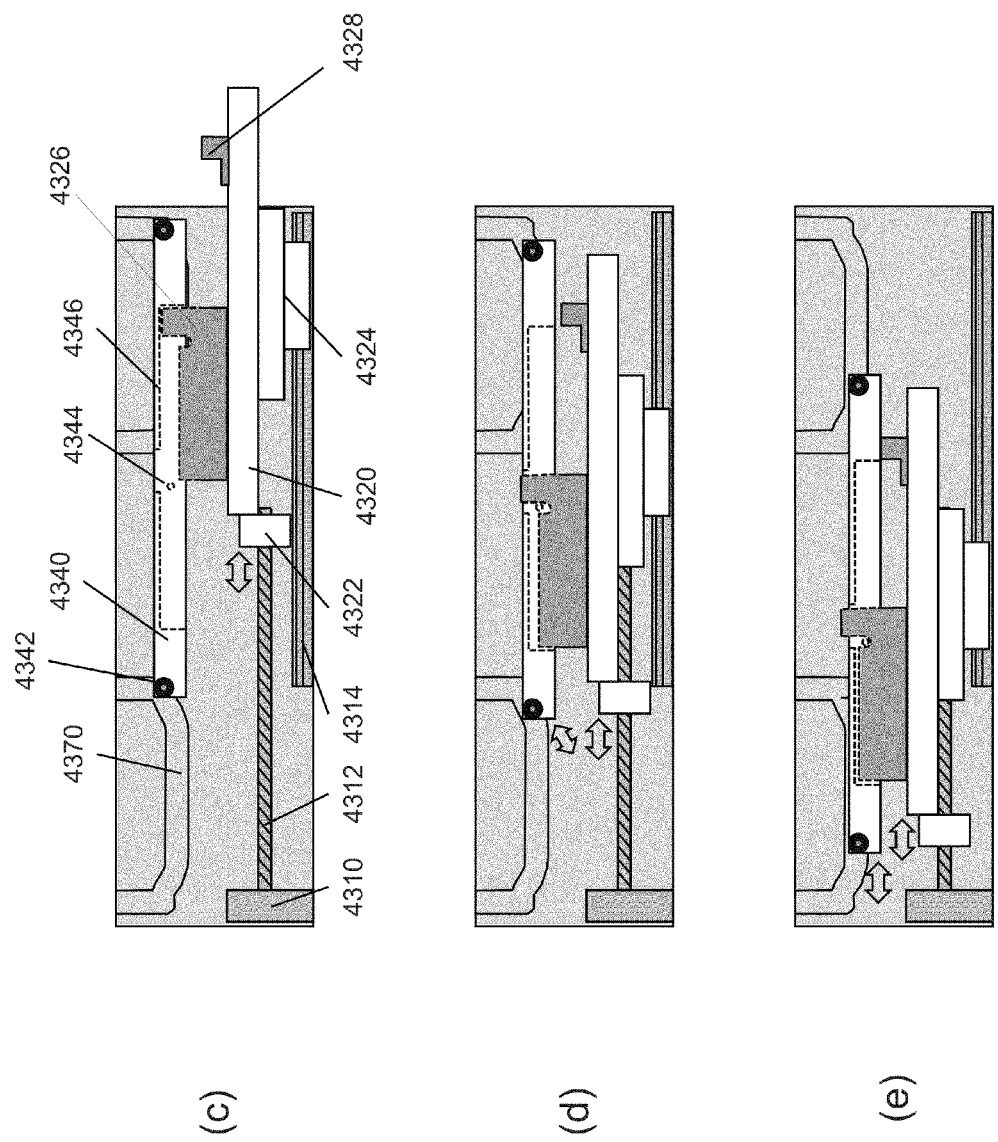
FIGS. 43(a)-(g) show cutaway views of one embodiment of a cartridge reader design with a cartridge tray in the fully extended and fully retracted positions (color FIGS. 43(a) and (b), respectively).
Figure 43F:
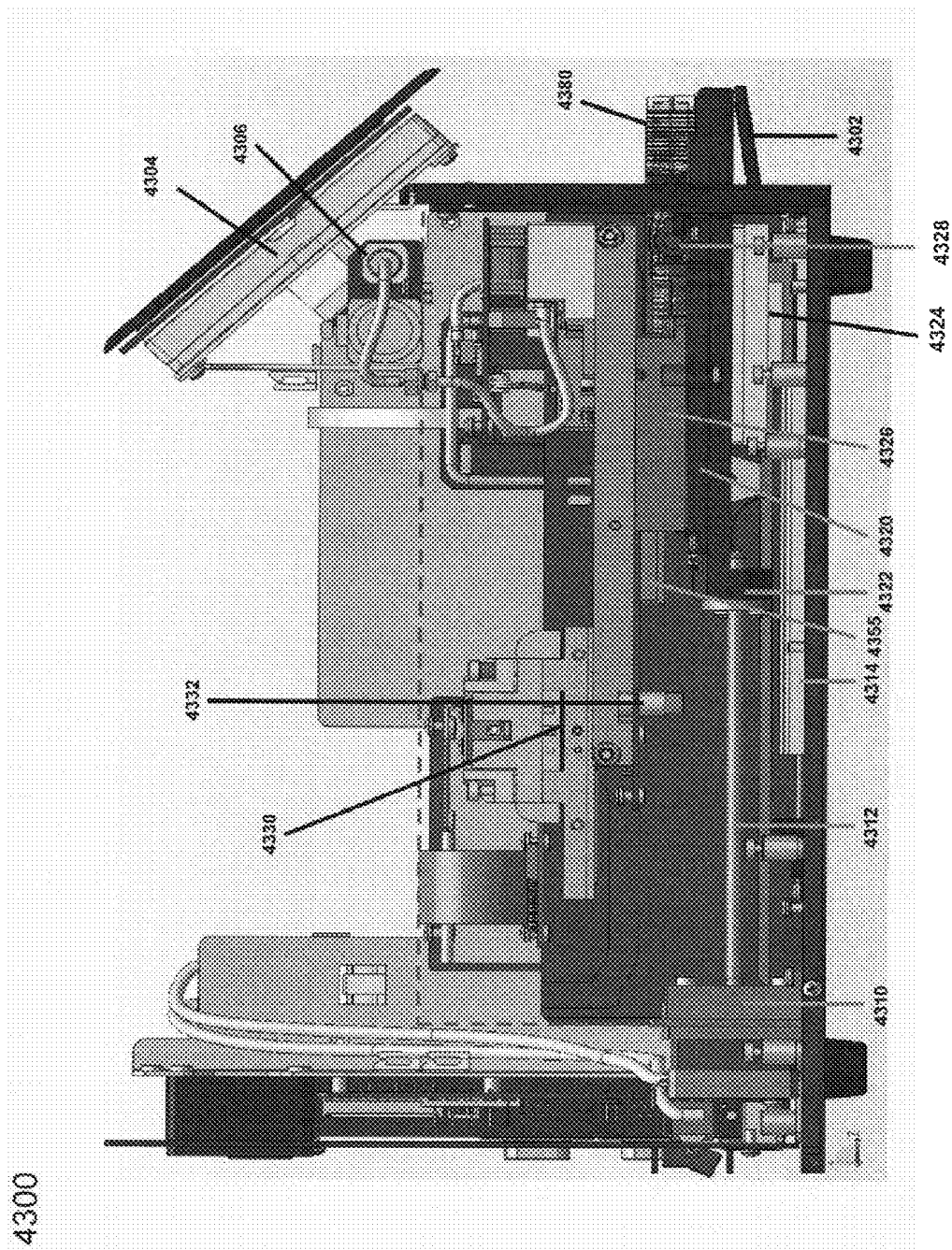
Figure 43G:
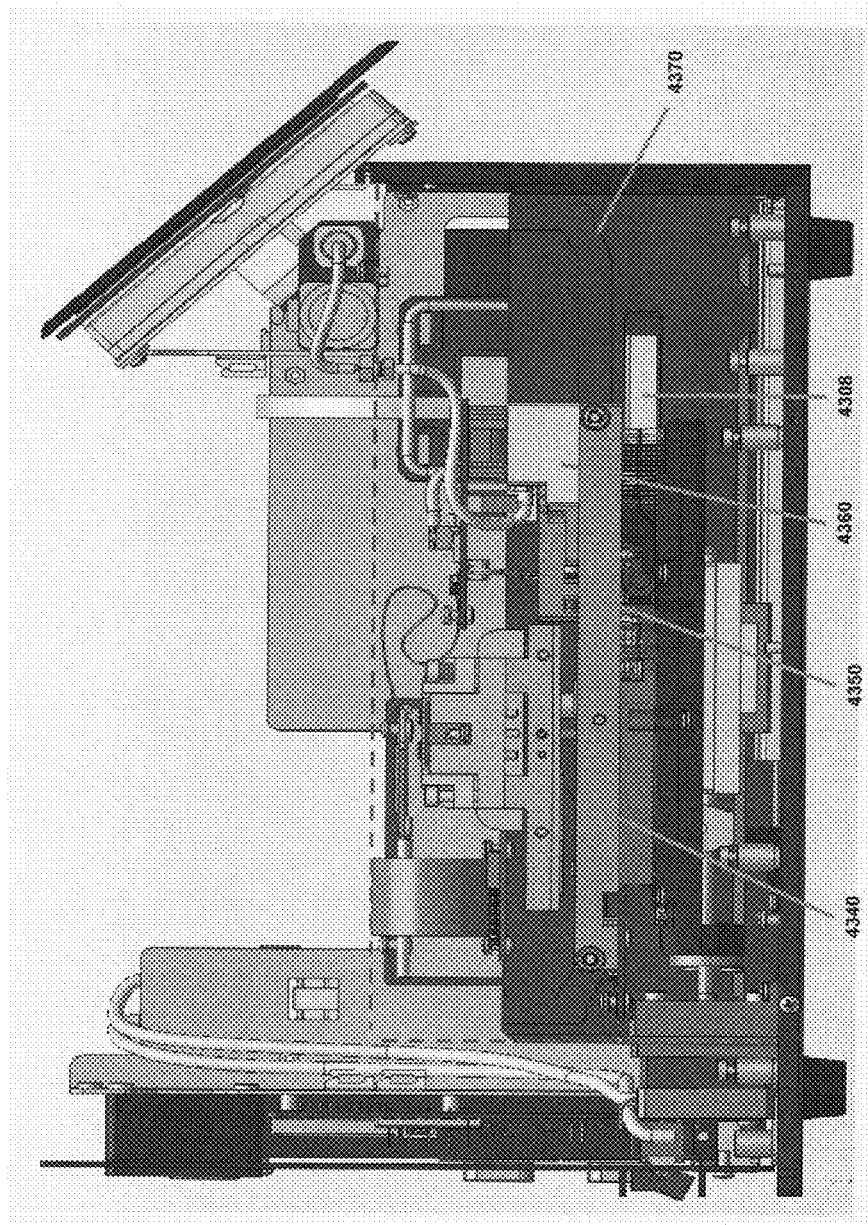

In accordance with another aspect of the present invention, a preferred cartridge reader is provided, as illustrated in FIGS. 43(*a*)-43(*g*). In this embodiment, a preferred cartridge reader receives the assay cartridge and moves the assay cartridge into a light-tight enclosure, where the amount of ambient light that enters the reader is minimized. A cartridge tray supports the assay cartridge on the bottom and a top mounting tray is guided to enable the assay cartridge to be accessed and analyzed by a plurality of reader components within the cartridge reader. A photodiode assembly having at least one photodiode is capable of moving in a direction that is substantially orthogonal to the direction of the assay cartridge to provide multiple degrees of freedom for the sampling of the assay cartridge.

Referring to FIGS. 43(*a*)-(*g*), a preferred embodiment of a cartridge reader is illustrated, which describes preferred approaches to loading and aligning assay cartridges in the reader. In FIGS. 43(*a*) and 43(*b*), cartridge reader 4300 is shown for clarity without the external case or housing and without the walls that define a light-tight enclosure within cartridge reader 4300 (the locations of which are shown as a dotted line). The reader includes cartridge tray 4320 for holding cartridge 4380, which may be a liquid sample or swab sample cartridge as described above, e.g., swab cartridge 3700 shown in FIG. 37(*b*). Tray 4320 is mounted, via guide block 4324 onto linear rail 4314 to provide for linear motion of the tray in and out of the light-tight enclosure. While the motion of tray 4320 is preferably linear, it is not so limited and rail 4314 and motion of tray 1320 can be along any paths, including linear, segmented or curvilinear paths. Movement of tray 4320 along the rail is driven by motor 4310 which turns lead screw 4312 and translates lead screw nut 4322 which is mounted on tray 4320. Other methods of moving tray 4320 can also be used. As cartridge tray 4320 is retracted from the fully extended position shown in FIG. 43(*a*), and the tray is pulled into the light-tight enclosure shown in FIG. 43(*b*), door 4302 closes to provide a light-tight seal to the light tight enclosure.

Therefore, cartridge reader 4300 is configured to analyze an assay conducted in an assay cartridge and the cartridge reader comprises (a) an enclosure; (b) cartridge tray for holding a cartridge during analysis in the cartridge reader; (c) a rail in the enclosure, wherein the cartridge tray is mounted on the rail such that the tray can move in and out of the enclosure by moving along the rail; (d) an actuator to move the cartridge tray along the rail; (e) a mounting frame in the enclosure, the mounting frame is configured to align the cartridge with one or more reader components; and (f) an alignment guide attached to the cartridge tray that is configured to engage with and control movement of the mounting frame. Cartridge reader 4300 includes a plurality of reader components, such as bar code reader 4308, which reads bar codes or other identifying information on the sides of cartridges as the cartridge tray is pulled into the reader. Other reader components present in the light-tight enclosure within cartridge reader 4300 include, but are not limited to, (i) photodiode assembly 4330, which supports at least one photodiode and aligns it with assay locations in the cartridge (which includes a photodiode optical coupler and shield, 4332), (ii) mounting frame 4340 on which is mounted ampoule breaking mechanism 4350, e.g., the ampoule breaker described in FIG. 42, (iii) electrode contact pin assembly 4355, which supports the conductive pins making electrical contact to the cartridge electrodes, and (iv) fluidic manifold 4360. Fluidic manifold 4360 includes fluidic connectors (not shown) that mate to the vent ports in the cartridge when the cartridge is fully inserted, e.g., using gaskets or o-rings to provide leak-free seals. The fluidic manifold is also linked to air cylinder pump 4306, which provides the pressure/vacuum source for driving fluid motion in the cartridge. Valves in the manifold determine whether a specific vent port on the cartridge is sealed, open to the atmosphere (ambient) or connected to the air cylinder. In one exemplary embodiment, the valves and fluid lines are configured according to the valve diagram in FIG. 37, which allows all the vent ports to be sealed or opened to ambient pressure and also allows the left waste, right waste, wash buffer and collection component ports, e.g., as described above in connection with cartridge 3700, to be connected to the air cylinder so as to allow for pushing or pulling of liquids in the cartridge from these ports. Cartridge reader 4300 also includes electronics, such as a microprocessor or computer for controlling the operation of the cartridge reader and a user interface (touch-screen 4304, a keyboard, a stylus or an electronic mouse). In addition, communication interfaces (RS-232, Ethernet, USB, etc.) may be provided for communicating with a network or Laboratory Information System. The cartridge reader may also provide interfaces to external memory devices such as memory cards, EEPROMs, REID devices, external hard drives, USB drives, etc. that may be used to import lot-specific parameters, e.g., assay identity information, lot-specific assay thresholds, calibration data, etc., associated with a lot of cartridges. Such memory devices could be provided as a separate component to a kit, e.g., a box containing one or more cartridges could come with one or more memory devices containing lot-specific parameters for the assay cartridges in the box. Alternatively, the memory device could be attached to the cartridge itself and cartridge reader 4300 is configured to read the lot-specific information when assay cartridge 4380 is inserted into the cartridge processing slot of the cartridge reader or into a separate memory reading slot. In this regard, reference is made to U.S. Provisional Application Ser. No. 61/271,873, filed Jul. 27, 2009, the disclosure of which is incorporated by reference herein in its entirety.

In the embodiment shown in FIGS. 43(a)-(b), the mechanical motions needed to properly move and position assay cartridge 4380 and to align reader components, e.g., the ampoule breaking mechanism 4350, fluidic manifold 4360, electrode contact assembly 4355 and photodiode assembly 4330, relative to assay cartridge 4380 are coupled to the linear motion of the cartridge tray 4320, allowing these operations to be carried out with a single motor 4310. The mechanical design that properly aligns the components on mounting frame 4340, including ampoule breaking assembly 4350 and fluidic manifold 4360, is illustrated in FIGS. 43(c)-43(e). Mounting frame 4340 includes rollers 4342 that each ride on separate tracks present in track walls 4370 on either side of the mounting frame. Only the track wall on one side of the mounting frame is shown to illustrate the moving components, and although multiple tracks 4370 are shown, a single track with multiple linear or non-linear segments can also be used. The tracks are roughly U-shaped and include, in order moving away from the front of cartridge reader 4300 or door 4302, an elevated shelf region, a descending sloping region and an extended flat region at the bottom of the U-shaped track. Movement of mounting frame 4340 is driven by alignment guide 4326 mounted on cartridge tray 4320.

When the cartridge tray is fully extended as shown in FIGS. 43(a) and 43(c), rollers 4342 of mounting frame 4340 are resting on the elevated shelf positions, keeping the mounting frame 4340 in an elevated position relative to the cartridge in the cartridge tray. As cartridge tray 1320 is initially retracted into cartridge reader 4300, alignment guide 4326 moves freely along groove 4346 in mounting frame 4340 without contacting or engaging mounting frame 4340, and the mounting frame remains stationary. As cartridge tray 4320 continues to retract, a vertical tab in alignment guide 4326 contacts pin 4344 mounted on mounting frame 4340 that spans groove 4346 and moves mounting frame 4340 at the same speed as the cartridge tray 4320. As best shown in FIG. 43(d), rollers 4342 descend along the descending portion of the tracks in the track wall 4370 shown by the oblique arrow. This descending movement causes pin 4344 to descend into a notch in the alignment guide 4326 adjacent to the vertical tab, and thereby provide precise alignment of mounting frame 4340 relative to cartridge tray 4320 along the axis of motion. In other words, at this stage mounting frame 4340 moves closer to cartridge tray 4320, and when pin 1344 is received within the notch in alignment guide 4326 and releasably held therewithin, the movements of mounting frame 4340 and of cartridge tray 4320 coincide with each other. FIG. 43(a) also shows guide 4328 that is used to guide the cartridge into the tray and ensure that the cartridge can be inserted into the tray only in the correct orientation. When mounting frame 4340 is at its lowest position, ampoule breaking assembly 4350 is properly positioned to break the ampoules in cartridge 4380 present in cartridge tray 4320; fluidic manifold 4360 is pressed down onto cartridge 4380 to provide leak-free seals to the cartridge vent ports; and electrode contact assembly 4355 is positioned so as to make proper contact to the cartridge electrodes. As cartridge tray 4320 retracts further into the reader, rollers 4312 ride in the extended flat portion of the track 4370, and mounting frame 4340 and cartridge tray 4320 remain in alignment and move at the same speed and direction, but allowing for positioning of specific assay locations, e.g., electrodes or array elements in the cartridge, under photodiode assembly 4330. Elevation and release of mounting frame 4340 during extension of the cartridge tray follows the reverse of the process described for retraction of the tray.

Figure 44B:
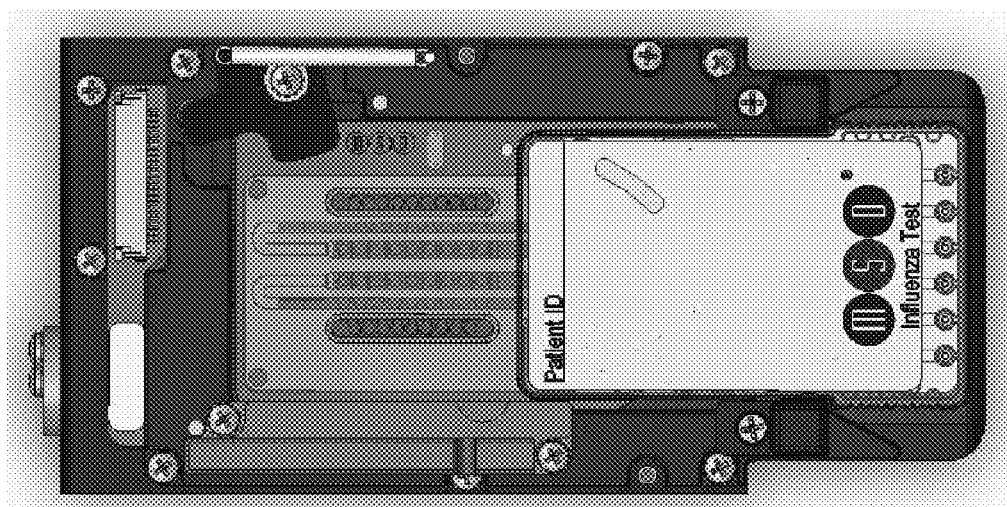

FIGS. 44(a)-(b) provide a top view of cartridge tray 4320 and illustrate features present on the tray to allow a user to reproducibly and accurately position and lock cartridge 1380 in place on cartridge tray 4320. FIG. 44a shows a cartridge that is partially inserted in the tray, similar to that shown in FIGS. 43(a) and 43(c). Cartridge 4380 has a skirt and preferably a narrow skirt along both sides of the cartridge that slides into slots along both sides of cartridge tray 4320. The back end of the cartridge is patterned to provide a visual and tactile cue to help the operator hold and orient the cartridge for proper insertion into the instrument. The skirt does not extend along the entire length of the cartridge but ends before this ergonomic zone. As cartridge 4380 is fully inserted into the tray, it also passes under cartridge latch 4420 and contacts pin 4424, which extends under latch 4420 causing the latch to pivot on its axis. This pivoting movement causes a second pin, pin 4426, to insert into notch 4382 on the side of cartridge 4380, releasably locking the cartridge into place, as shown in FIG. 44(b). Spring 4428 is initially stretched by the pivoting motion adding resistance to the rotating motion, and the stretching is reduced as the spring passes the axis of rotation and begins to aid in the rotation instead of resisting it. Pin 4426 is inserted in the notch, thus transferring the spring force to the cartridge and drawing the cartridge in until it meets a reference surface. The spring force maintains the cartridge the locked position and provides positive feedback to the user that the cartridge is correctly positioned. The user may pull the cartridge out of the tray by providing a pulling force sufficient to compensate for the spring force keeping the cartridge in the locked position.

Latch 4420 has tab 4422 that in the locked position shown in FIG. 44(b) covers optical sensor 4430 to enable cartridge reader 4300's electronics to check that the cartridge is correctly inserted. The tab may have a pin (as shown in the figure) that extends down toward the sensor to provide a stronger optical signal. The tray has additional optical sensors as indicated in FIG. 37(b) and associated text) including sensors 1110 for use in controlling the movement of fluid slugs in the cartridge. Cartridge tray 4320 may also include integrated heaters (not shown) for maintaining the cartridge at set temperatures during processing. The vertical guides have lateral cutouts that allow the thin skirt region of the cartridge to be inserted but not the tall ergonomic zone. This ensures that the cartridge can be inserted in only one orientation into the instrument. Optionally, the cartridge tray is coated with a water resistant seal to prevent any fluid leakage from affecting the optical sensors and other electronics in cartridge tray 4320. The seal material (which may be a polymeric film) transmits infra-red light used by the optical sensor. Preferably, the seal does not transmit visible light. FIG. 44(a) also shows alignment guide 4326 and vertical guides 4328a and 4328b on each side of the tray, as described above. Optionally, as the cartridge is inserted into cartridge tray 4320, a cartridge cap passes in close proximity to a surface of cartridge tray 4320, shown in FIGS. 44(a)-(b) as a surface of vertical guide 4328a, so as to prevent insertion of a cartridge that is not properly capped.

Figure 45:
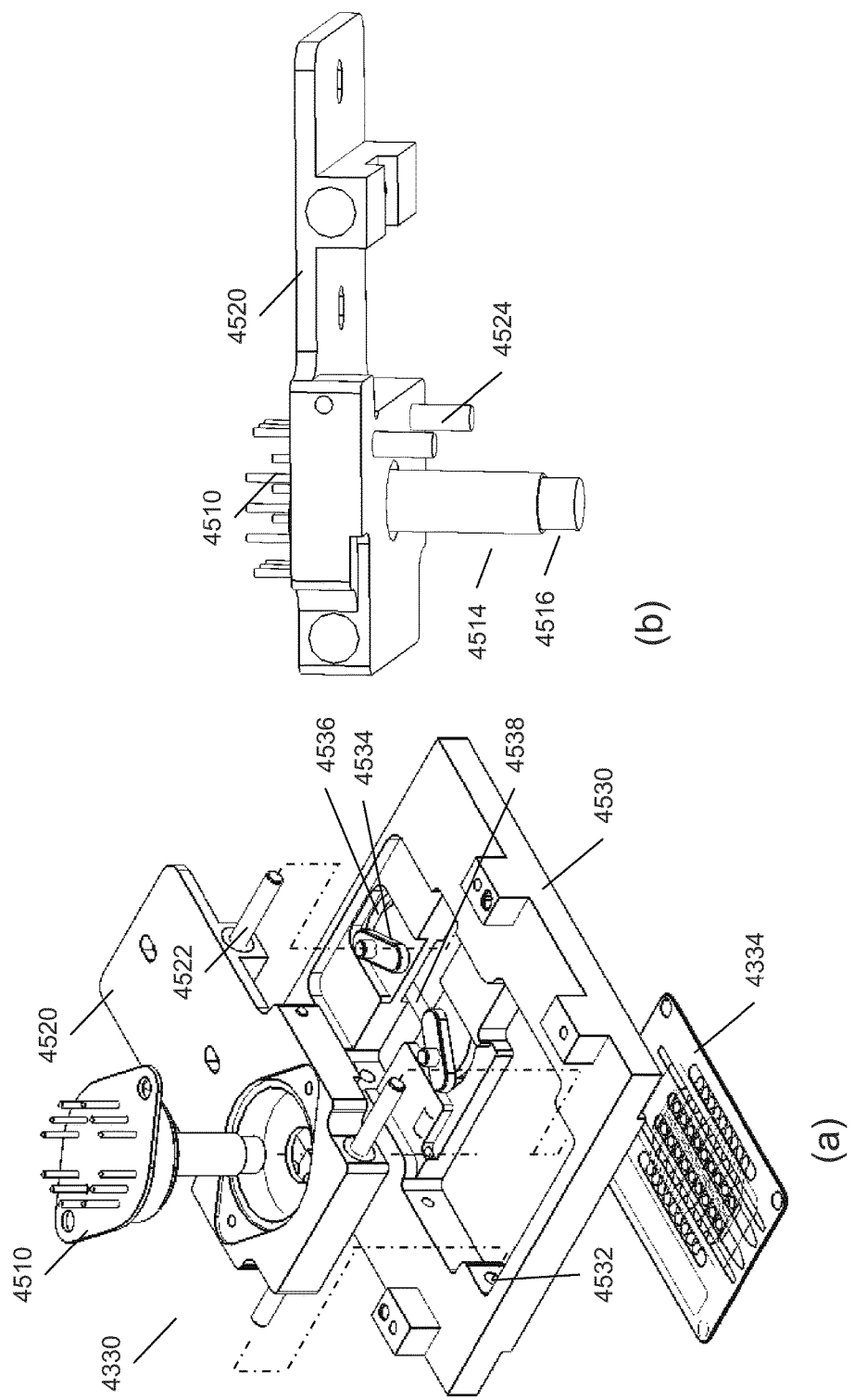
FIGS. 45(a)-(b) show one embodiment of a mechanism for supporting a photodiode within a cartridge reader and for aligning the photodiode with array elements or electrodes within the cartridge.

FIGS. 45(a)-(b) provide two views of components of photodiode assembly 4330 that are used to align photodiode 4510 with specific assay regions on cartridge 4380. Photodiode 4510 is mated to optical coupler 4516, a light guide used to maximize the efficiency of light collection while not requiring photodiode 4510 to be located directly adjacent to cartridge 4380. Most of the length of optical coupler 4516 is surrounded by cylindrical conductive shield 4514 to shield the photodiode from capacitive pickup. Photodiode 4510 is mounted in traveler block 4520, which can translate side-to-side or in a transverse direction along guide cylinders 4522 which are slidingly mounted into photodiode assembly frame 4530. Traveler block 4520 is spring loaded such that traveler block 4520 latches at the two extreme side-to-side positions and a force sufficient to overcome the spring force must be applied to move the traveler from one side to the other. In one embodiment, this spring force is provided by latching levers 4534 mounted in photodiode assembly frame 4530. Pins on levers 4534 engage slots in assembly frame 4530 such that the side-to-side motion of the traveler block causes the latches to pivot and stretch spring 4538. Electrodes 4334 from the electrode array of cartridge 4380 are shown in the exploded view of FIG. 45(a) to show their positions relative to photodiode 4510.

Figure 46:
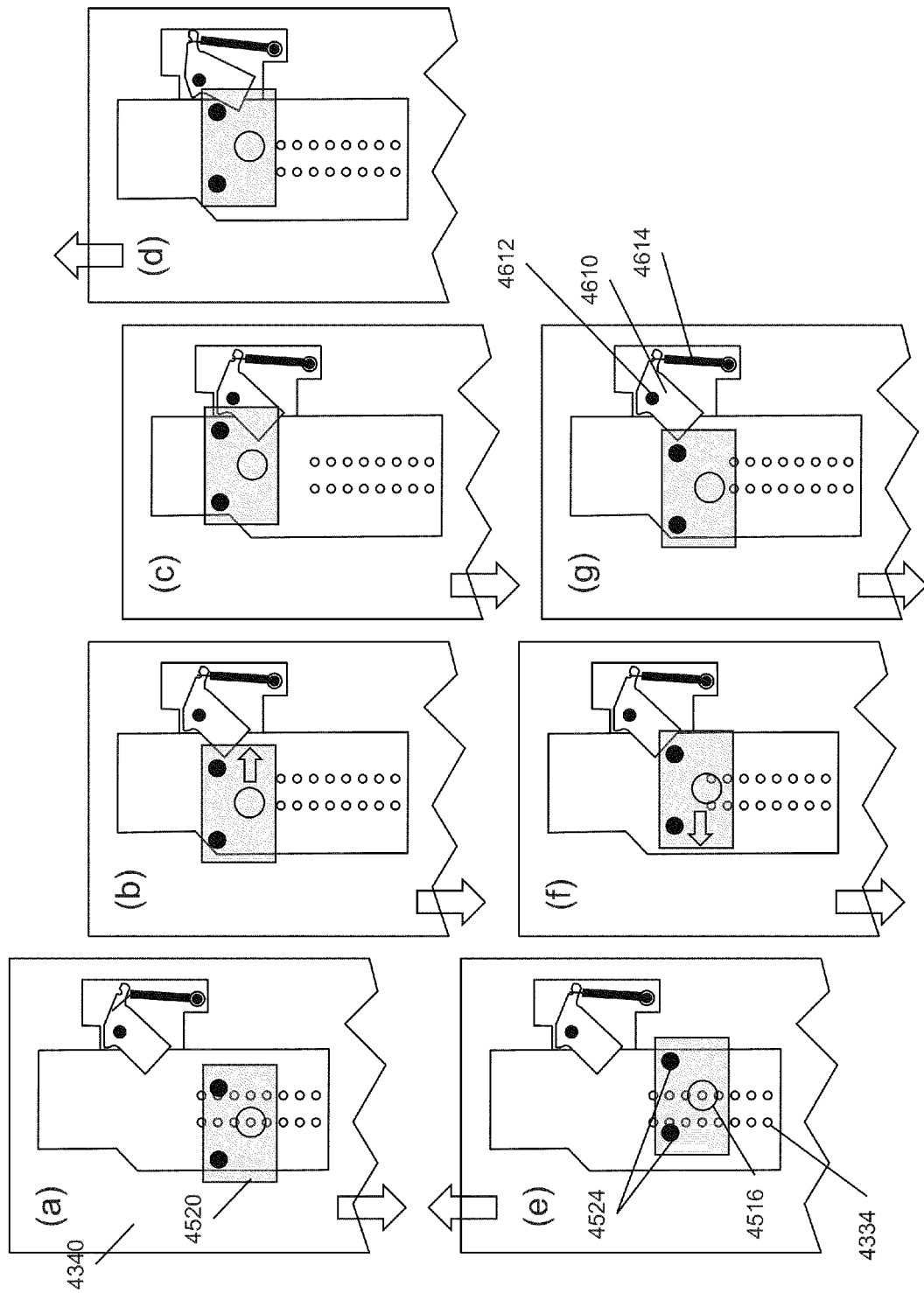
FIGS. 46(a)-(g) show a schematic representation of the operation of the photodiode alignment mechanism of FIG. 45.

Traveler block 4520 as shown in FIG. 45(b) illustrates photodiode positioning pins 4524, which extend downwardly from traveler block 4520 and couple the motion of mounting frame 4340 to the side-to-side motion of the traveler block. This coupled motion is shown schematically in FIGS. 46(a)-(g). When mounting frame 4340 is in the lowered position, as shown in FIGS. 43(d) and (e), movement of cartridge tray 4320 along its axis causes an inserted cartridge 4380 represented schematically by two linear arrays of electrodes 4334, and mounting frame 4340 to move or translate at the same speed. In FIGS. 46(a)-(g), traveler block 4520 is represented by a rectangular shape, and positioning pins 4524 are represented by two dark spots. In FIG. 46(a), traveler block 4520 is positioned in the leftmost position and movement or translation of cartridge tray 4320 aligns the photodiode or preferably optical coupler 4516 with any of the electrodes in the left flow cell. As the cartridge tray is moved toward the extended position shown in FIG. 46(b), traveler block 4520 remains in the left position until left positioning pin 4524 hits a slanted control surface defined in mounting frame 4340, driving traveler block 4520 to the right position, as shown in FIG. 46(c). Retraction of the tray can be used to align the photodiode or optical coupler 4516 with electrodes in the right flow cell. During this movement, right positioning pin 4524 contacts spring loaded pivot cam 4610, which is mounted on mounting frame 4340, causing pivot cam 4610 to pivot around pivot 4612, as shown in FIG. 46(d). The spring three provided by spring 4614 is selected to be low enough that the traveler block remains in the rightmost position, as shown in FIGS. 46(d) and 46(c). As shown in FIGS. 46(f) and 46(g), traveler block 4520 is shuttled back to the far left position by extending the tray until right positioning pin 4524 contacts a slanted control surface located on the bottom of pivot cam 4610 driving traveler block 4520 to the left position, as shown in FIG. 46(f). As shown, pivot cam 4610 is mounted such that it can pivot in response to a retracting tray but not in response to an extending tray. 1n other words, pivot cam 4610 slips or pivots when cartridge tray 4320 retracts as illustrated in FIGS. 46(c)-(d), but remains rigid to push traveler block 4520 when cartridge tray extends as illustrated, in FIGS. 46(e)-(f).

Figure 26A:
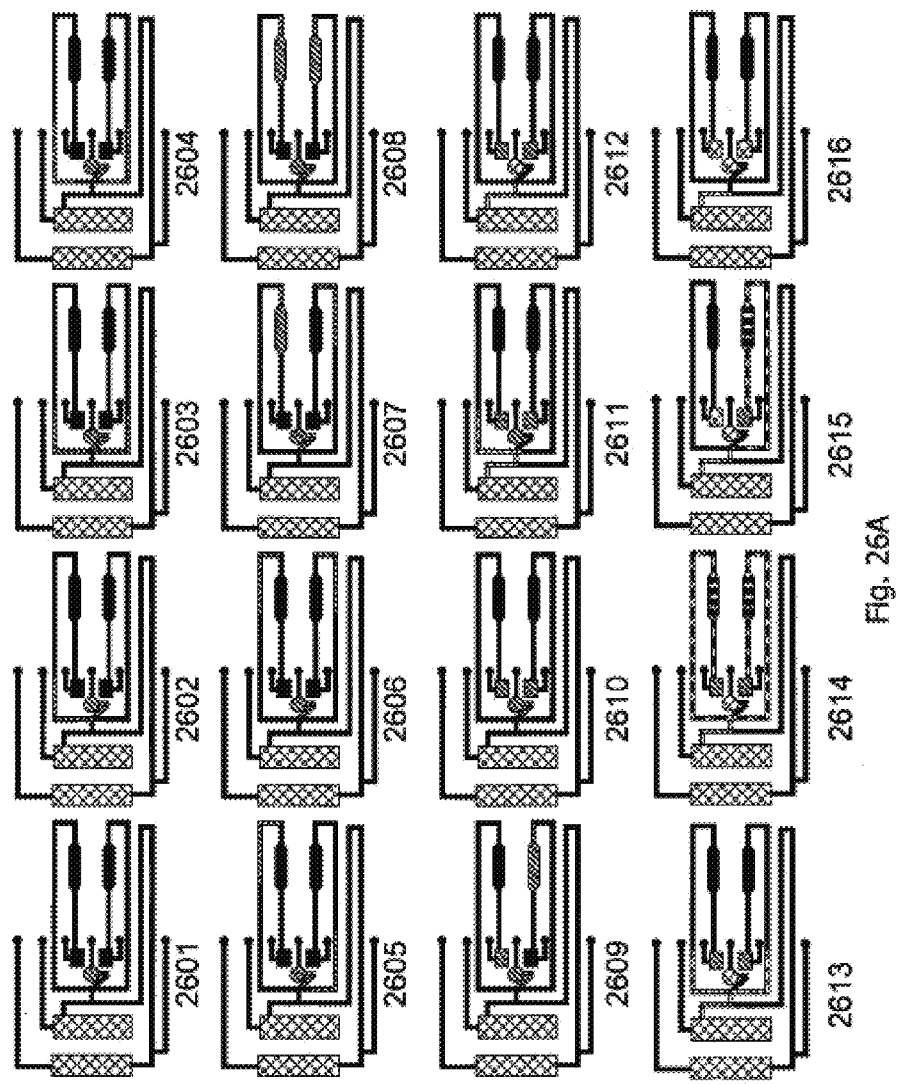
FIGS. 26a through 26c illustrate one preferred manner of operating the assay cartridge depicted in FIG. 25.
Figure 26B:
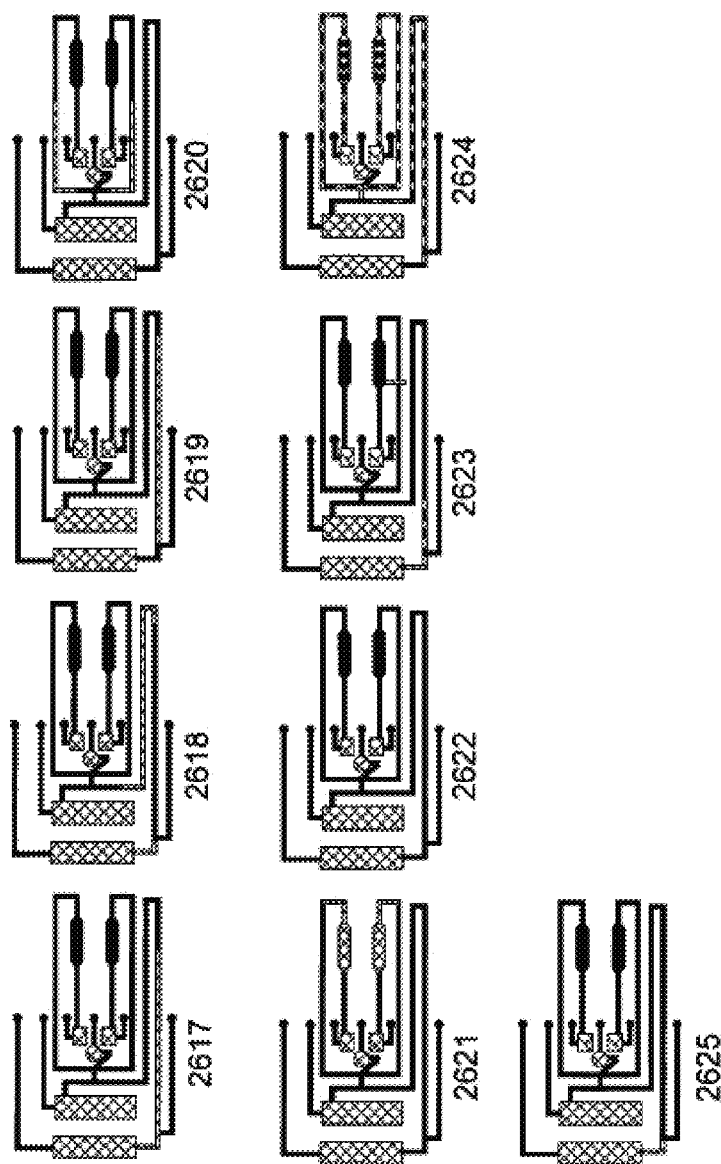
Figure 26C:
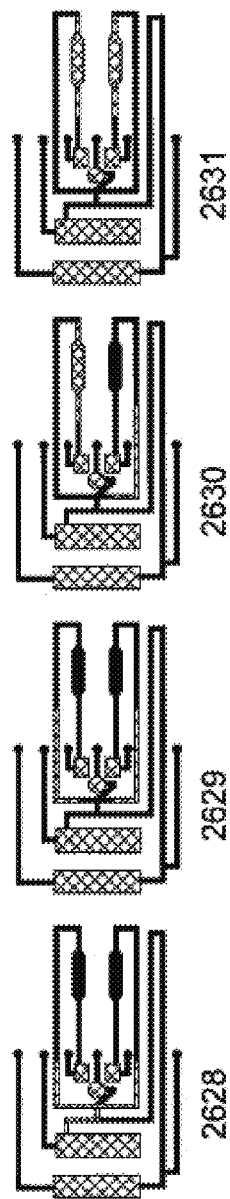

With reference to FIGS. 24 through 26, performance of an assay using a preferred cartridge of the invention will be described. This exemplary method will be described in the context of a two-step multiplexed binding assay using antibodies as binding reagents and ECL as the detection methodology, however, it will be readily apparent to the skilled practitioner that the described fluidic operations can be used in a variety of different assay formats (e.g., binding assays using other classes of binding reagents, enzymatic assays, etc.) and with a variety of different detection technologies. It is also apparent that the sequence of operation discussed below may vary according to differences in the configuration of a particular cartridge as well as differences in the particular assay to be performed.

During operation, the pump vent line valve may be used to enable and disable pressurization of the system for more precise fluid control; when the pump's vent is opened, the system returns to ambient pressure very quickly. Typical fluid draw operations, i.e., routing of fluid within and throughout the fluid network, involve closing the pump vent valve and opening i) one or more (preferably, one) cartridge vent valves, e.g., the sample, air, reagent chamber A and/or reagent chamber B vent valves and ii) one or more (preferably, one) control valves, e.g., waste chamber A or waste chamber B control valves. Therefore, a slug of fluid will move along a path through the fluid network in the cartridge when the fluid channels comprising that path is vented to air at one end and subjected to either pressure or vacuum at the other end.

A user selects the appropriate cartridge for carrying out a desired measurement and introduces sample to the sample introduction port of a cartridge and, preferably, seals a closure on the sample introduction port. The cartridge is inserted into the cartridge reader. Preferably, the cartridge will include features that ensure the cartridge is inserted in the proper orientation; e.g., by incorporating identifying marks to show which direction it should be placed on the tray and/or mechanical features that guide the user to place it in the correct orientation. After the user has successfully prepared and inserted the cartridge, reading/processing of the cartridge is performed by the cartridge reader upon receiving an indication from the user that the read cycle should commence (alternatively, the reader may automatically begin operation upon confirming that a properly prepared cartridge has been properly inserted into the cartridge reader). The subsequent reading of the cartridge is preferably automated; e.g., the cartridge reader's electronic control system (computerized control system or the like) automatically processes and reads the cartridge.

The automated sequence of operations to be performed by the cartridge reader will now be described. Preferably the cartridge includes machine readable indicia, e.g., barcode, that is detected and processed by the cartridge reader. For example, processing of the machine readable indicia may allow the cartridge reader to verify that a valid, readable barcode has been detected and thereafter determine the operational parameters for the present read cycle; i.e., determine the set of assays/tests to be performed, extract any relevant instrument configuration parameters and verify the expiration date. In certain preferred embodiments, the cartridge reader may prompt the user for any data that it requires; e.g., operator ID, sample or patient ID, and the like. Additionally, if the cartridge is capable of running a panel of test, the user may be able to select which test(s) within the panel should want be performed.

Preferably, the reader has a cartridge handling subsystem that mechanically engages the cartridges and moves/aligns it into position. Preferably, this process includes positioning the cartridge within a light-tight enclosure. The reader also makes the appropriate fluidic and/or electronic connections to the cartridge and, optionally, breaks or pierces any reagent modules (e.g., reagent ampoules) present in cartridge reagent chambers. As discussed above, in one preferred embodiment, the cartridge handler's motion would be physically coupled to the fluidic and electronic handlers (and, optionally, the reagent module release mechanism) such that upon positioning the cartridge within the light tight enclosure the electrical contacts and the fluidics manifold engage the cartridge at their respective engagement points (and, optionally, the reagent module release mechanisms releases reagent from any reagent modules). Next, where required or preferred, the electronic control system begins operating a heater in order to bring the cartridge to the appropriate predetermined temperature and maintain the cartridge at such target temperature. In certain preferred embodiments temperature regulation may be controlled by a microprocessor employing a proportional derivative control to control a heater that will maintain the target temperature; preferably a suitable algorithm is employed.

Once the cartridge has been maintained at the target temperature for a predetermined amount of time, the fluid handler may begin processing the cartridge for reading; i.e., assemble the assay. Reference to FIG. 26 will be made to illustrate the intermediary states of the cartridge reader and the position of fluid within the fluid network of cartridge 2500 during a 2-step assay format. As presented in FIG. 26, the starting state of the cartridge 2500 (panel 2601) is illustrated and depicts the location of the constituent fluids within the fluidic network. Assay assembly preferably consists of metering specific volumes of sample fluid, reconstituting dried reagents in the sample fluid and incubating the sample fluid in the detection chambers. Predetermined valves are opened in a prescribed sequence in accordance with the desired fluid flow paths to be assumed by the constituent fluids.

According to the present embodiment in which two read chambers are present and will be utilized for testing the sample, two equal lengths of sample fluid (i.e., slugs) will be drawn; the length of the sample slugs is determined by the volume of the read chambers. The sample slugs are delimited from one another by introducing a slug of air between the two sample slugs. Accordingly, sample chamber vent valve 2412 and a waste chamber vent valve 2442A are opened and the pump vent is closed. The pump is subsequently activated to aspirate/draw the sample from sample chamber 2510 (preferably, overcoming a capillary break provided by a Z-transition that is used to prevent leakage of the sample from the sample chamber) into sample conduit branch 2515A. In this and other pumping steps, a pressure sensor (not shown), preferably, detects the pressure created by the operation and provides confirmation that the pump is aspirating/dispensing fluid properly. When fluid is detected at sensor 3 (see FIG. 26, 2602), the pump vent valve is opened and the pump motor is deactivated. The sample chamber vent valve 2412 and waste chamber vent valve 2442A are then closed. Similarly, sample is drawn into sample conduit branch 2515B by operating the pump with sample chamber vent valve 2412 and waste chamber B vent valve 2442B open (see FIG. 26, panel 2603). Defined slugs of sample fluid are drawn into the sample conduit branches by operating the pump with air vent valve 2422 open as well as the waste chamber A and B vent valves 2442A-B (see FIG. 26, panel 2604). In this and subsequent steps, two slugs may be moved simultaneously through sample conduit branches 2515A and B by holding both waste chamber vent valves open or sequentially through the branches by opening one at a time.

The sample conduit branches, preferably, comprise dry reagent pills (preferably containing one or reagents selected from blocking agents, pH buffers, salts, labeled binding reagents, and the like). One or more of the conduit branches may also comprise spiked analyte for spike recovery controls. In order to reconstitute the dried reagent, the two sample fluid slugs are moved back and forth across the pill zone a predetermined number of times by opening air vent valve 2422 and waste chamber vent valves 2442A and/or B and operating the pump to alternate between applying positive and negative pressure to the waste chamber vents (FIG. 26, panels 2605-2606). The two sample fluid slugs may be moved back and forth simultaneously or mixing of the two slugs may be accomplished in series. The number of repetitions that the sample fluid is cycled across the pill zone may be dependent upon a number of factors, including but not limited to, size/volume of reagent dried reagent pill, composition of reagent pill, drying method employed at the time of reagent deposition/pill formation, and the like. In accordance with preferred embodiments, the number of repetitions that need to be carried out by the fluid handler subsystem can be cartridge specific and can be automatically ascertained by the cartridge reader from the information encoded in the machine-readable indicia affixed/incorporated onto the cartridge. The number of repetitions may be predetermined through empirical results but may also be determined in-situ through the use of one or more sensors adapted and configured to measure the degree of mixing of the reagent(s) and sample fluid; e.g., use of optical sensors (transmittance or reflectance), electrical sensors (impedance, conductance, resistance, and the like).

The sample fluid slugs are now moved into their detection chambers 2550A and 2550B by operating the pump with air vent valve 2422 and waste chamber vent valve 2442A open until the sample slug is detected at sensor 7 and by operating the pump with air vent valve 2422 and waste chamber vent valve 2442B open until the sample slug is detected at sensor 8 (FIG. 26, panels 2607-2608). The sample slugs are incubated in the detection chambers to allow constituents of the sample (e.g., labeled binding reagents, analyte, control analyte, etc.) and immobilized binding reagents within the detection chamber to bind to form binding complexes in the detection chamber. Preferably, a mixing operation is employed to enhance the rate of these binding reactions. Preferably, mixing is achieved by moving the fluid slugs back and forth in the detection chamber by a process analogous to that described for reconstituting the reagent pill (optionally, using sensors 1, 2, 11 and 12 to provide stopping points in each direction). The aspirate and dispense operations are repeated a predetermined number of times, or until the degree of mixing desired has been achieved/detected. After completion of the incubation step, the air and waste chamber vent valves are used to draw the slugs out of the detection chambers and into waste chambers 2540A and B (FIG. 26, panels 2609-2610).

Preferably (as shown), the assay process includes a wash step for removing sample and unbound labeled reagents from the detection chamber. The wash uses a wash reagent (preferably, a buffered solution, more preferably comprising anon-ionic surfactant such as Triton X-100 and most preferably comprising an ECL coreactant such as TPA or PIPES) stored in reagent chamber A 2530A. If the wash reagent is in a reagent module (preferably, ampoule) and the module hasn't been opened, it is opened now. Optionally, the remaining sample fluid is first routed back into the sample chamber to prevent contamination of the wash reagent: first wash reagent is drawn from reagent chamber A 2530A into one of the sample conduit branches by operating the pump to apply negative pressure with reagent chamber A vent valve 2432A and the corresponding waste chamber vent valve 2442A or B open and, preferably, overcoming a capillary break provided by a Z-transition in the reagent conduit); then excess sample is drawn into the sample chamber by operating the pump to apply positive pressure to the waste chamber vent with the sample chamber vent valve open (FIG. 26, panels 2611-26120. Wash reagent is then drawn from reagent chamber A 2530A, through detection chambers 2550A and 2550B and into waste chambers 2540A and 2540B by operating the pump with reagent chamber A vent valve 2432A and waste chamber vent valves 2442A and/or 2442B (simultaneously or sequentially) open (FIG. 26, panels 2613-1616). As shown, in particularly preferred embodiments, the wash fluid may be segmented, i.e., broken up by one or more slugs of air. It has been observed that wash fluid alternating with air within the detection chambers increases the effectiveness of the clean cycle. Segmenting the wash fluid can be accomplished by periodically and temporarily opening the air vent valve 2422 and simultaneously closing the reagent chamber A vent valve 24324 so that air is drawn into the sample conduit. Timing and duration of these operations would dictate the size and frequency of the air slugs introduced into the segmented wash fluid slug.

In the two step format, one or more labeled detection reagents may be incubated in the detection chambers in an additional incubation step. Preferably, the detection reagent solution is prepared by reconstituting a dry reagent pill comprising the detection reagents with an assay diluent contained within reagent chamber B 2530B. If the assay diluent is in a reagent module (preferably an ampoule) and it is not already broken, it is broken now. The assay diluent is drawn into elongated reagent conduit 2535 by aspirating at one of the waste chamber vents while opening reagent chamber B vent valve 2432B until the assay diluent reaches sensor 13 (FIG. 26, panel 2617), A defined volume of assay diluent is prepared by closing reagent chamber B vent valve 2432B and opening air vent valve 2422 and continuing to aspirate at the waste chamber vent; reconstitution of the dry reagent in the elongated reagent conduit is promoted by alternating the pump between positive and negative pressure so as to move the slug back and forth over the dry reagent pill (FIG. 26, panel 2618-2619). In a process analogous to the introduction of sample to the detection chambers, the slug of detection reagent solution is i) distributed between the sample conduit branches 2515 A and B, ii) introduced to the detection chambers (2550 A and B), incubated in the detection chambers while moving the slugs back in forth in the chambers to increase the rate of the binding of the detection reagents to immobilized assay components in the chambers, and iii) expelled from the detection chambers to the waste chambers 2540 A and B (FIG. 26, panels 2620-2622). Optionally, residual detection reagent solution is washed from the detection chambers 2550A and B by aspirating at the waste chamber vents with the reagent chamber B vent valve 2432B open (and, preferably, alternating opening reagent chamber B vent valve 2432B and air vent valve 2422 so as to segment the fluid stream) and then with air vent valve 2422 continuously open to draw the excess assay diluent into the waste chambers (FIG. 26, panels 2623-2625). Alternatively, washing can be accomplished using the wash reagent by repeating the steps in panels 2613-2616.

To provide an appropriate environment for the ECL measurement, detection chambers 2550A and 2550B are filled with the wash reagent (which preferably, is an ECL read buffer comprising an ECL coreactant). Accordingly, wash reagent is introduced into the detection chambers by operating the pump with reagent A chamber vent valve 2432A and waste chamber vent valves 2442A and/or 2442B open so as to aspirate wash reagent into sample conduit branches 2515A and 2515B. Operating the pump with air vent valve 2422 and waste chamber valves 2442A and/or 2442B open introduces slugs wash fluid into the detection chambers (FIG. 16, panels 2628-2631). The above assay is described for a two-step assay that employs two binding steps. An analogous protocol may be used for a one step protocol with one binding step, preferably, by omitting the steps in FIG. 26, panels 2617-2625. In the one step format, all the detection reagents used in the assay are, preferably, stored as dry reagents in sample conduit branches 2515A and 2515B so that they are reconstituted during passage of the sample through the branches. Optionally, reagent chamber B 2530B may be omitted.

Preferably, an ECL measurement is conducted by stimulating/firing working electrodes in the detection chamber. Preferably, the immobilized binding reagents of the detection chambers are immobilized on one or more working electrodes, more preferably on an array of electrodes, most preferably an array of electrodes configured to be fired in a pair-wise fashion (as described above). Electrical potential is applied to the working electrodes to stimulate ECL, preferably in the pair-wise fashion discussed above. The light so generated is detected using an optical detector, e.g., using a photodiode or the like. The cartridge and/or light detector may be moved during the pair-wise firing process so as to align the active electrode with the light detector. Optionally, an array of light detectors or a sufficiently large light detector is used so that movement of the cartridge and/or light detector is not required, Predefined assay-specific conversion parameters may be used to derive concentrations/results from the measured ECL counts; e.g., empirically derived from test data or computed from theoretical predictions/models. In particularly preferred embodiments different types of cartridges may have different electrode patterns but would preferably employ a common cartridge electrode contact pattern/area. Some of the electrode contacts may not be used for lower density cartridge formats.

A preferred sequence of operations that one embodiment of the cartridge reader may employ for firing each read location will now be described. The discussion will reference a photodiode as the optical detector but it should be understood that any suitable optical detector know in the art may be employed. The photodiode assembly (or alternatively, the cartridge) is moved into position; e.g., to the appropriate side of the cartridge's electrode array. The cartridge is then positioned such that the first read location to be processed is brought into a predetermined alignment position with the photodiode (e.g., positioned in registered alignment) and electrical contact is made to the electrode contacts. Once the contact has been made, the reader preferably performs a diagnostic measurement to detect potential anomalies that may interfere with proper operation of the electrode array and/or its components (leads, contacts, electrodes, etc.). Anomalies that are preferably detected include manufacturing defects, surface bubbles, or the like. This diagnostic measurement may be accomplished by preferably applying either a 500 Hz AC voltage or a very low voltage (e.g., less than 100 mV), low current (e.g., less than 1 µA) DC signal to the electrodes and measuring the surface capacitance. An appropriate predetermined algorithm could then be utilized to determine the presence and/or effect of any such anomalies; e.g., compare measured signal to fixed thresholds, or the like. Preferably, if anomalies are detected, the cartridge reader would record the error and proceed accordingly; e.g., if the anomaly is isolated to a particular electrode/electrode pair, the cartridge reader would skip reading this location and proceed to the next pair and/or next operation. Upon confirming operational status, ECL from the first pair of electrodes is initiated by application of a voltage waveform; data acquisition from the light detector is also begun. After completion of the ECL measurement, the cartridge/light detector are realigned to measure ECL from the second electrode pair and the ECL induction/measurement process is repeated. The cycle is repeated for each electrode pair to be analyzed.

In certain preferred embodiments, once a full set of data points has been acquired, the cartridge reader can either store the acquired data later retrieval/inspection, preferably on machine readable storage medium, and conclude the read cycle by performing the necessary finalization steps (detailed below) or can post-process, preferably performed in real-time, the acquired data and store either the post-processed data alone or in combination with the raw acquired data. Since it is often times important to inspect raw data (e.g., troubleshooting, diagnostics, data cleansing/filtering, and the like), where data is stored only in post-processed format, the corresponding parameters utilized in converting the data may be stored as well so that the raw acquired data can be computed/determined as needed. Alternatively, both the raw acquired data as well as the post-processed data may be stored. Still further, the raw acquired data may only be subjected to a subset of predetermined data conversion/analysis operations in real-time and stored for further post-processing offline, i.e., not in real time; post-processing can be performed by the cartridge reader itself or another device, e.g., a general purpose programmable computer.

In certain preferred embodiments employing ECL detection technology, data conversion/analysis operations may include one or more of: background subtraction; conversion to ECL counts; conversion of ECL counts to concentrations; and/or performance of quality checks on the acquired data.

Since it is preferable that the resulting data set represents only the light generated by ECL background subtraction is employed to adjust the measured light to correct for the influence of ambient light or "background" signal. Background subtraction consists of subtracting the background signal from the photodiode signal.

ECL counts are preferably converted to concentrations using predetermined calibration parameters; calibration parameter may be dependent upon one or more factors, e.g., the particular assay/assay format to be performed within the cartridge, the assay reagents employed, the detection technology/techniques employed, cartridge configuration, and the like. Preferably, the calibration parameters are ascertained from machine readable indicia associated with the cartridge, e.g., a barcode affixed to or inscribed on the cartridge body, it should be recognized that conversion to ECL counts can occur in a number of differing ways, including, converting all the acquired data points after acquiring all data, converting each individually acquired data point as it is acquired, converting groups/groupings of acquired data points (e.g., if the cartridge employs a dual read chamber design, converting to ECL counts upon acquiring the data for each read chamber), etc.

In certain preferred embodiments it is preferable to perform quality checks, i.e., assess the quality of the acquired data. Where ECL detection technology is employed, useful quality checks can be performed on the acquired voltage and current data, including: short circuit detection; open circuit detection; voltage following confirmation; and peak current detection. For open and short circuit detection, the output voltage and monitored current are preferably integrated for each acquired data point and the ratio of these two values current relative to applied voltage can then be compared against threshold values; these threshold values may be assay-dependent. Results with very low relative current are preferably flagged as probable open circuit conditions while results with very high relative current are preferably flagged as probable short circuits. This information can be stored in relational form for later review/consideration. Alternatively, if either condition is detected, the results can be considered invalid and concentrations for those measurements not reported/computed.

In the case where a voltage following quality assessment is to be employed, each point of the acquired voltage waveform is preferably compared to its corresponding point in a sampled output waveform. Preferably, a predetermined fixed voltage following limit value is defined for the instrument (i.e., cartridge reader/cartridge) and if any pair of points differs by more than that predetermined value (i.e., $|v(t)_{defined} - v(t)_{measured}| <$ voltage following limit), the results are preferably flagged or considered invalid. If the results are flagged, this information can be stored in relational form for later review/consideration. If the results are considered invalid, the computed results for those data points are preferably not reported/computed.

Finalization of the cartridge read operation can occur once all of the requisite measurements have been made and all the requisite fluid processing has occurred (e.g., once the final measurements have been made, route all remaining fluid(s) within the channels and/or read chamber(s) into the waste chamber(s)) the cartridge may be ejected from the reader. The cartridge ejection operation preferably occurs in reverse of the operation used to draw the cartridge within the reader. Specifically, the cartridge reader controller ensures that the pump vent is open and that all other valves are closed. Confirmation that the pump is stopped and all electrode contacts are tri-stated is obtained and, if a cartridge heater is present and employed, deactivate the cartridge heater. The cartridge is then preferably moved back onto the reader tray and the reader tray is ejected leaving the cartridge external to the reader and ready for the user, or optionally an automated system, to remove the cartridge from the tray and dispose of it properly.

A preferred embodiment of the performance of an assay using cartridge 3200 is described below, the description focusing on aspects that differ from the operational steps described for cartridge 2500. The operational description includes the use of a preferred valve configuration in the cartridge reader that is similar to that described in FIG. 24 except that it is configured so that air vent port 3244 and air bubble trap vent port 3266 can be connected to the pump, sealed or vented to the atmosphere. In view of the operational description provided for cartridge 2500, the basic operations that are used to move fluid in this preferred embodiment (i.e., opening vent ports on one side of the fluid to be moved to air and applying positive or negative pressure to a vent port on the other side of the liquid) will be apparent and are not always described.

A sample, preferably a sample comprising and/or collected on a solid matrix, is inserted in sample chamber 3220 and cap 3297 is closed. In an especially preferred embodiment, the sample (most preferably an upper respiratory sample and/or a sample suspected of containing a *streptococcus* strain) was collected on an applicator stick (preferably a swab), the applicator stick preferably comprises a pre-defined weak point and the sample chamber is curved as shown in FIG. 33, in this especially preferred embodiment, insertion of the stick into the curved chamber causes the shaft to break. The shaft segment is then, preferably, removed and the head segment is sealed in the chamber by closing cap 3297.

The cartridge is inserted into a reader and mated to the appropriate electrical and fluidic connections as described above for cartridge 2500. The cartridge preferably holds ampoules of extraction and wash buffer in, respectively, reagent chambers 3210 and 3240 which are preferably broken now (or alternatively any time before they are required). The extraction reagent (preferably, nitrous acid, more preferably, nitrous acid made from a liquid acid in a reagent ampoule and a dry nitrate salt present outside the ampoule in chamber 3210) is pulled from its reagent chamber 3210 by opening vent port 3212 to air, vent port 3244 or 3264 to the pump, and operating the pump to draw the extraction reagent through the swab. To eliminate bubbles in the sample, the pump is operated until fluid from the swab is detected at sensor position #1. The fluid is then pushed into bubble trap 3226 by opening vent port 3266 to air and operating the pump to apply positive pressure at vent port 3244 or 3264 (or the reverse, i.e., applying negative pressure at vent port 3266 and opening vent port 3244 or 3264 to air). In bubble trap 3226, the bubbles rise to the top of the trap leaving bubble free liquid at the bottom of the trap. More fluid from the swab is pulled up to sensor in and again pushed into the bubble trap. This is repeated as often as necessary to ensure enough bubble-free liquid is collected in the bubble trap to conduct the assay.

Bubble-free sample liquid is then drawn from the bottom of nibble trap 3226 (by aspirating from vent port 3244 or 3264 with vent port 3266 open to air) until the fluid front reaches sensor #1. Vent port 3266 is closed and vent port 3262 is opened to air and the defined slug of sample is drawn forward, pulling air behind it from vent port 3262. This process accurately measures out a defined volume of sample liquid. The sample slug is then drawn across dry assay reagent 3225 to dissolve it—this reagent preferably includes buffers, labeled binding reagents (preferably antibodies) for the assays, stabilizing reagents, and/or other additives such as blocking reagents. For assays employing nitrous acid as an extraction reagent, the dry assay reagent preferably comprises sufficient base (preferably, the base form a pH buffer such as Tris, Hepes, phosphate, PIPES, etc.) to bring the pH of the sample to between 4-10, more preferably between 5-9, more preferably between 6-8. The dissolved reagents may be mixed into the sample by moving the sample back and forth in the fluid line, using sensors to ensure that the liquid remains within a defined region of conduit.

The sample containing the reconstituted assay reagents is then drawn into detection chamber 3230, where immobilized binding agents (preferably antibodies) are present on individual binding zones that are, more preferably, located on electrodes in an electrode array. The sample is incubated for a specific time period over the binding zones, either in a static mode or under mixing, during which time the analyte and labeled binding reagent can bind to each other and/or to the individual binding zones. Mixing is performed by moving the sample back-and-forth between sensors at the end of the read chamber.

Sometime before, during, or after sample incubation, a positive control assay is also performed in the other binding chamber: wash buffer is pulled from the wash buffer storage chamber 3240 to sensor #2 by pulling vacuum on vent port 3264 with vent port 3241 open to air. A fluid slug is metered by closing vent port 3241 and opening vent port 3244 to introduce air behind the metered fluid as it is drawn toward control detection chamber 3250. The metered fluid slug is then drawn over and dissolves dry control reagents 3252. These reagents, preferably, include labeled binding reagents (preferably antibodies), defined amounts of the analytes for the assays (to provide positive controls), stabilizing reagents and/or other assay reagents. The positive control sample, comprising the metered wash buffer slug and rehydrated control reagents, is then incubated in the control detection chamber 3250 either in a static fashion or with mixing by moving the sample between sensors located at the end of the control binding zone.

Following the incubation steps, the positive control sample is drawn into waste chamber 3254 and the extracted swab sample is drawn into the waste chamber 3228. Both detection chambers are washed in a consecutive or simultaneous manner by drawing wash buffer from wash buffer chamber 3240 through the detection chambers and into their corresponding waste chambers (waste chamber 3228 for detection chamber 3230 and waste chamber 3254 for control detection chamber 3250). The wash reagent used during the wash step is preferably segmented by introducing air at vent port 3244. After washing, both the control and sample binding zones are filled with wash buffer to complete the fluid sequence. Advantageously, wash reagent flows through detection chamber 3230 in a direction opposite that in which sample was introduced into chamber 3230. This reverse flow wash ensures the efficient removal of any components in the sample and/or extraction buffer that could interfere with a measurement in the detection chamber.

Preferably, the binding of analyte and/or labeled binding reagents to binding domains in the detection chambers is measured by an ECL measurement as described above for cartridge 2500. ECL is initiated by applying the desired electrical potentials to electrodes supporting the binding zones. The positive control binding zones in detection chamber 3250 will provide a positive signal for each assay and may be used to provide assurance that the assay reagents onboard the cartridge have not degraded. The ECL signal from any of the sample binding zones in detection chamber 3230 indicates the presence of analyte binds to that capture zone or competes with the binding of a labeled reagent to that capture zone.

A preferred embodiment of the performance of an assay using cartridge 3700 and reader 4300 is described below, the description focusing on aspects that differ from the operational steps described above for other embodiments of the cartridge and reader. The operational description includes the use of a preferred valve configuration shown in FIG. 37. The basic operations that are used to move fluid in this preferred embodiment (i.e., opening vent ports on one side of the fluid to be moved to air and applying positive or negative pressure to a vent port on the other side of the liquid) will be apparent and are not always described. During operation, the instrument continually monitors to make sure that fluid fronts pass appropriate optical sensors and do not pass by the protection sensors at the vent ports. If inappropriate fluid movement is detected, the instrument may stop the processing of a cartridge or implement corrective actions.

Figure 44C:
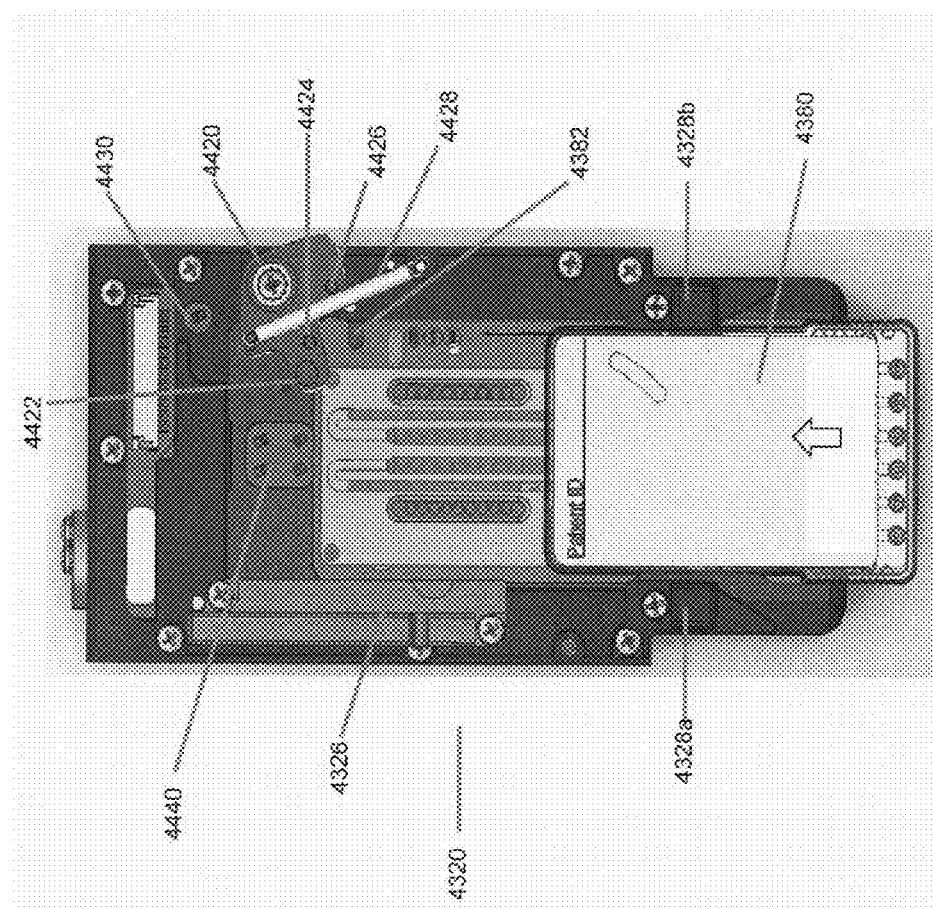
Figure 44D:
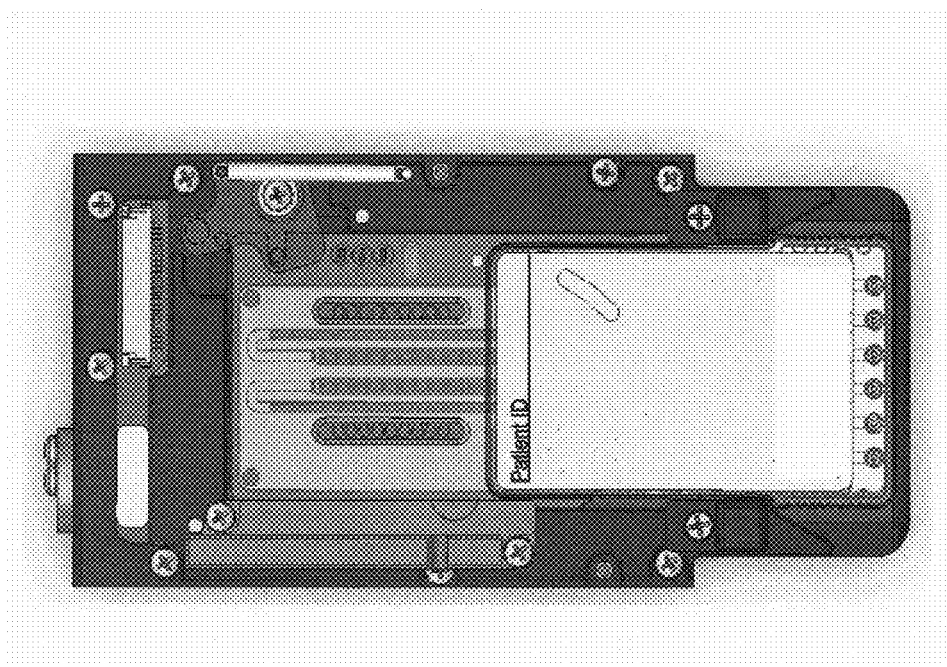

A sample is collected on a swab with a pre-defined weak point (as described in the text above) is inserted in sample chamber 3720. During insertion into the curved chamber, the swab head breaks of and is retained by retaining features 3721a and 3721b as the swab shaft is removed. The cartridge cap is then sealed. If lot-specific parameters for the lot of cartridges are not stored on the instrument, the user can download, them onto the instrument through its network interface or through connection of an external memory device (EEPROM, memory chip, RFID, barcode, etc.). Alternatively, these settings are stored on memory attached to the cartridge. The user may enter patient and operator information into the reader GUI, if desired, and then inserts the cartridge into cartridge tray 4320 until latched in place with latch 4420 (as shown in FIG. 44). Through the GUI, the user instructs the reader to begin processing and the cartridge tray is drawn into the reader and aligned with the reader's cartridge processing sub-components (as described in FIG. 43 and the associated text description) which includes mating the cartridge to the appropriate electrical and fluidic connections.

Once the cartridge is correctly positioned, the reader uses ampoule breaking assembly 4200 to break the extraction reagent buffer ampoule (which in the case of a typing/subtyping panel is, preferably, a low pH buffer as described above). The pump is used to aspirate air from the extraction reagent chamber through the sample chamber and into collection component 3726 until liquid reaches the collection component optical sensor indicating that the correct volume of extracted sample has been collected (described in greater detail in FIG. 38 and the accompanying description). Optionally, the extraction process can use an air-segmented stream of extraction buffer by alternating between aspirating from the extraction buffer chamber vent and the air port vent.

The sample is metered into the assay flow cell channels by applying pressure at the collection component vent and connecting the left or right waste vents to ambient (to meter into the left or right channels) until the sample fronts reach optical sensors 2a and 2b in the two channels (as numbered in FIG. 37(b) and in annotated FIG. 37(c)). Air is drawn to the collection chamber vent from the air port vent to finish the metering process. Air is then pulled from the air port vent toward the right waste chamber vent until the fluid front reaches sensor 4a. Air is then pulled from the air port vent toward the left waste chamber vent until the fluid front reaches sensor 4b. As shown in FIG. 37(b), sensors 2a and 2b are at staggered positions within their respective channels to compensate for the dead volume in fluidic junctions 3728 and 3729; the amount of sample metered into the right and left channels is the same (although, optionally, sensor placement can be selected to meter different volumes into the two chambers). After the sample splitting process is complete air is drawn to the collection chamber vent from the air port vent to clear unused sample from the fluidic lines.

The dry reagent pills in the left and right flow chambers are rehydrated by moving the sample slugs back and forth so that the leading and trailing liquid fronts move between sensors 4a and 3a in the right channel (3730a) and 4b and 3b in the left channel (3730b). For one step immunoassays, the dry pill may contain labeled antibodies, in the specific case of an influenza typing/subtyping panel, the dry pill may contain a neutralizing buffer to compensate for the low pH of the extraction buffer.

Right and left ECL detection chambers 3731a and 3731b are filled with sample by pulling the respective fluid slugs until the trailing edges reach optical sensors 5a and 5b. The slugs are then moved back and forth in the channels such that the trailing edges move between sensors 5a and 4a (right) and 5b and 4b (left). This process is continued for the prescribed assay incubation time to allow binding reactions to occur at the electrodes in the detection channels. Optionally, the cycling process is stopped occasionally and i) air is pulled from the air port vent to the collection component vent to prevent any wicking of fluid out of the collection component and/or ii) the extraction reagent vent is briefly opened to ambient to prevent pressure build-up in the chamber. During back and forth movement of the sample slugs, the reader control system may monitor cycle time and use the observed timing to adjust pump speed to hit a specified fluid flow speed.

On completion of the incubation phase, the samples are cleared from the detection chambers by aspiration of air from the air port to the respective waste ports. A fluidic design with hydrodynamic matching regions is used to provide for even fluidic flow during sample clearing (see FIG. 40 and accompanying text). The wash reagent ampoule (which, for ECL assays, preferably also acts as an ECL read buffer) is then broken and the fluidic lines are primed with wash reagent by pulling wash reagent from the wash reagent chamber toward the waste chambers until optical sensors 2a and 2b detect the fluid fronts. The wash buffer is then cleared through the detection chambers by aspirating fluid toward the right waste chamber from the air port vent and then toward the left waste chamber. To carry out an air-segmented wash of a detection chamber, fluid is aspirated toward the respective waste chamber while alternating between opening the wash buffer vent and the air port vent to ambient pressure. This segmented wash slug is generated until sensor 5a (right chamber) or 5b (left chamber) detects the fluid front. The prepared air-segmented slug is then pulled through the detection chamber and cleared by aspirating toward the respective waste chamber while opening the air port vent to ambient pressure. This process is repeated a pre-determined number of times (e.g., twice) for each detection chamber.

To fill the detection chambers with the wash/read buffer for an ECL measurement, the wash buffer fluid front is first pulled back towards the read buffer chamber while opening the air port vent to ambient. The wash buffer is then metered by applying pressure to the wash buffer chamber vent and moving fluid toward the waste chamber vents until optical sensors 2a and 2b detect the fluid front. The tail of the slug is pulled into the collection component after connecting the air port vent to ambient. The slug in the right channel is then moved into the right detection chamber by aspirating toward the right waste chamber while opening the airport vent to ambient until optical sensor 5a detects the trailing edge of the metered slug. The slug in the left channel is then moved into the left detection chamber by aspirating toward the left waste chamber while opening the airport vent to ambient until optical sensor 5b detects the trailing edge of the metered slug. Optionally, the control electronics checks for the presence of bubbles in the fluid slugs by looking for transient changes in the signal at optical sensors 4a or 4b that are followed by a similar change in the signal at optical sensors 5a or 5b, respectively, where the timing of the changes is consistent with the flow rate of the fluid slugs.

Once the wash/read buffer has been positioned into the detection chambers, ECL analysis is carried out. The photodiode is aligned with an assay electrode in one of the two detection chambers, the appropriate electrical potential is applied to the electrode (preferably, using an adjacent electrode as the counter electrode) and the resulting ECL is measured. By translating the cartridge tray, each assay electrode in the chamber may be aligned with the photodiode and analyzed in a serial fashion. Preferably, after each electrode is analyzed, it is used as the counter electrode for analyzing the adjacent electrode (as described above). When analysis of one channel is complete, the photodiode is shuttled into alignment with the other channel using the photodiode shuttling mechanism described in FIGS. 45 and 46 and the accompanying text. ECL is then induced and measured from the electrodes in the second channel as described for the first channel. Optionally, after ECL analysis is complete, the photodiode is shuttled back to its original position.

Subsequent to ECL analysis, the fluids in the channels may be aspirated into their respective waste chambers and the cartridge tray is extended, allowing the user to remove the cartridge. Assay results are then displayed on the GUI and may also be saved to memory and/or transferred to a network or server. In one embodiment of the invention, the cartridge contains assays for i) detection and typing influenza (for example, assays for influenza nucleoproteins or matrix proteins or other proteins that show high degrees of conservation across an influenza type) and ii) assays for specific influenza subtypes (e.g., assays for specific hemagglutinin or neuraminidase subtypes). Optionally, the typing and subtyping assays are separated into different channels of the cartridge. The ECL signals that are generated are compared to assay thresholds (which may be provided as lot specific parameters) and the GUI reports samples with signals above the thresholds as being positive for the respective influenza type or subtype. In one specific embodiment, the subtyping assays are assays for different influenza A hemagglutinin subtypes and the GUI only reports subtyping results if the typing result is positive for influenza A.

The assay modules (preferably assay cartridges) of the invention may be used to carry out a variety of different assay formats for measuring analytes interest, preferably formats based on electrode induced luminescence measurements. The assays, preferably, comprise the steps of introducing a sample, and optionally one or more solution phase assay reagents, into an detection chamber (preferably a flow cell) that comprises one or more assay domains (preferably a plurality of assay domains) comprising immobilized assay reagents that bind (with at least some degree of selectivity) with analytes of interest. Preferably, there are at least two assay domains that comprise binding immobilized binding reagents that differ in their selectivity for analytes. Preferably, there is a patterned array of immobilized binding reagents. The detection chamber preferably comprises a plurality of electrodes including one or more assay working electrodes having assay domains. In such a case, electrical energy is applied to the electrodes in a pair wise fashion as described above) to induce an assay dependent signal (e.g., an electrochemical signal such as a current or potential or, preferably, an electrode induced luminescence signal, most preferably an electrochemiluminescence signal) at the electrodes which is dependent on the amounts of the analytes of interest present in the sample. The assay dependent signal is measured to determine the amounts of the analytes of interest. The assays may comprise the step of washing the electrodes with a wash solution or they may be carried out in a non-wash format. In washed electrochemiluminescence assays, the assay preferably comprises the steps of washing the electrodes with a solution comprising an electrochemiluminescence coreactant (e.g., a tertiary alkyl amine such as tripropylamine or PIPES; for other examples of suitable coreactants see copending U.S. patent application Ser. No. 10/238,437 filed Sep. 10, 2002) and inducing ECL in the presence of the coreactant. In non-washed ECL assays, a coreactant is preferably introduced into the detection chamber with the sample or is present in the detection chamber prior to the introduction of the sample. Advantageously, assay modules comprising a plurality of assay domains, preferably on a plurality of electrodes, may be used to conduct assays for a plurality of analytes of interest.

In preferred embodiments of the invention, the assay modules (preferably, assay cartridges) of the invention are used to carry out binding assays, most preferably sandwich or competitive binding assays, preferably sandwich or competitive immunoassays. Such assays may, optionally, comprise the step of introducing into the detection chamber labeled binding reagents such as a labeled binding partner of the analyte of interest or a labeled competitor that competes with the analyte of interest for a binding partner of the analyte of interest. Alternatively, these reagents may be stored in dry or wet form in the detection chamber. For more information on the conduct of binding assays, particularly using electrochemiluminescence based detection, see copending U.S. patent application Ser. No. 10/185,274, filed Jun. 28, 2002 and copending U.S. patent application Ser. No. 10/238,391, filed Sep. 10, 2002, these patent applications hereby incorporated by reference.

The assay modules (preferably, assay cartridges) may be used to carry out panels of assays. Suitable panels include panels of assays for analytes or activities associated with a specific biochemical system, biochemical pathway, tissue, organism, cell type, organelle, disease state, class of receptors, class of enzymes, class of pathogen, environmental sample, food sample, etc. Preferred panels include immunoassay for cytokines and/or their receptors (e.g., one or more of TNF-$\alpha$, TNF-$\beta$, IL1-$\alpha$, IL1-$\beta$, IL2, IL4, IL6, IL10, IFN-$\gamma$, etc.), growth factors and/or their receptors (e.g., one or more of EGF, VGF, TGF, VEGF, etc.), second messengers cAMP, cGMP, phosphorylated forms of inositol and phosphatidyl inositol, etc.) drugs of abuse, therapeutic drugs, auto-antibodies (e.g., one or more antibodies directed against the Sm, RNP, SS-A, SS-B Jo-1, and Scl-70 antigens), allergen specific antibodies, tumor markers, cardiac markers (e.g., one or more of Troponin T, Troponin I, myoglobin, CKMB, etc.), markers associated with hemostasis (e.g., one or more of Fibrin monomer, D-dimer, thrombin-antithrombin complex, prothrombin fragments 1 & 2, anti-Factor Xa, etc.), markers of acute viral hepatitis infection (e.g., one or more of IgM antibody to hepatitis A virus, IgM antibody to hepatitis B core antigen, hepatitis B surface antigen, antibody to hepatitis C virus, etc.), markers of Alzheimers Disease (β-amyloid, tau-protein, etc.), markers of osteoporosis (e.g., one or more of cross-linked N or C-telopeptides, total deoxypyridinoline, free deoxypyridinoline, osteocalein, alkaline phosphatase, C-terminal propeptide of type I collagen, bone-specific alkaline phosphatase, etc.), markers of fertility (e.g., one or more of Estradiol, progesterone, follicle stimulating hormone (FSH), luetenizing hormone (LH), prolactin, β-hCG, testosterone, etc.), markers of congestive heart failure (e.g., one or more of β-natriuretic protein (BNP), a-natriuretic protein (ANP), endothelin, aldosterone, etc.), markers of thyroid disorders (e.g., one or more of thyroid stimulating hormone (TSH), Total T3, Free T3, Total T4, Free T4, and reverse T3), and markers of prostrate cancer (e.g., one or more of total PSA, free PSA, complexed PSA, prostatic acid phosphatase, creatine kinase, etc.), pathogens associated with upper respiratory infection (e.g., influenza A, influenza B, Respiratory Syncytial Virus, Streptococci species), pathogens found in food and water (e.g. *salmonella, listeria, eryptosporidia, campylobacter, E. Coli* 0157, etc.), sexually transmitted diseases (e.g., lily, syphilis, herpes, gonorrhea, HPV, etc.), blood borne pathogens and potential bioterrorism agents (e.g., pathogens and toxins in the CDC lists of Select A, B and C agents such as *B. anthracis, Y. pestis*, small pox, *F. tularensis*, ricin, botulinum toxins, staph enterotoxins, etc.). Preferred panels also include nucleic acid arrays for measuring mRNA levels of mRNA coding for cytokines, growth factors, components of the apoptosis pathway, expression of the P450 enzymes, expression of tumor related genes, pathogens (e.g. the pathogens listed above), etc. Preferred panels also include nucleic acid arrays for genotyping individuals (e.g., SNP analysis), pathogens, tumor cells, etc. Preferred panels also include libraries of enzymes and/or enzyme substrates (e.g., substrates and/or enzymes associated with ubiquitination, protease activity, kinase activity, phosphatase activity, nucleic acid processing activity, GTPase activity, guanine nucleotide exchange activity, GTPase activating activity, etc.). Preferred panels also include libraries of receptors or ligands (e.g., panels of G-protein coupled receptors, tyrosine kinase receptors, nuclear hormone receptors, cell adhesion molecules (integrins, VCAM, CD4, CD8), major histocompatibility complex proteins, nicotinic receptors, etc.). Preferred panels also include libraries of cells, cell membranes, membrane fragments, reconstituted membranes, organelles, etc. from different sources (e.g., from different cell types, cell lines, tissues, organisms, activation states, etc.).

The present invention also includes kits. The kits may include disassembled components necessary to make an assay module of the invention. Alternatively, the kits may comprise, in one or more containers, an assay module of the invention and at least one additional assay reagent necessary to carry out an assay. The one or more assay reagents may include, but are not limited to, binding reagents (preferably, labeled binding reagents, more preferably binding reagents labeled with electrochemiluminescent labels) specific for analyte of interest, ECL coreactants, enzymes, enzyme substrates, extraction reagents, assay calibration standards or controls, wash solutions, diluents, buffers, labels (preferably, electrochemiluminescent labels), etc. Preferred kits of the invention include cartridges adapted for extracting samples (as described in detail above), preferably samples collected on applicator sticks. These kits preferably include applicator sticks (more preferably swabs) that have properties that are matched to the specific cartridge. Most preferably, the applicator sticks have weak points that are matched to the geometry of a sample introduction chamber in the cartridge such that i) the sticks may be inserted and cleaved in the cartridge to form a head segment and ii) the head segment can be sealed in the sample chamber. Such kits may also include extraction buffers for extracting the sample on the applicator stick. One embodiment of the invention is a kit for measuring upper respiratory pathogens or pathogens that may be found in mucus-containing samples. The kit includes an applicator stick (preferably, a swab) for collecting the sample (the stick preferably comprising a weak point) and a cartridge for measuring a panel of pathogens (e.g., a panel of upper respiratory pathogens, a panel of sexually transmitted diseases, a panel of pathogens that dwell in mucous membranes, etc.), the cartridge preferably comprising one or more binding domains containing binding reagents that bind markers of these pathogens. The kit may also contain (in the cartridge or as a separate component), one or more labeled binding reagents against markers of these pathogens.

The invention includes assay modules (preferably assay cartridges) and module readers (preferably cartridge readers) as described above. These may be supplied as separate components. The invention also includes assays systems that comprise an assay module (preferably a cartridge) and a module reader (preferably a cartridge reader).

The present invention is not to be limited in scope by the specific embodiments described herein. Indeed, various modifications of the invention in addition to those described herein will become apparent to those skilled in the art from the foregoing description and accompanying figures. Such modifications are intended to fall within the scope of the claims. Various publications are cited herein, the disclosures of which are incorporated by reference in their entireties.

What is claimed is:
1. An assay cartridge comprising:
a sample chamber connected to a collection component comprising a collection chamber and a sensing chamber, wherein the assay cartridge comprises a top longitudinal plane and an opposite bottom,
wherein a collection conduit connects the sample chamber to the collection chamber proximate to a top of said collection chamber, and
an output conduit is connected proximate to a bottom of said collection chamber,
wherein a sensing conduit fluidly connects the collection chamber to the sensing chamber, wherein said sensing conduit comprises a tube that connects near the top of the collection chamber and extends into the collection chamber toward the bottom of said collection chamber and terminates before reaching the bottom of said collection chamber, wherein at least a portion of the tube extends in a lateral direction wherein said sensing chamber also connects to a sensing chamber vent, and
wherein a sample comprising at least a liquid is capable of being drawn from the sample chamber into the collection chamber through the collection conduit and a portion of the sample is capable of being drawn to the sensing chamber through the sensing conduit when the sample chamber is fluidly connected to a vent and the sensing chamber vent is exposed to a vacuum, and
wherein a portion of the collection conduit, a portion of the sending conduit, a portion of the sensing chamber vent and a portion of the output conduit are substantially parallel to each other.

2. The assay cartridge of claim 1 wherein said collection chamber further comprises a baffle positioned between said collection and sensing conduits.

3. The assay cartridge of claim 2, wherein the approximate ratio of the dimensional measurements in the assay cartridge of the liquid volume to the air head space volume in the collection chamber is about 1:2 after liquid has reached a distal end of the sensing conduit.

4. The assay cartridge of claim 3, wherein the liquid volume is about 125 µL and the air head space volume is about 250 µL.

5. The assay cartridge of claim 1 wherein the cartridge is adapted to have a portion of said liquid in the sensing chamber detected by an optical sensor.

6. The assay cartridge of claim 5 wherein the optical sensor is contained in the cartridge.

7. The assay cartridge of claim 1 further comprising a detection chamber and a distribution conduit interconnected to a plurality of fluid conduits comprising said output conduit, a detection chamber conduit connected to said detection chamber.

8. The assay cartridge of claim 7 wherein said distribution conduit comprises a Z-transition.

9. The assay cartridge of claim 8 wherein said cartridge comprises an air vent and said plurality of fluid conduits include an air vent conduit connected to said air vent, wherein said detection chamber conduit is distal from said air vent conduit.

10. The assay cartridge of claim 9 wherein said cartridge comprises a wash buffer chamber and said plurality of fluid conduits comprise a wash buffer chamber conduit connected to said wash buffer chamber, wherein said wash buffer chamber conduit is proximal to said air vent conduit and distal to said detection chamber conduit.

11. The assay cartridge of claim 1, wherein at least a portion of said sample exits said collection chamber through said output conduit when said output conduit is exposed to a vacuum source and the sensing chamber vent is vented.

12. The assay cartridge of claim 1, wherein at least a portion of said sample exits said collection chamber through said output conduit when said output conduit is vented and the sensing chamber vent is exposed to a positive pressure source.

13. The assay cartridge of claim 1 wherein an optical sensor located on a cartridge reader is adapted to detect the presence of liquid in said sensing chamber.

14. The assay cartridge of claim 1, wherein the approximate ratio of the dimensional measurements in the assay cartridge of the liquid volume to the air head space volume in the collection chamber is about 1:2 after liquid has reached a distal end of the sensing conduit.

15. An assay cartridge comprising:
a sample chamber connected to a collection component comprising a collection chamber and a sensing chamber, wherein the assay cartridge comprises a top longitudinal plane and an opposite bottom,
wherein a collection conduit connects the sample chamber to the collection chamber proximate to a top of said collection chamber, and
an output conduit is connected proximate to a bottom of said collection chamber;
wherein a sensing conduit fluidly connects the collection chamber to the sensing chamber, wherein said sensing conduit extends near the top of the collection chamber into the collection chamber toward the bottom of said collection chamber and terminates before reaching the bottom of said collection chamber, wherein at least a portion of the sensing conduit extends in a lateral direction wherein said sensing chamber also connects to a sensing chamber vent, and
wherein a sample comprising at least a liquid is capable of being drawn from the sample chamber into the collection chamber through the collection conduit and a portion of the sample is capable of being drawn to the sensing chamber through the sensing conduit when the sample chamber is fluidly connected to a vent and the sensing chamber vent is exposed to a vacuum, and
wherein a portion of the collection conduit, a portion of the sending conduit, a portion of the sensing chamber vent and a portion of the output conduit are substantially parallel to each other.

16. The assay cartridge of claim 15, wherein said collection chamber further comprises a baffle positioned between said collection and sensing conduits.

17. The assay cartridge of claim 15 wherein an optical sensor is adapted to detect the presence of a portion of said liquid in said sensing chamber.

18. The assay cartridge of claim 15, wherein at least a portion of said sample exits said collection chamber through said output conduit when said output conduit is exposed to a vacuum source and the sensing chamber vent is vented.

19. The assay cartridge of claim 15, wherein at least a portion of said sample exits said collection chamber through said output conduit when said output conduit is vented and the sensing chamber vent is exposed to a positive pressure source.

* * * * *

UNITED STATES PATENT AND TRADEMARK OFFICE
CERTIFICATE OF CORRECTION

PATENT NO. : 10,184,884 B2
APPLICATION NO. : 12/959952
DATED : January 22, 2019
INVENTOR(S) : Anderson et al.

Page 1 of 1

It is certified that error appears in the above-identified patent and that said Letters Patent is hereby corrected as shown below:

In the Specification

Column 1, Lines 21-24, under the heading STATEMENT REGARDING FEDERALLY SPONSORED RESEARCH:
"This invention was made with federal support under HHS 200-2007-19346 awarded by the Department of Health and Human Services. The U.S. government has certain rights in the invention."

Should be replaced with:
-- This invention was made with government support under contract 200-2007-19346 awarded by the Centers for Disease Control and Prevention (CDC) and contract AI067203 awarded by the National Institutes of Health (NIH). The U.S. government has certain rights in the invention. --

Signed and Sealed this
Nineteenth Day of April, 2022

Katherine Kelly Vidal
*Director of the United States Patent and Trademark Office*